US010240153B2

(12) United States Patent
Weiler et al.

(10) Patent No.: US 10,240,153 B2
(45) Date of Patent: Mar. 26, 2019

(54) ORGANIC COMPOSITIONS TO TREAT APOC3-RELATED DISEASES

(71) Applicant: Arrowhead Pharmaceuticals, Inc., Pasadena, CA (US)

(72) Inventors: Jan Weiler, Newton, MA (US); William Chutkow, Needham, MA (US); Jeremy Lee Baryza, Quincy, MA (US); Andrew Krueger, Cambridge, MA (US); Junping Zhao, Arlington, MA (US)

(73) Assignee: Arrowhead Pharmaceuticals, Inc., Pasadena, CA (US)

( * ) Notice: Subject to any disclaimer, the term of this patent is extended or adjusted under 35 U.S.C. 154(b) by 0 days.

(21) Appl. No.: 15/403,919

(22) Filed: Jan. 11, 2017

(65) Prior Publication Data

US 2017/0137814 A1    May 18, 2017

Related U.S. Application Data

(63) Continuation of application No. PCT/US2015/040517, filed on Jul. 15, 2015.

(60) Provisional application No. 62/025,164, filed on Jul. 16, 2014.

(51) Int. Cl.
*C12N 15/113*   (2010.01)
*C07H 21/02*    (2006.01)
*A61K 31/713*   (2006.01)

(52) U.S. Cl.
CPC .......... *C12N 15/113* (2013.01); *A61K 31/713* (2013.01); *C07H 21/02* (2013.01); *C12N 2310/14* (2013.01); *C12N 2310/321* (2013.01); *C12N 2310/322* (2013.01); *C12N 2310/341* (2013.01); *C12N 2310/344* (2013.01); *C12N 2310/351* (2013.01); *C12N 2310/3515* (2013.01); *C12N 2320/31* (2013.01)

(58) Field of Classification Search
None
See application file for complete search history.

(56) References Cited

U.S. PATENT DOCUMENTS

| | | | |
|---|---|---|---|
| 5,030,453 A | 7/1991 | Lenk et al. | |
| 5,962,016 A | 10/1999 | Willis | |
| 6,680,068 B2 | 1/2004 | Campbell et al. | |
| 8,084,600 B2 | 12/2011 | Natt et al. | |
| 8,097,716 B2 | 1/2012 | Weiler et al. | |
| 8,344,128 B2 | 1/2013 | Natt et al. | |
| 8,404,831 B2 | 3/2013 | Natt et al. | |
| 2002/0162126 A1 | 10/2002 | Beach et al. | |
| 2003/0012812 A1 | 1/2003 | Tormo et al. | |
| 2004/0072779 A1 | 4/2004 | Kreutzer et al. | |
| 2004/0142025 A1 | 7/2004 | Maclachlan et al. | |
| 2004/0147475 A1 | 7/2004 | Li et al. | |
| 2004/0204377 A1 | 10/2004 | Rana | |
| 2004/0208921 A1 | 10/2004 | Ho et al. | |
| 2004/0234586 A1 | 11/2004 | Meloche et al. | |
| 2005/0008617 A1 | 1/2005 | Chen et al. | |
| 2005/0069577 A1 | 3/2005 | Diamond et al. | |
| 2006/0240093 A1 | 10/2006 | Maclachlan et al. | |
| 2007/0135372 A1 | 6/2007 | Maclachlan et al. | |
| 2007/0203084 A1 | 8/2007 | Weiler et al. | |
| 2009/0182136 A1 | 7/2009 | Wengel et al. | |
| 2009/0209626 A1 | 8/2009 | Khvorova et al. | |
| 2009/0291131 A1 | 11/2009 | Maclachlan et al. | |
| 2010/0015705 A1 | 1/2010 | Vodyanyk et al. | |
| 2010/0056768 A1 | 3/2010 | Wengel | |
| 2011/0200582 A1 | 8/2011 | Baryza et al. | |
| 2012/0184595 A1* | 7/2012 | MacDonald | ......... A61K 9/1272 514/44 A |

FOREIGN PATENT DOCUMENTS

| | | |
|---|---|---|
| WO | 2010083615 A1 | 7/2010 |
| WO | 2012177947 A2 | 12/2012 |
| WO | 2013165816 A2 | 11/2013 |
| WO | 2015051366 A2 | 4/2015 |

OTHER PUBLICATIONS

Bernstein, et al.; "Role for a bidentate ribonuclease in the initiation step of RNA interference"; 2001; Nature; 409:363-366.
Burgin et al. 1996 Biochemistry 35: 14090-14097.
Caplen et al. 2001 Proc. Natl. Acad. Sci. (USA), 98: 9742-9747.
Chu and Rana; "Potent RNAi by short RNA triggers"; RNA; 2008; 14: 1714-1719.
Dammerman, M et al.; "An apolipoprotein CIII haplotype protective against hypertriglyceridemia is specified by promoter and 3' untranslated region polymorphisms"; Proc. Natl. Acad. Sci. U.S.A.; vol. 90; pp. 4562-4566; 1993.
De Silva et al.; "Overexpression of Human Apolipoprotein C-III in Transgenic Mice Results in an Accumulation of Apolipoprotein B48 Remnants That Is Corrected by Excess Apolipoprotein E"; J. Biol. Chem.; 1994; vol. 269; pp. 2324-2335.
Donze and Picard, 2002, 30(10): e46.
Dowler et al.; Nucleic Acids Research; 2006; vol. 34; No. 6; 1669-1675.
Duxbury et al., J. Surgical Research, 2004, 117: 339-344.
Elbashir et al. 2001 Genes Dev. 15: 188-200.
Elbashir et al. 2001 EMBO J. 20: 6877-6888.
Elbashir et al. 2001 Nature 411: 494-498.
Farhood, et al., Biochimica et Biophysica Acta, 1235, (1995), 289-295.
Gamblilng et al.; Kidney International, vol. 65; 2004; pp. 1774-1781.

(Continued)

*Primary Examiner* — Tracy Vivlemore
(74) *Attorney, Agent, or Firm* — Robert M. Teigen; Paul VanderVelde

(57) ABSTRACT

The present disclosure relates to compositions and methods for treating APOC3-related diseases such as: hypertriglyceridemia (e.g., Type V Hypertriglyceridemia), abnormal lipid metabolism, abnormal cholesterol metabolism, atherosclerosis, hyperlipidemia, diabetes, including Type 2 diabetes, obesity, cardiovascular disease, and coronary artery disease, among other disorders relating to abnormal metabolism or otherwise, using a therapeutically effective amount of a RNAi agent to APOC3.

17 Claims, 12 Drawing Sheets

Specification includes a Sequence Listing.

(56) References Cited

OTHER PUBLICATIONS

Gautier et al. 1987 Nucleic Acids. Res. 15: 6625-6641.
Henschel et al.; "DEQOR: a web-based tool for the design and quality control of siRNAs"; Nucleic Acids Research; vol. 32; Web Server Issue: W113-W120; 2004.
Hertz et al.; "Mode of Action of Peroxisome Proliferators as Hypolipidemic Drugs"; J. Biol. Chem.; vol. 270; No. 22; Issue of Jun. 2; pp. 13470-13475; 1995.
Hutvagner et al. 2001 Science 293: 834-838.
Inoue et al. 1987 Nucleic Acids Res. 15: 6131-6148.
Inoue et al. 1987 FEBS Lett 215: 327-330.
Ito et al.; "Hypertriglyceridemia as a Result of Human Apo CIII Gene Expression in Transgenic Mice"; Science; 1990; 249; pp. 790-793.
Karathanasis; "Apolipoprotein multigene family: Tandem organization of human apolipoprotein AI, CIII, and AIV genes"; Proc. Natl. Acad. Sci. U.S.A.; vol. 82; pp. 6374-6378; Oct. 1985.
Kardassis et al.; "SMAD Proteins Transactivate the Human ApoCIII Promoter by Interacting Physically and Functionally with Hepatocyte Nuclear Factor 4"; J. Biol. Chem.; vol. 275; No. 52; Issue of Dec. 29; pp. 41405-41414; 2000.
Kardassis et al.; "Direct Physical Interactions between HNF-4 and Sp1 Mediate Synergistic Transactivation of the Apolipoprotein CIII Promoter"; Biochemistry; 2002; 41; 1217-1228.
Kraynack et al. 2006 RNA 12:163-176.
Li et al.; "Common Genetic Variation in the Promoter of the Human apo CIII Gene Abolishes Regulation by Insulin and May Contribute to Hypertriglyceridemia"; J. Clin. Invest.; vol. 96; 1995; pp. 2601-2605.
Maeda et al.; "Molecular cloning of a human apoC-III variant: Thr 74-Ala 74 mutation prevents O-glycosylation"; J. Lipid Res.; vol. 28; 1987; 1405-1409.
Maeda et al.; "Targeted Disruption of the Apolipoprotein C-III Gene in Mice Results in Hypotriglyceridemia and Protection from Postprandial Hypertriglyceridemia"; J. Biol. Chem.; vol. 269; No. 38; Issue of Sep. 23; pp. 23610-23616; 1994.
Miller, et al., Biochemistry, 1998, 37(37): 12875-83.
Nyakanen et al. 2001 Cell 107:309-321.
Ogami et al.; "Purification and Characterization of a Heat Stable Nuclear Factor CIIIb1 Involved in the Regulation of the Human ApoC-III Gene"; J. Biol. Chem.; vol. 266; No. 15; Issue of May 25; pp. 9640-9646; 1991.
Olivieri et al.; "ApoC-III gene polymorphisms and risk of coronary artery disease"; J. Lipid Res.; 2002; vol. 43; 1450-1457.
Parrish et al. 2000 Molecular Cell 6: 1077-1087.
Raspe et al.; "Identification of Rev-erbα as a physiological repressor of apoC-III gene transcription"; J. Lipid Res.; vol. 43; pp. 2172-2179; 2002.
Schiffelers et al. 2004 Nucl. Acids Res. 32: e149, pp. 1-10.
Schoonjans et al.; "3-Hydroxy-3-methyglutaryl CoA reductase inhibitors reduce serum triglyceride levels through modulation of apolipoprotein C-III and lipoprotein lipase"; FEBS Letters; 452; 1999; 160-1640.
Sharp et al.; "RNA interference-2001"; Genes & Development; 15:485-490; 2001.
Sharpe et al.; "Human apolipoproteins AI, AII, CII and CIII. cDNA sequences and mRNA abundance" Nucleic Acids Res.; 1984; 12(9): 3917-3932.
Sioud and Sorensen, Biochem Biophys Res Commun. 2003, 312(4):1220-1225.
Sioud 2005 J. Mol. Biol. 348:1079-1090.
Song et al.,2003 Nature Medicine, vol. 9, No. 3, 347-351.
Song et al. 2005 Nat Biotech. 23: 709-717.
Soutschek et al. 2004 Nature 432: 173-178.
Sun et al.; "Asymmetric RNA duplexes mediate RNA interference in mammalian cells"; Nature Biotechnology; vol. 26; No. 12; 2008; 1379-1382.
Usman et al.; TIBS; 1992; 17:334-339.
Usman et al. 1994 Nucleic Acids Symp. Ser. 31: 163-164.
Vu-Dac et al.; "Retinoids Increase Human Apo C-III Expression at the Transcriptional Level ia the Retinoid X Receptor"; J. Clin. Invest.; 1998; vol. 102; No. 3; pp. 625-632.
Yamato et al.; "Enhanced specificity of HPV16 E6E7 siRNA by RNA-DNA chimera modification"; Cancer Gene Therapy; 2011; 18; 587-597.
International Report and Written Opinion for corresponding Application No. PCT/US2015/040517, dated Jan. 17, 2017.
Levy-Wilson et al.; "Isoloation and DNA Sequence of Full-Lenghth cDNA for Human Preapolipoprotein CIII"; DNA; vol. 3; No. 5; 1984; pp. 359-364.
McCaffrey et al.; RNA interference in adult mice; Nature; vol. 418; Jul. 4, 2002; pp. 38-39.
Protter et al.; "Isoloation and Sequence Analysis of the Human Apolipoprotein CIII Gene and the Intergenic Region between the Apo AI and Apo CIII Genes"; DNA; vol. 3; No. 6; 1984; pp. 449-456.
Shachter, Neil S.; "Apolipoproteins C-I and C-III as important modulators of lipoprotein metabolism"; Current Opinion in Lipidology; 2001; 12: 297-304.
Liu et al.; "RNA duplexes with abasic substitutions are potent and allele-selective inhibitors of huntingtin and ataxin-3 expression"; Nucleic Acids Research; vol. 41, No. 18; pp. 8788-8801; 2013.
Supplementary European Search Report for corresponding Application No. EP 15822399 dated Feb. 8, 2018.

* cited by examiner

A.
AS 5'          pa Gf c Af c Uf g Af g Af a Uf a Cf u Gf u Cf c Cf u Uf u sUf sa          SEQ ID NO:135
S  3' X1053-Uf su sUf c Gf u Gf a Cf u Cf u Uf a Uf g Af c Af g Gf g Af a     Af          SEQ ID NO:260

B.
AS 5'          pa Gf c Af c Uf g Af g Af a Uf a Cf u Gf u Cf c Cf u Uf u sUf sa          SEQ ID NO:135
S  3' X1053-Uf c Gf u Gf a Cf u Cf u Uf a Uf g Af c Af g Gf g Af a     Af              SEQ ID NO:259

C.
AS 5'          pa Gf c Af c Uf g Af g Af a Uf a Cf u Gf u Cf c Cf u Uf U sUf sa          SEQ ID NO:135
S  3' X1053-Uf c Gf u Gf a Cf u Cf u Uf a Uf g Af c Af g Gf g                        SEQ ID NO:258

D.
AS 5'          pa Gf c Af c Uf g Af g Af a Uf a Cf u Gf u Cf c sUf su                    SEQ ID NO:137
S  3' X1053-X Uf c Gf u Gf a Cf u Cf u Uf a Uf g Af c Af                              SEQ ID NO:238

FIG. 1

A.  AS 5' pAf Gf c  Af c  Af X  Uf g  Af g  Af a  Uf a  Cf u  Gf u  Gf Um Cm sX sPAZ          SEQ ID NO:223
    S  3' X1053-X Um Cm Gf u  Gf a  Cf u  Cf u  Uf a  Uf a  Af a  Uf g  Af c  a  g           SEQ ID NO:217

B.  AS 5' pAf Gf c  a  X  Uf g  Af g  Af a  Uf a  Cf u  Gf u  Cm sX sPAZ                     SEQ ID NO:223
    S  3' X1082-X Um Cm Gf u  Gf a  Cf u  Cf u  Uf a  Uf a  Af a  Uf g  Af c  a  g           SEQ ID NO:217

C.  AS 5' pAf Gf c  Af c  X  g  Af g  Af a  Uf a  Cf u  Gf u  Um Cm sX sPAZ                  SEQ ID NO:224
    S  3' X1053-X Um Cm Gf u  Gf a  Cf u  Cf u  Uf a  Uf a  Af a  Uf g  Af c  a  g           SEQ ID NO:217

D.  AS 5' pAf Gf c  Af c  Uf g  Af g  Af a  Uf a  Cf u  Gf X  Cm sX sPAZ                     SEQ ID NO:235
    S  3' X1053-X Um Cm Gf u  Gf a  Cf u  Cf u  Uf a  Uf a  Af a  Uf g  Af c  a  g           SEQ ID NO:217

E.  AS 5' pAf Gf c  Af c  Uf g  Af g  Af a  Uf a  Cf u  Gf u  X  sX sPAZ                     SEQ ID NO:236
    S  3' X1053-X Um Cm Gf u  Gf a  Cf u  Cf u  Uf a  Uf a  Af a  Uf g  Af c  a  g           SEQ ID NO:217

F.  AS 5' pa  Gf c  Af c  Uf g  Af g  Af a  Uf a  Cf u  Cf c  Cf u  Uf u  Uf a-X058          SEQ ID NO

| | | | SEQ ID NO:148 |
|---|---|---|---|
| A. | AS 5' | H-c Af a Uf u Uf a Gf c Af c Uf g Af a Af g Af a Uf a Cf u Gf u Cf c-X058 | SEQ ID NO:148 |
| | S 3' | X003-Gf u Uf a Af a Uf c Gf a Uf u Cf u Cf u Uf a Uf g Af c Af g Gf | SEQ ID NO:257 |
| B. | AS 5' | H-C Af a Uf u Uf a Gf c Af c Uf g Af a Af g Af a Uf a Cf u Gf u Cf c-X058 | SEQ ID NO:148 |
| | S 3' | X003-Gu Uf a Af a Uf c Gf a Uf u Cf u Cf u Uf g Uf g Af c Af g Gf | SEQ ID NO:257 |
| C. | AS 5' | H-A a Uf u Uf a Gf c Af c Uf g Af a Af g Af a Uf a Cf u Gf u Cf c-X058 | SEQ ID NO:148 |
| | S 3' | X003-G U Uf a Af a Uf c Gf a Uf u Cf u Cf u Uf a Uf g Af c Af g Gf | SEQ ID NO:257 |
| D. | AS 5' | H-C A Af u Uf a Gf c Af c Uf g Af a Af g Af a Uf a Cf u Gf u Cf c-X058 | SEQ ID NO:148 |
| | S 3' | X003-G U U a Af a Uf c Gf u Uf a Cf u Cf u Uf a Uf g Af c Af g Gf | SEQ ID NO:257 |
| E. | AS 5' | H-C A A Uf u Uf a Gf c Af c Uf g Af a Af g Af a Uf a Cf u Gf u Cf c-X058 | SEQ ID NO:148 |
| | S 3' | X003-G U U A Af a Uf c Gf a Uf a Cf u Cf u Uf a Uf g Af c Af g Gf | SEQ ID NO:257 |
| F. | AS 5' | H-C A A U Uf u Uf a Gf c Af c Uf g Af a Af g Af a Uf a Cf u Gf u Cf c-X058 | SEQ ID NO:148 |
| | S 3' | X003-G U U A A Af a Uf c Gf u Cf u Cf u Uf a Uf g Af c Af g Gf | SEQ ID NO:257 |
| G. | AS 5' | H-C A A U U Uf a Gf c Af c Uf g Af a Af g Af a Uf a Cf u Gf u Cf c-X058 | SEQ ID NO:148 |
| | S 3' | X003-G U U A A A Af c Gf a Uf a Cf u Cf u Uf a Uf g Af c Af g Gf | SEQ ID NO:257 |
| H. | AS 5' | H-C A A U U U Uf a Gf c Af c Uf g Af a Af g Af a Uf a Cf u Gf u Cf c-X058 | SEQ ID NO:148 |
| | S 3' | X003-G U U A A A A Gf c Gf u Cf u Cf u Uf a Uf g Af c Af g Gf | SEQ ID NO:257 |
| I. | AS 5' | H-c Af u Uf u Uf a Gf c Af c Uf g Af a Af g Af a Uf a Cf u Gf u Cf c-H | SEQ ID NO:148 |
| | S 3' | X003-G U U A A A U Gf a Uf c Gf u Cf u Cf u Uf a Uf g Af c Af g Gf | SEQ ID NO:257 |
| J. | AS 5' | H-c Af u Uf u Uf a Gf c Af c Uf g Af a Af g Af a Uf a Cf u Gf u Cf c-X058 | SEQ ID NO:148 |
| | S 3' | X003-G U U A A U A Gf c Gf u Uf a Cf u Cf u Uf a Uf g Af c Af g Gf | SEQ ID NO:257 |
| K. | AS 5' | H-c Af u Uf u Uf a Gf c Af c Uf g Af a Af g Af a Uf a Cf u Gf u Cf c-H | SEQ ID NO:148 |
| | S 3' | X003-Gm Um Uf a Af a Uf c Gf a Uf a Cf u Cf u Uf a Uf g Af c Af g Gf | SEQ ID NO:257 |
| L. | AS 5' | H-c Af u Uf u Uf a Gf c Af c Uf g Af a Af g Af a Uf a Cf u Gf u Cf c-X058 | SEQ ID NO:148 |
| | S 3' | X003-G U U A A A a Gf c Gf u Cf u Cf u Uf a Uf g Af c Af g Gf | SEQ ID NO:257 |

FIG. 3A

| | | | |
|---|---|---|---|
| M. | AS 5' | H-c Af a U U U A Gf c Af c Uf g Af a Cf u Gf u Cf c-X058 | SEQ ID NO:148 |
| | S 3' | X003 Gf u Uf A A A A U c Gf u Cf a Cf u Uf a Uf a Af c Af g Gf | SEQ ID NO:257 |
| N. | AS 5' | H-c Af a U U U A Gf c Af c Uf g Af a Cf u Gf u Cf c-X058 | SEQ ID NO:148 |
| | S 3' | X003 Gf u Uf A Af a Uf u Af a Cf u Gf a Uf g Af c Af g Gf | SEQ ID NO:257 |
| O. | AS 5' | H-c Af a Af u U A Gf c Af c Uf g Af a Cf u Gf u Cf c-X058 | SEQ ID NO:255 |
| | S 3' | X003 Gf u Uf A A a Uf c Gf u Cf a Cf u Uf a Uf a Af g Gf | SEQ ID NO:257 |
| P. | AS 5' | H-c Af a Uf u Uf a Gf c Af c Uf g Af a Cf u Gf u Cf c-X058 | SEQ ID NO:256 |
| | S 3' | X003 X Gm Um Uf a Af a Uf c Gf u Cf a Cf u Af c Af u Gf | SEQ ID NO:261 |
| Q. | AS 5' | H-c Af a Uf u Uf a Gf c Af c Uf g Af a Cf u Gf u Cf c-X058 | SEQ ID NO:256 |
| | S 3' | X003 X Gm Um Uf a Af a Uf c Gf u Cf a Uf g Af c Af u Gf | SEQ ID NO:261 |
| R. | AS 5' | H-C A A U U A G C A C U G A G A A U A C U G U C C-X058 | SEQ ID NO:148 |
| | S 3' | X003 G U U A A A U C G U C A U U A C U G Cm Cm X-X058 | SEQ ID NO:257 |
| S. | AS 5' | H-C A A U U A G C A C U G A G A A U A C U G U C C-H | SEQ ID NO:148 |
| | S 3' | X003 G U U A A A U C G U C A U U A C U G Cm Cm X-X058 | SEQ ID NO:257 |
| T. | AS 5' | H-C A A U U A G C A C U G A G A A U A C U G U C C-X058 | SEQ ID NO:148 |
| | S 3' | X003 G u u A A A u C G u C A u u A C u G A C A G G | SEQ ID NO:257 |
| U. | AS 5' | H-C A A U U A G C A C U G A G A A U A C U G U C C-H | SEQ ID NO:148 |
| | S 3' | X003-G u u A A A u C G u C A u u A C u G A C A G G | SEQ ID NO:257 |
| V. | AS 5' | H-C A A U U A G C A C U G A G A A U A C U G U C C-X058 | SEQ ID NO:148 |
| | S 3' | X003-dG dU U A A A U C G U C A U U A C U G A C A G G | SEQ ID NO:257 |

FIG. 3B

|   |         |                                                                                                 |                          |
|---|---------|-------------------------------------------------------------------------------------------------|--------------------------|
| A.| AS 5'   | H-a Gf c Af c Uf g Af a Af g Af a Cf u Gf u Cf c Cf u Uf u Uf a-X058                            | SEQ ID NO:252            |
|   | S 3'    | X003-Uf c Gf u Gf a Cf u Cf u Uf a Uf g Af c Uf g Af g Gf a Af a Af a Uf                        | SEQ ID NO:250            |
| B.| AS 5'   | H-A Gf c Af c Uf g Af g Af a Uf a Cf u Gf u Cf u Cf u Uf u Uf a-X058                            | SEQ ID NO:252            |
|   | S 3'    | X003-U c Gf u Gf a Cf u Cf u Uf a Uf g Af a Uf g Af g Gf a Af a Af a Uf                         | SEQ ID NO:250            |
| C.| AS 5'   | H-A G c Af c Uf g Af g Af a Uf a Cf u Gf u Cf c Cf u Uf u Uf a-X058                             | SEQ ID NO:252            |
|   | S 3'    | X003-U c Gf u Gf a Cf u Cf u Uf a Uf g Af c Uf g Af g Gf a Af a Af a Uf                         | SEQ ID NO:250            |
| D.| AS 5'   | H-A G C Af c Uf g Af g Af a Uf a Cf u Gf u Cf c Cf u Uf u Uf a-X058                             | SEQ ID NO:252            |
|   | S 3'    | X003-U C Gf u Gf a Cf u Cf u Uf a Uf g Af c Uf g Af g Gf a Af a Af a Uf                         | SEQ ID NO:250            |
| E.| AS 5'   | H-A G C A c Uf g Af g Af a Uf a Cf u Gf u Cf c Cf u Uf u Uf a-X058                              | SEQ ID NO:252            |
|   | S 3'    | X003-U C G u Gf a Cf u Cf u Uf a Uf g Af c Uf g Af g Gf a Af a Af a Uf                          | SEQ ID NO:250            |
| F.| AS 5'   | H-A G C A C Uf g Af g Af a Uf a Cf u Gf u Cf c Cf u Uf u Uf a-X058                              | SEQ ID NO:252            |
|   | S 3'    | X003-U C G U Gf a Cf u Cf u Uf a Uf g Af c Uf g Af g Gf a Af a Af a Uf                          | SEQ ID NO:250            |
| G.| AS 5'   | H-A G C A C U g Af g Af a Uf a Cf u Gf u Cf c Cf u Uf u Uf a-X058                               | SEQ ID NO:252            |
|   | S 3'    | X003-U C G U G a Cf u Cf u Uf a Uf g Af c Uf g Af g Gf a Af a Af a Uf                           | SEQ ID NO:250            |
| H.| AS 5'   | H-A G C A C U G Af g Af a Uf a Cf u Gf u Cf c Cf u Uf u Uf a-X058                               | SEQ ID NO:252            |
|   | S 3'    | X003-U C G U G A Cf u Cf u Uf a Uf g Af c Uf g Af g Gf a Af a Af a Uf                           | SEQ ID NO:250            |
| I.| AS 5'   | H-a Gf c Af c Uf g Af g Af a Uf a Cf u Gf u Cf u Cf u Uf u Uf a-H                               | SEQ ID NO:252            |
|   | S 3'    | X003-Uf c Gf u Gf a Cf u Cf u Uf a Uf g Af c Uf g Af g Gf a Af a Af a Uf                        | SEQ ID NO:250            |
| J.| AS 5'   | H-A G C A C U G A g Af a Uf a Cf u Gf u Cf c Cf u Uf u Uf a-X058                                | SEQ ID NO:252            |
|   | S 3'    | X003-U C G U G A C u Cf u Uf a Uf g Af c Uf g Af g Gf a Af a Af a Uf                            | SEQ ID NO:250            |
| K.| AS 5'   | H-a Gf c Af c Uf g Af g Af a Uf a Cf u Gf u Cf c Cf u Uf u Uf a-X058                            | SEQ ID NO:252            |
|   | S 3'    | X003-Um Cm Gf u Gf a Cf u Cf u Uf a Uf g Af c Uf g Af g Gf a Af a Af a Uf                       | SEQ ID NO:250            |
| L.| AS 5'   | H-A G C A C U g Af g Af a Uf a Cf u Gf u Cf c Cf u Uf u Uf a-X058                               | SEQ ID NO:252            |
|   | S 3'    | X003-U C G U G a Cf u Cf u Uf a Uf g Af c Uf g Af g Gf a Af a Af a Uf                           | SEQ ID NO:250            |

FIG. 4A

```
M.  AS 5'      H-a Gf c A C  U G Af g Af a Uf a Cf u Gf c Cf u Uf u Uf a-X058              SEQ ID NO:252
    S  3' X003-Uf c Gf u Gf a Cf u Uf a Uf g Af c Af g Gf a Af a Uf                         SEQ ID NO:250

N.  AS 5'      H-a Gf c A C U G Af a Uf a Cf u Gf u Cf c Cf u Uf u Uf a-X058                SEQ ID NO:252
    S  3' X003-Uf c Gf u Gf a Cf u Uf a Uf g Af c Af g Gf a Af a Uf                         SEQ ID NO:250

O.  AS 5'      H-a    Gf c Af c Uf g Af Af a Cf u Gf u Cf c Cf u Uf u Um Am rib-X058        SEQ ID NO:253
    S  3' X003-rib Um Cm Gf u Gf a Cf u Uf a Uf g Af c Af g Gf g Af a Af a Uf                SEQ ID NO:251

P.  AS 5'      H-a    Gf c Af c Uf g Af Af a Cf u Gf u Cf c Cf u Uf u Um Am rib-X003        SEQ ID NO:253
    S  3' X003-rib Um Cm Gf u Gf a Cf u Uf a Uf g Af c Af g Gf g Af a Af a Uf                SEQ ID NO:251

Q.  AS 5'      H-A G C A C U G A A U A C U G U C C C U U U U A-X058                         SEQ ID NO:252
    S  3' X003-U C G U G A C U U A U G A C A G G G A A A A U                                 SEQ ID NO:250

R.  AS 5'      H-A G C A C U G A A U A C U G U C C C U U U U A-H                             SEQ ID NO:252
    S  3' X003-U C G U G A C U U A U G A C A G G G A A A A U                                 SEQ ID NO:250

S.  AS 5'      H-A G C A C U G A A u A C U G u C C C u u u u A-X058                         SEQ ID NO:252
    S  3' X003-u C G u G A C u u u A u G A C A G G G A A A A u                                 SEQ ID NO:250

T.  AS 5'      H-A G C A C U G A A u A C U G u C C C u u u u A-H                             SEQ ID NO:252
    S  3' X003-u C G u G A C u u u A u G A C A G G G A A A A u                                 SEQ ID NO:250
```

FIG. 4B.

| | | |
|---|---|---|
| A. | AS 5' H-Af Gf c Af c Uf g Af g Af a Cf u Gf Um Cm-rib-PAZ | SEQ ID NO:218 |
| | S 3' X003-rib-Um Cm Gf u Gf a Cf u Cf u Uf a Af c a g | SEQ ID NO:217 |
| B. | AS 5' H-rib Gf c Af c Uf g Af g Af a Cf u Gf Um Cm-rib-PAZ | SEQ ID NO:219 |
| | S 3' X003-rib-Um Cm Gf u Gf a Cf u Cf u Uf a Af c a g | SEQ ID NO:217 |
| C. | AS 5' H-Af rib c Af c Uf g Af g Af a Cf u Gf Um Cm-rib-PAZ | SEQ ID NO:220 |
| | S 3' X003-rib-Um Cm Gf u Gf a Cf u Cf u Uf a Af c a g | SEQ ID NO:217 |
| D. | AS 5' H-Af Gf rib Af c Uf g Af g Af a Cf u Gf Um Cm-rib-PAZ | SEQ ID NO:221 |
| | S 3' X003-rib-Um Cm Gf u Gf a Cf u Cf u Uf a Af c a g | SEQ ID NO:217 |
| E. | AS 5' H-Af Gf c rib c Uf g Af g Af a Cf u Gf Um Cm-rib-PAZ | SEQ ID NO:222 |
| | S 3' X003-rib-Um Cm Gf u Gf a Cf u Cf u Uf a Af c a g | SEQ ID NO:217 |
| F. | AS 5' H-Af Gf c Af rib Uf g Af g Af a Cf u Gf Um Cm-rib-PAZ | SEQ ID NO:223 |
| | S 3' X003-rib-Um Cm Gf u Gf a Cf u Cf u Uf a Af c a g | SEQ ID NO:217 |
| G. | AS 5' H-Af Gf c Af c rib g Af g Af a Cf u Gf Um Cm-rib-PAZ | SEQ ID NO:224 |
| | S 3' X003-rib-Um Cm Gf u Gf a Cf u Cf u Uf a Af c a g | SEQ ID NO:217 |
| H. | AS 5' H-Af Gf c Af c Uf rib Af g Af a Cf u Gf Um Cm-rib-PAZ | SEQ ID NO:225 |
| | S 3' X003-rib-Um Cm Gf u Gf a Cf u Cf u Uf a Af c a g | SEQ ID NO:217 |
| I. | AS 5' H-Af Gf c Af c Uf g rib g Af a Cf u Gf Um Cm-rib-PAZ | SEQ ID NO:226 |
| | S 3' X003-rib-Um Cm Gf u Gf a Cf u Cf u Uf a Af c a g | SEQ ID NO:217 |
| J. | AS 5' H-Af Gf c Af c Uf g Af rib Af a Cf u Gf Um Cm-rib-PAZ | SEQ ID NO:227 |
| | S 3' X003-rib-Um Cm Gf u Gf a Cf u Cf u Uf a Af c a g | SEQ ID NO:217 |

| | | | | | | | | | | | | | | | | | | |
|---|---|---|---|---|---|---|---|---|---|---|---|---|---|---|---|---|---|---|
| K. | AS 5' | H-Af | Gf | c | Af | c | Uf | g | Af | g | rib a | Uf | a | Cf | u | Gf | u | Cm-rib-PAZ | SEQ ID NO:228 |
| | S 3' | X003-rib-Um | Cm | Gf | u | Cf | a | Cf | u | Uf | a | Uf | g | Cf | u | Af | c | a g | SEQ ID NO:217 |
| L. | AS 5' | H-Af | Gf | c | Af | c | Uf | g | Af | rib | Uf | a | Cf | u | Gf | u | Cm-rib-PAZ | | SEQ ID NO:229 |
| | S 3' | X003-rib-Um | Cm | Gf | u | Cf | a | Cf | u | a | Uf | g | Cf | u | Af | c | a g | | SEQ ID NO:217 |
| M. | AS 5' | H-Af | Gf | c | Af | c | Uf | g | Af | a | rib | Cf | u | Gf | u | Cm-rib-PAZ | | | SEQ ID NO:230 |
| | S 3' | X003-rib-Um | Cm | Gf | u | Cf | a | Cf | u | Uf | a | a | Uf | g | Cf | u | Af | c a g | SEQ ID NO:217 |
| N. | AS 5' | H-Af | Gf | c | Af | c | Uf | g | Af | a | Uf | rib | Cf | u | Gf | u | Cm-rib-PAZ | | SEQ ID NO:231 |
| | S 3' | X003-rib-Um | Cm | Gf | u | Cf | a | Cf | u | Uf | a | Uf | a | Cf | u | Af | c | a g | SEQ ID NO:217 |
| O. | AS 5' | H-Af | Gf | c | Af | c | Uf | g | Af | a | Uf | a | rib | u | Gf | u | Cm-rib-PAZ | | SEQ ID NO:232 |
| | S 3' | X003-rib-Um | Cm | Gf | u | Cf | a | Cf | u | Uf | a | Uf | a | Cf | u | Af | c | a g | SEQ ID NO:217 |
| P. | AS 5' | H-Af | Gf | c | Af | c | Uf | g | Af | a | Uf | a | Cf | rib | Gf | u | Cm-rib-PAZ | | SEQ ID NO:233 |
| | S 3' | X003-rib-Um | Cm | Gf | u | Cf | a | Cf | u | Uf | a | Uf | a | Cf | u | Af | c | a g | SEQ ID NO:217 |
| Q. | AS 5' | H-Af | Gf | c | Af | c | Uf | g | Af | a | Uf | a | Cf | u | rib | u | Cm-rib-PAZ | | SEQ ID NO:234 |
| | S 3' | X003-rib-Um | Cm | Gf | u | Cf | a | Cf | u | Uf | a | Uf | a | Cf | u | Af | c | a g | SEQ ID NO:217 |
| R. | AS 5' | H-Af | Gf | c | Af | c | Uf | g | Af | a | Uf | a | Cf | u | Gf | rib | Cm-rib-PAZ | | SEQ ID NO:235 |
| | S 3' | X003-rib-Um | Cm | Gf | u | Cf | a | Cf | u | Uf | a | Uf | a | Cf | u | Af | c | a g | SEQ ID NO:217 |
| S. | AS 5' | H-Af | Gf | c | Af | c | Uf | g | Af | a | Uf | a | Cf | u | Gf | u | rib-rib-PAZ | | SEQ ID NO:236 |
| | S 3' | X003-rib-Um | Cm | Gf | u | Cf | a | Cf | u | Uf | a | Uf | a | Cf | u | Af | c | a g | SEQ ID NO:217 |

| | | | | | | | | | | | | | | | | | | |
|---|---|---|---|---|---|---|---|---|---|---|---|---|---|---|---|---|---|---|
| A. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | a Cf | u Uf | g Af | a Cf | u Gf | Um | Cm-rib-PAZ | | | | | | SEQ ID NO:237 |
| B. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | a Uf | g Af | g Af | a Cf | u Gf | Um | Cm-rib-PAZ | | | | | | SEQ ID NO:238 |
| C. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | a Uf | g Af | a Cf | u Uf | g Af | a Cf | u Gf | Um | Cm-rib-PAZ | | | SEQ ID NO:239 |
| D. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | a Uf | a Af | g Af | a Cf | u Gf | Um | Cm-rib-PAZ | | | | | | SEQ ID NO:240 |
| E. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | a Uf | g Af | a Cf | u Gf | Um | Cm-rib-PAZ | | | | | | | SEQ ID NO:241 |
| F. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | a Uf | a Uf | a Af | a Cf | u Gf | Um | Cm-rib-PAZ | | | | | | SEQ ID NO:242 |
| G. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | a Uf | a Cf | u Gf | Um | Cm-rib-PAZ | | | | | | | | SEQ ID NO:243 |
| H. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | a Uf | a Cf u | Uf | Gf | Um | Cm-rib-PAZ | | | | | | | SEQ ID NO:244 |
| I. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | g Af | u Cf | u Gf | Um | Cm-rib-PAZ | | | | | | | | SEQ ID NO:245 |
| J. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf | a Uf | a Af | a Cf | u Gf | Um | Cm-rib-PAZ | | | | | | | | SEQ ID NO:246 |
| K. | AS 5' | H-Af | Gf c | Af c | Uf g | Af g | Af u | Uf a | Cf u | Gf | Um | Cm-rib-PAZ | | | | | | SEQ ID NO:249 |
| | S 3' | X003-rib-Um | Cm Gf | u Cf | a Uf | g Af | a Cf | u Gf | Um | Cm-rib-PAZ | | | | | | | | SEQ ID NO:247 |
| L. | AS 5' | H-Af | Gf c | Af c | Uf g | Af g | Af a | Uf a | Cf u | Gf | Um | Cm-rib-PAZ | | | | | | SEQ ID NO:249 |
| | S 3' | X003-rib-Um | Cm Gf | u Cf a | Cf g | Af g | Af a | Cf u | Gf | Um | Cm-rib-PAZ | | | | | | | SEQ ID NO:248 |

SEQUENCE LISTING

<160> NUMBER OF SEQ ID NOS: 546

<210> SEQ ID NO 1
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 1

-continued

```
aaacaugcug ucccuaauu                                                       19

<210> SEQ ID NO 2
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 2
aacaugcugu cccuaauau                                                       19

<210> SEQ ID NO 3
<211> LENGTH: 18
<212> TYPE: DNA
<213> ORGANISM: artificial sequence
<220> FEATURE:
<223> OTHER INFORMATION: RNAi agent sequence

<400> SEQUENCE: 3
aactcagaga acttgtcc                                                        18

<210> SEQ ID NO 4
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 4
aagcagcuag cuacuccau                                                       19

<210> SEQ ID NO 5
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 5
aaguuuacug acaaguucu                                                       19

<210> SEQ ID NO 6
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 6
aauaaagcug gacaagaau                                                       19

<210> SEQ ID NO 7
<211> LENGTH: 18
<212> TYPE: DNA
<213> ORGANISM: artificial sequence
<220> FEATURE:
<223> OTHER INFORMATION: RNAi agent sequence

<400> SEQUENCE: 7
acaacaagga gtacccgg                                                        18

<210> SEQ ID NO 8
<211> LENGTH: 18
<212> TYPE: RNA
```

<213> ORGANISM: artificial sequence
<220> FEATURE:
<223> OTHER INFORMATION: Unmodified NAi agent sequence

<400> SEQUENCE: 8
acaguauucu cagugcuu                                                   18

<210> SEQ ID NO 9
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 9
acaugcuguc ccuaauaau                                                  19

<210> SEQ ID NO 10
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 10
accaaccaac uccagcuau                                                  19

<210> SEQ ID NO 11
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 11
acuacuggag caccguuau                                                  19

<210> SEQ ID NO 12
<211> LENGTH: 18
<212> TYPE: DNA
<213> ORGANISM: artificial sequence
<220> FEATURE:
<223> OTHER INFORMATION: RNAi agent sequence

<400> SEQUENCE: 12
agaacttgtc cttaacgg                                                   18

<210> SEQ ID NO 13
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 13
agcaccguua aggacaagu                                                  19

<210> SEQ ID NO 14
<211> LENGTH: 18
<212> TYPE: DNA
<213> ORGANISM: artificial sequence
<220> FEATURE:
<223> OTHER INFORMATION: RNAi agent sequence

<400> SEQUENCE: 14
agcactgaga atactgtc                                                   18

```
<210> SEQ ID NO 15
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 15
agcuagcuac uccagguau                                                  19

<210> SEQ ID NO 16
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 16
agcuauugag ucgugagau                                                  19

<210> SEQ ID NO 17
<211> LENGTH: 21
<212> TYPE: RNA
<213> ORGANISM: artificial sequence
<220> FEATURE:
<223> OTHER INFORMATION: Unmodified RNAi agent sequence

<400> SEQUENCE: 17
agggacagua uucucagugc u                                               21

<210> SEQ ID NO 18
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 18
agggacagua uucucaguu                                                  19

<210> SEQ ID NO 19
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 19
aguauguucu caugucuuu                                                  19

<210> SEQ ID NO 20
<211> LENGTH: 16
<212> TYPE: RNA
<213> ORGANISM: artificial sequence
<220> FEATURE:
<223> OTHER INFORMATION: Unmodified RNAi agent sequence

<400> SEQUENCE: 20
aguauucuca gugcuu                                                     16

<210> SEQ ID NO 21
<211> LENGTH: 19
<212> TYPE: RNA
<213> ORGANISM: artificial sequence
<220> FEATURE:
```

```
<223> OTHER INFORMATION: Unmodified RNAi agent sequence

<400> SEQUENCE: 21
aguuuacuga caaguucau                                                    19

<210> SEQ ID NO 22
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 22
augcaggguu acaugaagu                                                    19

<210> SEQ ID NO 23
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 23
augcuguccc uaauaaagu                                                    19

<210> SEQ ID NO 24
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 24
auggacaauc acuucagau                                                    19

<210> SEQ ID NO 25
<211> LENGTH: 13
<212> TYPE: RNA
<213> ORGANISM: artificial sequence
<220> FEATURE:
<223> OTHER INFORMATION: Unmodified RNAi agent sequence

<400> SEQUENCE: 25
auucucagug cuu                                                          13

<210> SEQ ID NO 26
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 26
caaccaacuc cagcuauuu                                                    19

<210> SEQ ID NO 27
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 27
caaguuuacu gacaaguuu                                                    19
```

```
<210> SEQ ID NO 28
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 28
caauaaagcu ggacaagau                                              19

<210> SEQ ID NO 29
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 29
caccguuaag gacaaguuu                                              19

<210> SEQ ID NO 30
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 30
caccugccua uccauccuu                                              19

<210> SEQ ID NO 31
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 31
cagaucccug aaaggcuau                                              19

<210> SEQ ID NO 32
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 32
cagcuagcua cuccagguu                                              19

<210> SEQ ID NO 33
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 33
cagcuucaug caggguuau                                              19

<210> SEQ ID NO 34
<211> LENGTH: 19
<212> TYPE: RNA
<213> ORGANISM: artificial sequence
<220> FEATURE:
<223> OTHER INFORMATION: Unmodified RNAi agent sequence
```

```
<400> SEQUENCE: 34
caggaguccg auauagcuu                                                19

<210> SEQ ID NO 35
<211> LENGTH: 17
<212> TYPE: RNA
<213> ORGANISM: artificial sequence
<220> FEATURE:
<223> OTHER INFORMATION: Unmodified RNAi agent sequence

<400> SEQUENCE: 35
caguauucuc agugcuu                                                  17

<210> SEQ ID NO 36
<211> LENGTH: 8
<212> TYPE: RNA
<213> ORGANISM: artificial sequence
<220> FEATURE:
<223> OTHER INFORMATION: Unmodified RNAi agent sequence

<400> SEQUENCE: 36 cagugcuu                                                            8

<210> SEQ ID NO 37
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 37
caguucccug aaagacuau                                                19

<210> SEQ ID NO 38
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 38
caugcagggu uacaugaau                                                19

<210> SEQ ID NO 39
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 39
caugcugucc cuaauaaau                                                19

<210> SEQ ID NO 40
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 40
cauggaacaa gccuccaau                                                19

<210> SEQ ID NO 41
<211> LENGTH: 19
```

```
<212> TYPE: RNA
<213> ORGANISM: artificial sequence
<220> FEATURE:
<223> OTHER INFORMATION: Unmodified RNAi agent sequence

<400> SEQUENCE: 41
cccuagaucu caccuaaau                                                    19

<210> SEQ ID NO 42
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 42
ccggcuucug ggauucuau                                                    19

<210> SEQ ID NO 43
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 43
ccggguacuc cuuguuguu                                                    19

<210> SEQ ID NO 44
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 44
ccguuaagga caaguucuu                                                    19

<210> SEQ ID NO 45
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 45
ccuaauaaag cuggauaau                                                    19

<210> SEQ ID NO 46
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 46
ccuagaagca gcuagcuau                                                    19

<210> SEQ ID NO 47
<211> LENGTH: 21
<212> TYPE: RNA
<213> ORGANISM: artificial sequence
<220> FEATURE:
<223> OTHER INFORMATION: Unmodified RNAi agent sequence

<400> SEQUENCE: 47
```
ccuagaucuc accuaaacau u                                          21

<210> SEQ ID NO 48
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 48
ccuagaucuc accuaaacu                                             19

<210> SEQ ID NO 49
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 49
ccucccaaua aagcuggau                                             19

<210> SEQ ID NO 50
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 50
ccuucucagc uucaugcau                                             19

<210> SEQ ID NO 51
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 51
cggcuucugg gauucuaau                                             19

<210> SEQ ID NO 52
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 52
cggguacucc uuguuguuu                                             19

<210> SEQ ID NO 53
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 53
cgugcaggag uccgauauu                                             19

<210> SEQ ID NO 54
<211> LENGTH: 19
<212> TYPE: RNA
<213> ORGANISM: artificial sequence

```
<220> FEATURE:
<223> OTHER INFORMATION: Unmodified RNAi agent sequence

<400> SEQUENCE: 54
cuacuggagc aaguuuacu                                                    19

<210> SEQ ID NO 55
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 55
cuacuggagc accguuaau                                                    19

<210> SEQ ID NO 56
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 56
cuagaucuca ccuaaacau                                                    19

<210> SEQ ID NO 57
<211> LENGTH: 21
<212> TYPE: RNA
<213> ORGANISM: artificial sequence
<220> FEATURE:
<223> OTHER INFORMATION: Unmodified RNAi agent sequence

<400> SEQUENCE: 57
cuauaucaug gccgacaagu u                                                 21

<210> SEQ ID NO 58
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 58
cuauugaguc gugagacuu                                                    19

<210> SEQ ID NO 59
<211> LENGTH: 10
<212> TYPE: RNA
<213> ORGANISM: artificial sequence
<220> FEATURE:
<223> OTHER INFORMATION: Unmodified RNAi agent sequence

<400> SEQUENCE: 59
cucagugcuu                                                              10

<210> SEQ ID NO 60
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 60
cucccuagau cucaccuau                                                    19
```

```
<210> SEQ ID NO 61
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 61
cugaggucag accaacuuu                                                        19

<210> SEQ ID NO 62
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 62
cuggagcacc guuaaggau                                                        19

<210> SEQ ID NO 63
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 63
cuggauggac aaucacuuu                                                        19

<210> SEQ ID NO 64
<211> LENGTH: 21
<212> TYPE: RNA
<213> ORGANISM: artificial sequence
<220> FEATURE:
<223> OTHER INFORMATION: Unmodified RNAi agent sequence

<400> SEQUENCE: 64
cuuacuggcu uaucgaaauu u                                                     21

<210> SEQ ID NO 65
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 65
cuucaguucc cugaaagau                                                        19

<210> SEQ ID NO 66
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 66
cuucaugcag gguuacauu                                                        19

<210> SEQ ID NO 67
<211> LENGTH: 19
<212> TYPE: RNA
<213> ORGANISM: artificial sequence
<220> FEATURE:
<223> OTHER INFORMATION: Unmodified RNAi agent sequence
```

<400> SEQUENCE: 67
gaaaguaugu ucucauguu                                              19

<210> SEQ ID NO 68
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 68
gaacagaggu gccaugcau                                              19

<210> SEQ ID NO 69
<211> LENGTH: 18
<212> TYPE: DNA
<213> ORGANISM: artificial sequence
<220> FEATURE:
<223> OTHER INFORMATION: RNAi agent sequence

<400> SEQUENCE: 69
gaactcagag aacttgtc                                               18

<210> SEQ ID NO 70
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 70
gacaaguucu cugaguucu                                              19

<210> SEQ ID NO 71
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 71
gacaguauuc ucagugcuu                                              19

<210> SEQ ID NO 72
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 72
gacccugagg ucagaccau                                              19

<210> SEQ ID NO 73
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 73
gagcaccguu aaggacaau                                              19

<210> SEQ ID NO 74

```
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 74
gaggaccaac caacuccau                                             19

<210> SEQ ID NO 75
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 75
gaggucagac caacuucau                                             19

<210> SEQ ID NO 76
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 76
gaugugccug uuccuccau                                             19

<210> SEQ ID NO 77
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 77
gcaucugccc gagcugaau                                             19

<210> SEQ ID NO 78
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 78
gcgugcagga guccgauau                                             19

<210> SEQ ID NO 79
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 79
gcuacuggag caaguuuau                                             19

<210> SEQ ID NO 80
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 80
```

```
gcucaguuca ucccuagau                                              19

<210> SEQ ID NO 81
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 81
gcuguccCua auaaagcuu                                              19

<210> SEQ ID NO 82
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 82
gcuucaugca ggguuacau                                              19

<210> SEQ ID NO 83
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 83
ggaaaguaug uucucaugu                                              19

<210> SEQ ID NO 84
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 84
ggacaaguuc ucugaguuu                                              19

<210> SEQ ID NO 85
<211> LENGTH: 25
<212> TYPE: RNA
<213> ORGANISM: artificial sequence
<220> FEATURE:
<223> OTHER INFORMATION: Unmodified RNAi agent sequence

<400> SEQUENCE: 85
ggacaguauu cucagugcua aauug                                       25

<210> SEQ ID NO 86
<211> LENGTH: 26
<212> TYPE: RNA
<213> ORGANISM: artificial sequence
<220> FEATURE:
<223> OTHER INFORMATION: Unmodified RNAi agent sequence

<400> SEQUENCE: 86
ggacaguauu cucagugcua aauuga                                      26

<210> SEQ ID NO 87
<211> LENGTH: 21
<212> TYPE: RNA
```

```
<213> ORGANISM: artificial sequence
<220> FEATURE:
<223> OTHER INFORMATION: Unmodified RNAi agent sequence

<400> SEQUENCE: 87
ggacaguauu cucagugcuu u                                              21

<210> SEQ ID NO 88
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 88
ggcuacugga gcaaguuuu                                                 19

<210> SEQ ID NO 89
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 89
gggcucugua cagggcuau                                                 19

<210> SEQ ID NO 90
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 90
guacagggcu acauggaau                                                 19

<210> SEQ ID NO 91
<211> LENGTH: 15
<212> TYPE: RNA
<213> ORGANISM: artificial sequence
<220> FEATURE:
<223> OTHER INFORMATION: Unmodified RNAi agent sequence

<400> SEQUENCE: 91
guauucucag ugcuu                                                     15

<210> SEQ ID NO 92
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 92
gugcaggagu ccgauauau                                                 19

<210> SEQ ID NO 93
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 93
guugcagaug ugccuguuu                                                 19
```

```
<210> SEQ ID NO 94
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 94
uuuauuaggg acagcaugu                                              19

<210> SEQ ID NO 95
<211> LENGTH: 18
<212> TYPE: DNA
<213> ORGANISM: artificial sequence
<220> FEATURE:
<223> OTHER INFORMATION: RNAi agent sequence

<400> SEQUENCE: 95
taaccctgca tgaagctg                                               18

<210> SEQ ID NO 96
<211> LENGTH: 18
<212> TYPE: DNA
<213> ORGANISM: artificial sequence
<220> FEATURE:
<223> OTHER INFORMATION: RNAi agent sequence

<400> SEQUENCE: 96
tcttgtccag ctttattg                                               18

<210> SEQ ID NO 97
<211> LENGTH: 18
<212> TYPE: DNA
<213> ORGANISM: artificial sequence
<220> FEATURE:
<223> OTHER INFORMATION: RNAi agent sequence

<400> SEQUENCE: 97
ttcttgtcca gctttatt                                               18

<210> SEQ ID NO 98
<211> LENGTH: 25
<212> TYPE: RNA
<213> ORGANISM: artificial sequence
<220> FEATURE:
<223> OTHER INFORMATION: Unmodified RNAi agent sequence

<400> SEQUENCE: 98
uaaaagggac aguauucuca gugcu                                       25

<210> SEQ ID NO 99
<211> LENGTH: 26
<212> TYPE: RNA
<213> ORGANISM: artificial sequence
<220> FEATURE:
<223> OTHER INFORMATION: Unmodified RNAi agent sequence

<400> SEQUENCE: 99
uaaaagggac aguauucuca gugcua                                      26

<210> SEQ ID NO 100
<211> LENGTH: 19
<212> TYPE: RNA
<213> ORGANISM: artificial sequence
<220> FEATURE:
```

<223> OTHER INFORMATION: Unmodified RNAi agent sequence

<400> SEQUENCE: 100
uaauaaagcu ggauaagau                                          19

<210> SEQ ID NO 101
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 101
uacuggagca ccguuaagu                                          19

<210> SEQ ID NO 102
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 102
uagaucucac cuaaacauu                                          19

<210> SEQ ID NO 103
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 103
uagcgugcag gaguccgau                                          19

<210> SEQ ID NO 104
<211> LENGTH: 14
<212> TYPE: RNA
<213> ORGANISM: artificial sequence
<220> FEATURE:
<223> OTHER INFORMATION: Unmodified RNAi agent sequence

<400> SEQUENCE: 104
uauucucagu gcuu                                               14

<210> SEQ ID NO 105
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 105
uauugagucg ugagacuuu                                          19

<210> SEQ ID NO 106
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 106
ucacuucaga ucccugaau                                          19

```
<210> SEQ ID NO 107
<211> LENGTH: 9
<212> TYPE: RNA
<213> ORGANISM: artificial sequence
<220> FEATURE:
<223> OTHER INFORMATION: Unmodified RNAi agent sequence

<400> SEQUENCE: 107 ucagugcuu                                                                    9

<210> SEQ ID NO 108
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 108
uccaggaugc gcuaaguau                                                        19

<210> SEQ ID NO 109
<211> LENGTH: 21
<212> TYPE: RNA
<213> ORGANISM: artificial sequence
<220> FEATURE:
<223> OTHER INFORMATION: Unmodified RNAi agent sequence

<400> SEQUENCE: 109
ucccuagauc ucaccuaaau u                                                     21

<210> SEQ ID NO 110
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 110
ucccuagauc ucaccuaau                                                        19

<210> SEQ ID NO 111
<211> LENGTH: 11
<212> TYPE: RNA
<213> ORGANISM: artificial sequence
<220> FEATURE:
<223> OTHER INFORMATION: Unmodified RNAi agent sequence

<400> SEQUENCE: 111
ucucagugcu u                                                                11

<210> SEQ ID NO 112
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 112
ugaaagacua cuggagcau                                                        19

<210> SEQ ID NO 113
<211> LENGTH: 19
<212> TYPE: RNA
<213> ORGANISM: artificial sequence
<220> FEATURE:
<223> OTHER INFORMATION: Unmodified RNAi agent sequence
```

```
<400> SEQUENCE: 113
ugaaaggcua cuggagcau                                              19

<210> SEQ ID NO 114
<211> LENGTH: 12
<212> TYPE: RNA
<213> ORGANISM: artificial sequence
<220> FEATURE:
<223> OTHER INFORMATION: Unmodified RNAi agent sequence

<400> SEQUENCE: 114
uucucagugc uu                                                     12

<210> SEQ ID NO 115
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 115
aaacuugcuc caguagccu                                              19

<210> SEQ ID NO 116
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 116
aacaacaagg aguacccgg                                              19

<210> SEQ ID NO 117
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 117
aacaggcaca ucugcaaca                                              19

<210> SEQ ID NO 118
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 118
aacucagaga acuuguccu                                              19

<210> SEQ ID NO 119
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 119
aacuugucag uaaacuugc                                              19

<210> SEQ ID NO 120
<211> LENGTH: 19
```

```
<212> TYPE: RNA
<213> ORGANISM: artificial sequence
<220> FEATURE:
<223> OTHER INFORMATION: Unmodified RNAi agent sequence

<400> SEQUENCE: 120
aacuuguccu uaacggugc                                                    19

<210> SEQ ID NO 121
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 121
aagacaugag aacauacuu                                                    19

<210> SEQ ID NO 122
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 122
aagucucacg acucaauag                                                    19

<210> SEQ ID NO 123
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 123
aagugauugu ccauccagc                                                    19

<210> SEQ ID NO 124
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 124
aaguuggucu gaccucagg                                                    19

<210> SEQ ID NO 125
<211> LENGTH: 18
<212> TYPE: DNA
<213> ORGANISM: artificial sequence
<220> FEATURE:
<223> OTHER INFORMATION: RNAi agent sequence

<400> SEQUENCE: 125
aataaagctg gacaagaa                                                     18

<210> SEQ ID NO 126
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 126
```

| | | |
|---|---|---|
| aauagcugga guugguugg | | 19 |

```
<210> SEQ ID NO 127
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 127
```

| | | |
|---|---|---|
| acaacaagga gucccggg | | 19 |

```
<210> SEQ ID NO 128
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 128
```

| | | |
|---|---|---|
| acaugagaac auacuuucc | | 19 |

```
<210> SEQ ID NO 129
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 129
```

| | | |
|---|---|---|
| accuggagua gcuagcugc | | 19 |

```
<210> SEQ ID NO 130
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 130
```

| | | |
|---|---|---|
| acugagaaua cugucccuu | | 19 |

```
<210> SEQ ID NO 131
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 131
```

| | | |
|---|---|---|
| agaacuuguc cuuaacggu | | 19 |

```
<210> SEQ ID NO 132
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 132
```

| | | |
|---|---|---|
| agcacugaga auacugucc | | 19 |

```
<210> SEQ ID NO 133
<211> LENGTH: 21
<212> TYPE: RNA
<213> ORGANISM: artificial sequence
```

```
<220> FEATURE:
<223> OTHER INFORMATION: Unmodified RNAi agent sequence

<400> SEQUENCE: 133
agcacugaga auacuguccc u                                              21

<210> SEQ ID NO 134
<211> LENGTH: 23
<212> TYPE: RNA
<213> ORGANISM: artificial sequence
<220> FEATURE:
<223> OTHER INFORMATION: Unmodified RNAi agent sequence

<400> SEQUENCE: 134
agcacugaga auacuguccc uuu                                            23

<210> SEQ ID NO 135
<211> LENGTH: 25
<212> TYPE: RNA
<213> ORGANISM: artificial sequence
<220> FEATURE:
<223> OTHER INFORMATION: Unmodified RNAi agent sequence

<400> SEQUENCE: 135
agcacugaga auacuguccc uuuua                                          25

<210> SEQ ID NO 136
<211> LENGTH: 26
<212> TYPE: RNA
<213> ORGANISM: artificial sequence
<220> FEATURE:
<223> OTHER INFORMATION: Unmodified RNAi agent sequence

<400> SEQUENCE: 136
agcacugaga auacuguccc uuuuaa                                         26

<210> SEQ ID NO 137
<211> LENGTH: 21
<212> TYPE: RNA
<213> ORGANISM: artificial sequence
<220> FEATURE:
<223> OTHER INFORMATION: Unmodified RNAi agent sequence

<400> SEQUENCE: 137
agcacugaga auacuguccu u                                              21

<210> SEQ ID NO 138
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 138
agcuauaucg gacuccugc                                                 19

<210> SEQ ID NO 139
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 139
agcuuuauua gggacagca                                                 19
```

<210> SEQ ID NO 140
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 140
aggauggaua ggcaggugg                                            19

<210> SEQ ID NO 141
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 141
agucucacga cucaauagc                                            19

<210> SEQ ID NO 142
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 142
auaucggacu ccugcacgc                                            19

<210> SEQ ID NO 143
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 143
auguaacccu gcaugaagc                                            19

<210> SEQ ID NO 144
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 144
auguuuaggu gagaucuag                                            19

<210> SEQ ID NO 145
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 145
auuagggaca gcauguuua                                            19

<210> SEQ ID NO 146
<211> LENGTH: 21
<212> TYPE: RNA
<213> ORGANISM: artificial sequence
<220> FEATURE:
<223> OTHER INFORMATION: Unmodified RNAi agent sequence

```
<400> SEQUENCE: 146
auuucgauaa gccaguaagu u                                              21

<210> SEQ ID NO 147
<211> LENGTH: 18
<212> TYPE: DNA
<213> ORGANISM: artificial sequence
<220> FEATURE:
<223> OTHER INFORMATION: RNAi agent sequence

<400> SEQUENCE: 147
caataaagct ggacaaga                                                  18

<210> SEQ ID NO 148
<211> LENGTH: 25
<212> TYPE: RNA
<213> ORGANISM: artificial sequence
<220> FEATURE:
<223> OTHER INFORMATION: Unmodified RNAi agent sequence

<400> SEQUENCE: 148
caauuuagca cugagaauac ugucc                                          25

<210> SEQ ID NO 149
<211> LENGTH: 26
<212> TYPE: RNA
<213> ORGANISM: artificial sequence
<220> FEATURE:
<223> OTHER INFORMATION: Unmodified RNAi agent sequence

<400> SEQUENCE: 149
caauuuagca cugagaauac ugucca                                         26

<210> SEQ ID NO 150
<211> LENGTH: 18
<212> TYPE: DNA
<213> ORGANISM: artificial sequence
<220> FEATURE:
<223> OTHER INFORMATION: RNAi agent sequence

<400> SEQUENCE: 150
cagcttcatg cagggtta                                                  18

<210> SEQ ID NO 151
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 151
caugagaaca uacuuuccc                                                 19

<210> SEQ ID NO 152
<211> LENGTH: 18
<212> TYPE: DNA
<213> ORGANISM: artificial sequence
<220> FEATURE:
<223> OTHER INFORMATION: RNAi agent sequence

<400> SEQUENCE: 152
ccgggtactc cttgttgt                                                  18

<210> SEQ ID NO 153
```

```
<211> LENGTH: 18
<212> TYPE: DNA
<213> ORGANISM: artificial sequence
<220> FEATURE:
<223> OTHER INFORMATION: RNAi agent sequence

<400> SEQUENCE: 153
ccgttaagga caagttct                                              18

<210> SEQ ID NO 154
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 154
cuuaacggug cuccaguag                                             19

<210> SEQ ID NO 155
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 155
cuucauguaa cccugcaug                                             19

<210> SEQ ID NO 156
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 156
cuuguccuua acggugcuc                                             19

<210> SEQ ID NO 157
<211> LENGTH: 21
<212> TYPE: RNA
<213> ORGANISM: artificial sequence
<220> FEATURE:
<223> OTHER INFORMATION: Unmodified RNAi agent sequence

<400> SEQUENCE: 157
cuugucggcc augauauagu u                                          21

<210> SEQ ID NO 158
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 158
cuuuauuagg gacagcaug                                             19

<210> SEQ ID NO 159
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 159
```
gaacucagag aacuugucc                                          19

<210> SEQ ID NO 160
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 160
gaacuuguca guaaacuug                                          19

<210> SEQ ID NO 161
<211> LENGTH: 18
<212> TYPE: DNA
<213> ORGANISM: artificial sequence
<220> FEATURE:
<223> OTHER INFORMATION: RNAi agent sequence

<400> SEQUENCE: 161
gacaagttct ctgagttc                                           18

<210> SEQ ID NO 162
<211> LENGTH: 18
<212> TYPE: DNA
<213> ORGANISM: artificial sequence
<220> FEATURE:
<223> OTHER INFORMATION: RNAi agent sequence

<400> SEQUENCE: 162
gacagtattc tcagtgct                                           18

<210> SEQ ID NO 163
<211> LENGTH: 18
<212> TYPE: DNA
<213> ORGANISM: artificial sequence
<220> FEATURE:
<223> OTHER INFORMATION: RNAi agent sequence

<400> SEQUENCE: 163
ggacaagttc tctgagtt                                           18

<210> SEQ ID NO 164
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 164
guaaacuugc uccaguagc                                          19

<210> SEQ ID NO 165
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 165
guuuagguga gaucuaggg                                          19

<210> SEQ ID NO 166
<211> LENGTH: 19
<212> TYPE: RNA

<213> ORGANISM: artificial sequence
<220> FEATURE:
<223> OTHER INFORMATION: Unmodified RNAi agent sequence

<400> SEQUENCE: 166
uaaacuugcu ccaguagcc                                              19

<210> SEQ ID NO 167
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 167
uaacccugca ugaagcuga                                              19

<210> SEQ ID NO 168
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 168
uaacggugcu ccaguaguc                                              19

<210> SEQ ID NO 169
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 169
uaccuggagu agcuagcug                                              19

<210> SEQ ID NO 170
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 170
uacuuagcgc auccuggac                                              19

<210> SEQ ID NO 171
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 171
uagaauccca gaagccggu                                              19

<210> SEQ ID NO 172
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 172
uagcccugua cagagccca                                              19

```
<210> SEQ ID NO 173
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 173
uagccuuuca gggaucuga                                                        19

<210> SEQ ID NO 174
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 174
uagcuagcug cuucuaggg                                                        19

<210> SEQ ID NO 175
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 175
uagcuggagu ugguugguc                                                        19

<210> SEQ ID NO 176
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 176
uaggugagau cuagggagg                                                        19

<210> SEQ ID NO 177
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 177 uagcuuuca gggaacuga                                                         19

<210> SEQ ID NO 178
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 178
uauaucggac uccugcacg                                                        19

<210> SEQ ID NO 179
<211> LENGTH: 19
<212> TYPE: RNA
<213> ORGANISM: artificial sequence
<220> FEATURE:
```

<223> OTHER INFORMATION: Unmodified RNAi agent sequence

<400> SEQUENCE: 179
uaucggacuc cugcacgcu                                            19

<210> SEQ ID NO 180
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 180
uauuagggac agcauguuu                                            19

<210> SEQ ID NO 181
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 181
uccagcuuua uugggaggc                                            19

<210> SEQ ID NO 182
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 182
uccuuaacgg ugcuccagu                                            19

<210> SEQ ID NO 183
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 183
ucggacuccu gcacgcuac                                            19

<210> SEQ ID NO 184
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 184
ucuagggaug aacugagca                                            19

<210> SEQ ID NO 185
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 185
ucucacgacu caauagcug                                            19

```
<210> SEQ ID NO 186
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 186
ucugaaguga uuguccauc                                                    19

<210> SEQ ID NO 187
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 187
ucuuauccag cuuuauuag                                                    19

<210> SEQ ID NO 188
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 188
ucuuguccag cuuuauugg                                                    19

<210> SEQ ID NO 189
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 189
ucuuucaggg aacugaagc                                                    19

<210> SEQ ID NO 190
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 190
ugaacuuguc aguaaacuu                                                    19

<210> SEQ ID NO 191
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 191
ugaaguuggu cugaccuca                                                    19

<210> SEQ ID NO 192
<211> LENGTH: 19
<212> TYPE: RNA
<213> ORGANISM: artificial sequence
<220> FEATURE:
<223> OTHER INFORMATION: Unmodified RNAi agent sequence
```

```
<400> SEQUENCE: 192
ugcaugaagc ugagaaggg                                              19

<210> SEQ ID NO 193
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 193
ugcauggcac cucuguucc                                              19

<210> SEQ ID NO 194
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 194
ugcuccagua gccuuucag                                              19

<210> SEQ ID NO 195
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 195
ugcuccagua gucuuucag                                              19

<210> SEQ ID NO 196
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 196
uggaggaaca ggcacaucu                                              19

<210> SEQ ID NO 197
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 197
uggaguagcu agcugcuuc                                              19

<210> SEQ ID NO 198
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 198
uggaguuggu ugguccuca                                              19

<210> SEQ ID NO 199
<211> LENGTH: 19
```

```
<212> TYPE: RNA
<213> ORGANISM: artificial sequence
<220> FEATURE:
<223> OTHER INFORMATION: Unmodified RNAi agent sequence

<400> SEQUENCE: 199
uggucugacc ucaggqucc                                                    19

<210> SEQ ID NO 200
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 200
uguaacccug caugaagcu                                                    19

<210> SEQ ID NO 201
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 201
uguuuaggug agaucuagg                                                    19

<210> SEQ ID NO 202
<211> LENGTH: 21
<212> TYPE: RNA
<213> ORGANISM: artificial sequence
<220> FEATURE:
<223> OTHER INFORMATION: Unmodified RNAi agent sequence

<400> SEQUENCE: 202
uguuuaggug agaucuaggu u                                                 21

<210> SEQ ID NO 203
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 203
uuaacggugc uccaguagu                                                    19

<210> SEQ ID NO 204
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 204
uuagaauccc agaagccgg                                                    19

<210> SEQ ID NO 205
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 205
```
uuaggugaga ucuagggag                                                19

<210> SEQ ID NO 206
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 206
uuauccagcu uuauuaggg                                                19

<210> SEQ ID NO 207
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 207
uuauuaggga cagcauguu                                                19

<210> SEQ ID NO 208
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 208
uucagcucgg gcagaugcc                                                19

<210> SEQ ID NO 209
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 209
uucagggauc ugaagugau                                                19

<210> SEQ ID NO 210
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 210
uucauguaac ccugcauga                                                19

<210> SEQ ID NO 211
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 211
uuccauguag cccuguaca                                                19

<210> SEQ ID NO 212
<211> LENGTH: 19
<212> TYPE: RNA
<213> ORGANISM: artificial sequence

```
<220> FEATURE:
<223> OTHER INFORMATION: Unmodified RNAi agent sequence

<400> SEQUENCE: 212
uucuugucca gcuuuauug                                                    19

<210> SEQ ID NO 213
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 213
uuggaggcuu guuccaugu                                                    19

<210> SEQ ID NO 214
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 214
uuguccuuaa cggugcucc                                                    19

<210> SEQ ID NO 215
<211> LENGTH: 19
<212> TYPE: RNA
<213> ORGANISM: artificial sequence
<220> FEATURE:
<223> OTHER INFORMATION: Unmodified RNAi agent sequence

<400> SEQUENCE: 215
uuuaggugag aucuaggga                                                    19

<210> SEQ ID NO 216
<211> LENGTH: 21
<212> TYPE: RNA
<213> ORGANISM: artificial sequence
<220> FEATURE:
<223> OTHER INFORMATION: Unmodified RNAi agent sequence

<400> SEQUENCE: 216
uuuaggugag aucuagggau u                                                 21

<210> SEQ ID NO 217
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 217
nucgugacuc uuaugacag                                                    19

<210> SEQ ID NO 218
<211> LENGTH: 19
<212> TYPE: RNA
<213> ORGANISM: artificial sequence
<220> FEATURE:
<223> OTHER INFORMATION: RNAi agent sequence
<220> FEATURE:
```

```
<221> NAME/KEY: modified_base
<222> LOCATION: 19
<223> OTHER INFORMATION: /mod_base = "abasic corresponding nucleotide"

<400> SEQUENCE: 218
agcacugaga auacugucn                                                    19

<210> SEQ ID NO 219
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1,19
<223> OTHER INFORMATION: /mod_base = "abasic corresponding nucleotide"

<400> SEQUENCE: 219
ngcacugaga auacugucn                                                    19

<210> SEQ ID NO 220
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 2,19
<223> OTHER INFORMATION: /mod_base = "abasic corresponding nucleotide"

<400> SEQUENCE: 220
ancacugaga auacugucn                                                    19

<210> SEQ ID NO 221
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 3,19
<223> OTHER INFORMATION: /mod_base = "abasic corresponding nucleotide"

<400> SEQUENCE: 221
agnacugaga auacugucn                                                    19

<210> SEQ ID NO 222
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 4,19
<223> OTHER INFORMATION: /mod_base = "abasic corresponding nucleotide"

<400> SEQUENCE: 222
agcncugaga auacugucn                                                    19

<210> SEQ ID NO 223
<211> LENGTH: 19
<212> TYPE: RNA
<213> ORGANISM: artificial sequence
<220> FEATURE:
<223> OTHER INFORMATION: RNAi agent sequence
```

```
<220> FEATURE:
<221> NAME/KEY: modified_base
<222> LOCATION: 5,19
<223> OTHER INFORMATION: /mod_base = "abasic corresponding nucleotide"

<400> SEQUENCE: 223
agcanugaga auacugucn                                                    19

<210> SEQ ID NO 224
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 6,19
<223> OTHER INFORMATION: /mod_base = "abasic corresponding nucleotide"

<400> SEQUENCE: 224
agcacngaga auacugucn                                                    19

<210> SEQ ID NO 225
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 7,19
<223> OTHER INFORMATION: /mod_base = "abasic corresponding nucleotide"

<400> SEQUENCE: 225
agcacunaga auacugucn                                                    19

<210> SEQ ID NO 226
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 8,19
<223> OTHER INFORMATION: /mod_base = "abasic corresponding nucleotide"

<400> SEQUENCE: 226
agcacugnga auacugucn                                                    19

<210> SEQ ID NO 227
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 9,19
<223> OTHER INFORMATION: /mod_base = "abasic corresponding nucleotide"

<400> SEQUENCE: 227
agcacugana auacugucn                                                    19

<210> SEQ ID NO 228
<211> LENGTH: 19
<212> TYPE: RNA
<213> ORGANISM: artificial sequence
<220> FEATURE:
```

```
<223> OTHER INFORMATION: RNAi agent sequence
<220> FEATURE:
<221> NAME/KEY: modified_base
<222> LOCATION: 10,19
<223> OTHER INFORMATION: /mod_base = "abasic corresponding nucleotide"

<400> SEQUENCE: 228
agcacugagn auacugucn                                                      19

<210> SEQ ID NO 229
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 11,19
<223> OTHER INFORMATION: /mod_base = "abasic corresponding nucleotide"

<400> SEQUENCE: 229
agcacugaga nuacugucn                                                      19

<210> SEQ ID NO 230
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 12,19
<223> OTHER INFORMATION: /mod_base = "abasic corresponding nucleotide"

<400> SEQUENCE: 230
agcacugaga anacugucn                                                      19

<210> SEQ ID NO 231
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 13,19
<223> OTHER INFORMATION: /mod_base = "abasic corresponding nucleotide"

<400> SEQUENCE: 231
agcacugaga auncugucn                                                      19

<210> SEQ ID NO 232
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 14,19
<223> OTHER INFORMATION: /mod_base = "abasic corresponding nucleotide"

<400> SEQUENCE: 232
agcacugaga auanugucn                                                      19

<210> SEQ ID NO 233
<211> LENGTH: 19
<212> TYPE: RNA
<213> ORGANISM: artificial sequence
```

```
<220> FEATURE:
<223> OTHER INFORMATION: RNAi agent sequence
<220> FEATURE:
<221> NAME/KEY: modified_base
<222> LOCATION: 15,19
<223> OTHER INFORMATION: /mod_base = "abasic corresponding nucleotide"

<400> SEQUENCE: 233
agcacugaga auacngucn                                                19

<210> SEQ ID NO 234
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 16,19
<223> OTHER INFORMATION: /mod_base = "abasic corresponding nucleotide"

<400> SEQUENCE: 234
agcacugaga auacunucn                                                19

<210> SEQ ID NO 235
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 17,19
<223> OTHER INFORMATION: /mod_base = "abasic corresponding nucleotide"

<400> SEQUENCE: 235
agcacugaga auacugncn                                                19

<210> SEQ ID NO 236
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 18,19
<223> OTHER INFORMATION: /mod_base = "abasic corresponding nucleotide"

<400> SEQUENCE: 236
agcacugaga auacugunn                                                19

<210> SEQ ID NO 237
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 237
nucgugacuc uuaugacag                                                19

<210> SEQ ID NO 238
<211> LENGTH: 18
<212> TYPE: RNA
```

```
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 238
nucgugacuc uuaugaca                                                          18

<210> SEQ ID NO 239
<211> LENGTH: 17
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 239
nucgugacuc uuaugac                                                           17

<210> SEQ ID NO 240
<211> LENGTH: 16
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 240
nucgugacuc uuauga                                                            16

<210> SEQ ID NO 241
<211> LENGTH: 15
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 241
nucgugacuc uuaug                                                             15

<210> SEQ ID NO 242
<211> LENGTH: 14
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 242
nucgugacuc uuau                                                              14

<210> SEQ ID NO 243
<211> LENGTH: 13
```

```
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 243
nucgugacuc uua                                                          13

<210> SEQ ID NO 244
<211> LENGTH: 12
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 244
nucgugacuc uu                                                           12

<210> SEQ ID NO 245
<211> LENGTH: 11
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 245
nucgugacuc u                                                            11

<210> SEQ ID NO 246
<211> LENGTH: 10
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 246 nucgugacuc                                                              10

<210> SEQ ID NO 247
<211> LENGTH: 9
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 247 nucgugacu                                                                9

<210> SEQ ID NO 248
```

```
<211> LENGTH: 8
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 248 nucgugac                                                                    8

<210> SEQ ID NO 249
<211> LENGTH: 19
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 19
<223> OTHER INFORMATION: /mod_base = "abasic corresponding nucleotide"

<400> SEQUENCE: 249
agcacugaga auacugucn                                                       19

<210> SEQ ID NO 250
<211> LENGTH: 25
<212> TYPE: RNA
<213> ORGANISM: artificial sequence
<220> FEATURE:
<223> OTHER INFORMATION: RNAi agent sequence

<400> SEQUENCE: 250
ucgugacucu uaugacaggg aaaau                                                25

<210> SEQ ID NO 251
<211> LENGTH: 26
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 251
nucgugacuc uuaugacagg gaaaau                                               26

<210> SEQ ID NO 252
<211> LENGTH: 25
<212> TYPE: RNA
<213> ORGANISM: artificial sequence
<220> FEATURE:
<223> OTHER INFORMATION: RNAi agent sequence

<400> SEQUENCE: 252
agcacugaga auacuguccc uuuua                                                25

<210> SEQ ID NO 253
<211> LENGTH: 26
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
```

```
<222> LOCATION: 26
<223> OTHER INFORMATION: /mod_base = "abasic corresponding nucleotide"

<400> SEQUENCE: 253
agcacugaga auacuguccc uuuuan                                          26

<210> SEQ ID NO 254
<211> LENGTH: 25
<212> TYPE: RNA
<213> ORGANISM: artificial sequence
<220> FEATURE:
<223> OTHER INFORMATION: RNAi agent sequence

<400> SEQUENCE: 254
agcaaugaga auacuguccc uuuua                                           25

<210> SEQ ID NO 255
<211> LENGTH: 25
<212> TYPE: RNA
<213> ORGANISM: artificial sequence
<220> FEATURE:
<223> OTHER INFORMATION: RNAi agent sequence

<400> SEQUENCE: 255
caaauuagca cugagaauac ugucc                                           25

<210> SEQ ID NO 256
<211> LENGTH: 26
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 26
<223> OTHER INFORMATION: /mod_base = "abasic corresponding nucleotide"

<400> SEQUENCE: 256
caauuuagca cugagaauac ugucccn                                         26

<210> SEQ ID NO 257
<211> LENGTH: 25
<212> TYPE: RNA
<213> ORGANISM: artificial sequence
<220> FEATURE:
<223> OTHER INFORMATION: RNAi agent sequence

<400> SEQUENCE: 257
guuaaaucgu gacucuuaug acagg                                           25

<210> SEQ ID NO 258
<211> LENGTH: 20
<212> TYPE: RNA
<213> ORGANISM: artificial sequence
<220> FEATURE:
<223> OTHER INFORMATION: RNAi agent sequence

<400> SEQUENCE: 258
ucgugacucu uaugacaggg                                                 20

<210> SEQ ID NO 259
<211> LENGTH: 23
<212> TYPE: RNA
<213> ORGANISM: artificial sequence
<220> FEATURE:
<223> OTHER INFORMATION: RNAi agent sequence
```

```
<400> SEQUENCE: 259
ucgugacucu uaugacaggg aaa                                    23

<210> SEQ ID NO 260
<211> LENGTH: 25
<212> TYPE: RNA
<213> ORGANISM: artificial sequence
<220> FEATURE:
<223> OTHER INFORMATION: RNAi agent sequence

<400> SEQUENCE: 260
uuucgugacu cuuaugacag ggaaa                                  25

<210> SEQ ID NO 261
<211> LENGTH: 26
<212> TYPE: RNA
<213> ORGANISM: artificial sequence
<220> FEATURE:
<223> OTHER INFORMATION: RNAi agent sequence
<220> FEATURE:
<221> NAME/KEY: modified_base
<222> LOCATION: 1
<223> OTHER INFORMATION: /mod_base = "abasic corresponding nucleotide"

<400> SEQUENCE: 261
nguuaaaucg ugacucuuau gacagg                                 26

<210> SEQ ID NO 262
<211> LENGTH: 19
<212> TYPE: RNA
<213> ORGANISM: artificial sequence
<220> FEATURE:
<223> OTHER INFORMATION: RNAi agent sequence

<400> SEQUENCE: 262
gcucaguuca ucccuagau                                         19

<210> SEQ ID NO 263
<211> LENGTH: 19
<212> TYPE: RNA
<213> ORGANISM: artificial sequence
<220> FEATURE:
<223> OTHER INFORMATION: RNAi agent sequence

<400> SEQUENCE: 263
gaacagaggu gccaugcau                                         19

<210> SEQ ID NO 264
<211> LENGTH: 19
<212> TYPE: RNA
<213> ORGANISM: artificial sequence
<220> FEATURE:
<223> OTHER INFORMATION: RNAi agent sequence

<400> SEQUENCE: 264
ccggguacuc cuuguuguu                                         19

<210> SEQ ID NO 265
<211> LENGTH: 19
<212> TYPE: RNA
<213> ORGANISM: artificial sequence
<220> FEATURE:
<223> OTHER INFORMATION: RNAi agent sequence

<400> SEQUENCE: 265
cggguacucc uuguuguuu                                         19
```

<210> SEQ ID NO 266
<211> LENGTH: 19
<212> TYPE: RNA
<213> ORGANISM: artificial sequence
<220> FEATURE:
<223> OTHER INFORMATION: RNAi agent sequence

<400> SEQUENCE: 266
ccuucucagc uucaugcau                                            19

<210> SEQ ID NO 267
<211> LENGTH: 19
<212> TYPE: RNA
<213> ORGANISM: artificial sequence
<220> FEATURE:
<223> OTHER INFORMATION: RNAi agent sequence

<400> SEQUENCE: 267
cagcuucaug caggguuau                                            19

<210> SEQ ID NO 268
<211> LENGTH: 19
<212> TYPE: RNA
<213> ORGANISM: artificial sequence
<220> FEATURE:
<223> OTHER INFORMATION: RNAi agent sequence

<400> SEQUENCE: 268
gcuucaugca ggguuacau                                            19

<210> SEQ ID NO 269
<211> LENGTH: 19
<212> TYPE: RNA
<213> ORGANISM: artificial sequence
<220> FEATURE:
<223> OTHER INFORMATION: RNAi agent sequence

<400> SEQUENCE: 269
cuucaugcag gguuacauu                                            19

<210> SEQ ID NO 270
<211> LENGTH: 19
<212> TYPE: RNA
<213> ORGANISM: artificial sequence
<220> FEATURE:
<223> OTHER INFORMATION: RNAi agent sequence

<400> SEQUENCE: 270
caugcagggu uacaugaau                                            19

<210> SEQ ID NO 271
<211> LENGTH: 19
<212> TYPE: RNA
<213> ORGANISM: artificial sequence
<220> FEATURE:
<223> OTHER INFORMATION: RNAi agent sequence

<400> SEQUENCE: 271
augcaggguu acaugaagu                                            19

<210> SEQ ID NO 272
<211> LENGTH: 19
<212> TYPE: RNA
<213> ORGANISM: artificial sequence
<220> FEATURE:

```
<223> OTHER INFORMATION: RNAi agent sequence

<400> SEQUENCE: 272
cuucaguucc cugaaagau                                                 19

<210> SEQ ID NO 273
<211> LENGTH: 19
<212> TYPE: RNA
<213> ORGANISM: artificial sequence
<220> FEATURE:
<223> OTHER INFORMATION: RNAi agent sequence

<400> SEQUENCE: 273
caguucccug aaagacuau                                                 19

<210> SEQ ID NO 274
<211> LENGTH: 19
<212> TYPE: RNA
<213> ORGANISM: artificial sequence
<220> FEATURE:
<223> OTHER INFORMATION: RNAi agent sequence

<400> SEQUENCE: 274
ugaaagacua cuggagcau                                                 19

<210> SEQ ID NO 275
<211> LENGTH: 19
<212> TYPE: RNA
<213> ORGANISM: artificial sequence
<220> FEATURE:
<223> OTHER INFORMATION: RNAi agent sequence

<400> SEQUENCE: 275
acuacuggag caccguuau                                                 19

<210> SEQ ID NO 276
<211> LENGTH: 19
<212> TYPE: RNA
<213> ORGANISM: artificial sequence
<220> FEATURE:
<223> OTHER INFORMATION: RNAi agent sequence

<400> SEQUENCE: 276
cuacuggagc accguuaau                                                 19

<210> SEQ ID NO 277
<211> LENGTH: 19
<212> TYPE: RNA
<213> ORGANISM: artificial sequence
<220> FEATURE:
<223> OTHER INFORMATION: RNAi agent sequence

<400> SEQUENCE: 277
uacuggagca ccguuaagu                                                 19

<210> SEQ ID NO 278
<211> LENGTH: 19
<212> TYPE: RNA
<213> ORGANISM: artificial sequence
<220> FEATURE:
<223> OTHER INFORMATION: RNAi agent sequence

<400> SEQUENCE: 278
cuggagcacc guuaaggau                                                 19
```

```
<210> SEQ ID NO 279
<211> LENGTH: 19
<212> TYPE: RNA
<213> ORGANISM: artificial sequence
<220> FEATURE:
<223> OTHER INFORMATION: RNAi agent sequence

<400> SEQUENCE: 279
gagcaccguu aaggacaau                                            19

<210> SEQ ID NO 280
<211> LENGTH: 19
<212> TYPE: RNA
<213> ORGANISM: artificial sequence
<220> FEATURE:
<223> OTHER INFORMATION: RNAi agent sequence

<400> SEQUENCE: 280
agcaccguua aggacaagu                                            19

<210> SEQ ID NO 281
<211> LENGTH: 19
<212> TYPE: RNA
<213> ORGANISM: artificial sequence
<220> FEATURE:
<223> OTHER INFORMATION: RNAi agent sequence

<400> SEQUENCE: 281
caccguuaag gacaaguuu                                            19

<210> SEQ ID NO 282
<211> LENGTH: 19
<212> TYPE: RNA
<213> ORGANISM: artificial sequence
<220> FEATURE:
<223> OTHER INFORMATION: RNAi agent sequence

<400> SEQUENCE: 282
ccguuaagga caaguucuu                                            19

<210> SEQ ID NO 283
<211> LENGTH: 19
<212> TYPE: RNA
<213> ORGANISM: artificial sequence
<220> FEATURE:
<223> OTHER INFORMATION: RNAi agent sequence

<400> SEQUENCE: 283
ggacaaguuc ucugaguuu                                            19

<210> SEQ ID NO 284
<211> LENGTH: 19
<212> TYPE: RNA
<213> ORGANISM: artificial sequence
<220> FEATURE:
<223> OTHER INFORMATION: RNAi agent sequence

<400> SEQUENCE: 284
gacaaguucu cugaguucu                                            19

<210> SEQ ID NO 285
<211> LENGTH: 19
<212> TYPE: RNA
<213> ORGANISM: artificial sequence
<220> FEATURE:
<223> OTHER INFORMATION: RNAi agent sequence
```

```
<400> SEQUENCE: 285
gacccugagg ucagaccau                                              19

<210> SEQ ID NO 286
<211> LENGTH: 19
<212> TYPE: RNA
<213> ORGANISM: artificial sequence
<220> FEATURE:
<223> OTHER INFORMATION: RNAi agent sequence

<400> SEQUENCE: 286
cugaggucag accaacuuu                                              19

<210> SEQ ID NO 287
<211> LENGTH: 19
<212> TYPE: RNA
<213> ORGANISM: artificial sequence
<220> FEATURE:
<223> OTHER INFORMATION: RNAi agent sequence

<400> SEQUENCE: 287
gaggucagac caacuucau                                              19

<210> SEQ ID NO 288
<211> LENGTH: 19
<212> TYPE: RNA
<213> ORGANISM: artificial sequence
<220> FEATURE:
<223> OTHER INFORMATION: RNAi agent sequence

<400> SEQUENCE: 288
caccugccua uccauccuu                                              19

<210> SEQ ID NO 289
<211> LENGTH: 19
<212> TYPE: RNA
<213> ORGANISM: artificial sequence
<220> FEATURE:
<223> OTHER INFORMATION: RNAi agent sequence

<400> SEQUENCE: 289
agggacagua uucucaguu                                              19

<210> SEQ ID NO 290
<211> LENGTH: 19
<212> TYPE: RNA
<213> ORGANISM: artificial sequence
<220> FEATURE:
<223> OTHER INFORMATION: RNAi agent sequence

<400> SEQUENCE: 290
gacaguauuc ucagugcuu                                              19

<210> SEQ ID NO 291
<211> LENGTH: 19
<212> TYPE: RNA
<213> ORGANISM: artificial sequence
<220> FEATURE:
<223> OTHER INFORMATION: RNAi agent sequence

<400> SEQUENCE: 291
ccucccaaua aagcuggau                                              19

<210> SEQ ID NO 292
<211> LENGTH: 19
```

```
<212> TYPE: RNA
<213> ORGANISM: artificial sequence
<220> FEATURE:
<223> OTHER INFORMATION: RNAi agent sequence

<400> SEQUENCE: 292
caauaaagcu ggacaagau                                              19

<210> SEQ ID NO 293
<211> LENGTH: 19
<212> TYPE: RNA
<213> ORGANISM: artificial sequence
<220> FEATURE:
<223> OTHER INFORMATION: RNAi agent sequence

<400> SEQUENCE: 293
aauaaagcug gacaagaau                                              19

<210> SEQ ID NO 294
<211> LENGTH: 21
<212> TYPE: RNA
<213> ORGANISM: artificial sequence
<220> FEATURE:
<223> OTHER INFORMATION: RNAi agent sequence

<400> SEQUENCE: 294
ucccuagauc ucaccuaaau u                                           21

<210> SEQ ID NO 295
<211> LENGTH: 21
<212> TYPE: RNA
<213> ORGANISM: artificial sequence
<220> FEATURE:
<223> OTHER INFORMATION: RNAi agent sequence

<400> SEQUENCE: 295
ccuagaucuc accuaaacau u                                           21

<210> SEQ ID NO 296
<211> LENGTH: 21
<212> TYPE: RNA
<213> ORGANISM: artificial sequence
<220> FEATURE:
<223> OTHER INFORMATION: RNAi agent sequence

<400> SEQUENCE: 296
cuuacuggcu uaucgaaauu u                                           21

<210> SEQ ID NO 297
<211> LENGTH: 21
<212> TYPE: RNA
<213> ORGANISM: artificial sequence
<220> FEATURE:
<223> OTHER INFORMATION: RNAi agent sequence

<400> SEQUENCE: 297
cuauaucaug gccgacaagu u                                           21

<210> SEQ ID NO 298
<211> LENGTH: 19
<212> TYPE: RNA
<213> ORGANISM: artificial sequence
<220> FEATURE:
<223> OTHER INFORMATION: RNAi agent sequence

<400> SEQUENCE: 298
```
ccuagaagca gcuagcuau                              19

<210> SEQ ID NO 299
<211> LENGTH: 19
<212> TYPE: RNA
<213> ORGANISM: artificial sequence
<220> FEATURE:
<223> OTHER INFORMATION: RNAi agent sequence

<400> SEQUENCE: 299
aagcagcuag cuacuccau                              19

<210> SEQ ID NO 300
<211> LENGTH: 19
<212> TYPE: RNA
<213> ORGANISM: artificial sequence
<220> FEATURE:
<223> OTHER INFORMATION: RNAi agent sequence

<400> SEQUENCE: 300
cagcuagcua cuccagguu                              19

<210> SEQ ID NO 301
<211> LENGTH: 19
<212> TYPE: RNA
<213> ORGANISM: artificial sequence
<220> FEATURE:
<223> OTHER INFORMATION: RNAi agent sequence

<400> SEQUENCE: 301
agcuagcuac uccagguau                              19

<210> SEQ ID NO 302
<211> LENGTH: 19
<212> TYPE: RNA
<213> ORGANISM: artificial sequence
<220> FEATURE:
<223> OTHER INFORMATION: RNAi agent sequence

<400> SEQUENCE: 302
gcaucugccc gagcugaau                              19

<210> SEQ ID NO 303
<211> LENGTH: 19
<212> TYPE: RNA
<213> ORGANISM: artificial sequence
<220> FEATURE:
<223> OTHER INFORMATION: RNAi agent sequence

<400> SEQUENCE: 303
gggcucugua cagggcuau                              19

<210> SEQ ID NO 304
<211> LENGTH: 19
<212> TYPE: RNA
<213> ORGANISM: artificial sequence
<220> FEATURE:
<223> OTHER INFORMATION: RNAi agent sequence

<400> SEQUENCE: 304
guacagggcu acauggaau                              19

<210> SEQ ID NO 305
<211> LENGTH: 19
<212> TYPE: RNA
<213> ORGANISM: artificial sequence

```
<220> FEATURE:
<223> OTHER INFORMATION: RNAi agent sequence

<400> SEQUENCE: 305
cauggaacaa gccuccaau                                                    19

<210> SEQ ID NO 306
<211> LENGTH: 19
<212> TYPE: RNA
<213> ORGANISM: artificial sequence
<220> FEATURE:
<223> OTHER INFORMATION: RNAi agent sequence

<400> SEQUENCE: 306
uccaggaugc gcuaaguau                                                    19

<210> SEQ ID NO 307
<211> LENGTH: 19
<212> TYPE: RNA
<213> ORGANISM: artificial sequence
<220> FEATURE:
<223> OTHER INFORMATION: RNAi agent sequence

<400> SEQUENCE: 307
uagcgugcag gaguccgau                                                    19

<210> SEQ ID NO 308
<211> LENGTH: 19
<212> TYPE: RNA
<213> ORGANISM: artificial sequence
<220> FEATURE:
<223> OTHER INFORMATION: RNAi agent sequence

<400> SEQUENCE: 308
gcgugcagga guccgauau                                                    19

<210> SEQ ID NO 309
<211> LENGTH: 19
<212> TYPE: RNA
<213> ORGANISM: artificial sequence
<220> FEATURE:
<223> OTHER INFORMATION: RNAi agent sequence

<400> SEQUENCE: 309
cgugcaggag uccgauauu                                                    19

<210> SEQ ID NO 310
<211> LENGTH: 19
<212> TYPE: RNA
<213> ORGANISM: artificial sequence
<220> FEATURE:
<223> OTHER INFORMATION: RNAi agent sequence

<400> SEQUENCE: 310
gugcaggagu ccgauauau                                                    19

<210> SEQ ID NO 311
<211> LENGTH: 19
<212> TYPE: RNA
<213> ORGANISM: artificial sequence
<220> FEATURE:
<223> OTHER INFORMATION: RNAi agent sequence

<400> SEQUENCE: 311
caggaguccg auauagcuu                                                    19
```

<210> SEQ ID NO 312
<211> LENGTH: 19
<212> TYPE: RNA
<213> ORGANISM: artificial sequence
<220> FEATURE:
<223> OTHER INFORMATION: RNAi agent sequence

<400> SEQUENCE: 312
cuggauggac aaucacuuu                                                    19

<210> SEQ ID NO 313
<211> LENGTH: 19
<212> TYPE: RNA
<213> ORGANISM: artificial sequence
<220> FEATURE:
<223> OTHER INFORMATION: RNAi agent sequence

<400> SEQUENCE: 313
auggacaauc acuucagau                                                    19

<210> SEQ ID NO 314
<211> LENGTH: 19
<212> TYPE: RNA
<213> ORGANISM: artificial sequence
<220> FEATURE:
<223> OTHER INFORMATION: RNAi agent sequence

<400> SEQUENCE: 314
ucacuucaga ucccugaau                                                    19

<210> SEQ ID NO 315
<211> LENGTH: 19
<212> TYPE: RNA
<213> ORGANISM: artificial sequence
<220> FEATURE:
<223> OTHER INFORMATION: RNAi agent sequence

<400> SEQUENCE: 315
cagaucccug aaaggcuau                                                    19

<210> SEQ ID NO 316
<211> LENGTH: 19
<212> TYPE: RNA
<213> ORGANISM: artificial sequence
<220> FEATURE:
<223> OTHER INFORMATION: RNAi agent sequence

<400> SEQUENCE: 316
ugaaaggcua cuggagcau                                                    19

<210> SEQ ID NO 317
<211> LENGTH: 19
<212> TYPE: RNA
<213> ORGANISM: artificial sequence
<220> FEATURE:
<223> OTHER INFORMATION: RNAi agent sequence

<400> SEQUENCE: 317
ggcuacugga gcaaguuuu                                                    19

<210> SEQ ID NO 318
<211> LENGTH: 19
<212> TYPE: RNA
<213> ORGANISM: artificial sequence
<220> FEATURE:
<223> OTHER INFORMATION: RNAi agent sequence -continued

<400> SEQUENCE: 318
gcuacuggag caaguuuau                                                19

<210> SEQ ID NO 319
<211> LENGTH: 19
<212> TYPE: RNA
<213> ORGANISM: artificial sequence
<220> FEATURE:
<223> OTHER INFORMATION: RNAi agent sequence

<400> SEQUENCE: 319
cuacuggagc aaguuuacu                                                19

<210> SEQ ID NO 320
<211> LENGTH: 19
<212> TYPE: RNA
<213> ORGANISM: artificial sequence
<220> FEATURE:
<223> OTHER INFORMATION: RNAi agent sequence

<400> SEQUENCE: 320
caaguuuacu gacaaguuu                                                19

<210> SEQ ID NO 321
<211> LENGTH: 19
<212> TYPE: RNA
<213> ORGANISM: artificial sequence
<220> FEATURE:
<223> OTHER INFORMATION: RNAi agent sequence

<400> SEQUENCE: 321
aaguuuacug acaaguucu                                                19

<210> SEQ ID NO 322
<211> LENGTH: 19
<212> TYPE: RNA
<213> ORGANISM: artificial sequence
<220> FEATURE:
<223> OTHER INFORMATION: RNAi agent sequence

<400> SEQUENCE: 322
aguuuacuga caaguucau                                                19

<210> SEQ ID NO 323
<211> LENGTH: 19
<212> TYPE: RNA
<213> ORGANISM: artificial sequence
<220> FEATURE:
<223> OTHER INFORMATION: RNAi agent sequence

<400> SEQUENCE: 323
ccggcuucug ggauucuau                                                19

<210> SEQ ID NO 324
<211> LENGTH: 19
<212> TYPE: RNA
<213> ORGANISM: artificial sequence
<220> FEATURE:
<223> OTHER INFORMATION: RNAi agent sequence

<400> SEQUENCE: 324
cggcuucugg gauucuaau                                                19

<210> SEQ ID NO 325

```
<211> LENGTH: 19
<212> TYPE: RNA
<213> ORGANISM: artificial sequence
<220> FEATURE:
<223> OTHER INFORMATION: RNAi agent sequence

<400> SEQUENCE: 325
gaggaccaac caacuccau                                              19

<210> SEQ ID NO 326
<211> LENGTH: 19
<212> TYPE: RNA
<213> ORGANISM: artificial sequence
<220> FEATURE:
<223> OTHER INFORMATION: RNAi agent sequence

<400> SEQUENCE: 326
accaaccaac uccagcuau                                              19

<210> SEQ ID NO 327
<211> LENGTH: 19
<212> TYPE: RNA
<213> ORGANISM: artificial sequence
<220> FEATURE:
<223> OTHER INFORMATION: RNAi agent sequence

<400> SEQUENCE: 327
caaccaacuc cagcuauuu                                              19

<210> SEQ ID NO 328
<211> LENGTH: 19
<212> TYPE: RNA
<213> ORGANISM: artificial sequence
<220> FEATURE:
<223> OTHER INFORMATION: RNAi agent sequence

<400> SEQUENCE: 328
agcuauugag ucgugagau                                              19

<210> SEQ ID NO 329
<211> LENGTH: 19
<212> TYPE: RNA
<213> ORGANISM: artificial sequence
<220> FEATURE:
<223> OTHER INFORMATION: RNAi agent sequence

<400> SEQUENCE: 329
cuauugaguc gugagacuu                                              19

<210> SEQ ID NO 330
<211> LENGTH: 19
<212> TYPE: RNA
<213> ORGANISM: artificial sequence
<220> FEATURE:
<223> OTHER INFORMATION: RNAi agent sequence

<400> SEQUENCE: 330
uauugagucg ugagacuuu                                              19

<210> SEQ ID NO 331
<211> LENGTH: 19
<212> TYPE: RNA
<213> ORGANISM: artificial sequence
<220> FEATURE:
<223> OTHER INFORMATION: RNAi agent sequence

<400> SEQUENCE: 331
```

```
guugcagaug ugccuguuu                                              19

<210> SEQ ID NO 332
<211> LENGTH: 19
<212> TYPE: RNA
<213> ORGANISM: artificial sequence
<220> FEATURE:
<223> OTHER INFORMATION: RNAi agent sequence

<400> SEQUENCE: 332
gaugugccug uuccuccau                                              19

<210> SEQ ID NO 333
<211> LENGTH: 19
<212> TYPE: RNA
<213> ORGANISM: artificial sequence
<220> FEATURE:
<223> OTHER INFORMATION: RNAi agent sequence

<400> SEQUENCE: 333
ggaaaguaug uucucaugu                                              19

<210> SEQ ID NO 334
<211> LENGTH: 19
<212> TYPE: RNA
<213> ORGANISM: artificial sequence
<220> FEATURE:
<223> OTHER INFORMATION: RNAi agent sequence

<400> SEQUENCE: 334
gaaaguaugu ucucauguu                                              19

<210> SEQ ID NO 335
<211> LENGTH: 19
<212> TYPE: RNA
<213> ORGANISM: artificial sequence
<220> FEATURE:
<223> OTHER INFORMATION: RNAi agent sequence

<400> SEQUENCE: 335
aguauguucu caugucuuu                                              19

<210> SEQ ID NO 336
<211> LENGTH: 19
<212> TYPE: RNA
<213> ORGANISM: artificial sequence
<220> FEATURE:
<223> OTHER INFORMATION: RNAi agent sequence

<400> SEQUENCE: 336
cucccuagau cucaccuau                                              19

<210> SEQ ID NO 337
<211> LENGTH: 19
<212> TYPE: RNA
<213> ORGANISM: artificial sequence
<220> FEATURE:
<223> OTHER INFORMATION: RNAi agent sequence

<400> SEQUENCE: 337
ucccuagauc ucaccuaau                                              19

<210> SEQ ID NO 338
<211> LENGTH: 19
<212> TYPE: RNA
```

```
<213> ORGANISM: artificial sequence
<220> FEATURE:
<223> OTHER INFORMATION: RNAi agent sequence

<400> SEQUENCE: 338
cccuagaucu caccuaaau                                                 19

<210> SEQ ID NO 339
<211> LENGTH: 19
<212> TYPE: RNA
<213> ORGANISM: artificial sequence
<220> FEATURE:
<223> OTHER INFORMATION: RNAi agent sequence

<400> SEQUENCE: 339
ccuagaucuc accuaaacu                                                 19

<210> SEQ ID NO 340
<211> LENGTH: 19
<212> TYPE: RNA
<213> ORGANISM: artificial sequence
<220> FEATURE:
<223> OTHER INFORMATION: RNAi agent sequence

<400> SEQUENCE: 340
cuagaucuca ccuaaacau                                                 19

<210> SEQ ID NO 341
<211> LENGTH: 19
<212> TYPE: RNA
<213> ORGANISM: artificial sequence
<220> FEATURE:
<223> OTHER INFORMATION: RNAi agent sequence

<400> SEQUENCE: 341
uagaucucac cuaaacauu                                                 19

<210> SEQ ID NO 342
<211> LENGTH: 19
<212> TYPE: RNA
<213> ORGANISM: artificial sequence
<220> FEATURE:
<223> OTHER INFORMATION: RNAi agent sequence

<400> SEQUENCE: 342
aaacaugcug ucccuaauu                                                 19

<210> SEQ ID NO 343
<211> LENGTH: 19
<212> TYPE: RNA
<213> ORGANISM: artificial sequence
<220> FEATURE:
<223> OTHER INFORMATION: RNAi agent sequence

<400> SEQUENCE: 343
aacaugcugu cccuaauau                                                 19

<210> SEQ ID NO 344
<211> LENGTH: 19
<212> TYPE: RNA
<213> ORGANISM: artificial sequence
<220> FEATURE:
<223> OTHER INFORMATION: RNAi agent sequence

<400> SEQUENCE: 344
acaugcuguc ccuaauaau                                                 19
```

```
<210> SEQ ID NO 345
<211> LENGTH: 19
<212> TYPE: RNA
<213> ORGANISM: artificial sequence
<220> FEATURE:
<223> OTHER INFORMATION: RNAi agent sequence

<400> SEQUENCE: 345
caugcugucc cuaauaaau                                                19

<210> SEQ ID NO 346
<211> LENGTH: 19
<212> TYPE: RNA
<213> ORGANISM: artificial sequence
<220> FEATURE:
<223> OTHER INFORMATION: RNAi agent sequence

<400> SEQUENCE: 346
augcuguccc uaauaaagu                                                19

<210> SEQ ID NO 347
<211> LENGTH: 19
<212> TYPE: RNA
<213> ORGANISM: artificial sequence
<220> FEATURE:
<223> OTHER INFORMATION: RNAi agent sequence

<400> SEQUENCE: 347
gcugucccua auaaagcuu                                                19

<210> SEQ ID NO 348
<211> LENGTH: 19
<212> TYPE: RNA
<213> ORGANISM: artificial sequence
<220> FEATURE:
<223> OTHER INFORMATION: RNAi agent sequence

<400> SEQUENCE: 348 ccuauaaag cuggauaau                                                 19

<210> SEQ ID NO 349
<211> LENGTH: 19
<212> TYPE: RNA
<213> ORGANISM: artificial sequence
<220> FEATURE:
<223> OTHER INFORMATION: RNAi agent sequence

<400> SEQUENCE: 349
uaauaaagcu ggauaagau                                                19

<210> SEQ ID NO 350
<211> LENGTH: 19
<212> TYPE: RNA
<213> ORGANISM: artificial sequence
<220> FEATURE:
<223> OTHER INFORMATION: RNAi agent sequence

<400> SEQUENCE: 350
ucuagggaug aacugagca                                                19

<210> SEQ ID NO 351
<211> LENGTH: 19
<212> TYPE: RNA
<213> ORGANISM: artificial sequence
<220> FEATURE:
```

```
<223> OTHER INFORMATION: RNAi agent sequence

<400> SEQUENCE: 351
ugcauggcac cucuguucc                                                19

<210> SEQ ID NO 352
<211> LENGTH: 19
<212> TYPE: RNA
<213> ORGANISM: artificial sequence
<220> FEATURE:
<223> OTHER INFORMATION: RNAi agent sequence

<400> SEQUENCE: 352
acaacaagga guacccggg                                                19

<210> SEQ ID NO 353
<211> LENGTH: 19
<212> TYPE: RNA
<213> ORGANISM: artificial sequence
<220> FEATURE:
<223> OTHER INFORMATION: RNAi agent sequence

<400> SEQUENCE: 353
aacaacaagg aguacccgg                                                19

<210> SEQ ID NO 354
<211> LENGTH: 19
<212> TYPE: RNA
<213> ORGANISM: artificial sequence
<220> FEATURE:
<223> OTHER INFORMATION: RNAi agent sequence

<400> SEQUENCE: 354
ugcaugaagc ugagaaggg                                                19

<210> SEQ ID NO 355
<211> LENGTH: 19
<212> TYPE: RNA
<213> ORGANISM: artificial sequence
<220> FEATURE:
<223> OTHER INFORMATION: RNAi agent sequence

<400> SEQUENCE: 355
uaacccugca ugaagcuga                                                19

<210> SEQ ID NO 356
<211> LENGTH: 19
<212> TYPE: RNA
<213> ORGANISM: artificial sequence
<220> FEATURE:
<223> OTHER INFORMATION: RNAi agent sequence

<400> SEQUENCE: 356
uguaacccug caugaagcu                                                19

<210> SEQ ID NO 357
<211> LENGTH: 19
<212> TYPE: RNA
<213> ORGANISM: artificial sequence
<220> FEATURE:
<223> OTHER INFORMATION: RNAi agent sequence

<400> SEQUENCE: 357
auguaacccu gcaugaagc                                                19
```

```
<210> SEQ ID NO 358
<211> LENGTH: 19
<212> TYPE: RNA
<213> ORGANISM: artificial sequence
<220> FEATURE:
<223> OTHER INFORMATION: RNAi agent sequence

<400> SEQUENCE: 358
uucauguaac ccugcauga                                              19

<210> SEQ ID NO 359
<211> LENGTH: 19
<212> TYPE: RNA
<213> ORGANISM: artificial sequence
<220> FEATURE:
<223> OTHER INFORMATION: RNAi agent sequence

<400> SEQUENCE: 359
cuucauguaa cccugcaug                                              19

<210> SEQ ID NO 360
<211> LENGTH: 19
<212> TYPE: RNA
<213> ORGANISM: artificial sequence
<220> FEATURE:
<223> OTHER INFORMATION: RNAi agent sequence

<400> SEQUENCE: 360
ucuuucaggg aacugaagc                                              19

<210> SEQ ID NO 361
<211> LENGTH: 19
<212> TYPE: RNA
<213> ORGANISM: artificial sequence
<220> FEATURE:
<223> OTHER INFORMATION: RNAi agent sequence

<400> SEQUENCE: 361
uagucuuuca gggaacuga                                              19

<210> SEQ ID NO 362
<211> LENGTH: 19
<212> TYPE: RNA
<213> ORGANISM: artificial sequence
<220> FEATURE:
<223> OTHER INFORMATION: RNAi agent sequence

<400> SEQUENCE: 362
ugcuccagua gucuuucag                                              19

<210> SEQ ID NO 363
<211> LENGTH: 19
<212> TYPE: RNA
<213> ORGANISM: artificial sequence
<220> FEATURE:
<223> OTHER INFORMATION: RNAi agent sequence

<400> SEQUENCE: 363
uaacggugcu ccaguaguc                                              19

<210> SEQ ID NO 364
<211> LENGTH: 19
<212> TYPE: RNA
<213> ORGANISM: artificial sequence
<220> FEATURE:
<223> OTHER INFORMATION: RNAi agent sequence
```

```
<400> SEQUENCE: 364
uuaacggugc uccaguagu                                                    19

<210> SEQ ID NO 365
<211> LENGTH: 19
<212> TYPE: RNA
<213> ORGANISM: artificial sequence
<220> FEATURE:
<223> OTHER INFORMATION: RNAi agent sequence

<400> SEQUENCE: 365
cuuaacggug cuccaguag                                                    19

<210> SEQ ID NO 366
<211> LENGTH: 19
<212> TYPE: RNA
<213> ORGANISM: artificial sequence
<220> FEATURE:
<223> OTHER INFORMATION: RNAi agent sequence

<400> SEQUENCE: 366
uccuuaacgg ugcuccagu                                                    19

<210> SEQ ID NO 367
<211> LENGTH: 19
<212> TYPE: RNA
<213> ORGANISM: artificial sequence
<220> FEATURE:
<223> OTHER INFORMATION: RNAi agent sequence

<400> SEQUENCE: 367
uuguccuuaa cggugcucc                                                    19

<210> SEQ ID NO 368
<211> LENGTH: 19
<212> TYPE: RNA
<213> ORGANISM: artificial sequence
<220> FEATURE:
<223> OTHER INFORMATION: RNAi agent sequence

<400> SEQUENCE: 368
cuuguccuua acggugcuc                                                    19

<210> SEQ ID NO 369
<211> LENGTH: 19
<212> TYPE: RNA
<213> ORGANISM: artificial sequence
<220> FEATURE:
<223> OTHER INFORMATION: RNAi agent sequence

<400> SEQUENCE: 369
aacuugcccu uaacggugc                                                    19

<210> SEQ ID NO 370
<211> LENGTH: 19
<212> TYPE: RNA
<213> ORGANISM: artificial sequence
<220> FEATURE:
<223> OTHER INFORMATION: RNAi agent sequence

<400> SEQUENCE: 370
agaacuuguc cuuaacggu                                                    19

<210> SEQ ID NO 371
<211> LENGTH: 19
```

```
<212> TYPE: RNA
<213> ORGANISM: artificial sequence
<220> FEATURE:
<223> OTHER INFORMATION: RNAi agent sequence

<400> SEQUENCE: 371
aacucagaga acuuguccu                                                  19

<210> SEQ ID NO 372
<211> LENGTH: 19
<212> TYPE: RNA
<213> ORGANISM: artificial sequence
<220> FEATURE:
<223> OTHER INFORMATION: RNAi agent sequence

<400> SEQUENCE: 372
gaacucagag aacuugucc                                                  19

<210> SEQ ID NO 373
<211> LENGTH: 19
<212> TYPE: RNA
<213> ORGANISM: artificial sequence
<220> FEATURE:
<223> OTHER INFORMATION: RNAi agent sequence

<400> SEQUENCE: 373
uggucugacc ucaggaucc                                                  19

<210> SEQ ID NO 374
<211> LENGTH: 19
<212> TYPE: RNA
<213> ORGANISM: artificial sequence
<220> FEATURE:
<223> OTHER INFORMATION: RNAi agent sequence

<400> SEQUENCE: 374
aaguuggucu gaccucagg                                                  19

<210> SEQ ID NO 375
<211> LENGTH: 19
<212> TYPE: RNA
<213> ORGANISM: artificial sequence
<220> FEATURE:
<223> OTHER INFORMATION: RNAi agent sequence

<400> SEQUENCE: 375
ugaaguuggu cugaccuca                                                  19

<210> SEQ ID NO 376
<211> LENGTH: 19
<212> TYPE: RNA
<213> ORGANISM: artificial sequence
<220> FEATURE:
<223> OTHER INFORMATION: RNAi agent sequence

<400> SEQUENCE: 376
aggauggaua ggcaggugg                                                  19

<210> SEQ ID NO 377
<211> LENGTH: 19
<212> TYPE: RNA
<213> ORGANISM: artificial sequence
<220> FEATURE:
<223> OTHER INFORMATION: RNAi agent sequence

<400> SEQUENCE: 377
```
acugagaaua cugucccuu                                              19

<210> SEQ ID NO 378
<211> LENGTH: 19
<212> TYPE: RNA
<213> ORGANISM: artificial sequence
<220> FEATURE:
<223> OTHER INFORMATION: RNAi agent sequence

<400> SEQUENCE: 378
agcacugaga auacugucc                                              19

<210> SEQ ID NO 379
<211> LENGTH: 19
<212> TYPE: RNA
<213> ORGANISM: artificial sequence
<220> FEATURE:
<223> OTHER INFORMATION: RNAi agent sequence

<400> SEQUENCE: 379
uccagcuuua uugggaggc                                              19

<210> SEQ ID NO 380
<211> LENGTH: 19
<212> TYPE: RNA
<213> ORGANISM: artificial sequence
<220> FEATURE:
<223> OTHER INFORMATION: RNAi agent sequence

<400> SEQUENCE: 380
ucuuguccag cuuuauugg                                              19

<210> SEQ ID NO 381
<211> LENGTH: 19
<212> TYPE: RNA
<213> ORGANISM: artificial sequence
<220> FEATURE:
<223> OTHER INFORMATION: RNAi agent sequence

<400> SEQUENCE: 381
uucuugucca gcuuuauug                                              19

<210> SEQ ID NO 382
<211> LENGTH: 21
<212> TYPE: RNA
<213> ORGANISM: artificial sequence
<220> FEATURE:
<223> OTHER INFORMATION: RNAi agent sequence

<400> SEQUENCE: 382
uuuaggugag aucuagggau u                                           21

<210> SEQ ID NO 383
<211> LENGTH: 21
<212> TYPE: RNA
<213> ORGANISM: artificial sequence
<220> FEATURE:
<223> OTHER INFORMATION: RNAi agent sequence

<400> SEQUENCE: 383
uguuuaggug agaucuaggu u                                           21

<210> SEQ ID NO 384
<211> LENGTH: 21
<212> TYPE: RNA
<213> ORGANISM: artificial sequence

```
<220> FEATURE:
<223> OTHER INFORMATION: RNAi agent sequence

<400> SEQUENCE: 384
auuucgauaa gccaguaagu u                                              21

<210> SEQ ID NO 385
<211> LENGTH: 21
<212> TYPE: RNA
<213> ORGANISM: artificial sequence
<220> FEATURE:
<223> OTHER INFORMATION: RNAi agent sequence

<400> SEQUENCE: 385
cuugucggcc augauauagu u                                              21

<210> SEQ ID NO 386
<211> LENGTH: 19
<212> TYPE: RNA
<213> ORGANISM: artificial sequence
<220> FEATURE:
<223> OTHER INFORMATION: RNAi agent sequence

<400> SEQUENCE: 386
uagcuagcug cuucuaggg                                                 19

<210> SEQ ID NO 387
<211> LENGTH: 19
<212> TYPE: RNA
<213> ORGANISM: artificial sequence
<220> FEATURE:
<223> OTHER INFORMATION: RNAi agent sequence

<400> SEQUENCE: 387
uggaguagcu agcugcuuc                                                 19

<210> SEQ ID NO 388
<211> LENGTH: 19
<212> TYPE: RNA
<213> ORGANISM: artificial sequence
<220> FEATURE:
<223> OTHER INFORMATION: RNAi agent sequence

<400> SEQUENCE: 388
accuggagua gcuagcugc                                                 19

<210> SEQ ID NO 389
<211> LENGTH: 19
<212> TYPE: RNA
<213> ORGANISM: artificial sequence
<220> FEATURE:
<223> OTHER INFORMATION: RNAi agent sequence

<400> SEQUENCE: 389
uaccuggagu agcuagcug                                                 19

<210> SEQ ID NO 390
<211> LENGTH: 19
<212> TYPE: RNA
<213> ORGANISM: artificial sequence
<220> FEATURE:
<223> OTHER INFORMATION: RNAi agent sequence

<400> SEQUENCE: 390
uucagcucgg gcagaugcc                                                 19
```

<210> SEQ ID NO 391
<211> LENGTH: 19
<212> TYPE: RNA
<213> ORGANISM: artificial sequence
<220> FEATURE:
<223> OTHER INFORMATION: RNAi agent sequence

<400> SEQUENCE: 391
uagcccugua cagagccca                                                      19

<210> SEQ ID NO 392
<211> LENGTH: 19
<212> TYPE: RNA
<213> ORGANISM: artificial sequence
<220> FEATURE:
<223> OTHER INFORMATION: RNAi agent sequence

<400> SEQUENCE: 392
uuccauguag cccuguaca                                                      19

<210> SEQ ID NO 393
<211> LENGTH: 19
<212> TYPE: RNA
<213> ORGANISM: artificial sequence
<220> FEATURE:
<223> OTHER INFORMATION: RNAi agent sequence

<400> SEQUENCE: 393
uuggaggcuu guuccaugu                                                      19

<210> SEQ ID NO 394
<211> LENGTH: 19
<212> TYPE: RNA
<213> ORGANISM: artificial sequence
<220> FEATURE:
<223> OTHER INFORMATION: RNAi agent sequence

<400> SEQUENCE: 394
uacuuagcgc auccuggac                                                      19

<210> SEQ ID NO 395
<211> LENGTH: 19
<212> TYPE: RNA
<213> ORGANISM: artificial sequence
<220> FEATURE:
<223> OTHER INFORMATION: RNAi agent sequence

<400> SEQUENCE: 395
ucggacuccu gcacgcuac                                                      19

<210> SEQ ID NO 396
<211> LENGTH: 19
<212> TYPE: RNA
<213> ORGANISM: artificial sequence
<220> FEATURE:
<223> OTHER INFORMATION: RNAi agent sequence

<400> SEQUENCE: 396
uaucggacuc cugcacgcu                                                      19

<210> SEQ ID NO 397
<211> LENGTH: 19
<212> TYPE: RNA
<213> ORGANISM: artificial sequence
<220> FEATURE:
<223> OTHER INFORMATION: RNAi agent sequence

```
<400> SEQUENCE: 397
auaucggacu ccugcacgc                                              19

<210> SEQ ID NO 398
<211> LENGTH: 19
<212> TYPE: RNA
<213> ORGANISM: artificial sequence
<220> FEATURE:
<223> OTHER INFORMATION: RNAi agent sequence

<400> SEQUENCE: 398
uauaucggac uccugcacg                                              19

<210> SEQ ID NO 399
<211> LENGTH: 19
<212> TYPE: RNA
<213> ORGANISM: artificial sequence
<220> FEATURE:
<223> OTHER INFORMATION: RNAi agent sequence

<400> SEQUENCE: 399
agcuauaucg gacuccugc                                              19

<210> SEQ ID NO 400
<211> LENGTH: 19
<212> TYPE: RNA
<213> ORGANISM: artificial sequence
<220> FEATURE:
<223> OTHER INFORMATION: RNAi agent sequence

<400> SEQUENCE: 400
aagugauugu ccauccagc                                              19

<210> SEQ ID NO 401
<211> LENGTH: 19
<212> TYPE: RNA
<213> ORGANISM: artificial sequence
<220> FEATURE:
<223> OTHER INFORMATION: RNAi agent sequence

<400> SEQUENCE: 401
ucugaaguga uuguccauc                                              19

<210> SEQ ID NO 402
<211> LENGTH: 19
<212> TYPE: RNA
<213> ORGANISM: artificial sequence
<220> FEATURE:
<223> OTHER INFORMATION: RNAi agent sequence

<400> SEQUENCE: 402
uucagggauc ugaagugau                                              19

<210> SEQ ID NO 403
<211> LENGTH: 19
<212> TYPE: RNA
<213> ORGANISM: artificial sequence
<220> FEATURE:
<223> OTHER INFORMATION: RNAi agent sequence

<400> SEQUENCE: 403
uagccuuuca gggaucuga                                              19

<210> SEQ ID NO 404
```

```
<211> LENGTH: 19
<212> TYPE: RNA
<213> ORGANISM: artificial sequence
<220> FEATURE:
<223> OTHER INFORMATION: RNAi agent sequence

<400> SEQUENCE: 404
ugcuccagua gccuuucag                                                    19

<210> SEQ ID NO 405
<211> LENGTH: 19
<212> TYPE: RNA
<213> ORGANISM: artificial sequence
<220> FEATURE:
<223> OTHER INFORMATION: RNAi agent sequence

<400> SEQUENCE: 405
aaacuugcuc caguagccu                                                    19

<210> SEQ ID NO 406
<211> LENGTH: 19
<212> TYPE: RNA
<213> ORGANISM: artificial sequence
<220> FEATURE:
<223> OTHER INFORMATION: RNAi agent sequence

<400> SEQUENCE: 406
uaaacuugcu ccaguagcc                                                    19

<210> SEQ ID NO 407
<211> LENGTH: 19
<212> TYPE: RNA
<213> ORGANISM: artificial sequence
<220> FEATURE:
<223> OTHER INFORMATION: RNAi agent sequence

<400> SEQUENCE: 407
guaaacuugc uccaguagc                                                    19

<210> SEQ ID NO 408
<211> LENGTH: 19
<212> TYPE: RNA
<213> ORGANISM: artificial sequence
<220> FEATURE:
<223> OTHER INFORMATION: RNAi agent sequence

<400> SEQUENCE: 408
aacuugucag uaaacuugc                                                    19

<210> SEQ ID NO 409
<211> LENGTH: 19
<212> TYPE: RNA
<213> ORGANISM: artificial sequence
<220> FEATURE:
<223> OTHER INFORMATION: RNAi agent sequence

<400> SEQUENCE: 409
gaacuuguca guaaacuug                                                    19

<210> SEQ ID NO 410
<211> LENGTH: 19
<212> TYPE: RNA
<213> ORGANISM: artificial sequence
<220> FEATURE:
<223> OTHER INFORMATION: RNAi agent sequence

<400> SEQUENCE: 410
```
ugaacuuguc aguaaacuu                                                19

<210> SEQ ID NO 411
<211> LENGTH: 19
<212> TYPE: RNA
<213> ORGANISM: artificial sequence
<220> FEATURE:
<223> OTHER INFORMATION: RNAi agent sequence

<400> SEQUENCE: 411
uagaauccca gaagccggu                                                19

<210> SEQ ID NO 412
<211> LENGTH: 19
<212> TYPE: RNA
<213> ORGANISM: artificial sequence
<220> FEATURE:
<223> OTHER INFORMATION: RNAi agent sequence

<400> SEQUENCE: 412
uuagaauccc agaagccgg                                                19

<210> SEQ ID NO 413
<211> LENGTH: 19
<212> TYPE: RNA
<213> ORGANISM: artificial sequence
<220> FEATURE:
<223> OTHER INFORMATION: RNAi agent sequence

<400> SEQUENCE: 413
uggaguuggu ugguccuca                                                19

<210> SEQ ID NO 414
<211> LENGTH: 19
<212> TYPE: RNA
<213> ORGANISM: artificial sequence
<220> FEATURE:
<223> OTHER INFORMATION: RNAi agent sequence

<400> SEQUENCE: 414
uagcuggagu ugguugguc                                                19

<210> SEQ ID NO 415
<211> LENGTH: 19
<212> TYPE: RNA
<213> ORGANISM: artificial sequence
<220> FEATURE:
<223> OTHER INFORMATION: RNAi agent sequence

<400> SEQUENCE: 415
aauagcugga guugguugg                                                19

<210> SEQ ID NO 416
<211> LENGTH: 19
<212> TYPE: RNA
<213> ORGANISM: artificial sequence
<220> FEATURE:
<223> OTHER INFORMATION: RNAi agent sequence

<400> SEQUENCE: 416
ucucacgacu caauagcug                                                19

<210> SEQ ID NO 417
<211> LENGTH: 19
<212> TYPE: RNA

```
<213> ORGANISM: artificial sequence
<220> FEATURE:
<223> OTHER INFORMATION: RNAi agent sequence

<400> SEQUENCE: 417
agucucacga cucaauagc                                                19

<210> SEQ ID NO 418
<211> LENGTH: 19
<212> TYPE: RNA
<213> ORGANISM: artificial sequence
<220> FEATURE:
<223> OTHER INFORMATION: RNAi agent sequence

<400> SEQUENCE: 418
aagucucacg acucaauag                                                19

<210> SEQ ID NO 419
<211> LENGTH: 19
<212> TYPE: RNA
<213> ORGANISM: artificial sequence
<220> FEATURE:
<223> OTHER INFORMATION: RNAi agent sequence

<400> SEQUENCE: 419
aacaggcaca ucugcaaca                                                19

<210> SEQ ID NO 420
<211> LENGTH: 19
<212> TYPE: RNA
<213> ORGANISM: artificial sequence
<220> FEATURE:
<223> OTHER INFORMATION: RNAi agent sequence

<400> SEQUENCE: 420
uggaggaaca ggcacaucu                                                19

<210> SEQ ID NO 421
<211> LENGTH: 19
<212> TYPE: RNA
<213> ORGANISM: artificial sequence
<220> FEATURE:
<223> OTHER INFORMATION: RNAi agent sequence

<400> SEQUENCE: 421
caugagaaca uacuuuccc                                                19

<210> SEQ ID NO 422
<211> LENGTH: 19
<212> TYPE: RNA
<213> ORGANISM: artificial sequence
<220> FEATURE:
<223> OTHER INFORMATION: RNAi agent sequence

<400> SEQUENCE: 422
acaugagaac auacuuucc                                                19

<210> SEQ ID NO 423
<211> LENGTH: 19
<212> TYPE: RNA
<213> ORGANISM: artificial sequence
<220> FEATURE:
<223> OTHER INFORMATION: RNAi agent sequence

<400> SEQUENCE: 423
aagacaugag aacauacuu                                                19
```

<210> SEQ ID NO 424
<211> LENGTH: 19
<212> TYPE: RNA
<213> ORGANISM: artificial sequence
<220> FEATURE:
<223> OTHER INFORMATION: RNAi agent sequence

<400> SEQUENCE: 424
uaggugagau cugggagg                                                19

<210> SEQ ID NO 425
<211> LENGTH: 19
<212> TYPE: RNA
<213> ORGANISM: artificial sequence
<220> FEATURE:
<223> OTHER INFORMATION: RNAi agent sequence

<400> SEQUENCE: 425
uuaggugaga ucuagggag                                               19

<210> SEQ ID NO 426
<211> LENGTH: 19
<212> TYPE: RNA
<213> ORGANISM: artificial sequence
<220> FEATURE:
<223> OTHER INFORMATION: RNAi agent sequence

<400> SEQUENCE: 426
uuuaggugag aucuaggga                                               19

<210> SEQ ID NO 427
<211> LENGTH: 19
<212> TYPE: RNA
<213> ORGANISM: artificial sequence
<220> FEATURE:
<223> OTHER INFORMATION: RNAi agent sequence

<400> SEQUENCE: 427
guuuagguga gaucuaggg                                               19

<210> SEQ ID NO 428
<211> LENGTH: 19
<212> TYPE: RNA
<213> ORGANISM: artificial sequence
<220> FEATURE:
<223> OTHER INFORMATION: RNAi agent sequence

<400> SEQUENCE: 428
uguuuaggug agaucuagg                                               19

<210> SEQ ID NO 429
<211> LENGTH: 19
<212> TYPE: RNA
<213> ORGANISM: artificial sequence
<220> FEATURE:
<223> OTHER INFORMATION: RNAi agent sequence

<400> SEQUENCE: 429
auguuuaggu gagaucuag                                               19

<210> SEQ ID NO 430
<211> LENGTH: 19
<212> TYPE: RNA
<213> ORGANISM: artificial sequence
<220> FEATURE:

<223> OTHER INFORMATION: RNAi agent sequence

<400> SEQUENCE: 430
auuagggaca gcauguuua                           19

<210> SEQ ID NO 431
<211> LENGTH: 19
<212> TYPE: RNA
<213> ORGANISM: artificial sequence
<220> FEATURE:
<223> OTHER INFORMATION: RNAi agent sequence

<400> SEQUENCE: 431
uauuagggac agcauguuu                           19

<210> SEQ ID NO 432
<211> LENGTH: 19
<212> TYPE: RNA
<213> ORGANISM: artificial sequence
<220> FEATURE:
<223> OTHER INFORMATION: RNAi agent sequence

<400> SEQUENCE: 432
uuauuaggga cagcauguu                           19

<210> SEQ ID NO 433
<211> LENGTH: 19
<212> TYPE: RNA
<213> ORGANISM: artificial sequence
<220> FEATURE:
<223> OTHER INFORMATION: RNAi agent sequence

<400> SEQUENCE: 433
uuuauuaggg acagcaugu                           19

<210> SEQ ID NO 434
<211> LENGTH: 19
<212> TYPE: RNA
<213> ORGANISM: artificial sequence
<220> FEATURE:
<223> OTHER INFORMATION: RNAi agent sequence

<400> SEQUENCE: 434
cuuuauuagg gacagcaug                           19

<210> SEQ ID NO 435
<211> LENGTH: 19
<212> TYPE: RNA
<213> ORGANISM: artificial sequence
<220> FEATURE:
<223> OTHER INFORMATION: RNAi agent sequence

<400> SEQUENCE: 435
agcuuuauua gggacagca                           19

<210> SEQ ID NO 436
<211> LENGTH: 19
<212> TYPE: RNA
<213> ORGANISM: artificial sequence
<220> FEATURE:
<223> OTHER INFORMATION: RNAi agent sequence

<400> SEQUENCE: 436
uuauccagcu uuauuaggg                           19

```
<210> SEQ ID NO 437
<211> LENGTH: 19
<212> TYPE: RNA
<213> ORGANISM: artificial sequence
<220> FEATURE:
<223> OTHER INFORMATION: RNAi agent sequence

<400> SEQUENCE: 437
ucuuauccag cuuuauuag                                                    19

<210> SEQ ID NO 438
<211> LENGTH: 19
<212> TYPE: RNA
<213> ORGANISM: artificial sequence
<220> FEATURE:
<223> OTHER INFORMATION: RNAi agent sequence

<400> SEQUENCE: 438
gacaguauuc ucagugcuu                                                    19

<210> SEQ ID NO 439
<211> LENGTH: 19
<212> TYPE: RNA
<213> ORGANISM: artificial sequence
<220> FEATURE:
<223> OTHER INFORMATION: RNAi agent sequence

<400> SEQUENCE: 439
gacaguauuc ucagugcuu                                                    19

<210> SEQ ID NO 440
<211> LENGTH: 21
<212> TYPE: RNA
<213> ORGANISM: artificial sequence
<220> FEATURE:
<223> OTHER INFORMATION: RNAi agent sequence

<400> SEQUENCE: 440
ggacaguauu cucagugcuu u                                                 21

<210> SEQ ID NO 441
<211> LENGTH: 21
<212> TYPE: RNA
<213> ORGANISM: artificial sequence
<220> FEATURE:
<223> OTHER INFORMATION: RNAi agent sequence

<400> SEQUENCE: 441
ggacaguauu cucagugcuu u                                                 21

<210> SEQ ID NO 442
<211> LENGTH: 21
<212> TYPE: RNA
<213> ORGANISM: artificial sequence
<220> FEATURE:
<223> OTHER INFORMATION: RNAi agent sequence

<400> SEQUENCE: 442
agggacagua uucucagugc u                                                 21

<210> SEQ ID NO 443
<211> LENGTH: 25
<212> TYPE: RNA
<213> ORGANISM: artificial sequence
<220> FEATURE:
<223> OTHER INFORMATION: RNAi agent sequence
```

```
<400> SEQUENCE: 443
uaaaagggac aguauucuca gugcu                                              25

<210> SEQ ID NO 444
<211> LENGTH: 25
<212> TYPE: RNA
<213> ORGANISM: artificial sequence
<220> FEATURE:
<223> OTHER INFORMATION: RNAi agent sequence

<400> SEQUENCE: 444
uaaaagggac aguauucuca gugcu                                              25

<210> SEQ ID NO 445
<211> LENGTH: 26
<212> TYPE: RNA
<213> ORGANISM: artificial sequence
<220> FEATURE:
<223> OTHER INFORMATION: RNAi agent sequence

<400> SEQUENCE: 445
uaaaagggac aguauucuca gugcua                                             26

<210> SEQ ID NO 446
<211> LENGTH: 25
<212> TYPE: RNA
<213> ORGANISM: artificial sequence
<220> FEATURE:
<223> OTHER INFORMATION: RNAi agent sequence

<400> SEQUENCE: 446
uaaaagggac aguauucuca gugcu                                              25

<210> SEQ ID NO 447
<211> LENGTH: 25
<212> TYPE: RNA
<213> ORGANISM: artificial sequence
<220> FEATURE:
<223> OTHER INFORMATION: RNAi agent sequence

<400> SEQUENCE: 447
uaaaagggac aguauucuca gugcu                                              25

<210> SEQ ID NO 448
<211> LENGTH: 25
<212> TYPE: RNA
<213> ORGANISM: artificial sequence
<220> FEATURE:
<223> OTHER INFORMATION: RNAi agent sequence

<400> SEQUENCE: 448
uaaaagggac aguauucuca gugcu                                              25

<210> SEQ ID NO 449
<211> LENGTH: 25
<212> TYPE: RNA
<213> ORGANISM: artificial sequence
<220> FEATURE:
<223> OTHER INFORMATION: RNAi agent sequence

<400> SEQUENCE: 449
uaaaagggac aguauucuca gugcu                                              25

<210> SEQ ID NO 450
<211> LENGTH: 25
```

```
<212> TYPE: RNA
<213> ORGANISM: artificial sequence
<220> FEATURE:
<223> OTHER INFORMATION: RNAi agent sequence

<400> SEQUENCE: 450
uaaaagggac aguauucuca gugcu                                      25

<210> SEQ ID NO 451
<211> LENGTH: 25
<212> TYPE: RNA
<213> ORGANISM: artificial sequence
<220> FEATURE:
<223> OTHER INFORMATION: RNAi agent sequence

<400> SEQUENCE: 451
uaaaagggac aguauucuca gugcu                                      25

<210> SEQ ID NO 452
<211> LENGTH: 25
<212> TYPE: RNA
<213> ORGANISM: artificial sequence
<220> FEATURE:
<223> OTHER INFORMATION: RNAi agent sequence

<400> SEQUENCE: 452
uaaaagggac aguauucuca gugcu                                      25

<210> SEQ ID NO 453
<211> LENGTH: 25
<212> TYPE: RNA
<213> ORGANISM: artificial sequence
<220> FEATURE:
<223> OTHER INFORMATION: RNAi agent sequence

<400> SEQUENCE: 453
uaaaagggac aguauucuca gugcu                                      25

<210> SEQ ID NO 454
<211> LENGTH: 25
<212> TYPE: RNA
<213> ORGANISM: artificial sequence
<220> FEATURE:
<223> OTHER INFORMATION: RNAi agent sequence

<400> SEQUENCE: 454
uaaaagggac aguauucuca gugcu                                      25

<210> SEQ ID NO 455
<211> LENGTH: 25
<212> TYPE: RNA
<213> ORGANISM: artificial sequence
<220> FEATURE:
<223> OTHER INFORMATION: RNAi agent sequence

<400> SEQUENCE: 455
uaaaagggac aguauucuca gugcu                                      25

<210> SEQ ID NO 456
<211> LENGTH: 25
<212> TYPE: RNA
<213> ORGANISM: artificial sequence
<220> FEATURE:
<223> OTHER INFORMATION: RNAi agent sequence

<400> SEQUENCE: 456
```
ggacaguauu cucagugcua aauug                                              25

<210> SEQ ID NO 457
<211> LENGTH: 25
<212> TYPE: RNA
<213> ORGANISM: artificial sequence
<220> FEATURE:
<223> OTHER INFORMATION: RNAi agent sequence

<400> SEQUENCE: 457
ggacaguauu cucagugcua aauug                                              25

<210> SEQ ID NO 458
<211> LENGTH: 25
<212> TYPE: RNA
<213> ORGANISM: artificial sequence
<220> FEATURE:
<223> OTHER INFORMATION: RNAi agent sequence

<400> SEQUENCE: 458
ggacaguauu cucagugcua aauug                                              25

<210> SEQ ID NO 459
<211> LENGTH: 25
<212> TYPE: RNA
<213> ORGANISM: artificial sequence
<220> FEATURE:
<223> OTHER INFORMATION: RNAi agent sequence

<400> SEQUENCE: 459
ggacaguauu cucagugcua aauug                                              25

<210> SEQ ID NO 460
<211> LENGTH: 25
<212> TYPE: RNA
<213> ORGANISM: artificial sequence
<220> FEATURE:
<223> OTHER INFORMATION: RNAi agent sequence

<400> SEQUENCE: 460
ggacaguauu cucagugcua aauug                                              25

<210> SEQ ID NO 461
<211> LENGTH: 25
<212> TYPE: RNA
<213> ORGANISM: artificial sequence
<220> FEATURE:
<223> OTHER INFORMATION: RNAi agent sequence

<400> SEQUENCE: 461
ggacaguauu cucagugcua aauug                                              25

<210> SEQ ID NO 462
<211> LENGTH: 25
<212> TYPE: RNA
<213> ORGANISM: artificial sequence
<220> FEATURE:
<223> OTHER INFORMATION: RNAi agent sequence

<400> SEQUENCE: 462
ggacaguauu cucagugcua aauug                                              25

<210> SEQ ID NO 463
<211> LENGTH: 25
<212> TYPE: RNA
<213> ORGANISM: artificial sequence

```
<220> FEATURE:
<223> OTHER INFORMATION: RNAi agent sequence

<400> SEQUENCE: 463
ggacaguauu cucagugcua aauug                                              25

<210> SEQ ID NO 464
<211> LENGTH: 25
<212> TYPE: RNA
<213> ORGANISM: artificial sequence
<220> FEATURE:
<223> OTHER INFORMATION: RNAi agent sequence

<400> SEQUENCE: 464
ggacaguauu cucagugcua aauug                                              25

<210> SEQ ID NO 465
<211> LENGTH: 25
<212> TYPE: RNA
<213> ORGANISM: artificial sequence
<220> FEATURE:
<223> OTHER INFORMATION: RNAi agent sequence

<400> SEQUENCE: 465
ggacaguauu cucagugcua aauug                                              25

<210> SEQ ID NO 466
<211> LENGTH: 25
<212> TYPE: RNA
<213> ORGANISM: artificial sequence
<220> FEATURE:
<223> OTHER INFORMATION: RNAi agent sequence

<400> SEQUENCE: 466
ggacaguauu cucagugcua aauug                                              25

<210> SEQ ID NO 467
<211> LENGTH: 25
<212> TYPE: RNA
<213> ORGANISM: artificial sequence
<220> FEATURE:
<223> OTHER INFORMATION: RNAi agent sequence

<400> SEQUENCE: 467
ggacaguauu cucagugcua aauug                                              25

<210> SEQ ID NO 468
<211> LENGTH: 25
<212> TYPE: RNA
<213> ORGANISM: artificial sequence
<220> FEATURE:
<223> OTHER INFORMATION: RNAi agent sequence

<400> SEQUENCE: 468
ggacaguauu cucagugcua aauug                                              25

<210> SEQ ID NO 469
<211> LENGTH: 25
<212> TYPE: RNA
<213> ORGANISM: artificial sequence
<220> FEATURE:
<223> OTHER INFORMATION: RNAi agent sequence

<400> SEQUENCE: 469
ggacaguauu cucagugcua aauug                                              25
```

```
<210> SEQ ID NO 470
<211> LENGTH: 25
<212> TYPE: RNA
<213> ORGANISM: artificial sequence
<220> FEATURE:
<223> OTHER INFORMATION: RNAi agent sequence

<400> SEQUENCE: 470
ggacaguauu cucagugcua aauug                                                25

<210> SEQ ID NO 471
<211> LENGTH: 25
<212> TYPE: RNA
<213> ORGANISM: artificial sequence
<220> FEATURE:
<223> OTHER INFORMATION: RNAi agent sequence

<400> SEQUENCE: 471
ggacaguauu cucagugcua aauug                                                25

<210> SEQ ID NO 472
<211> LENGTH: 26
<212> TYPE: RNA
<213> ORGANISM: artificial sequence
<220> FEATURE:
<223> OTHER INFORMATION: RNAi agent sequence

<400> SEQUENCE: 472
ggacaguauu cucagugcua aauuga                                               26

<210> SEQ ID NO 473
<211> LENGTH: 18
<212> TYPE: RNA
<213> ORGANISM: artificial sequence
<220> FEATURE:
<223> OTHER INFORMATION: RNAi agent sequence

<400> SEQUENCE: 473
acaguauucu cagugcuu                                                        18

<210> SEQ ID NO 474
<211> LENGTH: 9
<212> TYPE: RNA
<213> ORGANISM: artificial sequence
<220> FEATURE:
<223> OTHER INFORMATION: RNAi agent sequence

<400> SEQUENCE: 474 ucagugcuu                                                                   9

<210> SEQ ID NO 475
<211> LENGTH: 10
<212> TYPE: RNA
<213> ORGANISM: artificial sequence
<220> FEATURE:
<223> OTHER INFORMATION: RNAi agent sequence

<400> SEQUENCE: 475
cucagugcuu                                                                 10

<210> SEQ ID NO 476
<211> LENGTH: 16
<212> TYPE: RNA
<213> ORGANISM: artificial sequence
<220> FEATURE:
<223> OTHER INFORMATION: RNAi agent sequence
```

-continued

```
<400> SEQUENCE: 476
aguauucuca gugcuu                                                  16

<210> SEQ ID NO 477
<211> LENGTH: 12
<212> TYPE: RNA
<213> ORGANISM: artificial sequence
<220> FEATURE:
<223> OTHER INFORMATION: RNAi agent sequence

<400> SEQUENCE: 477
uucucagugc uu                                                      12

<210> SEQ ID NO 478
<211> LENGTH: 8
<212> TYPE: RNA
<213> ORGANISM: artificial sequence
<220> FEATURE:
<223> OTHER INFORMATION: RNAi agent sequence

<400> SEQUENCE: 478 cagugcuu                                                            8

<210> SEQ ID NO 479
<211> LENGTH: 11
<212> TYPE: RNA
<213> ORGANISM: artificial sequence
<220> FEATURE:
<223> OTHER INFORMATION: RNAi agent sequence

<400> SEQUENCE: 479
ucucagugcu u                                                       11

<210> SEQ ID NO 480
<211> LENGTH: 15
<212> TYPE: RNA
<213> ORGANISM: artificial sequence
<220> FEATURE:
<223> OTHER INFORMATION: RNAi agent sequence

<400> SEQUENCE: 480
guauucucag ugcuu                                                   15

<210> SEQ ID NO 481
<211> LENGTH: 14
<212> TYPE: RNA
<213> ORGANISM: artificial sequence
<220> FEATURE:
<223> OTHER INFORMATION: RNAi agent sequence

<400> SEQUENCE: 481
uauucucagu gcuu                                                    14

<210> SEQ ID NO 482
<211> LENGTH: 17
<212> TYPE: RNA
<213> ORGANISM: artificial sequence
<220> FEATURE:
<223> OTHER INFORMATION: RNAi agent sequence

<400> SEQUENCE: 482
caguauucuc agugcuu                                                 17

<210> SEQ ID NO 483
```

```
<211> LENGTH: 13
<212> TYPE: RNA
<213> ORGANISM: artificial sequence
<220> FEATURE:
<223> OTHER INFORMATION: RNAi agent sequence

<400> SEQUENCE: 483
auucucagug cuu                                                          13

<210> SEQ ID NO 484
<211> LENGTH: 19
<212> TYPE: RNA
<213> ORGANISM: artificial sequence
<220> FEATURE:
<223> OTHER INFORMATION: RNAi agent sequence

<400> SEQUENCE: 484
agcacugaga auacugucc                                                    19

<210> SEQ ID NO 485
<211> LENGTH: 19
<212> TYPE: RNA
<213> ORGANISM: artificial sequence
<220> FEATURE:
<223> OTHER INFORMATION: RNAi agent sequence

<400> SEQUENCE: 485
agcacugaga auacugucc                                                    19

<210> SEQ ID NO 486
<211> LENGTH: 19
<212> TYPE: RNA
<213> ORGANISM: artificial sequence
<220> FEATURE:
<223> OTHER INFORMATION: RNAi agent sequence

<400> SEQUENCE: 486
agcacugaga auacugucc                                                    19

<210> SEQ ID NO 487
<211> LENGTH: 19
<212> TYPE: RNA
<213> ORGANISM: artificial sequence
<220> FEATURE:
<223> OTHER INFORMATION: RNAi agent sequence

<400> SEQUENCE: 487
agcacugaga auacugucc                                                    19

<210> SEQ ID NO 488
<211> LENGTH: 19
<212> TYPE: RNA
<213> ORGANISM: artificial sequence
<220> FEATURE:
<223> OTHER INFORMATION: RNAi agent sequence

<400> SEQUENCE: 488
agcacugaga auacugucc                                                    19

<210> SEQ ID NO 489
<211> LENGTH: 19
<212> TYPE: RNA
<213> ORGANISM: artificial sequence
<220> FEATURE:
<223> OTHER INFORMATION: RNAi agent sequence

<400> SEQUENCE: 489
```

```
agcacugaga auacugucc                                                19

<210> SEQ ID NO 490
<211> LENGTH: 19
<212> TYPE: RNA
<213> ORGANISM: artificial sequence
<220> FEATURE:
<223> OTHER INFORMATION: RNAi agent sequence

<400> SEQUENCE: 490
agcacugaga auacugucc                                                19

<210> SEQ ID NO 491
<211> LENGTH: 19
<212> TYPE: RNA
<213> ORGANISM: artificial sequence
<220> FEATURE:
<223> OTHER INFORMATION: RNAi agent sequence

<400> SEQUENCE: 491
agcacugaga auacugucc                                                19

<210> SEQ ID NO 492
<211> LENGTH: 19
<212> TYPE: RNA
<213> ORGANISM: artificial sequence
<220> FEATURE:
<223> OTHER INFORMATION: RNAi agent sequence

<400> SEQUENCE: 492
agcacugaga auacugucc                                                19

<210> SEQ ID NO 493
<211> LENGTH: 19
<212> TYPE: RNA
<213> ORGANISM: artificial sequence
<220> FEATURE:
<223> OTHER INFORMATION: RNAi agent sequence

<400> SEQUENCE: 493
agcacugaga auacugucc                                                19

<210> SEQ ID NO 494
<211> LENGTH: 19
<212> TYPE: RNA
<213> ORGANISM: artificial sequence
<220> FEATURE:
<223> OTHER INFORMATION: RNAi agent sequence

<400> SEQUENCE: 494
agcacugaga auacugucc                                                19

<210> SEQ ID NO 495
<211> LENGTH: 19
<212> TYPE: RNA
<213> ORGANISM: artificial sequence
<220> FEATURE:
<223> OTHER INFORMATION: RNAi agent sequence

<400> SEQUENCE: 495
agcacugaga auacugucc                                                19

<210> SEQ ID NO 496
<211> LENGTH: 19
<212> TYPE: RNA
```

```
<213> ORGANISM: artificial sequence
<220> FEATURE:
<223> OTHER INFORMATION: RNAi agent sequence

<400> SEQUENCE: 496
agcacugaga auacugucc                                               19

<210> SEQ ID NO 497
<211> LENGTH: 19
<212> TYPE: RNA
<213> ORGANISM: artificial sequence
<220> FEATURE:
<223> OTHER INFORMATION: RNAi agent sequence

<400> SEQUENCE: 497
agcacugaga auacugucc                                               19

<210> SEQ ID NO 498
<211> LENGTH: 19
<212> TYPE: RNA
<213> ORGANISM: artificial sequence
<220> FEATURE:
<223> OTHER INFORMATION: RNAi agent sequence

<400> SEQUENCE: 498
agcacugaga auacugucc                                               19

<210> SEQ ID NO 499
<211> LENGTH: 19
<212> TYPE: RNA
<213> ORGANISM: artificial sequence
<220> FEATURE:
<223> OTHER INFORMATION: RNAi agent sequence

<400> SEQUENCE: 499
agcacugaga auacugucc                                               19

<210> SEQ ID NO 500
<211> LENGTH: 19
<212> TYPE: RNA
<213> ORGANISM: artificial sequence
<220> FEATURE:
<223> OTHER INFORMATION: RNAi agent sequence

<400> SEQUENCE: 500
agcacugaga auacugucc                                               19

<210> SEQ ID NO 501
<211> LENGTH: 19
<212> TYPE: RNA
<213> ORGANISM: artificial sequence
<220> FEATURE:
<223> OTHER INFORMATION: RNAi agent sequence

<400> SEQUENCE: 501
agcacugaga auacugucc                                               19

<210> SEQ ID NO 502
<211> LENGTH: 19
<212> TYPE: RNA
<213> ORGANISM: artificial sequence
<220> FEATURE:
<223> OTHER INFORMATION: RNAi agent sequence

<400> SEQUENCE: 502
agcacugaga auacugucc                                               19
```

<210> SEQ ID NO 503
<211> LENGTH: 19
<212> TYPE: RNA
<213> ORGANISM: artificial sequence
<220> FEATURE:
<223> OTHER INFORMATION: RNAi agent sequence

<400> SEQUENCE: 503
agcacugaga auacugucc                                                    19

<210> SEQ ID NO 504
<211> LENGTH: 21
<212> TYPE: RNA
<213> ORGANISM: artificial sequence
<220> FEATURE:
<223> OTHER INFORMATION: RNAi agent sequence

<400> SEQUENCE: 504
agcacugaga auacuguccu u                                                 21

<210> SEQ ID NO 505
<211> LENGTH: 21
<212> TYPE: RNA
<213> ORGANISM: artificial sequence
<220> FEATURE:
<223> OTHER INFORMATION: RNAi agent sequence

<400> SEQUENCE: 505
agcacugaga auacugaccc u                                                 21

<210> SEQ ID NO 506
<211> LENGTH: 21
<212> TYPE: RNA
<213> ORGANISM: artificial sequence
<220> FEATURE:
<223> OTHER INFORMATION: RNAi agent sequence

<400> SEQUENCE: 506
agcacugaga auacuguccc u                                                 21

<210> SEQ ID NO 507
<211> LENGTH: 23
<212> TYPE: RNA
<213> ORGANISM: artificial sequence
<220> FEATURE:
<223> OTHER INFORMATION: RNAi agent sequence

<400> SEQUENCE: 507
agcacugaga auacuguccc uuu                                               23

<210> SEQ ID NO 508
<211> LENGTH: 25
<212> TYPE: RNA
<213> ORGANISM: artificial sequence
<220> FEATURE:
<223> OTHER INFORMATION: RNAi agent sequence

<400> SEQUENCE: 508
agcacugaga auacuguccc uuuua                                             25

<210> SEQ ID NO 509
<211> LENGTH: 25
<212> TYPE: RNA
<213> ORGANISM: artificial sequence
<220> FEATURE:

<223> OTHER INFORMATION: RNAi agent sequence

<400> SEQUENCE: 509
agcacugaga auacuguccc uuuua                                     25

<210> SEQ ID NO 510
<211> LENGTH: 25
<212> TYPE: RNA
<213> ORGANISM: artificial sequence
<220> FEATURE:
<223> OTHER INFORMATION: RNAi agent sequence

<400> SEQUENCE: 510
agcacugaga auacuguccc uuuua                                     25

<210> SEQ ID NO 511
<211> LENGTH: 25
<212> TYPE: RNA
<213> ORGANISM: artificial sequence
<220> FEATURE:
<223> OTHER INFORMATION: RNAi agent sequence

<400> SEQUENCE: 511
agcacugaga auacuguccc uuuua                                     25

<210> SEQ ID NO 512
<211> LENGTH: 26
<212> TYPE: RNA
<213> ORGANISM: artificial sequence
<220> FEATURE:
<223> OTHER INFORMATION: RNAi agent sequence

<400> SEQUENCE: 512
agcacugaga auacuguccc uuuuaa                                    26

<210> SEQ ID NO 513
<211> LENGTH: 26
<212> TYPE: RNA
<213> ORGANISM: artificial sequence
<220> FEATURE:
<223> OTHER INFORMATION: RNAi agent sequence

<400> SEQUENCE: 513
agcacugaga auacuguccc uuuuaa                                    26

<210> SEQ ID NO 514
<211> LENGTH: 25
<212> TYPE: RNA
<213> ORGANISM: artificial sequence
<220> FEATURE:
<223> OTHER INFORMATION: RNAi agent sequence

<400> SEQUENCE: 514
agcacugaga auacuguccc uuuua                                     25

<210> SEQ ID NO 515
<211> LENGTH: 25
<212> TYPE: RNA
<213> ORGANISM: artificial sequence
<220> FEATURE:
<223> OTHER INFORMATION: RNAi agent sequence

<400> SEQUENCE: 515
agcacugaga auacuguccc uuuua                                     25

```
<210> SEQ ID NO 516
<211> LENGTH: 25
<212> TYPE: RNA
<213> ORGANISM: artificial sequence
<220> FEATURE:
<223> OTHER INFORMATION: RNAi agent sequence

<400> SEQUENCE: 516
agcacugaga auacuguccc uuuua                                              25

<210> SEQ ID NO 517
<211> LENGTH: 25
<212> TYPE: RNA
<213> ORGANISM: artificial sequence
<220> FEATURE:
<223> OTHER INFORMATION: RNAi agent sequence

<400> SEQUENCE: 517
agcacugaga auacuguccc uuuua                                              25

<210> SEQ ID NO 518
<211> LENGTH: 25
<212> TYPE: RNA
<213> ORGANISM: artificial sequence
<220> FEATURE:
<223> OTHER INFORMATION: RNAi agent sequence

<400> SEQUENCE: 518
agcacugaga auacuguccc uuuua                                              25

<210> SEQ ID NO 519
<211> LENGTH: 25
<212> TYPE: RNA
<213> ORGANISM: artificial sequence
<220> FEATURE:
<223> OTHER INFORMATION: RNAi agent sequence

<400> SEQUENCE: 519
agcacugaga auacuguccc uuuua                                              25

<210> SEQ ID NO 520
<211> LENGTH: 25
<212> TYPE: RNA
<213> ORGANISM: artificial sequence
<220> FEATURE:
<223> OTHER INFORMATION: RNAi agent sequence

<400> SEQUENCE: 520
agcacugaga auacuguccc uuuua                                              25

<210> SEQ ID NO 521
<211> LENGTH: 25
<212> TYPE: RNA
<213> ORGANISM: artificial sequence
<220> FEATURE:
<223> OTHER INFORMATION: RNAi agent sequence

<400> SEQUENCE: 521
agcacugaga auacuguccc uuuua                                              25

<210> SEQ ID NO 522
<211> LENGTH: 25
<212> TYPE: RNA
<213> ORGANISM: artificial sequence
<220> FEATURE:
<223> OTHER INFORMATION: RNAi agent sequence
```

```
<400> SEQUENCE: 522
agcacugaga auacuguccc uuuua                                           25

<210> SEQ ID NO 523
<211> LENGTH: 25
<212> TYPE: RNA
<213> ORGANISM: artificial sequence
<220> FEATURE:
<223> OTHER INFORMATION: RNAi agent sequence

<400> SEQUENCE: 523
agcacugaga auacuguccc uuuua                                           25

<210> SEQ ID NO 524
<211> LENGTH: 25
<212> TYPE: RNA
<213> ORGANISM: artificial sequence
<220> FEATURE:
<223> OTHER INFORMATION: RNAi agent sequence

<400> SEQUENCE: 524
agcacugaga auacuguccc uuuua                                           25

<210> SEQ ID NO 525
<211> LENGTH: 25
<212> TYPE: RNA
<213> ORGANISM: artificial sequence
<220> FEATURE:
<223> OTHER INFORMATION: RNAi agent sequence

<400> SEQUENCE: 525
caauuuagca cugagaauac ugucc                                           25

<210> SEQ ID NO 526
<211> LENGTH: 25
<212> TYPE: RNA
<213> ORGANISM: artificial sequence
<220> FEATURE:
<223> OTHER INFORMATION: RNAi agent sequence

<400> SEQUENCE: 526
caauuuagca cugagaauac ugucc                                           25

<210> SEQ ID NO 527
<211> LENGTH: 25
<212> TYPE: RNA
<213> ORGANISM: artificial sequence
<220> FEATURE:
<223> OTHER INFORMATION: RNAi agent sequence

<400> SEQUENCE: 527
caauuuagca cugagaauac ugucc                                           25

<210> SEQ ID NO 528
<211> LENGTH: 25
<212> TYPE: RNA
<213> ORGANISM: artificial sequence
<220> FEATURE:
<223> OTHER INFORMATION: RNAi agent sequence

<400> SEQUENCE: 528
caauuuagca cugagaauac ugucc                                           25

<210> SEQ ID NO 529
<211> LENGTH: 25
```

```
<212> TYPE: RNA
<213> ORGANISM: artificial sequence
<220> FEATURE:
<223> OTHER INFORMATION: RNAi agent sequence

<400> SEQUENCE: 529
caauuuagca cugagaauac ugucc                                          25

<210> SEQ ID NO 530
<211> LENGTH: 25
<212> TYPE: RNA
<213> ORGANISM: artificial sequence
<220> FEATURE:
<223> OTHER INFORMATION: RNAi agent sequence

<400> SEQUENCE: 530
caauuuagca cugagaauac ugucc                                          25

<210> SEQ ID NO 531
<211> LENGTH: 25
<212> TYPE: RNA
<213> ORGANISM: artificial sequence
<220> FEATURE:
<223> OTHER INFORMATION: RNAi agent sequence

<400> SEQUENCE: 531
caauuuagca cugagaauac ugucc                                          25

<210> SEQ ID NO 532
<211> LENGTH: 25
<212> TYPE: RNA
<213> ORGANISM: artificial sequence
<220> FEATURE:
<223> OTHER INFORMATION: RNAi agent sequence

<400> SEQUENCE: 532
caauuuagca cugagaauac ugucc                                          25

<210> SEQ ID NO 533
<211> LENGTH: 25
<212> TYPE: RNA
<213> ORGANISM: artificial sequence
<220> FEATURE:
<223> OTHER INFORMATION: RNAi agent sequence

<400> SEQUENCE: 533
caauuuagca cugagaauac ugucc                                          25

<210> SEQ ID NO 534
<211> LENGTH: 25
<212> TYPE: RNA
<213> ORGANISM: artificial sequence
<220> FEATURE:
<223> OTHER INFORMATION: RNAi agent sequence

<400> SEQUENCE: 534
caauuuagca cugagaauac ugucc                                          25

<210> SEQ ID NO 535
<211> LENGTH: 25
<212> TYPE: RNA
<213> ORGANISM: artificial sequence
<220> FEATURE:
<223> OTHER INFORMATION: RNAi agent sequence

<400> SEQUENCE: 535
```
caauuuagca cugagaauac ugucc                                              25

<210> SEQ ID NO 536
<211> LENGTH: 25
<212> TYPE: RNA
<213> ORGANISM: artificial sequence
<220> FEATURE:
<223> OTHER INFORMATION: RNAi agent sequence

<400> SEQUENCE: 536
caauuuagca cugagaauac ugucc                                              25

<210> SEQ ID NO 537
<211> LENGTH: 25
<212> TYPE: RNA
<213> ORGANISM: artificial sequence
<220> FEATURE:
<223> OTHER INFORMATION: RNAi agent sequence

<400> SEQUENCE: 537
caauuuagca cugagaauac ugucc                                              25

<210> SEQ ID NO 538
<211> LENGTH: 25
<212> TYPE: RNA
<213> ORGANISM: artificial sequence
<220> FEATURE:
<223> OTHER INFORMATION: RNAi agent sequence

<400> SEQUENCE: 538
caauuuagca cugagaauac ugucc                                              25

<210> SEQ ID NO 539
<211> LENGTH: 25
<212> TYPE: RNA
<213> ORGANISM: artificial sequence
<220> FEATURE:
<223> OTHER INFORMATION: RNAi agent sequence

<400> SEQUENCE: 539
caauuuagca cugagaauac ugucc                                              25

<210> SEQ ID NO 540
<211> LENGTH: 25
<212> TYPE: RNA
<213> ORGANISM: artificial sequence
<220> FEATURE:
<223> OTHER INFORMATION: RNAi agent sequence

<400> SEQUENCE: 540
caauuuagca cugagaauac ugucc                                              25

<210> SEQ ID NO 541
<211> LENGTH: 26
<212> TYPE: RNA
<213> ORGANISM: artificial sequence
<220> FEATURE:
<223> OTHER INFORMATION: RNAi agent sequence

<400> SEQUENCE: 541
caauuuagca cugagaauac ugucca                                             26

<210> SEQ ID NO 542
<211> LENGTH: 26
<212> TYPE: RNA
<213> ORGANISM: artificial sequence

```
<220> FEATURE:
<223> OTHER INFORMATION: RNAi agent sequence

<400> SEQUENCE: 542
caauuuagca cugagaauac ugucca                                              26

<210> SEQ ID NO 543
<211> LENGTH: 18
<212> TYPE: RNA
<213> ORGANISM: artificial sequence
<220> FEATURE:
<223> OTHER INFORMATION: Unmodified RNAi agent sequence

<400> SEQUENCE: 543
agcacugaga auacuguc                                                       18

<210> SEQ ID NO 544
<211> LENGTH: 18
<212> TYPE: RNA
<213> ORGANISM: artificial sequence
<220> FEATURE:
<223> OTHER INFORMATION: RNAi agent sequence

<400> SEQUENCE: 544
agcacugaga auacuguc                                                       18

<210> SEQ ID NO 545
<211> LENGTH: 18
<212> TYPE: RNA
<213> ORGANISM: artificial sequence
<220> FEATURE:
<223> OTHER INFORMATION: Unmodified RNAi agent sequence

<400> SEQUENCE: 545
gacaguauuc ucagugcu                                                       18

<210> SEQ ID NO 546
<211> LENGTH: 18
<212> TYPE: RNA
<213> ORGANISM: artificial sequence
<220> FEATURE:
<223> OTHER INFORMATION: RNAi agent sequence

<400> SEQUENCE: 546
gacaguauuc ucagugcu                                                       18
```

ORGANIC COMPOSITIONS TO TREAT APOC3-RELATED DISEASES

CROSS-REFERENCE TO RELATED APPLICATIONS

This application is a continuation of International Patent Application No. PCT/US2015/040517, with an international filing date of 15 Jul. 2015, designating the United States, which is based on U.S. Provisional Patent Application No. 62/025,164, filed 16 Jul. 2014. The contents of these specifications are incorporated herein by reference.

SEQUENCE LISTING

This application contains a Sequence Listing which has been submitted electronically in ASCII format and is hereby incorporated by reference in its entirety.

BACKGROUND

Lipoproteins are globular, micelle-like particles that consist of a non-polar core of acylglycerols and cholesteryl esters surrounded by an amphiphilic coating of protein, phospholipid and cholesterol. Lipoproteins have been classified into five broad categories on the basis of their functional and physical properties: chylomicrons, which transport dietary lipids from intestine to tissues; very low density lipoproteins (VLDL), intermediate density lipoproteins (IDL), and low density lipoproteins (LDL), all of which transport triacylglycerols and cholesterol from the liver to tissues; and high density lipoproteins (HDL), which transport endogenous cholesterol from tissues to the liver.

Lipoprotein particles undergo continuous metabolic processing and have variable properties and compositions. Lipoprotein densities increase without decreasing particle diameter because the density of their outer coatings is less than that of the inner core. The protein components of lipoproteins are known as apolipoproteins. At least nine apolipoproteins are distributed in significant amounts among the various human lipoproteins.

Apolipoprotein C-III is a constituent of HDL and of triglyceride-rich lipoproteins and has a role in hypertriglyceridemia, a risk factor for coronary artery disease. Apolipoprotein C-III slows this clearance of triglyceride-rich lipoproteins by inhibiting lipolysis, both through inhibition of lipoprotein lipase and by interfering with lipoprotein binding to the cell-surface glycosaminoglycan matrix (Shachter, Curr. Opin. Lipidol., 2001, 12, 297-304).

The gene encoding human apolipoprotein C-III (also called APOC3, APOC-III, APO CIII, and APO C-III) was cloned in 1984 by three research groups (Levy-Wilson et al., DNA, 1984, 3, 359-364; Prater et al., DNA, 1984, 3, 449-456; Sharpe et al., Nucleic Acids Res., 1984, 12, 3917-3932). The coding sequence is interrupted by three introns (Prater et al., DNA, 1984, 3, 449-456). The human apolipoprotein C-III gene is located approximately 2.6 kB to the 3' direction of the apolipoprotein A-1 gene and these two genes are convergently transcribed (Karathanasis, Proc. Natl. Acad. Sci. U.S.A., 1985, 82, 6374-6378). Also cloned was a variant of human apolipoprotein C-III with a Thr74 to Ala74 mutation from a patient with unusually high level of serum apolipoprotein C-III. As the Thr74 is O-glycosylated, the Ala74 mutant therefore resulted in increased levels of serum apolipoprotein C-III lacking the carbohydrate moiety (Maeda et al., J. Lipid Res., 1987, 28, 1405-1409).

Five polymorphisms have been identified in the promoter region of the gene: C(−641) to A, G(−630) to A, T(−625) to deletion, C(−482) to T and T(−455) to C. All of these polymorphisms are in linkage disequilibrium with the SstI polymorphism in the 3' untranslated region. The SstI site distinguishes the S1 and S2 alleles and the S2 allele has been associated with elevated plasma triglyceride levels (Dammerman et al., Proc. Natl. Acad. Sci. U.S.A., 1993, 90, 4562-4566). The apolipoprotein C-III promoter is downregulated by insulin and this polymorphic site abolishes the insulin regulation. Thus the potential overexpression of apolipoprotein C-III resulting from the loss of insulin regulation may be a contributing factor to the development of hypertriglyceridemia associated with the S2 allele (Li et al., J. Clin. Invest., 1995, 96, 2601-2605). The T(−455) to C polymorphism has been associated with an increased risk of coronary artery disease (Olivieri et al., J. Lipid Res., 2002, 43, 1450-1457).

In addition to insulin, other regulators of apolipoprotein C-III gene expression have been identified. A response element for the nuclear orphan receptor rev-erb alpha has been located at positions −23/−18 in the apolipoprotein C-III promoter region and rev-erb alpha decreases apolipoprotein C-III promoter activity (Raspe et al., J. Lipid Res., 2002, 43, 2172-2179). The apolipoprotein C-III promoter region −86 to −74 is recognized by two nuclear factors CIIIB1 and CIIIB2 (Ogami et al., J. Biol. Chem., 1991, 266, 9640-9646). Apolipoprotein C-III expression is also upregulated by retinoids acting via the retinoid X receptor, and alterations in retinoid X receptor abundance affects apolipoprotein C-III transcription (Vu-Dac et al., J. Clin. Invest., 1998, 102, 625-632). Specificity protein 1 (Sp1) and hepatocyte nuclear factor-4 (HNF-4) have been shown to work synergistically to transactivate the apolipoprotein C-III promoter via the HNF-4 binding site (Kardassis et al., Biochemistry, 2002, 41, 1217-1228). HNF-4 also works in conjunction with SMAD3-SMAD4 to transactivate the apolipoprotein C-III promoter (Kardassis et al., J. Biol. Chem., 2000, 275, 41405-41414).

Transgenic and knockout mice have further defined the role of apolipoprotein C-III in lipolysis. Overexpression of apolipoprotein C-III in transgenic mice leads to hypertriglyceridemia and impaired clearance of VLDL-triglycerides (de Silva et al., J. Biol. Chem., 1994, 269, 2324-2335; Ito et al., Science, 1990, 249, 790-793). Knockout mice with a total absence of the apolipoprotein C-III protein exhibited significantly reduced plasma cholesterol and triglyceride levels compared with wild-type mice and were protected from postprandial hypertriglyceridemia (Maeda et al., J. Biol. Chem., 1994, 269, 23610-23616).

Currently, there are no known therapeutic agents that affect the function of apolipoprotein C-III. The hypolipidemic effect of the fibrate class of drugs has been postulated to occur via a mechanism where peroxisome proliferator activated receptor (PPAR) mediates the displacement of HNF-4 from the apolipoprotein C-III promoter, resulting in transcriptional suppression of apolipoprotein C-III (Hertz et al., J. Biol. Chem., 1995, 270, 13470-13475). The statin class of hypolipidemic drugs also lower triglyceride levels via an unknown mechanism, which results in increases in lipoprotein lipase mRNA and a decrease in plasma levels of apolipoprotein C-III (Schoonjans et al., FEBS Lett., 1999, 452, 160-164). Consequently, there remains a long felt need for additional agents capable of effectively inhibiting apolipoprotein C-III function.

SUMMARY

The present disclosure pertains to RNAi agents to Apolipoprotein III (APOC3).

In various embodiments, the disclosure pertains to an APOC3 RNAi agent comprising a first and a second strand, wherein the sequence of the first and/or second strand is that of any sequence disclosed herein.

In various embodiments, the disclosure pertains to APOC3 RNAi agents which comprise any sequence or an 18-nucleotide portion of any APOC3 RNAi agent sequence disclosed herein (e.g., nucleotides 1-18 or nucleotides 2-19 of any sequence disclosed herein). In various embodiments, these APOC3 RNAi agents are blunt-ended.

In various embodiments, the disclosure pertains to APOC3 RNAi agents which comprise any sequence of at least 14 contiguous nucleotides ("nt") of any APOC3 RNAi agent sequence disclosed herein (e.g., nt 1-14, 2-15, 3-16, etc., of any sequence disclosed herein).

In various embodiments, the disclosure relates to compositions comprising an APOC3 RNAi agent having any of various formats. In one embodiment, the APOC3 RNAi agent has the 18-mer format. In some embodiments, APOC3 RNAi agents comprise a sense and an anti-sense strand, each strand being an 18-mer and the strands together forming a blunt-ended duplex, wherein the 3' end of at least one strand terminates in a phosphate or modified internucleoside linker and further comprises, in 5' to 3' order: a spacer; a second phosphate or modified internucleoside linker; and a 3' end cap. In some embodiments, the 3' end of both the sense and anti-sense strand terminate in a phosphate or modified internucleoside linker and further comprise, in 5' to 3' order: a spacer; a second phosphate or modified internucleoside linker; and a 3' end cap. In some embodiments, the disclosure pertains to a RNAi agent that comprises a first and a second strand, wherein the first and second strand are both 18-mers, and the first and second strand together form a blunt-ended duplex, and wherein the 3' end of the first strand terminates in a phosphate or modified internucleoside linker and further comprises, in 5' to 3' order: a spacer, a phosphate or modified internucleoside linker, and a 3' end cap; and wherein the 3' end of the second strand terminates in a phosphate or modified internucleoside linker and further comprises a 3' end cap. In some embodiments, the disclosure pertains to a RNAi agent that comprises a first and a second strand, wherein the first and second strands are both 18-mers, and the first and second strand together form a blunt-ended duplex, and wherein the 3' end of both the first and second strand terminate in a phosphate or modified internucleoside linker and both further comprise a 3' end cap. In some embodiments the APOC3 RNAi agent has a 19-mer format; in this format, both the first and second strand are 19-mers, wherein the 3' terminus of one or both strands further comprises a 3' terminal dinucleotide, spacer, and/or a 3' end cap. In some embodiments, one or both strands are longer than 19-mers (e.g., a 20-, 21-, 22-, 23-, 24-, 25-, 26-, 27-, 28-, 29-, or 30-mer), wherein one or both ends of the RNAi comprises an overhang, 3' terminal dinucleotide, spacer, and/or 3' end cap. In some embodiments, the APOC3 RNAi agent has an internal spacer format; e.g., one or more subunits [sugar+base] of the first or second strand is/are replaced by a spacer.

Optionally, the 3' end of one or both strands further comprises a spacer and a 3' end cap. In various embodiments, the APOC3 RNAi agent has a shortened sense strand format; e.g., the sense strand is shortened (e.g., to a 18-, 17-, 16-, 15- or 14-mer). The disclosure also pertains to any RNAi agent of any sequence, to any target which has a shortened sense strand format. In this format, the sense strand is shortened (to, for example, a 14-, 15-, 16-, or 17-mer), and the anti-sense strand is an 18-mer or longer. In some embodiments, the first strand is the antisense strand and the second strand is the sense strand. In other embodiments, the first strand is the sense strand and the second strand is the antisense strand. The two strands can have the same or different spacers, phosphates or modified internucleoside linkers, and/or 3' end caps. The strands can be ribonucleotides, or, optionally, one or more nucleotide can be modified or substituted. Optionally, at least one nucleotide comprises a modified internucleoside linker. Optionally, the RNAi agent can be modified on one or both 5' end. Optionally, the sense strand can comprise a 5' end cap which reduces the amount of the RNA interference mediated by this strand. Optionally, the RNAi agent is attached to a ligand. The disclosure also relates to processes for making such compositions, and methods and uses of such compositions, e.g., to mediate RNA interference.

The present disclosure encompasses RNAi agents to APOC3, for inhibition of APOC3, and which are useful in treatment of an APOC3-related disease, such as obesity and metabolic-related disorders such as hyperlipidemia or hypertriglyceridemia (e.g., Type V Hypertriglyceridemia).

The present disclosure also encompasses a method for inhibiting and/or decreasing the expression and/or activity of APOC3 in a human subject. In various embodiments, the subject has an APOC3-related disease (a pathological state mediated at least in part by APOC3 over-expression or hyper-activity), and the method comprises the step of administering to the subject a therapeutically effective amount of a RNAi agent to APOC3. In various embodiments, the APOC3-related disease is selected from: hypertriglyceridemia (e.g., Type V Hypertriglyceridemia), abnormal lipid metabolism, abnormal cholesterol metabolism, atherosclerosis, hyperlipidemia, diabetes, including Type 2 diabetes, obesity, cardiovascular disease, and coronary artery disease, among other disorders relating to abnormal metabolism or otherwise.

In various embodiments, the present disclosure pertains to a RNAi agent to APOC3, comprising two strands, wherein the sequence of the first and/or second strand is, comprises, comprises 18 contiguous nt of, or comprises a sequence of 18 contiguous nt with 0-3 mismatches from, comprises 14 contiguous nt of, or comprises a sequence of 14 contiguous nt with 0-3 mismatches from: the sequence of any RNAi agent disclosed herein. In some embodiments, the disclosure pertains to an APOC3 RNAi agent comprising a first and second strand, wherein the sequence of the first and/or second strand is, comprises, or comprises 14 contiguous nt of any sequence of any APOC3 RNAi agent disclosed herein, except that one or both strands is nicked and/or one or more nt of the sequence disclosed herein has been replaced by a spacer (e.g., the first comprises the sequence of nt 1-3 and 5-14, nt 1-5 and 7-18, or of 1-4 and 6-18 of a sequence disclosed herein).

In some embodiments, the RNAi agent to APOC3 comprises a first strand and a second strand, wherein the sequence of the first strand comprises 14 contiguous nt of, or comprises 14 contiguous nt with 1-3 mismatches from any sequence of any APOC3 RNAi agent listed herein.

The present disclosure provides specific RNAi agents for inhibition of APOC3, and methods that are useful in reducing APOC3 levels in a subject, e.g., a mammal, such as a human. The present disclosure specifically provides double-stranded RNAi agents comprising at least 14, 15, 16, 17, 18, or 19 or more contiguous nucleotides of APOC3. In particular, the present disclosure provides agents comprising sequences of 14 or more contiguous nucleotides differing by 0, 1, 2 or 3 from those of any of the RNAi agents provided, e.g., in any table herein, or otherwise disclosed herein. The RNAi agents can in some embodiments comprise less than 30 nucleotides per strand, e.g., such as 17-23 nucleotides, 15-19, 18-22, and/or 19-21 nucleotides, and/or such as those provided herein, and modified and unmodified variants thereof (e.g., wherein the sense and/or anti-sense or first and/or second strand are modified or unmodified). The present disclosure also provides RNAi agents to APOC3 comprising a sense strand and an anti-sense strand, wherein the sense and/or the anti-sense strand comprise sequences of 19 or more contiguous nucleotides differing by 0, 1, 2 or 3 from those of the RNAi agents provided, and modified or unmodified variants thereof. The present disclosure also provides RNAi agents to APOC3 having a shortened sense strand format. In this format, the sense strand is shortened (to, for example, a 14-, 15-, 16-, or 17-mer), and the anti-sense strand is an 18-mer or longer.

The disclosure also pertains to any RNAi agent of any sequence, to any target which has a shortened sense strand format. In this format, the sense strand is shortened (to, for example, a 14-, 15-, 16-, or 17-mer), and the anti-sense strand is an 18-mer or longer.

The sense and anti-sense strand can be contiguous, or physically connected, e.g., by covalently bonds, a loop or linker. In some embodiments, the sense and/or anti-sense strand is discontinuous. Either strand can be nicked. In some embodiments, one or more nucleobase ([sugar+base]) is replaced by a spacer. In some embodiments, the sense strand can be shortened (e.g., to a 14-, 15-, 16-, 17- or 18-mer), for example, in the shortened sense strand format.

The double-stranded RNAi agents can have 0, 1 or 2 blunt ends, and/or overhangs of 1, 2, 3 or 4 nucleotides (i.e., 1 to 4 nt) from one or both 3' and/or 5' ends. The double-stranded RNAi agents can also optionally comprise one or two 3' caps and/or one or more modified nucleotides. Modified variants of sequences as provided herein include those that are otherwise identical but contain substitutions of a naturally-occurring nucleotide for a corresponding modified nucleotide.

Furthermore, the RNAi agent can either contain only nucleotides, e.g., naturally-occurring ribonucleotide subunits, or optionally one or more modifications to the sugar, phosphate or base of one or more of the substitute nucleotide subunits, whether they comprise ribonucleotide subunits or deoxyribonucleotide subunits. In some embodiments, modified variants of the disclosed RNAi agents have a thymidine (as RNA, or, preferably, DNA) replacing a uridine, or have an inosine base. In some aspects, the modified variants of the disclosed RNAi agents can have a nick in the passenger strand, mismatches between the guide and passenger strand, DNA replacing the RNA of a portion of both the guide and passenger strand (e.g., the seed region of nt 2-7 counting from the 5' end of the anti-sense strand), and/or a shortened passenger (sense) strand (e.g., 14, 15, 16, 17 or 18 nt). Once a functional guide strand is identified, modifications and variants of the RNAi agent can be readily made. Any two or more modifications which are not mutually exclusive can be combined (e.g., the combination of base modifications with shortened passenger strand; or nicked passenger strand and base modifications; or DNA replacing part or all of the seed region and base modifications in the remaining RNA; etc.).

In some embodiments, modified variants of the disclosed RNAi agents include RNAi agents with the same sequence (e.g., the same sequence of bases) as any RNAi agent disclosed in any of the tables herein or otherwise disclosed herein. It is also noted that various authors have shown that once a successful RNAi agent is designed, generally adding a few nt to one or both strands does not impair RNA activity. Lengthening one or both strands, e.g, to 24 or 25 nt, does not impair RNA interference activity. In addition, we show here that the sense strand can be shortened to a 14-, 15-, 16- or 17-mer (while the anti-sense strand is at least an 18-mer), and RNA interference activity is maintained. Thus, this disclosure encompasses RNAi agents comprising a first strand and a second strand, wherein the sequence of the first and/or second strand comprises the sequence of any APOC3 RNAi agent disclosed herein, further comprising 1-5 nt.

In some embodiments, modified variants of the disclosed RNAi agents include RNAi agents with the same sequence (e.g., the same sequence of bases) as any RNAi agent disclosed in any of the tables herein or otherwise disclosed herein, but with one or more modifications to one or more of the sugar or phosphate of one or more of the nucleotide subunits. In some embodiments, the modifications improve efficacy, stability (e.g., against nucleases in, for example, blood serum or intestinal fluid), and/or reduce immunogenicity of the RNAi agent. Some embodiments of the present disclosure relates to a double-stranded oligonucleotide comprising at least one non-natural nucleobase. In certain aspects, the non-natural nucleobase is difluorotolyl, nitroindolyl, nitropyrrolyl, or nitroimidazolyl. In a particular aspect, the non-natural nucleobase is difluorotolyl. In certain aspects, only one of the two oligonucleotide strands contains a non-natural nucleobase. In certain aspects, both of the oligonucleotide strands contain a non-natural nucleobase.

In various embodiments, the disclosure relates to compositions comprising an APOC3 RNAi agent having an 18-mer format. In some embodiments, APOC3 RNAi agents comprise a sense and an anti-sense strand, each strand being an 18-mer and the strands together forming a blunt-ended duplex, wherein the 3' end of at least one strand terminates in a phosphate or modified internucleoside linker and further comprises, in 5' to 3' order: a spacer; a second phosphate or modified internucleoside linker; and a 3' end cap. In some embodiments, the 3' end of both the sense and anti-sense strand terminate in a phosphate or modified internucleoside linker and further comprise, in 5' to 3' order: a spacer; a second phosphate or modified internucleoside linker; and a 3' end cap. In some embodiments, the disclosure pertains to an APOC3 RNAi agent that comprises a first and a second strand, wherein the first and second strand are both 18-mers, and the first and second strand together form a blunt-ended duplex, and wherein the 3' end of the first strand terminates in a phosphate or modified internucleoside linker and further comprises, in 5' to 3' order: a spacer, a phosphate or modified internucleoside linker, and a 3' end cap; and wherein the 3' end of the second strand terminates in a phosphate or modified internucleoside linker and further comprises a 3' end cap. In some embodiments, the disclosure pertains to an APOC3 RNAi agent that comprises a first and a second strand, wherein the first and second strands are both 18-mers, and the first and second strand together form a blunt-ended duplex, and wherein the 3' end of both the first and second strand terminate in a phosphate or modified internucleoside linker and both further comprise a 3' end cap. In some embodiments, the first strand is the antisense strand and the second strand is the sense strand. In other embodiments, the first strand is the sense strand and the second strand is the antisense strand. The two strands can have the same or different spacers, phosphates or modified internucleoside linkers, and/or 3' end caps. The strands can be ribonucleotides, or, optionally, one or more nucleotide can be modified or substituted. Optionally, at least one nucleotide comprises a modified internucleoside linker.

Optionally, the RNAi agent can be modified on one or both 5' end. Optionally, the sense strand can comprise a 5' end cap which reduces the amount of the RNA interference mediated by this strand. Optionally, the RNAi agent is attached to a ligand. The disclosure also relates to processes for making such compositions, and methods and uses of such compositions, e.g., to mediate RNA interference. In some embodiments, the disclosure pertains to any RNAi agent of any sequence which has the 18-mer format or any format disclosed herein (e.g., internal spacer format or shortened sense strand format). In some embodiments, the disclosure pertains to an APOC3 RNAi agent comprising a sense strand and an anti-sense strand, wherein each strand is an 18-mer, wherein one or more nucleoside subunit ([sugar+base]) of the 18-mer anti-sense strand is replaced by a spacer, and wherein the 3' terminus of one or both strands further comprises: a 3' end cap, or a spacer and a 3' end cap. In various embodiments, the nucleobase subunit ([sugar+base]) replaced by a spacer is at position 1, 3, 5, 6, 7, 15, 16, 17, or 18 (counting 5' to 3'). In various embodiments, the nucleobase subunit ([sugar+base]) replaced by a spacer is at position 5, 6, or 17 (counting 5' to 3'). In various embodiments, the spacer can be sugar, alkyl, cycloakyl, ribitol or other type of abasic nucleotide, 2'-deoxy-ribitol, diribitol, 2'-methoxyethoxy-ribitol (ribitol with 2'-MOE), C3, C4, C5, C6, or 4-methoxybutane-1,3-diol (5300). More than one different type of spacer can be incorporated into the same composition.

In some embodiments, the disclosure pertains to an RNAi agent to APOC3 having a shortened sense strand format. In this format, the sense strand is shortened to a 14-, 15-, 16-, or 17-mer, and the anti-sense strand is a 18-mer or longer. In some embodiments, the sense strand can comprise, in 5' to 3' order, a 14-mer which terminates at the 3' end with a phosphate or modified internucleoside linker, a spacer, a second phosphate or modified internucleoside linker, and a 3' end cap. In some embodiments, the sense strand can comprise, in 5' to 3' order, a 15-mer which terminates at the 3' end with a phosphate or modified internucleoside linker, a spacer, a second phosphate or modified internucleoside linker, and a 3' end cap. In some embodiments, the sense strand can comprise, in 5' to 3' order, a 16-mer which terminates at the 3' end with a phosphate or modified internucleoside linker, a spacer, a second phosphate or modified internucleoside linker, and a 3' end cap. In some embodiments, the sense strand can comprise, in 5' to 3' order, a 17-mer which terminates at the 3' end with a phosphate or modified internucleoside linker, a spacer, a second phosphate or modified internucleoside linker, and a 3' end cap. In various embodiments, the 14-, 15-, 16-, or 17-mer can comprise RNA, wherein one or more RNA subunits (nucleotides) has been modified or substituted. In some embodiments, the last 2 nucleotides on the 3' end of the anti-sense and sense strand are 2'-MOE (a 2'-MOE clamp). In various embodiments, with or without the 2'-MOE clamp, one or more nucleotides can be modified with a 2'-MOE, 2'-OMe, 2'-F, or substituted with DNA, a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), unlocked nucleic acid (UNA). The spacer can be a sugar, alkyl, cycloakyl, ribitol or other type of abasic nucleotide, 2'-deoxy-ribitol, diribitol, 2'-methoxyethoxy-ribitol (ribitol with 2'-MOE), C3, C4, C5, C6, or 4-methoxybutane-1,3-diol (5300). The 3' end cap can be selected from any of various 3' end caps described herein or known in the art. In various embodiments, the 3' end cap can be a PAZ ligand (e.g., X058 or X2). The shortened sense strand format is suitable for use with APOC3 RNAi agents, as disclosed herein, or with any RNAi agent of any sequence directed to any gene target.

The RNAi agent(s) can optionally be attached to a ligand selected to improve one or more characteristic, such as, e.g., stability, distribution and/or cellular uptake of the agent, e.g., cholesterol or a derivative thereof. The RNAi agent(s) can be isolated or be part of a pharmaceutical composition used for the methods described herein. Particularly, the pharmaceutical composition can be formulated for delivery to specific tissues (e.g., those afflicted with an APOC3-related disease) or formulated for parenteral administration. The pharmaceutical composition can optionally comprise two or more RNAi agents, each one directed to the same, overlapping or a different segment of the APOC3 mRNA. Optionally, the pharmaceutical composition can further comprise or be used in conjunction with any known treatment for any APOC3-related disease.

Second Agent or Treatment.

The method also optionally further comprises the step of administering a second agent or treatment. In some aspects, this second agent is another RNAi agent to APOC3. In various embodiments, the second agent or treatment is iron administration, chelation therapy, phlebotomy, erythropoiesis stimulating agent (ESA) (e.g., Epoetin alfa or darbepoetin alfa), anti-APOC3 antibody, hemodialysis, or hyperbaric oxygen. In other aspects, the second agent or treatment is directed to another target, which is also hyper-active, mutated and/or over-expressed in the pathological state.

Methods.

The present disclosure further provides methods for reducing the level of APOC3 mRNA in a cell, particularly in the case of a disease characterized by over-expression or hyper-activity of APOC3. Cells comprising an alteration such as a mutation, over-expression and/or hyperactivity of APOC3 are termed "APOC3-defective" cells. Such methods comprise the step of administering one or more of the RNAi agents of the present disclosure to an APOC3-defective cell, as further described below. The present methods utilize the cellular mechanisms involved in RNA interference to selectively degrade the target RNA in a cell and are comprised of the step of contacting a cell with one of the RNAi agents of the present disclosure.

The present disclosure also encompasses a method of treating a human subject having a pathological state mediated at least in part by APOC3 over-expression or hyper-activity, the method comprising the step of administering to the subject a therapeutically effective amount of a RNAi agent APOC3. Additional methods involve preventing, treating, modulating and/or ameliorating a pathological state wherein disease progression requires APOC3, although APOC3 is not amplified or over-expressed. Such methods comprise the step of administering one of the RNAi agents of the present disclosure to a subject, as further described below. Such methods can be performed directly on a cell or can be performed on a mammalian subject by administering to a subject one of the RNAi agents/pharmaceutical compositions of the present disclosure. Reduction of target APOC3 mRNA in a cell results in a reduction in the amount of encoded APOC3 protein produced. In an organism, this can result in restoration of balance in a pathway involving APOC3, and/or prevention of APOC3 accumulation, and/or a reduction in APOC3 activity and/or expression, and/or prevention of APOC3-mediated activation of other genes, and/or amelioration, treatment and/or prevention of an APOC3-related disease. In some embodiments, a reduction in APOC3 expression, level or activity can limit disease growth.

The methods and compositions of the present disclosure, e.g., the methods and APOC3 RNAi agent compositions, can be used in any appropriate dosage and/or formulation described herein or known in the art, as well as with any suitable route of administration described herein or known in the art.

The details of one or more aspects of the present disclosure are set forth in the accompanying drawings and the description below. Elements of the various aspects (e.g., sequences, modifications, formats [18-mer format, 19-mer format, internal spacer format, shortened sense strand format, etc.], substitutions, spacers, modified internucleoside linkers, endcaps, combinations of RNAi agents, delivery vehicles, combination therapy involving an APOC3 RNAi agent and another agent, etc.) disclosed herein or known in the art which are not mutually exclusive can be combined with each other, provided that the agent or agents are still capable of mediating RNA interference. For example, any RNAi agent sequence disclosed herein can be combined with any set of modifications or endcaps disclosed herein. Similarly, any combination of modifications, 5' end caps, and/or 3' end caps can be used with any RNAi agent sequence disclosed herein. Any RNAi agent disclosed herein (with any combination of modifications or endcaps or without either modifications or endcaps) can be combined with any other RNAi agent or other treatment composition or method disclosed herein.

Other features, objects, and advantages of the present disclosure will be apparent from this description, the drawings, and from the claims.

BRIEF DESCRIPTION OF THE FIGURES

FIG. 1. Various anti-ApoC3 RNAi agents.
FIG. 2. Various anti-ApoC3 RNAi agents.
FIG. 3B. Various anti-ApoC3 RNAi agents.
FIG. 3B. Various anti-ApoC3 RNAi agents.
FIG. 4A. Various anti-ApoC3 RNAi agents.
FIG. 4B. Various anti-ApoC3 RNAi agents.
FIG. 5A. Various anti-ApoC3 RNAi agents.
FIG. 5B. Various anti-ApoC3 RNAi agents.
FIG. 6. Various anti-ApoC3 RNAi agents.

DETAILED DESCRIPTION

Figure 7:
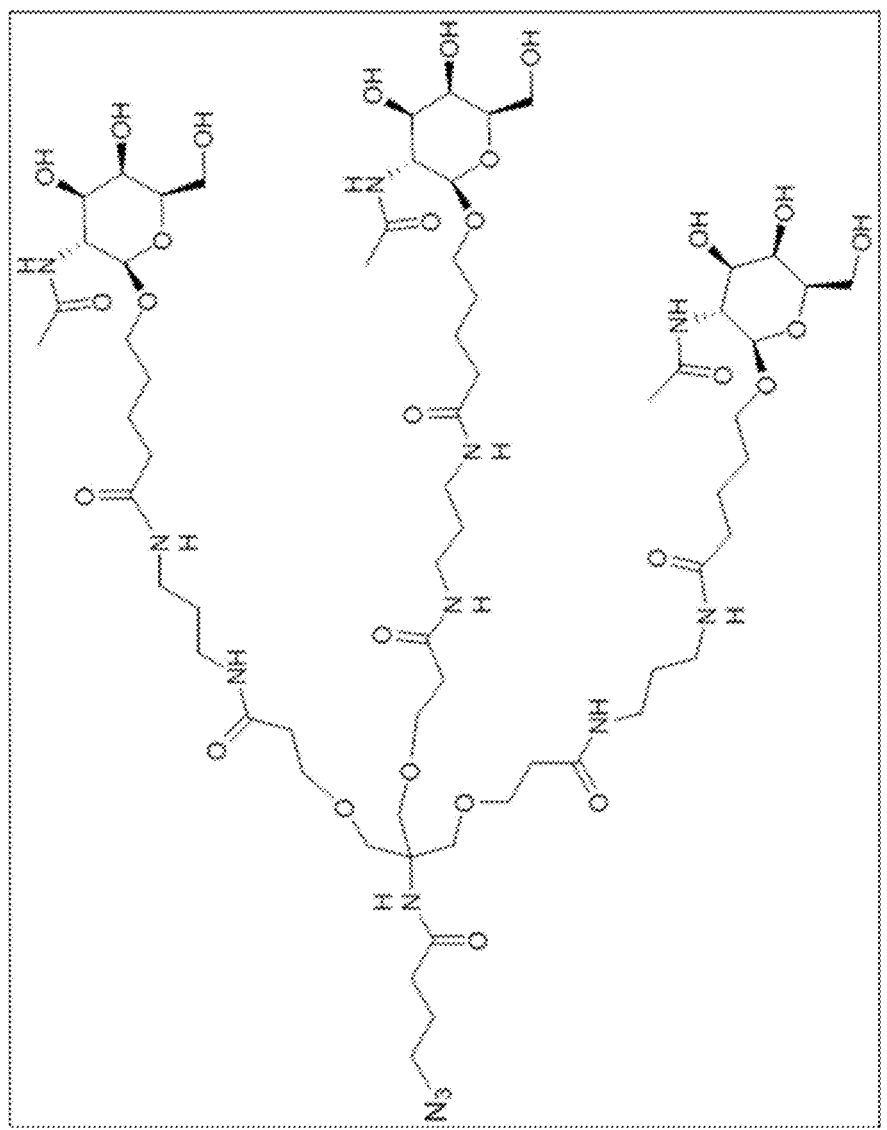
FIG. 7. Structure representing X1053.
Figure 8:
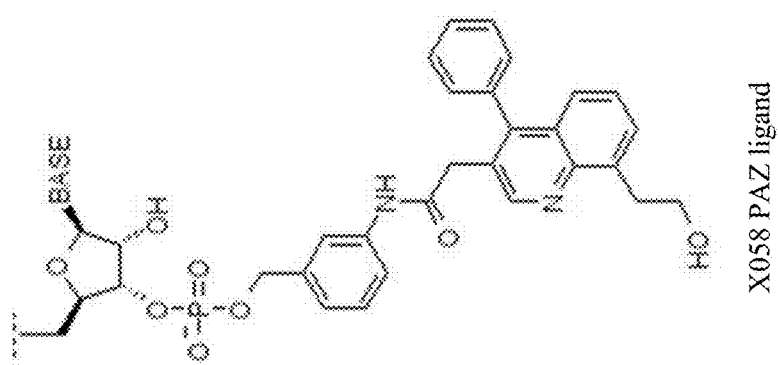
FIG. 8. Structure representing X058 PAZ ligand.
Figure 9:
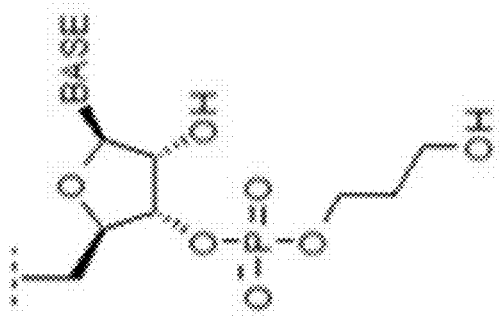
FIG. 9. Structure representing X003.
For each of FIGS. 1-6, p=phosphate, lower case letter=2'-O-Methyl nucleotide, Nf=2'-fluoro nucleotide, dN=deoxynucleotide, Nm=2'-MOE nucleotide, s=phosphorothioate, X=abasic ribose, and X1053, X003, X1082, X058, and PAZ=end modifications.

The present disclosure encompasses RNAi agents to APOC3, for targeting and inhibition of APOC3, which are useful in treatment of APOC3-related diseases (e.g., diseases associated with mutations in and/or altered expression, level and/or activity of APOC3, diseases requiring APOC3, diseases affected by a factor whose expression, over-expression, or hyper-activity is directly or indirectly affected by APOC3, and/or diseases treatable by modulating the expression, level and/or activity of APOC3). Such APOC3-related diseases include those listed herein or known in the art. The present disclosure also provides methods of treating a human subject having a pathological state mediated at least in part by APOC3 over-expression or hyper-activity, or requiring APOC3, the method comprising the step of administering to the subject a therapeutically effective amount of a RNAi agent to APOC3.

Various Aspects of the Disclosure Include the Following:

An RNAi agent comprising an antisense strand of an RNAi agent described herein.

In some embodiments, an aspect of the present disclosure relates to a composition comprising an RNAi agent comprising an antisense strand, wherein the antisense strand is, comprises, comprises at least 14 contiguous nucleotides (nt), or comprises at least 14 contiguous nucleotides differing by 0, 1, 2, or 3 nucleotides from the antisense strand of an RNAi agent to APOC3 selected from any sequence provided herein (e.g., in any of the tables herein). In some embodiments, the disclosure pertains to an APOC3 RNAi agent comprising a first and second strand, wherein the sequence of the first and/or second strand is, comprises, or comprises 14 contiguous nt of any sequence of any APOC3 RNAi agent disclosed herein, wherein one or both strands is nicked and/or one or more nt of the sequence disclosed herein has been replaced by a spacer (e.g., the first comprises the sequence of nt 1-5 and 7-18, or of 1-4 and 6-18 of a sequence disclosed herein). In another aspect, the present disclosure relates to a composition comprising an RNAi agent comprising a first strand and a second strand, wherein the first strand comprises at least 14 contiguous nucleotides differing by 0, 1, 2, or 3 nucleotides from the first strand of an RNAi agent to APOC3 from any sequence provided herein. In another aspect, the present disclosure relates to a composition comprising an RNAi agent comprising a sense strand and an antisense strand, wherein the sense strand comprises at least 14 contiguous nucleotides differing by 0, 1, 2, or 3 nucleotides from the sense strand and the antisense strand comprises at least 14 contiguous nucleotides differing by 0, 1, 2, or 3 nucleotides from the antisense strand of an RNAi agent to APOC3 listed immediately above. In some embodiments, one or both strands of the RNAi agent is an 18-mer. In one embodiment, both strands are 18-mers and together they form a blunt-ended duplex. In another aspect, the present disclosure relates to a composition comprising an RNAi agent comprising a first strand and a second strand, wherein the sequence of the first strand comprises the sequence of the first strand of any sequence provided herein. In another aspect, the present disclosure relates to a composition comprising an RNAi agent comprising a first strand and a second strand, wherein the sequence of the first strand is the sequence of the first strand of any sequence provided herein. In various aspects, the first and second strands are the anti-sense and sense strand, respectively, of any RNAi agent disclosed herein. In various aspects, the first and second strands are the sense and anti-sense strand, respectively, of any RNAi agent disclosed herein.

In various embodiments, the disclosure relates to compositions comprising an APOC3 RNAi agent having a novel format (the "18-mer format"). These APOC3 RNAi agents comprise a sense and an anti-sense strand, each strand being an 18-mer and the strands together forming a blunt-ended duplex, wherein the 3' end of at least one strand terminates in a phosphate or modified internucleoside linker and further comprises, in 5' to 3' order: a spacer; a second phosphate or modified internucleoside linker; and a 3' end cap. In some embodiments, the 3' end of both the sense and anti-sense strand terminate in a phosphate or modified internucleoside linker and further comprise, in 5' to 3' order: a spacer; a second phosphate or modified internucleoside linker; and a 3' end cap.

In some embodiments, the disclosure pertains to an APOC3 RNAi agent that comprises a first and a second strand, wherein the first and second strand are both 18-mers, and the first and second strand together form a blunt-ended duplex, and wherein the 3' end of the first strand terminates in a phosphate or modified internucleoside linker and further comprises, in 5' to 3' order: a spacer, a phosphate or modified internucleoside linker, and a 3' end cap; and wherein the 3' end of the second strand terminates in a phosphate or modified internucleoside linker and further comprises a 3' end cap. In some embodiments, the disclosure pertains to an APOC3 RNAi agent that comprises a first and a second strand, wherein the first and second strands are both 18-mers, and the first and second strand together form a blunt-ended duplex, and wherein the 3' end of both the first and second strand terminate in a phosphate or modified internucleoside linker and both further comprise a 3' end cap.

In some embodiments the APOC3 RNAi agent has a 19-mer format; in this format, both the first and second strand are 19-mers, wherein the 3' terminus of one or both strands further comprises a 3' terminal dinucleotide, spacer, and/or a 3' end cap. In some embodiments, one or both strands are longer than 19-mers (e.g., a 20-, 21-, 22-, 23-, 24-, 25-, 26-, 27-, 28-, 29-, or 30-mer), wherein one or both ends of the RNAi comprises an overhang, 3' terminal dinucleotide, spacer, and/or 3' end cap. In some embodiments, the APOC3 RNAi agent has an internal spacer format; e.g., one or more subunits [sugar+base] of the first or second strand is/are replaced by a spacer. Optionally, the 3' end of one or both strands further comprises another spacer and a 3' end cap. In various embodiments, the APOC3 RNAi agent has a shortened sense strand format; e.g., the sense strand is shortened (e.g., to a 18-, 17-, 16-, 15- or 14-mer). In some embodiments, the first strand is the antisense strand and the second strand is the sense strand. In other embodiments, the first strand is the sense strand and the second strand is the antisense strand. The two strands can have the same or different spacers, phosphates or modified internucleoside linkers, and/or 3' end caps. The strands can be ribonucleotides, or, optionally, one or more nucleotide can be modified or substituted. Optionally, at least one nucleotide comprises a modified internucleoside linker. Optionally, the RNAi agent can be modified on one or both 5' end. Optionally, the sense strand can comprise a 5' end cap which reduces the amount of the RNA interference mediated by this strand. Optionally, the RNAi agent is attached to a ligand. The disclosure also relates to processes for making such compositions, and methods and uses of such compositions, e.g., to mediate RNA interference.

In various embodiments, the disclosure relates to compositions comprising an APOC3 RNAi agent conjugated to GalNAc. N-Acetylgalactosamine (also known as GalNAc) (IUPAC name 2-(Acetylamino)-2-deoxy-D-galactose), is an amino sugar derivative of galactose. GalNAc is necessary for intercellular communication, and is concentrated in sensory nerve structures. It is typically the first monosaccharide that connects serine or threonine in particular forms of protein O-glycosylation. In humans it is the terminal carbohydrate forming the antigen of blood group A.

Particular duplexes include the unmodified (e.g., "generic") and example modified variants listed in the tables herein and otherwise disclosed herein; additional sequences and data for these RNAi agents are presented in the subsequent Tables. In addition to the described example modifications, other modified variants can be made using the nucleotide sequences provided.

TABLE 1

ANTI-APOC3 siRNA SEQUENCES

| Position | Location | Antisense generic sequence | SEQ ID NO: | Sense generic sequence | SEQ ID NO: | IC50 in Huh7 |
|---|---|---|---|---|---|---|
| 457 | 3'UTR | A GCACTG AGAATACT GTC | 14 | GACAGTATTCTCAGT GCT | 162 | 2.8 nM |
| 297 | CDS | A ACTCAG AGAACTTG TCC | 3 | GGACAAGTTCTCTGA GTT | 163 | 4.3 nM |
| 290 | CDS | A GAACTT GTCCTTAA CGG | 12 | CCGTTAAGGACAAGT TCT | 153 | 5.6 nM |
| 150 | CDS | T AACCCT GCATGAAG CTG | 95 | CAGCTTCATGCAGGG TTA | 150 | 4.6 nM |
| 524 | 3'UTR | T TCTTGT CCAGCTTT ATT | 97 | AATAAAGCTGGACAA GAA | 125 | 4.0 nM |
| 523 | 3'UTR | T CTTGTC CAGCTTTAT TG | 96 | CAATAAAGCTGGACA AGA | 147 | 3.8 nM |
| 298 | CDS | G AACTCA GAGAACTT GTC | 69 | GACAAGTTCTCTGAG TTC | 161 | 4.1 nM |
| 72 | CDS | A CAACAA GGAGTAC CCGG | 7 | CCGGGTACTCCTTGT TGT | 152 | 4.7 nM | boxed sequence = seed region
underline nucleotide = cyno/human mismatch
bold = GU wobble human --> mouse. In vivo data confirms active for mouse

TABLE 2

Knockdown of APOC3 mRNA in HUH7 cells with 30 nM of the described RNAi agents. siRNA SEQUENCE 1 HEAVY-STEM CHEMISTRIES RELATED, INCLUDING RIBITOL WALK AND 11-25MERS. The following are used in Table 2 to represent different chemistries and components of the sequences: N = RNA, n (lower case) = 2'-O-Methyl nucleotide, Nm = 2'-MOE nucleotide, X1 = abasic site with ribitol spacer, X2 = abasic site with 1,6-hexane-diol spacer.

| mRNA Position | % residual APOC3 mRNA ± SD | SEQ ID NO | Sense Sequence String | SEQ ID NO | Antisense Sequence String |
|---|---|---|---|---|---|
| 19 | 38.4 ± 5.5 | 262 (80 with shown modifications) | GcucAGuucAuc ccuAGmAmUX1 X2 | 350 (184 with shown modifications) | UCuAGGGAuGAACU GAGmCmAX1X2 |
| 51 | 69.6 ± 16.3 | 263 (68 with shown modifications) | GAAcAGAGGuG ccAuGCmAmUX 1X2 | 351 (193 with shown modifications) | UGCAuGGCACCuCUG uUmCmCX1X2 |
| 72 | 20.6 ± 3.5 | 264 (43 with shown modifications) | ccGGGuAcuccu uGuuGmUmUX 1X2 | 352 (127 with shown modifications) | ACAACAAGGAGuACC CGmGmGX1X2 |
| 73 | 34.5 ± 4.8 | 265 (52 with shown modifications) | cGGGuAcuccuu GuuGUmUmUX 1X2 | 353 (116 with shown modifications) | AACAACAAGGAGuAC CCmGmGX1X2 |
| 144 | 81.3 ± 9.2 | 266 (50 with shown modifications) | ccuucucAGcuuc AuGCmAmUX1 X2 | 354 (192 with shown modifications) | UGCAuGAAGCuGAG AAGmGmGX1X2 |
| 150 | 12.3 ± 5.5 | 267 (33 with shown modifications) | cAGcuucAuGcA GGGuUmAmUX 1X2 | 355 (167 with shown modifications) | UAACCCuGCAuGAAG CUmGmAX1X2 |
| 152 | 74.2 ± 7.8 | 268 (82 with shown modifications) | GcuucAuGcAG GGuuACmAmU X1X2 | 356 (200 with shown modifications) | UGuAACCCuGCAuGA AGmCmUX1X2 |
| 153 | 92.9 ± 15.2 | 269 (66 with shown modifications) | cuucAuGcAGG GuuAcAmUmU X1X2 | 357 (143 with shown modifications) | AUGuAACCCuGCAUG AAmGmCX1X2 |
| 156 | 113.1 ± 15.8 | 270 (38 with shown modifications) | cAuGcAGGGuu AcAuGmAmU X1X2 | 358 (210 with shown modifications) | UUCAuGuAACCCuGC AUmGmAX1X2 |
| 157 | 97.3 ± 10.1 | 271 (22 with shown modifications) | AuGcAGGGuuA cAuGAAmGmU X1X2 | 359 (155 with shown modifications) | CUuCAuGuAACCCUG CAmUmGX1X2 |
| 261 | 86.6 ± 11.9 | 272 (65 with shown modifications) | cuucAGuucccu GAAAGmAmUX 1X2 | 360 (189 with shown modifications) | UCuuuCAGGGAACUG AAmGmCX1X2 |
| 264 | 89.7 ± 12.6 | 273 (37 with shown modifications) | cAGuucccuGAA AGAcUmAmUX 1X2 | 361 (177 with shown modifications) | UAGuCuuuCAGGGAA CUmGmAX1X2 |
| 272 | 113.7 ± 21.6 | 274 (112 with shown modifications) | uGAAAGAcuAc uGGGAGCmAmU X1X2 | 362 (195 with shown modifications) | UGCuCCAGuAGuCUu uCmAmGX1X2 |
| 278 | 96.5 ± 13.5 | 275 (11 with shown modifications) | AcuAcuGGAGc AccGuUmAmU X1X2 | 363 (168 with shown modifications) | UAACGGuGCuCCAGu AGmUmCX1X2 |
| 279 | 96.1 ± 16.6 | 276 (55 with shown modifications) | cuAcuGGAGcAc cGuuAmAmUX 1X2 | 364 (203 with shown modifications) | UUAACGGuGCuCCAG uAmGmUX1X2 |
| 280 | 103.6 ± 14.9 | 277 (101 with shown modifications) | uAcuGGAGcAcc GuuAAmGmUX 1X2 | 365 (154 with shown modifications) | CUuAACGGuGCuCCA GUmAmGX1X2 |
| 282 | 102.5 ± 9.3 | 278 (62 with shown modifications) | cuGGAGcAccGu uAAGGmAmUX 1X2 | 366 (182 with shown modifications) | UCCuuAACGGuGCUC CAmGmUX1X2 |

TABLE 2-continued

Knockdown of APOC3 mRNA in HUH7 cells with 30 nM of the described RNAi agents. siRNA SEQUENCE 1 HEAVY-STEM CHEMISTRIES RELATED, INCLUDING RIBITOL WALK AND 11-25MERS. The following are used in Table 2 to represent different chemistries and components of the sequences: N = RNA, n (lower case) = 2'-O-Methyl nucleotide, Nm = 2'-MOE nucleotide, X1 = abasic site with ribitol spacer, X2 = abasic site with 1,6-hexane-diol spacer.

| mRNA Position | % residual APOCS mRNA ± SD | SEQ ID NO | Sense Sequence String | SEQ ID NO | Antisense Sequence String |
|---|---|---|---|---|---|
| 285 | 96.3 ± 10.8 | 279 (73 with shown modifications) | GAGcAccGuuA AGGAcAmAmU X1X2 | 367 (214 with shown modifications) | UUGuCCuuAACGGU GCUmCmCX1X2 |
| 286 | 90.4 ± 14.1 | 280 (13 with shown modifications) | AGcAccGuuAA GGAcAAmGmU X1X2 | 368 (156 with shown modifications) | CUuGuCCuuAACGGu GCmUmCX1X2 |
| 288 | 149.6 ± 13.2 | 281 (29 with shown modifications) | cAccGuuAAGG AcAAGUmUmU X1X2 | 369 (120 with shown modifications) | AACuuGuCCuuAACG GUmGmCX1X2 |
| 290 | 11.1 ± 2.0 | 282 (44 with shown modifications) | ccGuuAAGGAc AAGuuCmUmU X1X2 | 370 (131 with shown modifications) | AGAACuuGuCCuuAA CGmGmUX1X2 |
| 297 | 7.5 ± 3.9 | 283 (84 with shown modifications) | GGAcAAGuucu cuGAGUmUmU X1X2 | 371 (118 with shown modifications) | AACuCAGAGAACuUG uCmCmUX1X2 |
| 298 | 26.4 ± 5.3 | 284 (70 with shown modifications) | GAcAAGuucucu GAGuUmCmUX 1X2 | 372 (159 with shown modifications) | GAACuCAGAGAACUu GUmCmCX1X2 |
| 325 | 101.8 ± 3.8 | 285 (72 with show modifications) | GAcccuGAGGuc AGAcCmAmUX 1X2 | 373 (199 with shown modifications) | UGGuCuGACCuCAGG GUmCmCX1X2 |
| 329 | 105.7 ± 8.6 | 286 (61 with shown modifications) | cuGAGGucAGA ccAAcUmUmUX 1X2 | 374 (124 with shown modifications) | AAGuuGGuCuGACCu CAmGmGX1X2 |
| 331 | 111.6 ± 11.9 | 287 (75 with shown modifications) | GAGGucAGAcc AAcuuCmAmU X1X2 | 375 (191 with shown modifications) | UGAAGuuGGuCuGAC CUmCmAX1X2 |
| 383 | 111.5 ± 8.6 | 288 (30 with shown modifications) | cAccuGccuAucc AucCmUmUX1 X2 | 376 (140 with shown modification) | AGGAuGGAuAGGCA GGUmGmGX1X2 |
| 454 | 77.1 ± 2.4 | 289 (18 with shown modifications) | AGGGAcAGuAu ucucAGmUmU X1X2 | 377 (130 with shown modifications) | ACuGAGAAuACuGUC CCmUmUX1X2 |
| 457 | 4.6 ± 2.5 | 290 (71 with shown modifications) | GAcAGuAuucuc AGuGCmUmUX 1X2 | 378 (132 with shown modifications) | AGCACuGAGAAuACu GUmCmCX1X2 |
| 518 | 64.6 ± 3.8 | 291 (49 with shown modifications) | ccucccAAuAAA GcuGGmAmUX 1X2 | 379 (181 with shown modifications) | UCCAGCuuuAuuGGG AGmGmCX1X2 |
| 523 | 10.8 ± 2.6 | 292 (28 with shown modifications) | cAAuAAAGcuG GAcAAGmAmU X1X2 | 380 (188 with shown modifications) | UCuuGuCCAGCuuuA uUmGmGX1X2 |
| 524 | 13.5 ± 2.6 | 293 (6 with shown modifications) | AAuAAAGcuGG AcAAGAmAmU X1X2 | 381 (212 with shown modifications) | UUCuuGuCCAGCuUu AUmUmGX1X2 |
| 485 | 136.0 ± 12.7 | 294 (109 with shown modifications) | uCCCUAgAUCU CACCuAAAuu | 382 (216 with shown modifications) | UUUAGGuGAGAUCU AgGGAuu |

TABLE 2-continued

Knockdown of APOC3 mRNA in HUH7 cells with 30 nM of the described RNAi agents. siRNA SEQUENCE 1 HEAVY-STEM CHEMISTRIES RELATED, INCLUDING RIBITOL WALK AND 11-25MERS. The following are used in Table 2 to represent different chemistries and components of the sequences: N = RNA, n (lower case) = 2'-O-Methyl nucleotide, Nm = 2'-MOE nucleotide, X1 = abasic site with ribitol spacer, X2 = abasic site with 1,6-hexane-diol spacer.

| mRNA Position | % residual APOCS mRNA ± SD | SEQ ID NO | Sense Sequence String | SEQ ID NO | Antisense Sequence String |
|---|---|---|---|---|---|
| 485 | 136.8 ± 7.5 | 294 (109 with shown modifications) | uCCCUAgAUCU CACCuAAAuu | 382 (216 with shown modifications) | UUUAGGuGAGAUCU AgGGAuu |
| 485 | 123.8 ± 14.9 | 294 (109 with shown modifications) | uCCCUAgAUCU CACCuAAAuu | 382 (216 with shown modifications) | UUUAGGuGAGAUCU AgGGAuu |
| 487 | 196.3 ± 20.5 | 295 (47 with shown modifications) | CCUAGAuCUCA CCuAAACAuu | 383 (202 with shown modifications) | UGUUUAGGuGAGAU CuAGGuu |
| 487 | 176.3 ± 26.4 | 295 (47 with shown modifications) | CCUAGAuCUCA CCuAAACAuu | 383 (202 with shown modifications) | UGUUUAGGuGAGAU CuAGGuu |
| 487 | 187.6 ± 8.9 | 295 (47 with shown modifications) | CCUAGAuCUCA CCuAAACAuu | 383 (202 with shown modifications) | UGUUUAGGuGAGAU CuAGGuu |
| 1 | 102.3 ± 12.9 | 296 (64 with shown modifications) | CUUACUGGCU UAUCGAAAUuu | 384 (146 with shown modifications) | AUUUCGAUAAGCCA GUAAGuu |
| 1 | 89.8 ± 6.2 | 296 (64 with shown modifications) | CUUACUGGCU UAUCGAAAUuu | 384 (146 with shown modifications) | AUUUCGAUAAGCCA GUAAGuu |
| 1 | 101.7 ± 18.7 | 296 (64 with shown modifications) | CUUACUGGCU UAUCGAAAUuu | 384 (146 with shown modifications) | AUUUCGAUAAGCCA GUAAGuu |
| 471 | 62.9 ± 4.8 | 297 (57 with shown modifications) | CUAUAUCAUG GCCGACAAGuu | 385 (157 with shown modifications) | CUUGUCGGCCAUGA UAUAGuu |
| 471 | 52.1 ± 1.0 | 297 (57 with shown modifications) | CUAUAUCAUG GCCGACAAGuu | 385 (157 with shown modifications) | CUUGUCGGCCAUGA UAUAGuu |
| 471 | 63.1 ± 7.5 | 297 (57 with shown modifications) | CUAUAUCAUG GCCGACAAGuu | 385 (157 with shown modification) | CUUGUCGGCCAUGA UAUAGuu |
| 33 | 120.6 ± 10.4 | 298 (46 with shown modifications) | ccuAGAAGcAGc uAGcUmAmUX 1X2 | 386 (174 with shown modifications) | UAGCuAGCuGCuuCu AGmGmGX1X2 |
| 38 | 139.8 ± 17.6 | 299 (4 with shown modifications) | AAGcAGcuAGc uAcucCmAmUX 1X2 | 387 (197 with shown modifications) | UGGAGuAGCuAGCU GCUmUmCX1X2 |
| 41 | 143.4 ± 25.1 | 300 (32 with shown modifications) | cAGcuAGcuAcu ccAGGmUmUX 1X2 | 388 (129 with shown modifications) | ACCuGGAGuAGCuAG CUmGmCX1X2 |
| 42 | 116.9 ± 11.8 | 301 (15 with shown modifications) | AGcuAGcuAcuc cAGGUmUmUX 1X2 | 389 (169 with shown modifications) | UACCuGGAGuAGCUA GCmUmGX1X2 |
| 115 | 127.5 ± 18.0 | 302 (77 with shown modifications) | GcAucuGcccGA GcuGAmAmUX 1X2 | 390 (208 with shown modifications) | UUCAGCuCGGGCAG AuGmCmCX1X2 |

TABLE 2-continued

Knockdown of APOC3 mRNA in HUH7 cells with 30 nM of the described RNAi agents. siRNA SEQUENCE 1 HEAVY-STEM CHEMISTRIES RELATED, INCLUDING RIBITOL WALK AND 11-25MERS. The following are used in Table 2 to represent different chemistries and components of the sequences: N = RNA, n (lower case) = 2'-O-Methyl nucleotide, Nm = 2'-MOE nucleotide, X1 = abasic site with ribitol spacer, X2 = abasic site with 1,6-hexane-diol spacer.

| mRNA Position | % residual APOC5 mRNA ± SD | SEQ ID NO | Sense Sequence String | SEQ ID NO | Antisense Sequence String |
|---|---|---|---|---|---|
| 156 | 130.8 ± 8.3 | 303 (89 with shown modifications) | GGGcucuGuAc AGGGcUmAmU X1X2 | 391 (172 with shown modifications) | UAGCCCuGuACAGAG CCmCmAX1X2 |
| 163 | 151.0 ± 33.7 | 304 (90 with shown modifications) | GuAcAGGGcuA cAuGGAmAmU X1X2 | 392 (211 with shown modifications) | UUCCAuGuAGCCCUG uAmCmAX1X2 |
| 174 | 121.1 ± 20.0 | 305 (40 with shown modifications) | cAuGGAAcAAG ccuccAmAmUX 1X2 | 393 (213 with shown modifications) | UUGGAGGCuuGuuCC AUmGmUX1X2 |
| 197 | 103.0 ± 9.3 | 306 (108 with shown modifications) | uccAGGAuGcGc uAAGUmAmUX 1X2 | 394 (170 with shown modifications) | UACuuAGCGCAuCCu GGmAmCX1X2 |
| 213 | 122.7 ± 12.1 | 307 (103 with shown modifications) | uAGcGuGcAGG AGuccGmAmU X1X2 | 395 (183 with shown modification) | UCGGACuCCuGCACG CUmAmCX1X2 |
| 215 | 148.1 ± 22.2 | 308 (78 with shown modifications) | GcGuGcAGGAG uccGAUmAmU X1X2 | 396 (179 with shown modifications) | UAuCGGACuCCuGCA CGmCmUX1X2 |
| 216 | 139.8 ± 12.8 | 309 (53 with shown modifications) | cGuGcAGGAGu ccGAuAmUmU | 397 (142 with shown modifications) | AUAuCGGACuCCuGC ACmGmCX1X2 |
| 217 | 81.4 ± 10.0 | 310 (92 with shown modifications) | GuGcAGGAGuc cGAuAmUmAmU X1X2 | 398 (178 with shown modifications) | UAuAuCGGACuCCUG CAmGmGX1X2 |
| 220 | 104.2 ± 16.7 | 311 (34 with shown modifications) | cAGGAGuccGA uAuAGCmUmU | 399 (138 with shown modifications) | AGCuAuAuCGGACUC CUmGmCX1X2 |
| 252 | 129.3 ± 24.3 | 312 (63 with shown modifications) | cuGGAuGGAcA AucAcUmUmU X1X2 | 400 (123 with shown modifications) | AAGuGAuuGuCCAUC CAmGmCX1X2 |
| 256 | 116.8 ± 29.3 | 313 (24 with shown modifications) | AuGGAcAAucA cuucAGmAmUX 1X2 | 401 (186 with shown modifications) | UCuGAAGuGAuuGUC CAmUmCX1X2 |
| 264 | 133.4 ± 25.2 | 314 (106 with shown modifications) | ucAcuucAGAuc ccuGAmAmUX1 X2 | 402 (209 with shown modifications) | UUCAGGGAuCuGAA GuGmAmUX1X2 |
| 270 | 107.6 ± 11.0 | 315 (31 with shown modifications) | cAGAucccuGAA AGGcUmAmUX 1X2 | 403 (173 with shown modifications) | UAGCCuuuCAGGGAu CUmGmAX1X2 |
| 278 | 102.7 ± 23.2 | 316 (113 with shown modifications) | uGAAAGGcuAc uGGAGCmAmU X1X2 | 404 (194 with shown modifications) | UGCuCCAGuAGCCUu uCmAmGX1X2 |
| 283 | 104.3 ± 12.7 | 317 (88 with shown modifications) | GGcuAcuGGAG cAAGuUmUmU X1X2 | 405 (115 with shown modifications) | AAACuuGCuCCAGUA GCmCmUX1X2 |
| 284 | 110.8 ± 17.2 | 318 (79 with shown modifications) | GcuAcuGGAGc AAGuuUmAmU X1X2 | 406 (166 with shown modifications) | UAAACuuGCuCCAGu AGmCmCX1X2 |

TABLE 2-continued

Knockdown of APOC3 mRNA in HUH7 cells with 30 nM of the described RNAi agents. siRNA SEQUENCE 1 HEAVY-STEM CHEMISTRIES RELATED, INCLUDING RIBITOL WALK AND 11-25MERS. The following are used in Table 2 to represent different chemistries and components of the sequences: N = RNA, n (lower case) = 2'-O-Methyl nucleotide, Nm = 2'-MOE nucleotide, X1 = abasic site with ribitol spacer, X2 = abasic site with 1,6-hexane-diol spacer.

| mRNA Position | % residual APOCS mRNA ± SD | SEQ ID NO | Sense Sequence String | SEQ ID NO | Antisense Sequence String |
|---|---|---|---|---|---|
| 285 | 94.3 ± 12.7 | 319 (54 with shown modifications) | cuAcuGGAGcAuAmGmCX1X2 | 407 (164 with shown modifications) | GUAAACuuGCuCCAGAGuuuAmCmU |
| 294 | 91.9 ± 11.9 | 320 (27 with shown modifications) | cAAGuuuAcuGAcAAGUmUmUX1X2 | 408 (119 with shown modifications) | AACuuGuCAGuAAACuUmGmCX1X2 |
| 295 | 125.7 ± 18.8 | 321 (5 with shown modifications) | AAGuuuAcuGAcAAGuUmCmUX1X2 | 409 (160 with shown modifications) | GAACuuGuCAGuAAACUmUmGX1X2 |
| 296 | 106.8 ± 20.4 | 322 (21 with shown modifications) | AGuuuAcuGAcAAGuuCmAmUX1X2 | 410 (190 with shown modifications) | UGAACuuGuCAGuAAACmUmUX1X2 |
| 314 | 116.3 ± 18.0 | 323 (42 with shown modifications) | ccGGcuucuGGGAuucUmAmUX1X2 | 411 (171 with shown modifications) | UAGAAuCCCAGAAGCCGmGmUX1X2 |
| 315 | 117.1 ± 18.1 | 324 (51 with shown modifications) | cGGcuucuGGGAuucuAmAmUX1X2 | 412 (204 with shown modifications) | UUAGAAuCCCAGAAGCCmGmGX1X2 |
| 337 | 120.8 ± 18.1 | 325 (74 with shown modifications) | GAGGAccAAccAAcucCmAmUX1X2 | 413 (198 with shown modifications) | UGGAGuuGGuuGGUCCUmCmAX1X2 |
| 341 | 119.6 ± 6.4 | 326 (10 with shown modifications) | AccAAccAAcuccAGcUmAmUX1X2 | 414 (175 with shown modifications) | UAGCuGGAGuuGGUuGGmUmCX1X2 |
| 343 | 113.3 ± 26.7 | 327 (26 with shown modifications) | cAAccAAcuccAGcuAUmUmUX1X2 | 415 (126 with shown modifications) | AAuAGCuGGAGuuGGuUmGmCX1X2 |
| 354 | 128.0 ± 31.2 | 328 (16 with shown modifications) | AGcuAuuGAGucGuGAGmAmUX1X2 | 416 (185 with shown modifications) | UCuCACGACuCAAUAGCmUmGX1X2 |
| 356 | 117.4 ± 23.5 | 329 (58 with shown modifications) | cuAuuGAGucGuGAGACmUmUX1X2 | 417 (141 with shown modifications) | AGuCuCACGACuCAAuAmGmCX1X2 |
| 357 | 105.8 ± 25.2 | 330 (105 with shown modifications) | uAuuGAGucGuGAGAcUmUmUX1X2 | 418 (122 with shown modifications) | AAGuCuCACGACuCAAUmAmGX1X2 |
| 379 | 179.8 ± 20.4 | 331 (93 with shown modifications) | GuuGcAGAuGuGccuGUmUmUX1X2 | 419 (117 with shown modifications) | AACAGGCACAuCuGCAAmCmAX1X2 |
| 385 | 126.7 ± 30.2 | 332 (76 with shown modifications) | GAuGuGccuGuuccucCmAmUX1X2 | 420 (196 with shown modifications) | UGGAGGAACAGGCACAUmCmUX1X2 |
| 456 | 122.1 ± 19.4 | 333 (83 with shown modifications) | GGAAAGuAuGuucucAUmGmU | 421 (151 with shown modifications) | CAuGAGAACAuACUuuCmCmCX1X2 |
| 457 | 100.9 ± 1.4 | 334 (67 with shown modifications) | GAAAGuAuGuucucAuGmUmUX1X2 | 422 (128 with shown modifications) | ACAuGAGAACAuACuuUmCmCX1X2 |

TABLE 2-continued

Knockdown of APOC3 mRNA in HUH7 cells with 30 nM of the described RNAi agents. siRNA SEQUENCE 1 HEAVY-STEM CHEMISTRIES RELATED, INCLUDING RIBITOL WALK AND 11-25MERS. The following are used in Table 2 to represent different chemistries and components of the sequences: N = RNA, n (lower case) = 2'-O-Methyl nucleotide, Nm = 2'-MOE nucleotide, X1 = abasic site with ribitol spacer, X2 = abasic site with 1,6-hexane-diol spacer.

| mRNA Position | % residual APOCS mRNA ± SD | SEQ ID NO | Sense Sequence String | SEQ ID NO | Antisense Sequence String |
|---|---|---|---|---|---|
| 460 | 101.1 ± 20.2 | 335 (19 with shown modifications) | AGuAuGuucucA uGucUmUmUX1X2 | 423 (121 with shown modifications) | AAGACAuGAGAACAu ACmUmUX1X2 |
| 483 | 126.1 ± 18.3 | 336 (60 with shown modifications) | cucccuAGAucuc AccUmAmUX1X2 | 424 (176 with shown modifications) | UAGGuGAGAuCuAG GGAmGmGX1X2 |
| 484 | 132.5 ± 20.9 | 337 (110 with shown modifications) | ucccuAGAucuc AccUmAmAmUX1X2 | 425 (205 with shown modifications) | UUAGGuGAGAuCuA GGGmAmGX1X2 |
| 485 | 128.5 ± 13.2 | 338 (41 with shown modifications) | cccuAGAucucA ccuAAmAmUX1X2 | 426 (215 with shown modifications) | UUuAGGuGAGAuCU AGGmGmAX1X2 |
| 486 | 109.6 ± 14.5 | 339 (48 with shown modifications) | ccuAGAucucAc cuAAAmCmUX1X2 | 427 (165 with shown modifications) | GUuuAGGuGAGAuCu AGmGmGX1X2 |
| 487 | 107.5 ± 27.2 | 340 (56 with shown modifications) | cuAGAucucAcc uAAACmAmUX1X2 | 428 (201 with shown modifications) | UGuuuAGGuGAGAU CuAmGmGX1X2 |
| 488 | 112.6 ± 24.6 | 341 (102 with shown modifications) | uAGAucucAccu AAAcAmUmUX1X2 | 429 (144 with shown modifications) | AUGuuuAGGuGAGAu CUmAmGX1X2 |
| 500 | 112.9 ± 3.7 | 342 (1 with shown modifications) | AAAcAuGcuGuc ccuAAmUmUX1X2 | 430 (145 with shown modifications) | AUuAGGGACAGCAU GuUmUmAX1X2 |
| 501 | 116.4 ± 17.4 | 343 (2 with shown modifications) | AAcAuGcuGucc cuAAUmAmUX1X2 | 431 (180 with shown modifications) | UAuuAGGGACAGCAu GUmUmX1X2 |
| 502 | 108.2 ± 11.7 | 344 (9 with shown modifications) | AcAuGcuGuccc uAAuAmAmUX1X2 | 432 (207 with shown modifications) | UUAuuAGGGACAGC AuGmUmUX1X2 |
| 503 | 130.5 ± 18.2 | 345 (39 with shown modifications) | cAuGcuGucccu AAuAmAmUX1X2 | 433 (94 with shown modifications) | UUuAuuAGGGACAGC AUmGmUX1X2 |
| 504 | 92.4 ± 15.2 | 346 (23 with shown modifications) | AuGcuGucccuA AuAAAmGmUX1X2 | 434 (158 with shown modifications) | CUuuAuuAGGGACAG CAmUmGX1X2 |
| 506 | 115.7 ± 14.5 | 347 (81 with shown modifications) | GcuGucccuAAu AAAGCmUmUX1X2 | 435 (139 with shown modifications) | AGCuuuAuuAGGGAC AGmCmAX1X2 |
| 512 | 108.4 ± 16.5 | 348 (45 with shown modifications) | ccuAAuAAAGcu GGAuAmAmUX1X2 | 436 (206 with shown modifications) | UUAuCCAGCuuuAUu AGmGmGX1X2 |
| 514 | 109.9 ± 13.0 | 349 (100 with shown modifications) | uAAuAAAGcuG GAuAAGmAmUX1X2 | 437 (187 with shown modifications) | UCuuAuCCAGCuuuA uUmAmGX1X2 |

TABLE 3

Knockdown of APOC3 mRNA in HUH7 cells with 15 nM of the described RNAi agents. The following are used in Table 3 to represent different chemistries and components of the sequences: N = RNA, p = phosphate, n (lower case) = 2'-O-Methyl nucleotide, Nm = 2'-MOE nucleotide, Nf = 2'-fluoro nucleotide, dN = DNA, X1 = abasic site with ribitol spacer, X2 = abasic site with 1,6-hexane-diol spacer, X058 = 3' end cap

| % residual APOC3 mRNA ± SD | SEQ ID NO. | Sense Sequene String | SEQ ID NO. | Antisense Sequence String |
|---|---|---|---|---|
| 5.8 ± 2.8 | 438 (71 with shown modifications) | gacAfgUfaUfuCfuCfaGfuGfCmUmUX1X2 | 484 (132 with shown modifications) | AfGfcAfcUfgAfgAfaUfaCfuGfCmUmCX1CX1-3'cap |
| 3.4 ± 1.1 | 438 (71 with shown modifications) | gacAfgUfaUfuCfuCfaGfuGfCmUmUX1X2 | 485 (132 with shown modifications) | AfGfcAfcUfgAfgAfaUfaCfuGfUX1CmCX1-3'cap |
| 11.3 ± 2.1 | 438 (71 with shown modifications) | gacAfgUfaUfuCfuCfaGfuGfCmUmUX1X2 | 486 (132 with shown modifications) | AfGfcAfcUfgAfgAfaUfaCfuGX1UmCmCX1-3'cap |
| 9.5 ± 1.5 | 438 (71 with shown modifications) | gacAfgUfaUfuCfuCfaGfuGfCmUmUX1X2 | 487 (132 with shown modifications) | AfGfcAfcUfgAfgAfaUfaCfUX1GfUmCmCX1-3'cap |
| 25.6 ± 6.4 | 438 (71 with shown modifications) | gacAfgUfaUfuCfuCfaGfuGfCmUmUX1X2 | 488 (132 with shown modifications) | AfGfcAfcUfgAfgAfaUfaCX1uGfUmCmCX1-3'cap |
| 33.1 ± 8.1 | 438 (71 with shown modifications) | gacAfgUfaUfuCfuCfaGfuGfCmUmUX1X2 | 489 (132 with shown modifications) | AfGfcAfcUfgAfgAfaUfAX1CfuGfUmCmCX1-3'cap |
| 22 ± 9.1 | 438 (71 with shown modifications) | gacAfgUfaUfuCfuCfaGfuGfCmUmUX1X2 | 490 (132 with shown modifications) | AfGfcAfcUfgAfgAfaUX1aCfuGfUmCmCX1-3'cap |
| 23.8 ± 4.6 | 438 (71 with shown modifications) | gacAfgUfaUfuCfuCfaGfuGfCmUmUX1X2 | 491 (132 with shown modifications) | AfGfcAfcUfgAfgAfAX1UfaCfuGfUmCmCX1-3'cap |
| 56.7 ± 10.7 | 438 (71 with shown modifications) | gacAfgUfaUfuCfuCfaGfuGfCmUmUX1X2 | 492 (132 with shown modifications) | AfGfcAfcUfgAfgAX1aUfaCfuGfUmCmCX1-3'cap |
| 55 ± 10.8 | 438 (71 with shown modifications) | gacAfgUfaUfuCfuCfaGfuGfCmUmUX1X2 | 493 (132 with shown modifications) | AfGfcAfcUfgAfgGX1AfaUfaCfuGfUmCmCX1-3'cap |
| 22.3 ± 4.2 | 438 (71 with shown modifications) | gacAfgUfaUfuCfuCfaGfuGfCmUmUX1X2 | 494 (132 with shown modifications) | AfGfcAfcUfgAX1gAfaUfaCfuGfUmCmCX1-3'cap |
| 10.5 ± 1.5 | 438 (71 with shown modifications) | gacAfgUfaUfuCfuCfaGfuGfCmUmUX1X2 | 495 (132 with shown modifications) | AfGfcAfcUfGX1AfgAfaUfaCfuGfUmCmCX1-3'cap |
| 4.4 ± 0.7 | 438 (71 with shown modifications) | gacAfgUfaUfuCfuCfaGfuGfCmUmUX1X2 | 496 (132 with shown modifications) | AfGfcAfcUX1gAfgAfaUfaCfdUGfUmCmCX1-3'cap |
| 3.2 ± 0.4 | 438 (71 with shown modifications) | gacAfgUfaUfuCfuCfaGfuGfCmUmUX1X2 | 497 (132 with shown modifications) | AfGfcAfcCX1UfgAfgAfaUfaCfuGfUmCmCX1-3'cap |
| 18.3 ± 6 | 438 (71 with shown modifications) | gacAfgUfaUfuCfuCfaGfuGfCmUmUX1X2 | 498 (132 with shown modifications) | AfGfcAX1 cUfgAfgAfaUfaCfuGfUmCmCX1-3'cap |
| 6.8 ± 0.5 | 438 (71 with shown modifications) | gacAfgUfaUfuCfuCfaGfuGfCmUmUX1X2 | 499 (132 with shown modifications) | AfGfCX1AfcUfgAfgAfaUfaCfuGfUmCmCX1-3'cap |
| 57.4 ± 5.3 | 438 (71 with shown modifications) | gacAfgUfaUfuCfuCfaGfuGfCmUmUX1X2 | 500 (132 with shown modifications) | AfGX1cAfcUfgAfgAfaUfaCfuGfUmCmCX1-3'cap |

TABLE 3-continued

Knockdown of APOC3 mRNA in HUH7 cells with 15 nM of the described RNAi agents. The following are used in Table 3 to represent different chemistries and components of the sequences: N = RNA, p = phosphate, n (lower case) = 2'-O-Methyl nucleotide, Nm = 2'-MOE nucleotide, Nf = 2'-fluoro nucleotide, dN = DNA, X1 = abasic site with ribitol spacer, X2 = abasic site with 1,6-hexane-diol spacer, X058 = 3' end cap

| % residual APOC3 mRNA ± SD | SEQ ID NO. | Sense Sequene String | SEQ ID NO. | Antisense Sequence String |
|---|---|---|---|---|
| 7.6 ± 2 | 438 (71 with shown modifications) | gacAfgUfaUfuCfuCfaGfuGfCmUmUX1X2 | 501 (132 with shown modifications) | AX1GfcAfcUfgAfgAfaUfaCfuGfUmCmCX1-3'cap |
| 6.3 ± 1.4 | 438 (71 with shown modifications) | gacAfgUfaUfuCfuCfaGfuGfCmUmUX1X2 | 502 (132 with shown modifications) | AfGfcAfcUfgAfgAfaUfaCfuGfUmCmCX1-3'cap |
| 9.7 ± 1.9 | 439 (71 with shown modifications) | GAcAGuAuucucAGuGCmUmUX1X2 | 503 (132 with shown modifications) | dAGCACuGAGAAuACuGUmCmCX1-3'cap |
| 6.5 ± 1.4 | 440 (87 with shown modifications) | GGAcAGuAuucucAGuGcudUdU | 504 (137 with shown modifications) | AGCACuGAGAAuACuGuCCdUdU |
| 5.5 ± 1 | 441 (87 with shown modifications) | GfgAfcAfgUfaUfuCfuCfaGfuGfcUfuUfX2 | 505 (133 with shown modifications) | aGfcAfcUfgAfgAfaUfaCfuGfuCfcCfu |
| 5.4 ± 1.1 | 442 (17 with shown modifications) | AfgGfgAfcAfgUfaUfuCfuCfaGfuGfcUfX2 | 506 (133 with shown modifications) | aGfcAfcUfgAfgAfaUfaCfuGfuCfcCfu-3'cap |
| 5.4 ± 0.7 | 442 (17 with shown modifications) | AfgGfgAfcAfgUfaUfuCfuCfaGfuGfcUfX2 | 507 (134 with shown modifications) | aGfcAfcUfgAfgAfaUfaCfuGfuCfcCfuUfu |
| 7.2 ± 1.7 | 443 (98 with shown modifications) | uAAAAGGGAcAGuAuucucAGuGcuX2 | 508 (135 with shown modifications) | AGCACuGAGAAuACuGuCCCuuuuA |
| 9 ± 2.6 | 443 (98 with shown modifications) | uAAAAGGGAcAGuAuucucAGuGcuX2 | 509 (135 with shown modifications) | AGCACuGAGAAuACuGuCCCuuuuA-3'cap |
| 7.7 ± 1.1 | 444 (98 with shown modifications) | UAAAAGGGACAGUAUUCUCAGUGCUX2 | 510 (135 with shown modifications) | AGCACUGAGAAUACUGUCCCUUUUA |
| 6.4 ± 0.9 | 444 (98 with shown modifications) | UAAAAGGGACAGUAUUCUCAGUGCUX2 | 511 (135 with shown modifications) | AGCACUGAGAAUACUGUCCCUUUUA-3'cap |
| 180.2 ± 39.2 | 445 (99 with shown modifications) | UfaAfaAfgGfgAfcAfgUfaUfuCfuCfaGfuGfCmUmAX1X2 | 512 (136 with shown modifications) | aGfcAfcUfgAfgAfaUfaCfuGfuCfcCfuUfuUmAmAX1X2 |
| 141.5 ± 31 | 445 (99 with shown modifications) | UfaAfaAfgGfgAfcAfgUfaUfuCfuCfaGfuGfCmUmAX1X2 | 513 (136 with shown modifications) | aGfcAfcUfgAfgAfaUfaCfuGfuCfcCfuUfuUmAmAX1-3'cap |
| 6.7 ± 3.3 | 446 (98 with shown modifications) | UfaAfaAfgGfgAfcAfgUfaUfuCfuCfAGUGfcUfX2 | 514 (135 with shown modifications) | aGfcACUGAfgAfaUfaCfuGfuCfcCfuUfuUfa-3'cap |
| 5.5 ± 1.3 | 447 (98 with shown modifications) | UfaAfaAfgGfgAfcAfgUfaUfuCfuCfaGfuGfcUfX2 | 514 (135 with shown modifications) | aGfcACUGAfgAfaUfaCfuGfuCfcCfuUfuUfa-3'cap |
| 5.8 ± 2.5 | 448 (98 with shown modifications) | UfaAfaAfgGfgAfcAfgUfaUfuCfuCfaGUGCUX2 | 515 (135 with shown modifications) | AGCACUgAfgAfaUfaCfuGfuCfcCfuUfuUfa-3'cap |

TABLE 3-continued

Knockdown of APOC3 mRNA in HUH7 cells with 15 nM of the described RNAi agents. The following are used in Table 3 to represent different chemistries and components of the sequences: N = RNA, p = phosphate, n (lower case) = 2'-O-Methyl nucleotide, Nm = 2'-MOE nucleotide, Nf = 2'-fluoro nucleotide, dN = DNA, X1 = abasic site with ribitol spacer, X2 = abasic site with 1,6-hexane-diol spacer, X058 = 3' end cap

| % residual APOC3 mRNA ± SD | SEQ ID NO. | Sense Sequene String | SEQ ID NO. | Antisense Sequence String |
|---|---|---|---|---|
| 10.6 ± 3.6 | 449 (98 with shown modifications) | UfaAfaAfgGfgAfcAfg UfaUfuCfuCfaGfuGfC mUmX2 | 516 (135 with shown modifications) | aGfcAfcUfgAfgAfaUfa CfuGfuCfcCfuUfuUfa- 3'cap |
| 3.9 ± 1.2 | 450 (98 with shown modifications) | UfaAfaAfgGfgAfcAfg UfaUfuCfuCfCAGUGCU X2 | 517 (135 with shown modifications) | AGCACUGAfgAfaUfa CfuGfuCfcCfuUfuUfa |
| 9.1 ± 5.6 | 447 (98 with shown modifications) | UfaAfaAfgGfgAfcAfg UfaUfuCfuCfaGfuGfc UfX2 | 518 (135 with shown modifications) | aGfcAfcUfgAfgAfaUfa CfuGfuCfcCfuUfuUfa |
| 6.3 ± 1 | 450 (98 with shown modifications) | UfaAfaAfgGfgAfcAfg UfaUfuCfuCfCAGUGCU X2 | 519 (135 with shown modifications) | AGCACUGAfgAfaUfa CfuGfuCfcCfuUfuUfa- 3'cap |
| 7.2 ± 2.5 | 451 (98 with shown modifications) | UfaAfaAfgGfgAfcAfg UfaUfuCfuCfCfAGUGC UX2 | 515 (135 with shown modifications) | AGCACUgAfgAfaUfaC fuGfuCfcCfuUfuUfa- 3'cap |
| 6 ± 1.8 | 448 (98 with shown modifications) | UfaAfaAfgGfgAfcAfg UfaUfuCfuCfCfaGUGCU X2 | 520 (135 with shown modifications) | AGCACUfgAfgAfaUfa CfuGfuCfcCfuUfuUfa- 3'cap |
| 15.2 ± 1.5 | 452 (98 with shown modifications) | UfaAfaAfgGfgAfcAfg UfaUfuCfuCfCfaGfUGC UX2 | 521 (135 with shown modifications) | AGCAcUfgAfgAfaUfaC fuGfuCfcCfuUfuUfa- 3'cap |
| 9 ± 2.9 | 453 (98 with shown modifications) | UfaAfaAfgGfgAfcAfg UfaUfuCfuCfCfaGfuGCU X2 | 522 (135 with shown modifications) | AGCAfcUfgAfgAfaUfa CfuGfuCfcCfuUfuUfa- 3'cap |
| 7.5 ± 2.7 | 454 (98 with shown modifications) | UfaAfaAfgGfgAfcAfg UfaUfuCfuCfCfaGfuGfC UX2 | 523 (135 with shown modifications) | AGcAfcUfgAfgAfaUfa CfuGfuCfcCfuUfuUfa- 3'cap |
| 10.6 ± 2.1 | 455 (98 with shown modifications) | UfaAfaAfgGfgAfcAfg UfaUfuCfuCfCfaGfuGfc UX2 | 524 (135 with shown modifications) | AGfcAfcUfgAfgAfaUfa CfuGfuCfcCfuUfuUfa- 3'cap |
| 7.1 ± 0.4 | 447 (98 with shown modifications) | UfaAfaAfgGfgAfcAfg UfaUfuCfuCfCfaGfuGfc UfX2 | 516 (135 with shown modifications) | aGfcAfcUfgAfgAfaUfa CfuGfuCfcCfulffuUfa- 3'cap |
| 9 ± 1.9 | 456 (85 with shown modifications) | GGACAGUAUUCUC AGUGCUAAAUdUdG X2 | 525 (148 with shown modifications) | CAAUUUAGCACUGA GAAUACUGUCC- 3'cap |
| 88.9 ± 16.4 | 457 (85 with shown modifications) | GGAcAGuAuucucAGu GcuAAAuuGX2 | 526 (148 with shown modifications) | CAAuuuAGCACuGAG AAuACuGuCC |
| 84.9 ± 6.9 | 457 (85 with shown modifications) | GGAcAGuAuucucAGu GcuAAAuuGX2 | 527 (148 with shown modifications) | CAAuuuAGCACuGAG AAuACuGuCC-3'cap |
| 15.9 ± 6.3 | 458 (85 with shown modifications) | GGACAGUAUUCUC AGUGCUAAAUUGX 2 | 528 (148 with shown modifications) | CAAUUUAGCACUGA GAAUACUGUCC |
| 7.9 ± 4 | 458 (85 with shown modifications) | GGACAGUAUUCUC AGUGCUAAAUUGX 2 | 525 (148 with shown modifications) | CAAUUUAGCACUGA GAAUACUGUCC- 3'cap |

TABLE 3-continued

Knockdown of APOC3 mRNA in HUH7 cells with 15 nM of the described RNAi agents. The following are used in Table 3 to represent different chemistries and components of the sequences: N = RNA, p = phosphate, n (lower case) = 2'-O-Methyl nucleotide, Nm = 2'-MOE nucleotide, Nf = 2'-fluoro nucleotide, dN = DNA, X1 = abasic site with ribitol spacer, X2 = abasic site with 1,6-hexane-diol spacer, X058 = 3' end cap

| % residual APOC3 mRNA ± SD | SEQ ID NO. | Sense Sequene String | SEQ ID NO. | Antisense Sequence String |
|---|---|---|---|---|
| 14.9 ± 3.7 | 472 (86 with shown modifications) | GfgAfcAfgUfaUfuCfu CfaGfuGfcUfaAfaUfU mGmAX1X2 | 541 (149 with shown modifications) | cAfaUfuUfaGfcAfcUfg AfgAfaUfaCfuGfuCmC mAX1X2 |
| 12.6 ± 3.1 | 472 (86 with shown modifications) | GfgAfcAfgUfaUfuCfu CfaGfuGfcUfaAfaUfU mGmAX1X2 | 542 (149 with shown modifications) | cAfaUfuUfaGfcAfcUfg AfgAfaUfaCfuGfuCmC mAX1-3'cap |
| 17.1 ± 3.9 | 459 (85 with shown modifications) | GfgAfcAfgUfaUfuCfu CfaGfuGfcUfaAAUfu GfX2 | 529 (148 with shown modifications) | cAfaUfuUAGfcAfcUfg AfgAfaUfaCfuGfuCfc-3'cap |
| 11.8 ± 2.1 | 460 (85 with shown modifications) | GfgAfcAfgUfaUfuCfu CfaGfuGfcUfaAfaUfu GfX2 | 530 (148 with shown modifications) | cAfaUUUAGfcAfcUfgA fgAfaUfaCfuGfuCfc-3'cap |
| 10.5 ± 0.7 | 461 (85 with shown modifications) | GfgAfcAfgUfaUfuCfu CfaGfuGfcUAAAUfuG fx2 | 530 (148 with shown modifications) | cAfaUUUAGfcAfcUfgA fgAfaUfaCfuGfuCfc-3'cap |
| 6.2 ± 0.7 | 462 (85 with shown modifications) | GfgAfcAfgUfaUfuCfu CfaGfuGfcUfaAAUUG X2 | 531 (148 with shown modifications) | CAAUUUaGfcAfcUfgA fgAfaUfaCfuGfuCfc-3'cap |
| 16 ± 2.9 | 463 (85 with shown modifications) | GfgAfcAfgUfaUfuCfu CfaGfuGfcUfaAfaUfU mGmX2 | 532 (148 with shown modifications) | cAfaUfuUfaGfcAfcUfg AfgAfaUfaCfuGfuCfc-3'cap |
| 128.6 ± 24.3 | 464 (85 with shown modifications) | GfgAfcAfgUfaUfuCfu CfaGfuGfcUAAAUUG X2 | 533 (148 with shown modifications) | CAAUUUAGfcAfcUfg AfgAfaUfaCfuGfuCfc |
| 35.8 ± 12.6 | 460 (85 with shown modifications) | GfgAfcAfgUfaUfuCfu CfaGfuGfcUfaAfaUfu GfX2 | 534 (148 with shown modifications) | cAfaUfuUfaGfcAfcUfg AfgAfaUfaCfuGfuCfc |
| 6 ± 2.4 | 463 (85 with shown modifications) | GfgAfcAfgUfaUfuCfu CfaGfuGfcUAAAUUG X2 | 535 (148 with shown modifications) | CAAUUUAGfcAfcUfg AfgAfaUfaCfuGfuCfc-3'cap |
| 7.8 ± 1.6 | 465 (85 with shown modifications) | GfgAfcAfgUfaUfuCfu CfaGfuGfcUfAAAUU GX2 | 531 (148 with shown modifications) | CAAUUUaGfcAfcUfgA fgAfaUfaCfuGfuCfc-3'cap |
| 7 ± 0.9 | 466 (85 with shown modifications) | GfgAfcAfgUfaUfuCfu CfaGfuGfcUfaAAUUG X2 | 536 (148 with shown modifications) | CAAUUUfaGfcAfcUfg AfgAfaUfaCfuGfuCfc-3'cap |
| 9.2 ± 2.6 | 467 (85 with shown modifications) | GfgAfcAfgUfaUfuCfu CfaGfuGfcUfaAfAUU GX2 | 537 (148 with shown modifications) | CAAUuUfaGfcAfcUfgA fgAfaUfaCfuGfuCfc-3'cap |
| 9.2 ± 2.3 | 468 (85 with shown modifications) | GfgAfcAfgUfaUfuCfu CfaGfuGfcUfaAfaUUG X2 | 538 (148 with shown modifications) | CAAUfuUfaGfcAfcUfg AfgAfaUfaCfuGfuCfc-3'cap |
| 12.7 ± 3 | 469 (85 with shown modifications) | GfgAfcAfgUfaUfuCfu CfaGfuGfcUfaAfaUfU GX2 | 539 (148 with shown modifications) | CAaUfuUfaGfcAfcUfg AfgAfaUfaCfuGfuCfc-3'cap |
| 24.2 ± 2 | 470 (85 with shown modifications) | GfgAfcAfgUfaUfuCfu CfaGfuGfcUfaAfaUfu G-3'cap | 540 (148 with shown modifications) | CAfaUfuUfaGfcAfcUfg AfgAfaUfaCfuGfuCfc-3'cap |

TABLE 3-continued

Knockdown of APOC3 mRNA in HUH7 cells with 15 nM of the described RNAi agents. The following are used in Table 3 to represent different chemistries and components of the sequences: N = RNA, p = phosphate, n (lower case) = 2'-O-Methyl nucleotide, Nm = 2'-MOE nucleotide, Nf = 2'-fluoro nucleotide, dN = DNA, X1 = abasic site with ribitol spacer, X2 = abasic site with 1,6-hexane-diol spacer, X058 = 3' end cap

| % residual APOC3 mRNA ± SD | SEQ ID NO. | Sense Sequene String | SEQ ID NO. | Antisense Sequence String |
|---|---|---|---|---|
| 16.6 ± 2 | 471 (85 with shown modifications) | GfgAfcAfgUfaUfuCfu CfaGfuGfcUfaAfaUfu GfX2 | 532 (148 with shown modifications) | cAfaUfuUfaGfcAfcUfg AfgAfaUfaCfuGfuCfc-3'cap |
| 4.8 ± 1.6 | 473 (8 with shown modifications) | acAfgUfaUfuCfuCfaGf uGfCmUmUX1X2 | 502 (132 with shown modifications) | AfGfcAfcUfgAfgAfaUf aCfuGfUmCmCX1-3'cap |
| 126.5 ± 17.1 | 474 (107 with shown modifications) | uCfaGfuGfCmUmUX1 X2 | 502 (132 with shown modifications) | AfGfcAfcUfgAfgAfaUf aCfuGfUmCmCX1-3'cap |
| 99.4 ± 8.2 | 475 (59 with shown modifications) | CfuCfaGfuGfCmUmU X1X2 | 502 (132 with shown modifications) | AfGfcAfcUfgAfgAfaUf aCfuGfUmCmCX1-3'cap |
| 5.5 ± 1.5 | 476 (20 with shown modifications) | AfgUfaUfuCfuCfaGfu GfCmUmUX1X2 | 502 (132 with shown modifications) | AfGfcAfcUfgAfgAfaUf aCfuGfUmCmCX1-3'cap |
| 58.9 ± 7.7 | 477 (114 with shown modificaitons) | UfuCfuCfaGfuGfCmU mUX1X2 | 502 (132 with shown modifications) | AfGfcAfcUfgAfgAfaUf aCfuGfUmCmCX1-3'cap |
| 121.9 ± 16.7 | 478 (36 with shown modifications) | CfaGfuGfCmUmUX1X 2 | 502 (132 with shown modifications) | AfGfcAfcUfgAfgAfaUf aCfuGfUmCmCX1-3'cap |
| 96.6 ± 12.3 | 479 (111 with shown modifications) | uCfuCfaGfuGfCmUm UX1X2 | 502 (132 with shown modifications) | AfGfcAfcUfgAfgAfaUf aCfuGfUmCmCX1-3'cap |
| 4.7 ± 2.6 | 438 (71 with shown modifications) | gacAfgUfaUfuCfuCfaG fuGfCmUmUX1X2 | 502 (132 with shown modifications) | AfGfcAfcUfgAfgAfaUf aCfuGfUmCmCX1-3'cap |
| 6 ± 0.9 | 480 (91 with shown modifications) | gUfaUfuCfuCfaGfuGf CmUmUX1X2 | 502 (132 with shown modifications) | AfGfcAfcUfgAfgAfaUf aCfuGfUmCmCX1-3'cap |
| 37.8± 7.1 | 481 (104 with shown modifications) | UfaUfuCfuCfaGfuGfC mUmUX1X2 | 502 (132 with shown modifications) | AfGfcAfcUfgAfgAfaUf aCfuGfUmCmCX1-3'cap |
| 6.6 ± 0.4 | 482 (35 with shown modifications) | cAfgUfaUfuCfuCfaGfu GfCmUmUX1X2 | 502 (132 with shown modifications) | AfGfcAfcUfgAfgAfaUf aCfuGfUmCmCX1-3'cap |
| 68.9 ± 6.4 | 483 (25 with shown modifications) | aUfuCfuCfaGfuGfCm UmUX1X2 | 502 (132 with shown modifications) | AfGfcAfcUfgAfgAfaUf aCfuGfUmCmCX1-3'cap |
| 5.6 ± 1.5 | 473 (8 with shown modifications) | acAfgUfaUfuCfuCfaGf uGfCmUmUX1X2 | 502 (132 with shown modifications) | AfGfcAfcUfgAfgAfaUf aCfuGfUmCmCX1-3'cap |
| 105.3 ± 21.7 | 475 (59 with shown modifications) | CfuCfaGfuGfCmUmU X1X2 | 502 (132 with shown modifications) | AfGfcAfcUfgAfgAfaUf aCfuGfUmCmCX1-3'cap |
| 78.7 ± 8.2 | 477 (114 with shown modifications) | UfuCfuCfaGfuGfCmU mUX1X2 | 502 (132 with shown modifications) | AfGfcAfcUfgAfgAfaUf aCfuGfUmCmCX1-3'cap |

TABLE 3-continued

Knockdown of APOC3 mRNA in HUH7 cells with 15 nM of the described RNAi agents. The following are used in Table 3 to represent different chemistries and components of the sequences: N = RNA, p = phosphate, n (lower case) = 2'-O-Methyl nucleotide, Nm = 2'-MOE nucleotide, Nf = 2'-fluoro nucleotide, dN = DNA, X1 = abasic site with ribitol spacer, X2 = abasic site with 1,6-hexane-diol spacer, X058 = 3' end cap

| % residual APOC3 mRNA ± SD | SEQ ID NO. | Sense Sequene String | SEQ ID NO. | Antisense Sequence String |
|---|---|---|---|---|
| 105.7 ± 6.2 | 479 (111 with shown modifications) | uCfuCfaGfuGfCmUm UX1X2 | 502 (132 with shown modifications) | AfGfcAfcUfgAfgAfaUf aCfuGfUmCmCX1-3'cap |
| 9 ± 1 | 480 (91 with shown modifications) | gUfaUfuCfuCfaGfuGf CmUmUX1X2 | 502 (132 with shown modifications) | AfGfcAfcUfgAfgAfaUf aCfuGfUmCmCX1-3'cap |
| 5.5 ± 2 | 482 (35 with shown modifications) | cAfgUfaUfuCfuCfaGfu GfCmUmUX1X2 | 502 (132 with shown modifications) | AfGfcAfcUfgAfgAfaUf aCfuGfUmCmCX1-3'cap |
| 4.7 ± 0.9 | 439 (71 with shown modifications) | GAcAGuAuucucAGuG CmUmUX1X2 | 503 (132 with shown modifications) | dAGCACuGAGAAuAC uGUmCmCX1-3'cap |
| 5.1 ± 1.6 | 439 (71 with shown modifications) | GAcAGuAuucucAGuG CmUmUX1X2 | 503 (132 with shown modifications) | dAGCACuGAGAAuAC uGUmCmCX1-3'cap |
| 3.3 ± 0.9 | 438 (71 with shown modifications) | gacAfgUfaUfuCfuCfaG fuGfCmUmUX1X2 | 502 (132 with shown modifications) | AfGfcAfcUfgAfgAfaUf aCfuGfUmCmCX1-3'cap |
| 4.2 ± 0.5 | 438 (71 with shown modifications) | gacAfgUfaUfuCfuCfaG fuGfCmUmUX1X2 | 502 (132 with shown modifications) | AfGfcAfcUfgAfgAfaUf aCfuGfUmCmCX1-3'cap |

One or both strands of the 18-mer format can comprise, in various embodiments, in 5' to 3' order, a 18-mer, a spacer, and a 3' end cap. The 18-mer can be modified or unmodified. In various embodiments, the modifications include the two nt on the 3' end being 2'-MOE (a "2-MOE clamp"). In various embodiments, with or without the 2'-MOE clamp, various nucleotides can be modified with a 2'-MOE, 2'-OMe, 2'-F, or substituted with DNA, a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), unlocked nucleic acid (UNA). The spacer can be a sugar, alkyl, cycloakyl, ribitol or other type of abasic nucleotide, 2'-deoxy-ribitol, diribitol, 2'-methoxyethoxy-ribitol (ribitol with 2'-MOE), C3, C4, C5, C6, or 4-methoxybutane-1,3-diol (5300). The 3' end cap can be selected from any of various 3' end caps described herein or known in the art.

Various non-limiting examples of modified forms of sequences are shown in FIGS. 1-5.

In one embodiment, at least one nucleotide of the RNAi agent is modified.

In one embodiment, said at least one modified nucleotide is selected from among 2' alkoxyribonucleotide, 2' alkoxyalkoxy ribonucleotide, or 2'-fluoro ribonucleotide. In another embodiment, said at least one modified nucleotide is selected from 2'-OMe, 2'-MOE and 2'-H. In various aspects, the nucleotide subunit is chemically modified at the 2' position of the sugar. In some embodiments, the 2' chemical modification is selected from a halo, a C1-10 alkyl, a C1-10 alkoxy, a halo, and the like. In specific aspects, the 2' chemical modification is a C1-10 alkoxy selected from —OCH$_3$ (i.e., "OMe"), —OCH$_2$CH$_3$ (i.e., "OEt") or —CH$_2$OCH$_2$CH$_3$ (i.e., methoxyethyl or "MOE"); or is a halo selected from F.

In various embodiments, one of more nucleotides is DNA or is replaced by a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), and/or unlocked nucleic acid (UNA); and/or at least one nucleotide comprises a modified internucleoside linker (e.g., wherein at least one phosphate of a nucleotide is replaced by a modified internucleoside linker), wherein the modified internucleoside linker is selected from phosphorothioate, phosphorodithioate, phosphoramidate, boranophosphonate, an amide linker, and a compound of formula (I) (as described elsewhere herein).

In one embodiment, the first two base-pairing nucleotides on the 3' end of the first and/or second strand are modified.

In one embodiment, the first two base-pairing nucleotides on the 3' end of the first and/or second strand are 2'-MOE.

In various sequences disclosed herein, lower-case letters (e.g., c, u) indicate modified nucleotides while upper case letters (e.g., C, U, A, G) indicate unmodified nucleotides. In various Tables disclosed herein, example modified versions of the sequences are shown. However, the present disclosure also contemplates and encompasses unmodified versions of these sequences and other versions which comprise additional or alternative modifications.

In various sequences disclosed herein, the modified and unmodified variants can optionally further comprise the sequence "TT", "dTdT", "dTsdT" or "UU" as a single-stranded overhang at the 3' end, also termed herein a terminal dinucleotide or 3' terminal dinucleotide. dT is 2'-deoxy-thymidine-5'-phosphate and sdT is 2'-deoxy Thymidine 5'-phosphorothioate. In the disclosed sequences, terminal dinucleotide "UU" is UU or 2'-OMe-U 2'-OMe-U, and the terminal TT and the terminal UU can be in the inverted/reverse orientation. The terminal dithymidine (e.g., UU) is not part of the APOC3 target sequence, but is a modified variant of the dithymidine dinucleotide commonly placed as an overhang to protect the ends of siRNAs from nucleases (see, for example, Elbashir et al. 2001 Nature 411: 494-498; Elbashir et al. 2001 EMBO J. 20: 6877-6888; and Kraynack et al. 2006 RNA 12:163-176). A terminal dinucleotide is known from these references to enhance nuclease resistance but not contribute to target recognition. Thus, the present disclosure also encompasses any modified or any unmodified variant disclosed herein, wherein the modified variant comprises a terminal TT, dTdT, sdT, dTsdT, sdTsdT, sdTdT, or the like which may be in either the inverted/reverse orientation or in the same 5' to 3' orientation as the APOC3 specific sequence in the duplex. In addition, terminology used herein referring to "the APOC3 portion of a RNAi agent sequence" and the like indicate the portion of the sequence of a RNAi agent which is derived from APOC3 (thus "the APOC3 portion of a RNAi agent sequence" does not include, for example, a terminal dTdT, TT, UU, U (2'-OMe) dT, U (2'-OMe) U (2'-OMe), T(2'-OMe) T (2'-OMe), T(2'-OMe) dT, or the like, but does include the portion of the RNAi agent that corresponds to or is complementary to a portion of the APOC3 gene sequence or mRNA sequence). In some embodiments, the composition comprises a RNAi agent comprising a first and a second strand, wherein the sequence of the first strand and the sequence of the second strand are the sequences of the first and second strand, respectively, of any RNAi agent provided herein, further comprising a 3' terminal dinucleotide (a single-stranded overhang comprising 2 nt at the 3' end). In some embodiments, the composition comprises a RNAi agent comprising a first and a second strand, wherein the sequence of the first strand and the sequence of the second strand are the sequences of the first and second strand, respectively, of any RNAi agent provided herein, further comprising a 3' terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT. In some embodiments, the composition comprises a RNAi agent comprising a first and a second strand, wherein the sequence of the first strand and the sequence of the second strand are the sequences of the first and second strand, respectively, of any RNAi agent provided herein, further comprising a 3' terminal UU dinucleotide.

On any modified or unmodified variant, a 3' end cap, as is known in the art, can be used instead of or in addition to a terminal dinucleotide to stabilize the end from nuclease degradation provided that the 3' end cap is able to both stabilize the RNAi agent (e.g., against nucleases) and not interfere excessively with siRNA activity. Thus, the present disclosure also encompasses any modified or any unmodified variant disclosed herein, wherein the modified variant further comprises a terminal 3' end cap.

An RNAi Agent Comprising an Antisense Strand of an RNAi Agent Described Herein.

In some embodiments, the present disclosure relates to a composition comprising an RNAi agent comprising an antisense strand, wherein the antisense strand comprises at least 14 contiguous nucleotides differing by 0, 1, 2, or 3 nucleotides from the antisense strand of an RNAi agent to APOC3 selected from those antisense strands in the specific duplexes provided herein.

Various aspects of some embodiments are described below.

In some embodiments, the composition further comprises a second RNAi agent to APOC3. In various aspects, the second RNAi agent is physically separate from the first, or the two are physically connected (e.g., covalently linked or otherwise conjugated).

In some embodiments, the composition comprises a RNAi agent to APOC3 comprising a first and a second strand, wherein the sequence of the first strand and the sequence of the second strand are the sequences of the first and second strand, respectively, of any RNAi agent provided herein. In some embodiments, the composition comprises a RNAi agent comprising a first and a second strand, wherein the sequence of the first strand and the sequence of the second strand are the sequences of the first and second strand, respectively, of any RNAi agent provided herein, further comprising an additional about 6 to 20 nucleotides on one or both strands (e.g., about 6, 7, 8, 9, 10, 11, 12, 13, 14, 15, 16, 17, 18, 19 or 20 nt). In some embodiments, the composition comprises a RNAi agent comprising a first and a second strand, wherein the sequence of the first strand and the sequence of the second strand are the sequences of the first and second strand, respectively, of any RNAi agent provided herein, further comprising a 3' terminal dinucleotide.

In some embodiments, the composition comprises a RNAi agent comprising a first and a second strand, wherein the sequence of the first strand and the sequence of the second strand are the sequences of the first and second strand, respectively, of any RNAi agent provided herein, further comprising a 3' terminal dinucleotide selected from TT, UU, U (2'-OMe) dT, U (2'-OMe) U (2'-OMe), T(2'-OMe) T (2'-OMe), T(2'-OMe) dT, dTdT, sdT, dTsdT, sdTsdT, and sdTdT. In some embodiments, the composition comprises a RNAi agent comprising a first and a second strand, wherein the sequence of the first strand and the sequence of the second strand are the sequences of the first and second strand, respectively, of any RNAi agent provided herein, further comprising a 3' terminal UU dinucleotide. In various aspects, the first and second strands are the sense and anti-sense strands listed herein, respectively. In various aspects, the first and second strands are the anti-sense and sense strands listed herein, respectively.

In some embodiments, the sense strand is about 30 or fewer nucleotides (nt) in length.

In some embodiments, the antisense strand is about 30 or fewer nucleotides in length.

In some embodiments, the antisense strand forms a duplex region with a sense strand, wherein the duplex region is about 15 to 30 nucleotide pairs in length.

In some embodiments, the antisense strand is about 15 to about 30 nucleotides in length, including 18, about 18, and about 19 to about 23 nucleotides in length. In some embodiments, the antisense strand has at least the length selected from about 15 nucleotides, about 16 nucleotides, about 17 nucleotides, 18 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides and 30 nucleotides. In various aspects, the anti-sense strand is a 17-, 18-, 19-, 20-, 21-, 22-, 23-, 24-, 25-, 26-, 27-, 28-, 29- or 30-mer.

In various aspects, the sense strand can be shorter than the anti-sense strand. In various aspects, the sense strand is a 14-, 15-, 16-, 17-, 18-, 19-, 20-, 21-, 22-, 23-, 24-, 25-, 26-, 27-, 28-, 29- or 30-mer.

In some embodiments, the RNAi agent comprises a modification that causes the RNAi agent to have increased stability in a biological sample or environment (e.g., cytoplasm, interstitial fluid, blood serum, or lung or intestinal lavage).

In some embodiments, the RNAi agent comprises at least one sugar backbone modification (e.g., phosphorothioate linkage) or at least one 2'-modified nucleotide.

In some embodiments, the RNAi agent comprises: at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide. These dinucleotide motifs are particularly prone to serum nuclease degradation (e.g. RNase A). Chemical modification at the 2'-position of the first pyrimidine nucleotide in the motif prevents or slows down such cleavage. This modification recipe is also known under the term 'endo light'.

In some embodiments, the RNAi agent comprises a 2'-modification selected from the group consisting of: 2'-deoxy, 2'-deoxy-2'-fluoro, 2'-O-methyl (2'-OMe or 2'OMe), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In some embodiments, all pyrimidines (uridine and cytidine) are 2' O-methyl-modified nucleosides.

In some embodiments, the RNAi agent comprises at least one blunt end.

In some embodiments, the RNAi agent comprises an overhang having 1 nt to 4 nt unpaired.

In some embodiments, the RNAi agent comprises an overhang at the 3'-end of the antisense strand of the RNAi agent.

In some embodiments, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

In some embodiments, the RNAi agent is capable of inhibiting expression of APOC3 by at least about 50% in Huh-7 cells in nude mice.

In some embodiments, the RNAi agent is capable of inhibiting expression of APOC3 by at least about 70% at a concentration of 10 nM in Huh-7 cells in vitro.

In some embodiments, the RNAi agent is capable of inhibiting expression of APOC3 by at least about 75% at a concentration of 10 nM in Huh-7 cells in vitro.

In some embodiments, the RNAi agent is capable of inhibiting expression of APOC3 by at least about 80% at a concentration of 10 nM in Huh-7 cells in vitro.

In some embodiments, the RNAi agent is capable of inhibiting expression of APOC3 by at least about 90% at a concentration of 10 nM in Huh-7 cells in vitro.

In some embodiments, the RNAi agent is capable of inhibiting expression of APOC3 by at least about 95% at a concentration of 10 nM in Huh-7 cells in vitro.

In some embodiments, the RNAi agent is capable of inhibiting expression of APOC3 by at least about 99% at a concentration of 10 nM in Huh-7 cells in vitro.

In some embodiments, the RNAi has an EC50 of no more than about 0.1 nM in Huh-7 cells in vitro. EC50 is effective concentration to reduce gene expression by 50%.

In some embodiments, the RNAi has an EC50 of no more than about 0.01 nM in Huh-7 cells in vitro.

In some embodiments, the RNAi has an EC50 of no more than about 0.001 nM in Huh-7 cells in vitro.

An RNAi Agent Comprising a Sense and Antisense Strand of an RNAi Described Herein.

In some embodiments aspect, the present disclosure relates to a composition comprising a RNAi agent comprising a first strand and a second strand, wherein the sequence of the first strand and/or second strand comprise at least 14 contiguous nucleotides, differing by 0, 1, 2, or 3 nucleotides from the sequence of the first and/or second strand of a RNAi agent to APOC3 selected from the specific duplexes provided herein.

In some embodiments, the present disclosure relates to a composition comprising a RNAi agent comprising a first strand and a second strand, wherein the sequence of the first strand and/or second strand comprise the sequence of the first and/or second strand, respectively, of a RNAi agent to APOC3 selected from the specific duplexes provided herein.

In some embodiments, the present disclosure relates to a composition comprising a RNAi agent comprising a first strand and a second strand, wherein the sequence of the first strand and/or second strand are the sequence of the first and/or second strand, respectively, of a RNAi agent to APOC3 selected from the specific duplexes provided herein.

In some embodiments, the present disclosure relates to a composition comprising a RNAi agent comprising a first strand and a second strand, wherein the sequence of the first strand and/or second strand are the sequence of the first and/or second strand, respectively, of a RNAi agent to APOC3 selected from the specific duplexes provided herein, wherein the sequence of the first and/or second strand further comprise a terminal dinucleotide.

In some embodiments, the present disclosure relates to a composition comprising a RNAi agent comprising a first strand and a second strand, wherein the sequence of the first strand and/or second strand are the sequence of the first and/or second strand, respectively, of a RNAi agent to APOC3 selected from the specific duplexes provided herein, wherein the sequence of the first and/or second strand further comprise a terminal UU dinucleotide.

In some embodiments, the present disclosure relates to a composition comprising an RNAi agent comprising a sense strand and an antisense strand, wherein the sense strand and antisense strand comprise at least 14 contiguous nucleotides differing by 0, 1, 2, or 3 nucleotides, from the sense and antisense strand, respectively, of an RNAi agent to APOC3 selected from the specific duplexes provided herein.

Various aspects of some embodiments are described below.

In some embodiments, the composition comprises a second RNAi agent to APOC3. In various aspects, the second RNAi agent is physically separate from the first, or the two are physically connected (e.g., chemically linked or otherwise conjugated). In some aspects, the first and second RNAi agents are combined within the same composition (e.g., both in the same lipid nanoparticle).

In some embodiments, the antisense strand is about 30 or fewer nucleotides in length.

In some embodiments, the sense strand and the antisense strand form a duplex region about 15 to about 30 nucleotide pairs in length.

In some embodiments, the antisense strand is about 15 to about 36 nt in length including about 18 to about 23 nt in length, and including about 19 to about 21 nt in length and about 19 to about 23 nt in length. In some embodiments, the antisense strand has at least the length selected from about 15 nt, about 16 nt, about 17 nt, 18, about 18 nt, about 19 nt, about 20 nt, about 21 nt, about 22 nt, about 23 nt, about 24 nt, about 25 nt, about 26 nt, about 27 nt, about 28 nt, about 29 nt and about 30 nt. In various aspects, the anti-sense strand is a 17-, 18-, 19-, 20-, 21-, 22-, 23-, 24-, 25-, 26-, 27-, 28-, 29- or 30-mer.

In various aspects, the sense strand can be shorter than the anti-sense strand. In various aspects, the sense strand is a 14-, 15-, 16-, 17-, 18-, 19-, 20-, 21-, 22-, 23-, 24-, 25-, 26-, 27-, 28-, 29- or 30-mer.

In some embodiments, the RNAi agent comprises a modification that causes the RNAi agent to have increased stability in a biological sample or environment.

In some embodiments, the RNAi agent comprises a modified sugar backbone such as, e.g., a phosphorothioate linkage, or comprises a 2'-modified nucleotide.

In some embodiments, the RNAi agent comprises: at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; or at least one 5'-uridine-uridine-3' (5'-uu-3') dinucleotide, wherein the 5'-uridine is a 2'-modified nucleotide.

In some embodiments, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA). In some embodiments, all pyrimidines (uridine and cytidine) are 2' O-methyl-modified nucleosides.

In some embodiments, the RNAi agent comprises at least one blunt end.

In some embodiments, the RNAi agent comprises an overhang having 1 to 4 nt unpaired.

In some embodiments, the RNAi agent comprises an overhang at the 3'-end of the antisense strand of the RNAi agent.

In some embodiments, the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

A Method of Treatment Using a Composition Comprising a RNAi Agent Described Herein.

In some embodiments, the present disclosure relates to a method of treating an APOC3-related disease in an individual, comprising the step of administering to the individual a therapeutically effective amount of a composition comprising an RNAi agent comprising an antisense strand, wherein the antisense strand comprises at least 14 contiguous nucleotides differing by 0, 1, 2, or 3 nucleotides from the antisense strand of an RNAi agent to APOC3 selected from those specific duplexes provided above and as listed in any of the tables herein. In some embodiments, the RNAi agent to APOC3 comprises an antisense strand duplexed with a sense strand, wherein the sense and antisense strands are selected from one or more of the sequences provided in any of the tables herein.

Various aspects of some embodiments are described below. Any aspects disclosed herein that are not mutually exclusive can be combined.

In some embodiments, the present disclosure relates to such a method, wherein the composition comprising a RNAi agent further comprises a sense strand, wherein the sense strand comprises at least 14 contiguous nucleotides differing by 0, 1, 2, or 3 nucleotides from the sense strand of a RNAi agent to APOC3 selected from the specific duplexes provided herein and as listed, e.g., in any Table herein.

In some embodiments of the method, the RNAi agent comprises at least an anti-sense strand, and/or comprises a sense and an anti-sense strand, wherein the sequence of the sense and/or anti-sense strand is the sequence of the sense and/or the anti-sense strand of a RNAi agent to APOC3 selected from those specific duplex provided herein and as listed, e.g., in Tables 1-3, wherein the composition further comprises a pharmaceutically effective formulation.

In some embodiments of the method, the RNAi agent comprises at least an anti-sense strand, and/or comprises a sense and an anti-sense strand, wherein the sequence of the sense and/or anti-sense strand comprises the sequence of the sense and/or the anti-sense strand of a RNAi agent to APOC3 selected from those specific duplex provided herein and as listed, e.g., in any of the tables herein, wherein the composition further comprises a pharmaceutically effective formulation.

In some embodiments, the APOC3-related disease is selected from hypertriglyceridemia (e.g., Type V Hypertriglyceridemia), abnormal lipid metabolism, abnormal cholesterol metabolism, atherosclerosis, hyperlipidemia, diabetes, including Type 2 diabetes, obesity, cardiovascular disease, and coronary artery disease, among other disorders relating to abnormal metabolism or otherwise.

In some embodiments, the method further comprises the step of administering an additional treatment.

In some embodiments, the additional treatment is a method (or procedure). In some embodiments, the additional treatment is a therapeutically effective dose of a composition.

In some embodiments, the additional treatment and the RNAi agent can be administered in any order, or can be administered simultaneously.

In some embodiments, the method further comprises the step of administering an additional treatment for an APOC3-related disease.

In some embodiments, the method further comprises the step of administering an additional treatment. A RNAi agent to APOC3 can be used in conjunction with any additional treatment disclosed herein, as appropriate for the disease, optionally, in further conjunction with one or more additional RNAi agents to APOC3.

It will be understood that references to any additional treatment are meant to also include the pharmaceutically acceptable salts of any of the active substances. If active substances comprised by components (a) and/or (b) have, for example, at least one basic center, they can form acid addition salts. Corresponding acid addition salts can also be formed having, if desired, an additionally present basic center. Active substances having an acid group, e.g., COOH, can form salts with bases. The active substances comprised in components (a) and/or (b) or a pharmaceutically acceptable salts thereof may also be used in form of a hydrate or include other solvents used for crystallization.

In some embodiments, the composition comprises a second RNAi agent to APOC3. In various aspects, the second RNAi agent is physically distinct from the first, or the two are physically connected (e.g., linked or conjugated). In some aspects, the first and second RNAi agents are combined within the same composition (e.g., both in the same lipid nanoparticle).

A Method of Inhibiting the Expression of APOC3, Using an RNAi Composition Comprising an RNAi Agent Described Herein.

In some embodiments, the present disclosure relates to a method of inhibiting the expression of APOC3 in an individual, comprising the step of administering to the individual a therapeutically effective amount of a composition comprising an RNAi agent of the disclosure. In some embodiments, the RNAi agent comprises a sense strand and an antisense strand, wherein the antisense strand comprises at least 14 contiguous nucleotides differing by 0, 1, 2, or 3 nucleotides from the antisense strand of an RNAi agent to APOC3 selected from those specific duplexes provided above and as listed in any of the tables herein.

In some embodiments of the method, the RNAi agent comprises at least an anti-sense strand, and/or comprises a sense and an anti-sense strand, wherein the sequence of the sense and/or anti-sense strand is the sequence of the sense and/or the anti-sense strand of a RNAi agent to APOC3 selected from those specific duplex provided herein and as listed, e.g., in any of the tables herein, wherein the composition is in a pharmaceutically effective formulation.

In some embodiments of the method, the RNAi agent comprises at least an anti-sense strand, and/or comprises a sense and an anti-sense strand, wherein the sequence of the sense and/or anti-sense strand comprises the sequence of the sense and/or the anti-sense strand of a RNAi agent to APOC3 selected from those specific duplex provided herein and as listed, e.g., in any of the tables herein, wherein the composition is in a pharmaceutically effective formulation.

Various aspects of some embodiments are described below.

In some embodiments, the individual is afflicted with or susceptible to an APOC3-related disease.

In some embodiments, the APOC3-related disease is selected from hypertriglyceridemia (e.g., Type V Hypertriglyceridemia), abnormal lipid metabolism, abnormal cholesterol metabolism, atherosclerosis, hyperlipidemia, diabetes, including Type 2 diabetes, obesity, cardiovascular disease, and coronary artery disease, among other disorders relating to abnormal metabolism or otherwise.

In some embodiments, the method further comprises the step of administering an additional treatment.

In some embodiments, the additional treatment and the RNAi agent can be administered in any order or can be administered simultaneously.

In some embodiments, the method further comprises the step of administering an additional treatment for an ApoC3 condition such as hypertriglyceridemia (e.g., Type V Hypertriglyceridemia), abnormal lipid metabolism, abnormal cholesterol metabolism, atherosclerosis, hyperlipidemia, diabetes, including Type 2 diabetes, obesity, cardiovascular disease, and coronary artery disease, among other disorders relating to abnormal metabolism or otherwise.

In some embodiments, the composition comprises a second RNAi agent to APOC3. In various aspects, the second RNAi agent is physically separate from the first, or the two are physically connected (e.g., covalently linked or otherwise conjugated). In some aspects, the first and second RNAi agents are combined within the same composition (e.g., both in the same lipid nanoparticle).

In some embodiments, the method further comprises the step of administering an additional RNAi agent which comprises at least 14 contiguous nucleotides differing by 0, 1, 2, or 3 nucleotides from the antisense strand of a RNAi agent to APOC3 selected from the specific duplexes provided herein and as listed, e.g., in any Table herein.

Pharmaceutical Compositions of a RNAi Agent to APOC3

In some embodiments, the present disclosure relates to a composition comprising a RNAi agent of the present disclosure. In some embodiments, the RNAi agent comprises at least an anti-sense strand, and/or comprises a sense and an anti-sense strand, wherein the anti-sense strand comprises at least 14 contiguous nucleotides differing by 0, 1, 2, or 3 nucleotides from the anti-sense strand of a RNAi agent to APOC3 selected from those specific duplex provided herein and as listed, e.g., in any of the tables herein, wherein the composition is in a pharmaceutically effective formulation.

In some embodiments, the RNAi agent comprises at least an anti-sense strand, and/or comprises a sense and an anti-sense strand, wherein the sequence of the sense and/or anti-sense strand is the sequence of the sense and/or the anti-sense strand of a RNAi agent to APOC3 selected from those specific duplex provided herein and as listed, e.g., in any of the tables herein, wherein the composition is in a pharmaceutically effective formulation.

In some embodiments, the RNAi agent comprises at least an anti-sense strand, and/or comprises a sense and an anti-sense strand, wherein the sequence of the sense and/or anti-sense strand comprises the sequence of the sense and/or the anti-sense strand of a RNAi agent to APOC3 selected from those specific duplex provided herein and as listed, e.g., in any of the tables herein, wherein the composition is in a pharmaceutically effective formulation.

In some embodiments, the present disclosure pertains to the use of a RNAi agent in the manufacture of a medicament for treatment of an APOC3-related disease, wherein the RNAi agent comprises a sense strand and an antisense strand, wherein the antisense strand comprises at least 14 contiguous nucleotides differing by 0, 1, 2, or 3 nucleotides from the antisense strand of a RNAi agent to APOC3 selected from those specific duplex provided herein and as listed, e.g., in any Table herein.

Specific Aspects of RNAi Agents to APOC3 Comprising Mismatches from the Disclosed Sequences Various specific aspects of a RNAi agent to APOC3 are disclosed herein. The present disclosure encompasses the example modified variants provided in any of the tables herein, and the corresponding unmodified sequences and other modified variants. Specific aspects of the present disclosure include RNAi agents which comprise sequences differing by 0, 1, 2, or 3 nt (nucleotides) or bp [basepair(s)] (e.g., with 0, 1, 2 or 3 mismatches) from any of the RNAi agents listed in any of the tables herein, and modified and unmodified variants thereof. As described in additional detail below, a mismatch is defined herein as a difference between the base sequence (e.g., A instead of G) or length when two sequences are maximally aligned and compared. In addition, as described in more detail below, an "unmodified variant" is a variant in which the base sequence is identical, but none of the bases are modified; this includes, for example, a sequence identical to the corresponding portion of the wild-type APOC3 mRNA or gene. A "modified variant" contains one or more modifications (or one or more fewer or different modifications) to a nucleotide, sugar, phosphate or backbone, and/or addition of one or more moieties; but without a change, substitution, addition, or deletion to the base sequence. A particular sequence and its modified or unmodified variants have 0 mismatches among them.

In some embodiments, the present disclosure comprises a RNAi agent comprising a sense and an anti-sense strand, wherein the sense and/or anti-sense strand comprises at least 14 contiguous nucleotides differing by 0, 1, 2, or 3 nt from the sequence of the sense and/or anti-sense strand of: any of the RNAi agents listed in any of the tables herein, and modified and unmodified variants thereof.

In another particular aspect, the RNAi agent comprises a sense strand comprising at least 14 contiguous nucleotides differing by 0, 1, 2, or 3 nt from the sense strand of any of the RNAi agents listed in any of the tables herein, and modified and unmodified variants thereof.

Other Aspects

Various aspects of this disclosure are described below. Any aspects disclosed herein that are not mutually exclusive can be combined.

In some embodiments, the disclosure pertains to a composition according to any of the above aspects, for use in a method of treating an APOC3-related disease in an individual, the method comprising the step of administering to the individual a therapeutically effective amount of a composition according to any of the claims.

Various aspects of some embodiments are described below.

In some embodiments, the disclosure pertains to the composition according to any of the above aspects, for use in a method of inhibiting the expression of APOC3 in an individual, the method comprising the step of administering to the individual a therapeutically effective amount of a composition according to any of the above aspects.

Some embodiments of the disclosure is the use of a composition according to any of the above aspects, in the manufacture of a medicament for treatment of an APOC3-related disease.

In some embodiments, the APOC3-related disease is selected from any disease listed herein.

In some embodiments, the disclosure pertains to the composition of any of the above aspects, for use in the treatment of an APOC3-related disease.

In some embodiments, the APOC3-related disease is selected from any disease listed herein.

In some embodiments, the disclosure relates to a method of inhibiting the expression of APOC3 in an cell, comprising the step of introducing into the cell a composition comprising an RNAi agent comprising an antisense strand, wherein the antisense strand comprises at least 14 contiguous nucleotides differing by 0, 1, 2, or 3 nucleotides from the antisense strand of an RNAi agent to APOC3 selected from the APOC3 siRNAs disclosed herein.

In some embodiments, the disclosure relates to a method of inhibiting the expression of APOC3 in an cell, comprising the step of introducing into the cell a composition comprising an RNAi agent comprising a sense strand and an antisense strand, wherein the antisense strand comprises at least 14 contiguous nucleotides differing by 0, 1, 2, or 3 nucleotides from the antisense strand, and the sense strand comprises at least 14 contiguous nucleotides differing by 0, 1, 2, or 3 nucleotides from the sense strand of an RNAi agent to APOC3 selected from the APOC3 siRNAs disclosed herein.

Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

APOC3-Related Diseases siRNAs to APOC3 can be used to treat APOC3-related diseases. An "APOC3-related disease" is any disease associated with APOC3 and/or a mutation and/or an over-expression of a wild-type and/or mutant APOC3, and/or diseases wherein disease progression is enhanced by or prognosis worsened by the presence of APOC3 and/or a mutation and/or an over-expression of wild-type and/or mutant APOC3. Non-limiting examples of APOC3-related diseases include: hypertriglyceridemia (e.g., Type V Hypertriglyceridemia), abnormal lipid metabolism, abnormal cholesterol metabolism, atherosclerosis, hyperlipidemia, diabetes, including Type 2 diabetes, obesity, cardiovascular disease, and coronary artery disease, among other disorders relating to abnormal metabolism or otherwise.

In various aspects, the present disclosure pertains to the use of APOC3 RNAi agents in inhibiting and/or reducing the level and/or activity of APOC3, for treatment of APOC3-related diseases, particularly those diseases in which the level and/or activity of APOC3 is excessive. Such diseases include hypertriglyceridemia (e.g., Type V Hypertriglyceridemia), abnormal lipid metabolism, abnormal cholesterol metabolism, atherosclerosis, hyperlipidemia, diabetes, including Type 2 diabetes, obesity, cardiovascular disease, and coronary artery disease, among other disorders relating to abnormal metabolism or otherwise.

Thus, the present disclosure encompasses APOC3 RNAi agents and the uses thereof for APOC3-related diseases.

Use of APOC3 RNAi Agents to Treat APOC3-Related Diseases

In various aspects, the present disclosure pertains to the use of APOC3 RNAi agents, which inhibit and/or decrease the level and/or activity of APOC3, to treat APOC3-related diseases.

In earlier studies, inhibiting or decreasing the level and/or activity of APOC3 have been shown to be effective in treatment of APOC3 related diseases.

APOC3 RNAi Agent for Use in Treating Various APOC3-Related Diseases

In some embodiments, the APOC3 RNAi agent of the present disclosure comprises a sequence disclosed herein and is administered to a patient in need thereof (e.g., a patient suffering from an APOC3-related disease disclosed herein or known in the literature). In some embodiments, the APOC3 RNAi agent of the present disclosure is administered to a patient in need thereof, along with one or more additional pharmaceutical agent appropriate for that disease. For example, a patient suffering from an APOC3-related disease can be administered a pharmacologically effective amount of one or more APOC3 RNAi agent along with a pharmacologically effective amount of one or more of any APOC3-related disease treatment listed herein, and/or any other APOC3-related disease treatment known in the art.

A patient suffering from an APOC3-related disease can be administered one or more RNAi agents to APOC3 and one or more additional APOC3-related disease treatments. This one or more additional treatments can be selected from the list of any disease treatment listed herein, and/or any anti-APOC3-related disease treatment known in the art.

The APOC3 RNAi agents of the instant disclosure can be administered along with (as part of the same therapeutic treatment regimen, prior to, simultaneously with, or after) one or more additional therapeutics to treat an APOC3-related disease. These one or more additional therapeutics can be selected from: iron administration, chelation therapy, phlebotomy, erythropoiesis stimulating agent (ESA) (e.g., Epoetin alfa or darbepoetin alfa), anti-APOC3 antibody, hemodialysis, and hyperbaric oxygen.

The patient can also be administered more than one RNAi agent to APOC3.

In the case of APOC3-related diseases, the RNAi agent(s) and additional disease treatment(s) can be administered in any order, simultaneously or sequentially, or in multiple doses over time. Administration of the RNAi agent and the additional treatment can be, for example, simultaneous, concurrent, separate or sequential.

Simultaneous administration may, e.g., take place in the form of one fixed combination with two or more active ingredients, or by simultaneously administering two or more active ingredients that are formulated independently. Sequential use (administration) preferably means administration of one (or more) components of a combination at one time point, other components at a different time point, that is, in a chronically staggered manner, preferably such that the combination shows more efficiency than the single compounds administered independently (especially showing synergism). Separate use (administration) preferably means administration of the components of the combination independently of each other at different time points, preferably meaning that the components (a) and (b) are administered such that no overlap of measurable blood levels of both compounds are present in an overlapping manner (at the same time).

Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

The term "delay of progression" as used herein means administration of the combination to patients being in a pre-stage or in an early phase, of the first manifestation or a relapse of the disease to be treated, in which patients, e.g., a pre-form of the corresponding disease is diagnosed or which patients are in a condition, e.g., during a medical treatment or a condition resulting from an accident, under which it is likely that a corresponding disease will develop.

"Jointly therapeutically active" or "joint therapeutic effect" means that the compounds may be given separately (in a chronically staggered manner, especially a sequence-specific manner) in such time intervals that they preferably, in the warm-blooded animal, especially human, to be treated, still show a (preferably synergistic) interaction (joint therapeutic effect). Whether this is the case, can inter alia be determined by following the blood levels, showing that both compounds are present in the blood of the human to be treated at least during certain time intervals.

Methods of Identifying APOC3 RNAi Agents

Any method known in the art can be used to identify efficacious APOC3 RNAi agents useful for treating APOC3-related diseases. A few non-limiting examples of such methods are disclosed herein. Any one or more of the following, in addition to other methods known in the art, can be used.

For example: In various steps, APOC3 RNAi agents are tested for efficacy and tolerance to modifications and modification from 19-mer to 18-mer format.

For example: APOC3 RNAi candidates can be tested by target knockdown in Huh7 cells and primary hepatocytes. This can be tested using any method known in the art, including but not limited to RNAi Max. Preferably, the RNAi candidate demonstrates at least about 80% mRNA knockdown at 48 hours. The mechanism can optionally be confirmed to be RNAi (RNA interference) by identifying specific cleavage products using RACE.

Cross-reactivity with cyno monkeys can be assessed in primary cyno hepatocytes at 48 hours. Optionally, the IC50 can be within five-fold of human siRNA activity.

Off-target effects of the candidate APOC3 RNAi agent can be assessed. For example, cell growth in non-ApoC3-expressing cells can be tested. Preferably, there is no effect relative to, for example, YFP siRNA.

Immune stimulation by the candidate RNAi agent can be tested using whole blood assay. Preferably, there would be no detectable activation of cytokine expression.

Toxicity can also be assessed. MTD (maximum tolerated dosage) can be assessed in mice. A Mini-tox study can be performed for 2 weeks. Optionally, a conjugate can be used.

Efficacy in animal models can be assessed. For example, a conjugate can be used to deliver mouse ApoC3 siRNA to liver and effectively knockdown the target. Preferably, the mRNA knockdown will be at least about 80% at 96 hours.

Efficacy in cyno monkeys can also be tested.

PK (pharmacokinetics) and bio-distribution of formulated RNAi agents can be tested, for example, in rodents, using, for example, LNP (lipid nanoparticle)-formulated RNAi agents. Preferably, the RNAi targets the liver.

These examples are meant to be non-limiting examples of methods that can be used to test candidate or potential APOC3 RNAi agents.

These and other methods known in the art and/or known or available to one of ordinary skill can be used to test candidate APOC3 RNAi agents.

ApoC3 RNAi Agent Candidate Chemistry Optimization

In particular, several steps can be performed for optimizing the chemistry of the lead(s) APOC3 RNAi agent(s):

APOC3 sequences are identified, including various lead sequences. Serum stability highlights the 5' terminal U as a fragile site.

Tolerance for chemical modification is assessed. Many APOC3 sequences appear to be the tolerant for chemical modification. Indirect evidence shows that 5' dT vs 5'U does stabilize the 5' end of the guide strand. No "more modified" format did improve potency.

The 3' overhang is optimized, e.g., PAZ ligands are screened.

Passenger strand optimization is done. For example, this was done using the asymmetrical design.

Internal modifications for stabilization are assessed. For example, chemical stabilization at the cleavage sites is tested.

These and other tests available or known to one of ordinary skill in the art can be used to evaluate and modify the chemistry of a candidate APOC3 RNAi agent.

APOC3 RNAi Agent Candidate Selection

The instant disclosure pertains to RNAi agents to APOC3 for use in treating APOC3-related diseases. In some embodiments, these agents have various structural properties, such as having an 18-mer sequence. Optionally, the agent is modified, including but not limited to, modifications of one or more sugar or phosphate, and with, in 3' order, a linker and a 3' end cap. The 5' and/or 3' end of the sense strand can be conjugated to other components which increase targeting to and/or uptake by the liver.

The disclosure also pertains to compositions comprising the RNAi agent to APOC3 and, for example, an excipient or pharmaceutically acceptable carrier.

The APOC3 mRNA is unusually short, thus leaving only a small room for siRNA design, and very small room for pan-specific siRNAs (those which target both humans and one or more test animals).

In this work, using the human sequence, 419 possible 19-mer APOC3 RNAi agents were identified.

A subset of these were selected and tested. These sequences are shown in Table 1 (as DNA 19-mers) and Table 2 (as RNA 19-mers).

Various APOC3 RNAi Agents

As noted above, the disclosure thus relates to compositions comprising an APOC3 RNAi agent. These comprise a first strand and a second strand, wherein the sequence of the first and/or second strand is, comprises, comprises 15 contiguous nt of, or comprises 15 contiguous nt of (with 1-3 mismatches from) any sequence of any APOC3 RNAi agent listed herein. In some embodiments, the disclosure pertains to an APOC3 RNAi agent comprising a first and second strand, wherein the sequence of the first and/or second strand is, comprises, or comprises 15 contiguous nt of any sequence of any APOC3 RNAi agent disclosed herein, except that one or both strands is nicked and/or one or more nt of the sequence disclosed herein has been replaced by a spacer (e.g., the first comprises the sequence of nt 1-5 and 7-18, or of 1-4 and 6-18 of a sequence disclosed herein). These APOC3 RNAi agents can be of any format described herein or known in the art. These include the 18-mer format, the 19-mer format, the internal spacer format, the shortened sense strand format, a format comprising a nicked strand, or any other format or length of RNAi agent known in the art. RNAi agents of the various formats can comprise strands of various lengths, one or more spacer, modified internucleoside linker, and 3' end cap. RNAi agents of the 18-mer format, for example, comprise a sense and an anti-sense strand, each strand being an 18-mer and the strands together forming a blunt-ended duplex, wherein the 3' end of at least one strand terminates in a phosphate or modified internucleoside linker and further comprises, in 5' to 3' order: a spacer; a second phosphate or modified internucleoside linker; and a 3' end cap. In some embodiments, the 3' end of both the sense and anti-sense strand further comprise, in 5' to 3' order: a spacer; a second phosphate or modified internucleoside linker; and a 3' end cap. The two strands can have the same or different spacers, phosphate or modified internucleoside linker, and/or 3' end caps. In various embodiments, one or more nt can be modified and/or substituted. Various formats, spacers, modified internucleoside linkers and 3' end caps are described below.

Various Formats of RNAi AGENTS: 18-Mer Format

The present disclosure contemplates a variety of different formats for APOC3 RNAi agents, including various formats using any APOC3 RNAi agent sequence disclosed herein.

A particular novel format, designated the 18-mer format, has been developed. This and any other format can be used for an APOC3 RNAi agent.

siRNAs naturally generated in a cell by Dicer typically comprise two 21-nt RNA strands, which form a 19-bp duplex region and two dinucleotide overhangs. This is the so-called "canonical" siRNA structure. (See, for example, Elbashir et al. 2001 Nature 411: 494-498; Elbashir et al. 2001 EMBO J. 20: 6877). This is the so-called "canonical" structure or "21-mer" format of siRNAs.

The two dinucleotide overhangs do not contribute to target specificity. (Elbashir et al. 2001 Nature 411: 494-498; Elbashir et al. 2001 EMBO J. 20: 6877-6888; and Kraynack et al. 2006 RNA 12:163-176). They do, however, help protect the ends of the siRNA from nuclease degradation and sometimes improve activity. However, these di-nucleotides can optionally be replaced by 3' end caps. Ideal 3' end caps allow RNA interference activity, while increasing stability, e.g., against nucleases such as those in blood serum or intestinal fluid. (U.S. Pat. Nos. 8,097,716; and 8,084,600). Novel 3' end caps (some described as "PAZ ligands") are disclosed herein; these can be used in place of or in addition to a 3' end cap in APOC3 RNAi agents. It is noted that, although some 3' end caps are designated "PAZ ligands", this disclosure is not bound by any particular theory.

As noted above, the canonical siRNA structure comprises two strands, each a 19-mer with a 2 nt overhang. Strands of shorter length, e.g., 18-mers, are less commonly produced by a cell.

While a few 18-mer RNAi agents have shown to have efficacy, many do not. Disclosed herein in some embodiments is a 18-mer format shown to be efficacious in producing functional RNAi agents to a variety of different targets, with a variety of different sequences.

In some embodiments, the disclosure thus relates to compositions comprising an APOC3 RNAi agent having a novel format (the "18-mer format"). These RNAi agents comprise a sense and an anti-sense strand, each strand being an 18-mer and the strands together forming a blunt-ended duplex, wherein the 3' end of at least one strand further comprises, in 5' to 3' order: a spacer; a phosphate or modified internucleoside linker; and a 3' end cap. In some embodiments, each strand terminates at the 5' end with a hydroxyl, optionally linked to a 5' end cap or a ligand, and terminates at the 3' end with a phosphate or modified internucleoside linker. In some embodiments, the 3' end of both the sense and anti-sense strand further comprise, in 5' to 3' order: a spacer; a phosphate or modified internucleoside linker; and a 3' end cap. The two strands can have the same or different spacers, phosphate or modified internucleoside linker, and/or 3' end caps. The strands can be ribonucleotides, or, optionally, one or more nucleotide can be modified or substituted. Optionally, at least one nucleotide comprises a modified internucleoside linker. Optionally, the RNAi agent can be modified on one or both 5' end. Optionally, the sense strand can comprise a 5' end cap which reduces the amount of the RNA interference mediated by this strand. Optionally, the RNAi agent is attached to a ligand. The disclosure also relates to processes for making such compositions, and methods and uses of such compositions, e.g., to mediate RNA interference.

In one embodiment, the 3' end of both the sense and anti-sense strand terminate in a phosphate or modified internucleoside linker and further comprise in 5' to 3' order: a spacer, a phosphate or modified internucleoside linker, and a 3' end cap.

In various embodiments, the spacer is a sugar, alkyl, cycloakyl, ribitol or other type of abasic nucleotide, 2'-deoxy-ribitol, diribitol, 2'-methoxyethoxy-ribitol (ribitol with 2'-MOE), C3, C4, C5, C6, or 4-methoxybutane-1,3-diol (5300). In various embodiments, the spacers on the sense and anti-sense strands can be the same or different.

In various embodiments, the modified internucleoside linker is selected from phosphorothioate, phosphorodithioate, phosphoramidate, boranophosphonoate, an amide linker, and a compound of formula (I):

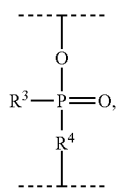

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$. The internucleoside linker of formula (I) can be used in any RNAi agent of any format, e.g., any APOC3 RNAi agent disclosed herein of any format disclosed herein.

RNAi Agent Format: Internal Spacer

As noted above, the present disclosure contemplates a variety of different formats for APOC3 RNAi agents, including various formats using any APOC3 RNAi agent sequence disclosed herein.

A particular novel format, designated the internal spacer, has been developed.

In this format, one or more nucleoside subunits ([sugar+base]) of one or both strands has been replaced by a spacer. In various embodiments, the nucleobase subunit ([sugar+base]) replaced by a spacer is at position 1, 3, 5, 6, 7, 15, 16, 17, or 18 (counting 5' to 3'). In various embodiments, the nucleobase subunit ([sugar+base]) replaced by a spacer is at position 5, 6, or 17 (counting 5' to 3'). In various embodiments, the spacer can be sugar, alkyl, cycloakyl, ribitol or other type of abasic nucleotide, 2'-deoxy-ribitol, diribitol, 2'-methoxyethoxy-ribitol (ribitol with 2'-MOE), C3, C4, C5, C6, or 4-methoxybutane-1,3-diol (5300), or any other spacer described herein or known in the art. More than one different type of spacer can be incorporated into the same composition.

The internal spacer format can be combined with other formats. For example, the internal spacer format can be combined with the 19-mer format. This produces a RNAi agent comprising a first strand and a second strand, wherein the first and second strand each comprise a 19-mer (optionally further comprising a 3' end and/or 3' terminal dinucleotide), wherein one or more nucleoside subunits of the first and/or second strand are replaced by a spacer.

The internal spacer format can also be combined, for example, with the 18-mer format. For example, the APOC3 RNAi agent can comprise a first and a second strand, wherein the both strands are 18-mers, and wherein the first strand is the anti-sense strand and a nucleoside subunit ([consisting of a sugar and base]) at any of positions 1 to 18 is replaced by a spacer. One or more nucleoside subunits can be replaced. Alternatively, one or more nucleoside subunits on the first and/or second strand can be replaced by a spacer.

Non-limiting examples of APOC3 RNAi agents having an internal spacer format are described herein.

This disclosure also pertains to any RNAi agent of any sequence, targeting any target, which has the internal spacer format. For example, if the anti-sense strands of two different duplexes are identical except that, at one position, the nucleobase unit (i.e., sugar+base) has been replaced by a spacer (e.g., a spacer described herein), the sequences are considered to have one mismatch (e.g., to differ by 1 nt). Thus, a first sequence comprising at least 14 contiguous nt differing by 0, 1, 2 or 3 nt from a second sequence can have any combination of 0, 1, 2 or 3 internal spacer, substitution, and/or other position wherein the base at one sequence does not match the corresponding base at the other sequence.

This disclosure also notes that, for the purposes of counting mismatches between sequences, the replacement of a nt with a spacer would count as a mismatch.

RNAi Agent Format: Shortened Sense Strand

As noted above, the present disclosure contemplates a variety of different formats for APOC3 RNAi agents, including various formats using any APOC3 RNAi agent sequence disclosed herein.

A particular novel format, designated the shortened sense strand, has been developed.

In various embodiments, the APOC3 RNAi agent comprises an anti-sense and a sense strand, wherein the sense strand has been shortened. In various embodiments, the sense strand is a 14-, 15-, 16-, or 17-mer.

The shortened sense strand format can be combined with any RNAi agent format known. This includes but is not limited to the 18-mer format.

For example, an APOC3 RNAi agent can comprise an anti-sense strand which is an 18-mer (or longer), and a sense strand which is a 14-, 15-, 16-, or 17-mer. The anti-sense strand can be an 18-, 19-, 20, 21-, 22-, 23-, 24-, 25-, 26-, 27-, 28-, 29-, or 30-mer or longer. The 3' terminus of the anti-sense and/or sense strand can optionally terminate a phosphate or modified internucleoside linker and further comprise: (a) a 3' end cap; or (b) a spacer, a second phosphate or modified internucleoside linker, and a 3' end cap (in 5' to 3' order). The spacer, modified internucleoside linker and 3' end cap can be any of those elements detailed herein or known in the art. A RNAi agent of the shortened sense strand format can comprise RNA subunits (ribonucleotides) wherein one or more ribonucleotides is modified and/or substituted by any modification or substitution described herein or known in the art.

The efficacy of various APOC3 RNAi agents having a shortened sense strand format is shown herein.

The disclosure also pertains to a RNAi agent of any sequence, targeting any gene target, which has a shortened sense strand format.

Components of APOC3 RNAi Agents

As noted above, APOC3 RNAi agents can pertain to sequences disclosed herein, and be of any of several formats described herein or known in the art.

Components of these various RNAi agents include different 3' end caps, spacers, and modified internucleoside linkers. Components can be mixed and matched.

These components are described in additional detail below.

3' End Caps

Various formats, each useful for producing an APOC3 RNAi agent comprise a 3' end cap. One or both strands of an APOC3 RNAi agent can comprise, at the 3' terminus: a 3' end cap; or a spacer, a phosphate or internucleoside linker, and a 3' end cap.

Any of the various 3' end caps disclosed herein or known in the art can be used to prepare an APOC3 RNAi agent. In various embodiments, the 3' end cap is selected from those represented by formula Ia or Ib, disclosed in Tables 5A, 5B, 5C, 5D, 5E, or otherwise described herein. In various embodiments, the 3' end caps on the sense and anti-sense strands can be the same or different.

In one embodiment, the 3' end cap encompasses a compound of formula Ia:

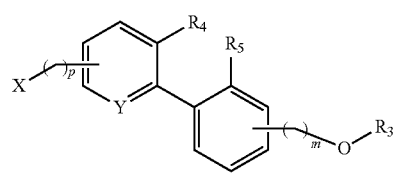

Ia in which:

X is a 3' end of molecule comprising: a strand of an APOC3 RNAi agent, wherein the 3' end of the strand terminates in a phosphate or modified internucleoside linker and optionally further comprises, in 5' to 3' order: a spacer and a second phosphate or modified internucleoside linker;

Y is selected from CH and N;

m is selected from 0 and 1;

p is selected from 1, 2 and 3;

$R_3$ is selected from hydrogen, 2-(hydroxy-methyl)-benzyl, 3-(hydroxy-methyl)-benzyl and succinate; or is attached to a solid support; wherein the $(CH_2)_m$—O—$R_3$ moiety is attached to the phenyl ring at position 3 or 4;

$R_4$ is hydrogen;

$R_5$ is hydrogen; or $R_4$ and $R_5$, together with the phenyl rings to which $R_4$ and $R_5$ are attached, form 6H-benzo[c]chromene.

In various embodiments, the 3' end cap encompasses a compound selected from Table 5A.

TABLE 5A

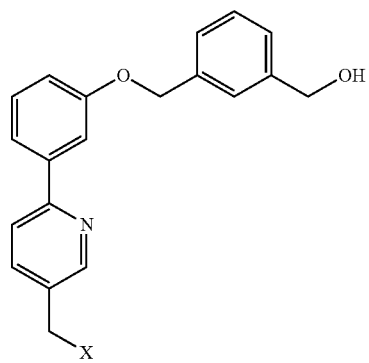

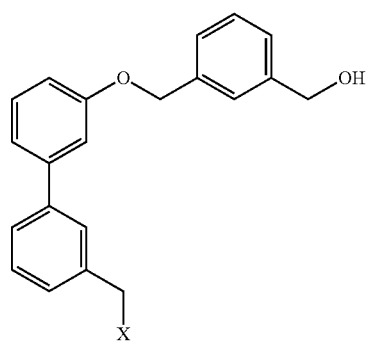

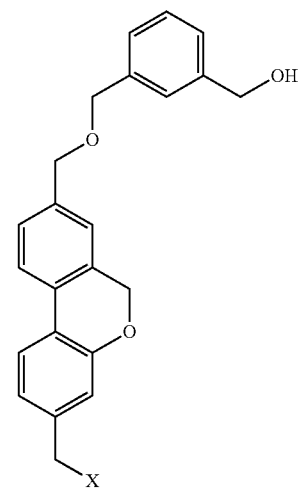

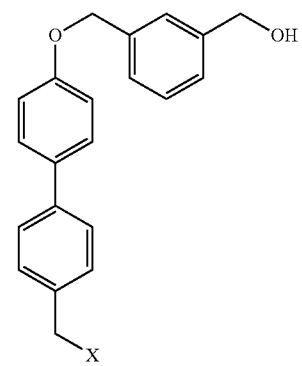

TABLE 5A-continued
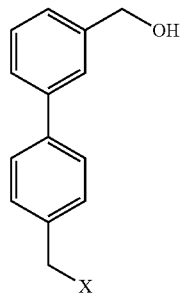
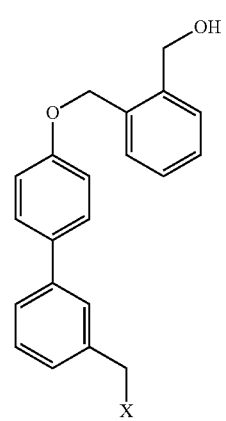
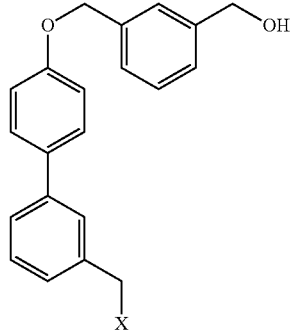
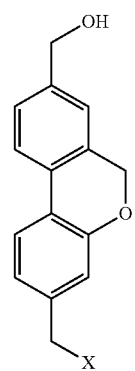
TABLE 5A-continued
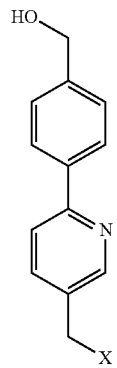
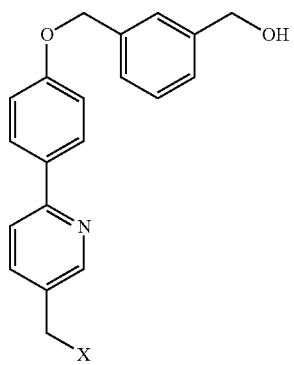
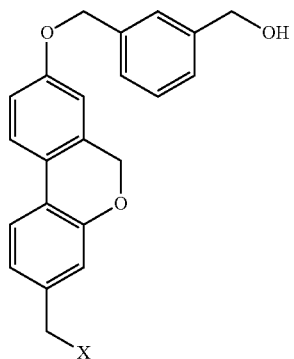
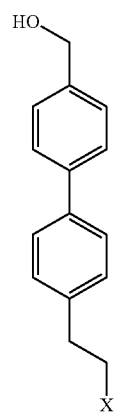

TABLE 5A-continued

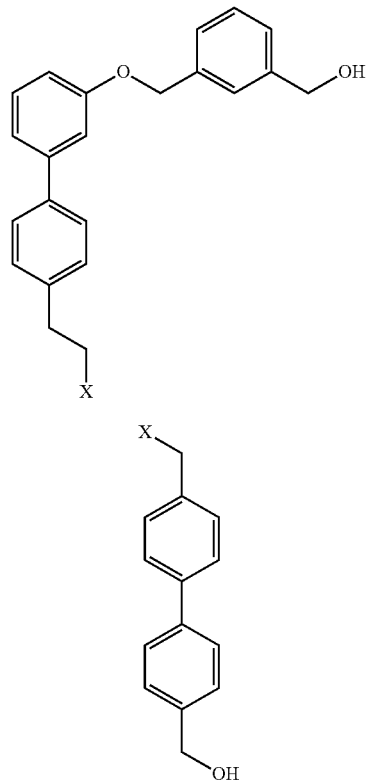

in which:

X is a 3' end of a molecule comprising: a strand of an APOC3 RNAi agent, wherein the 3' end of the strand terminates in a phosphate or modified internucleoside linker and optionally further comprises, in 5' to 3' order: a spacer and a second phosphate or modified internucleoside linker.

In one embodiment, the 3' end cap encompasses a compound of formula Ib:

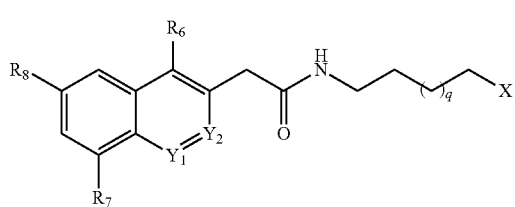

in which:

X is a 3' end of a molecule comprising: a strand of an APOC3 RNAi agent, wherein the 3' end of the strand terminates in a phosphate or modified internucleoside linker and optionally further comprises, in 5' to 3' order: a spacer and a second phosphate or modified internucleoside linker;

q is selected from 0, 1 and 2;

$R_6$ is selected from phenyl which is unsubstituted or substituted with benzoxy;

$R_7$ is selected from hydrogen and hydroxy-ethyl, wherein if $R_7$ is hydroxy-ethyl, the hydroxyl can be optionally functionalized as succinate or attached to a solid support;

$R_8$ is selected from hydrogen and methoxy;

$Y_1$ is selected from CH and N; and $Y_2$ is selected from N and $CR_9$; wherein $R_9$ is selected from hydrogen and methyl.

In various embodiments, the 3' end cap encompasses a compound selected from Table 5B.

TABLE 5B

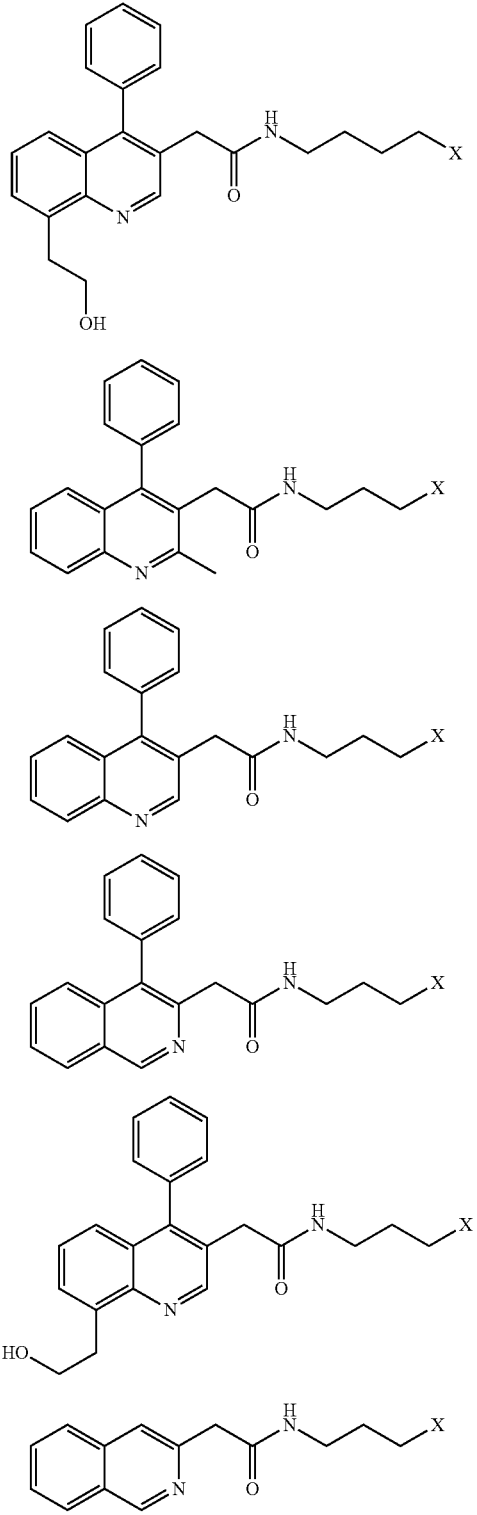

TABLE 5B-continued
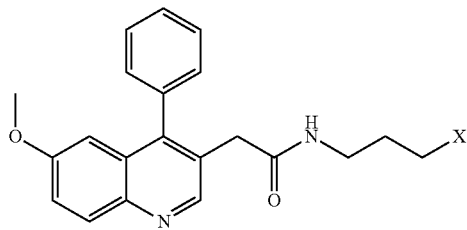
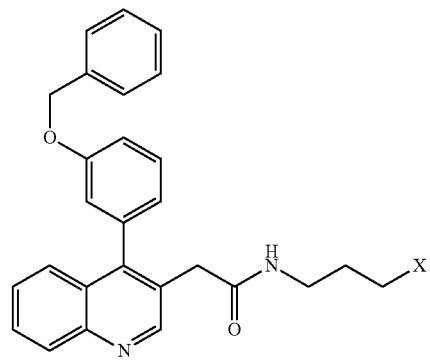
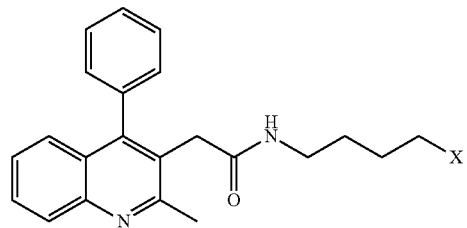
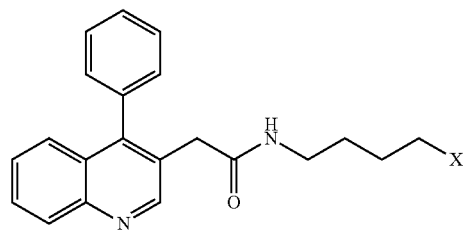
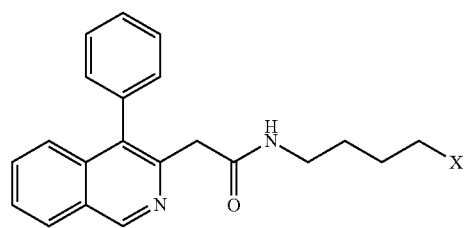
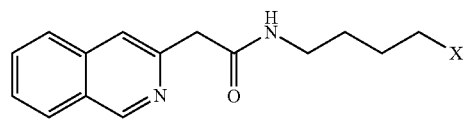
TABLE 5B-continued
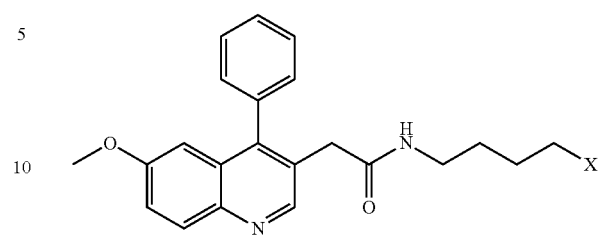
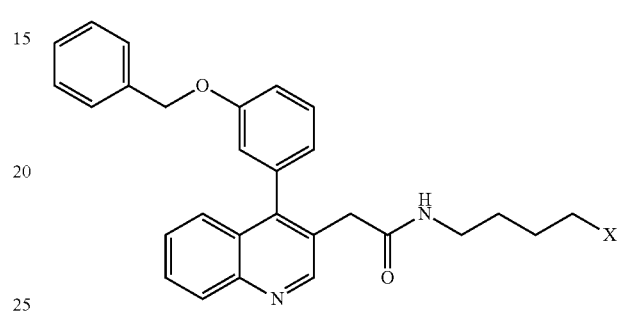
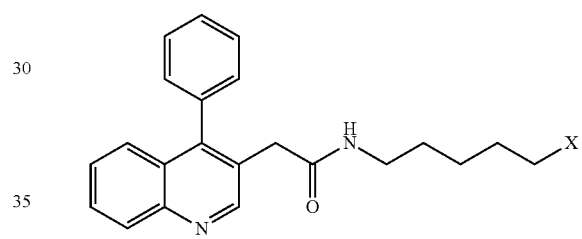
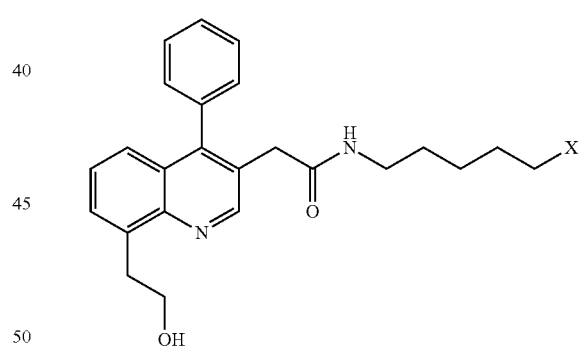
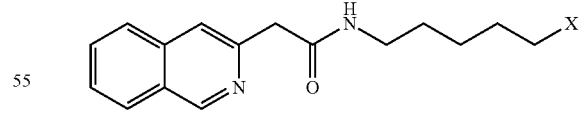
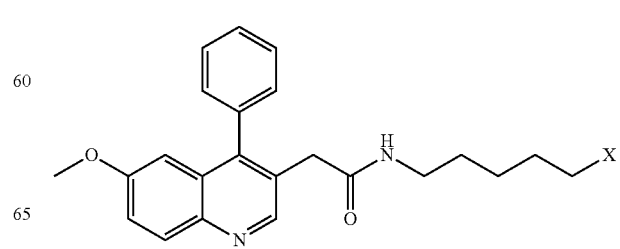

TABLE 5B-continued

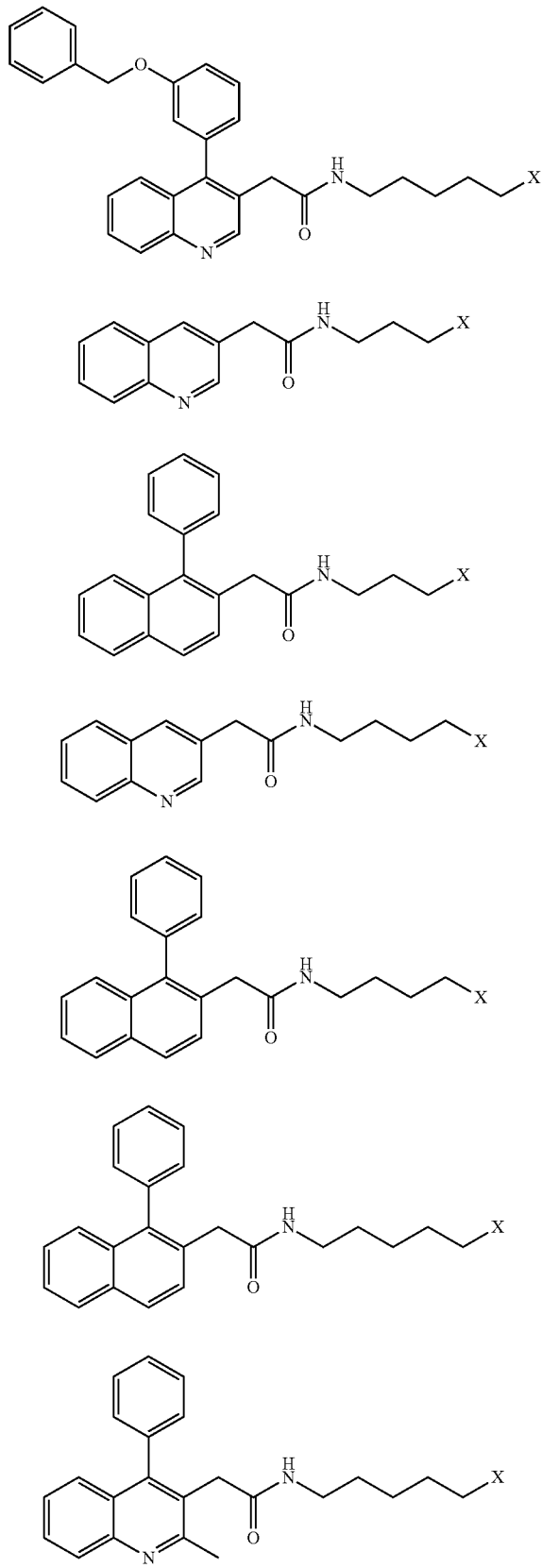

TABLE 5B-continued

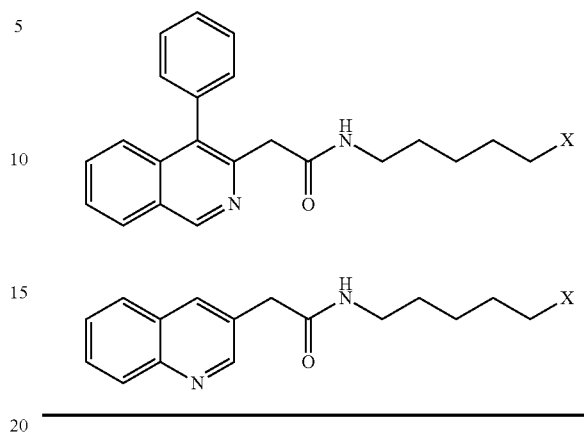

in which:

X is a 3' end of a molecule comprising: a strand of an APOC3 RNAi agent, wherein the 3' end of the strand terminates in a phosphate or modified internucleoside linker and optionally further comprises, in 5' to 3' order: a spacer and a second phosphate or modified internucleoside linker.

In various embodiments, the 3' end cap encompasses a compound selected from Table 5C.

TABLE 5C

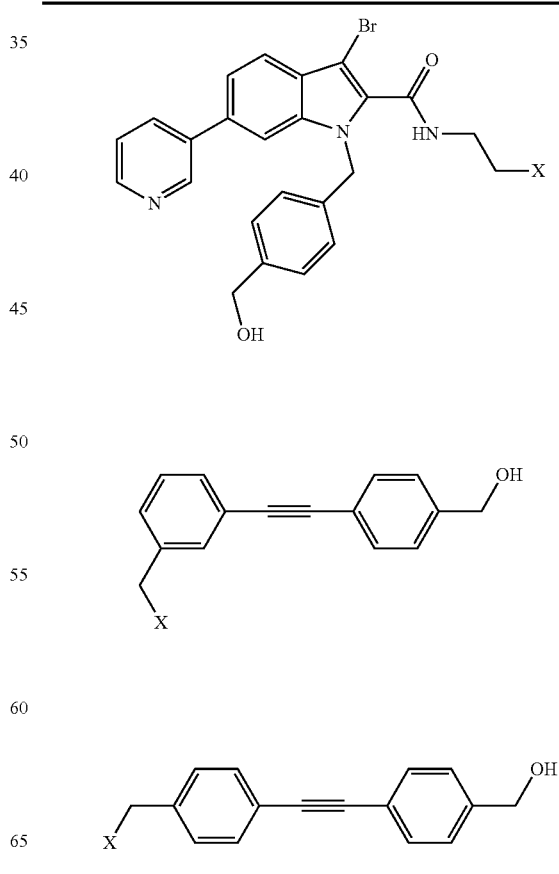

TABLE 5C-continued

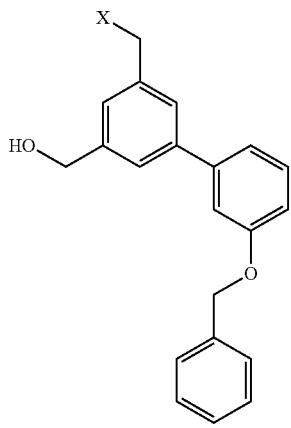

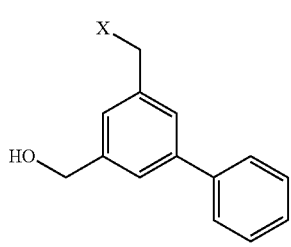

in which:

X is a 3' end of a molecule comprising: a strand of an APOC3 RNAi agent, wherein the 3' end of the strand terminates in a phosphate or modified internucleoside linker and optionally further comprises, in 5' to 3' order: a spacer and a second phosphate or modified internucleoside linker, and q is selected from 1 and 2.

In various embodiments, the 3' end cap encompasses a compound selected from Table 5D.

TABLE 5D

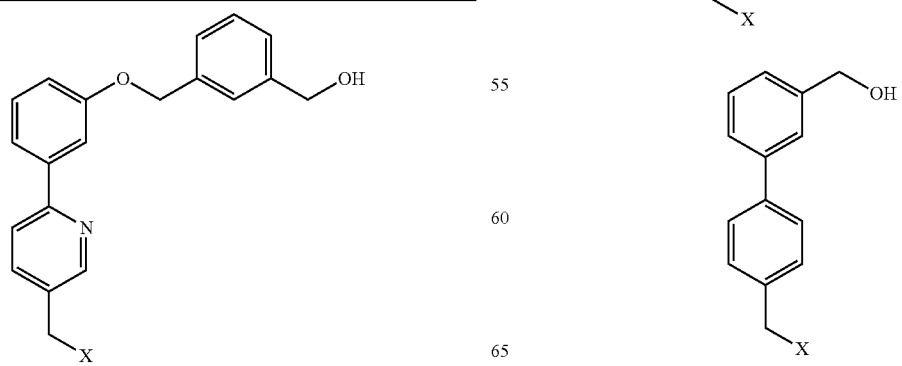

TABLE 5D-continued

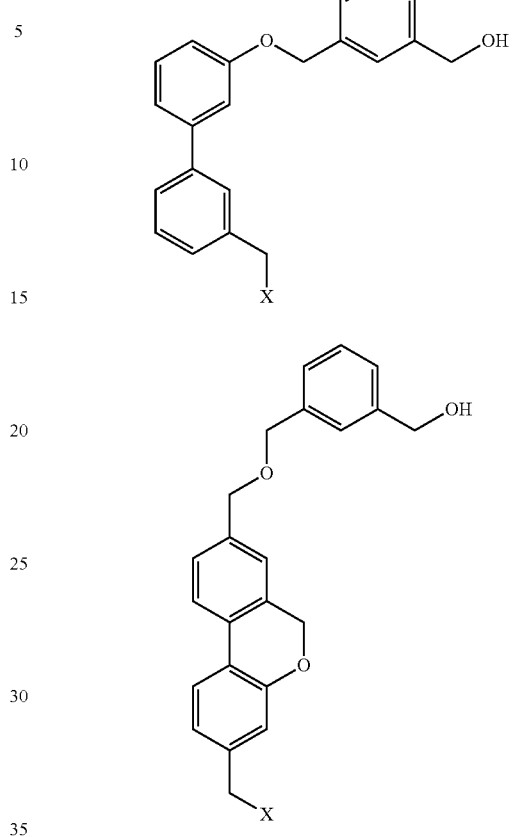

TABLE 5D-continued
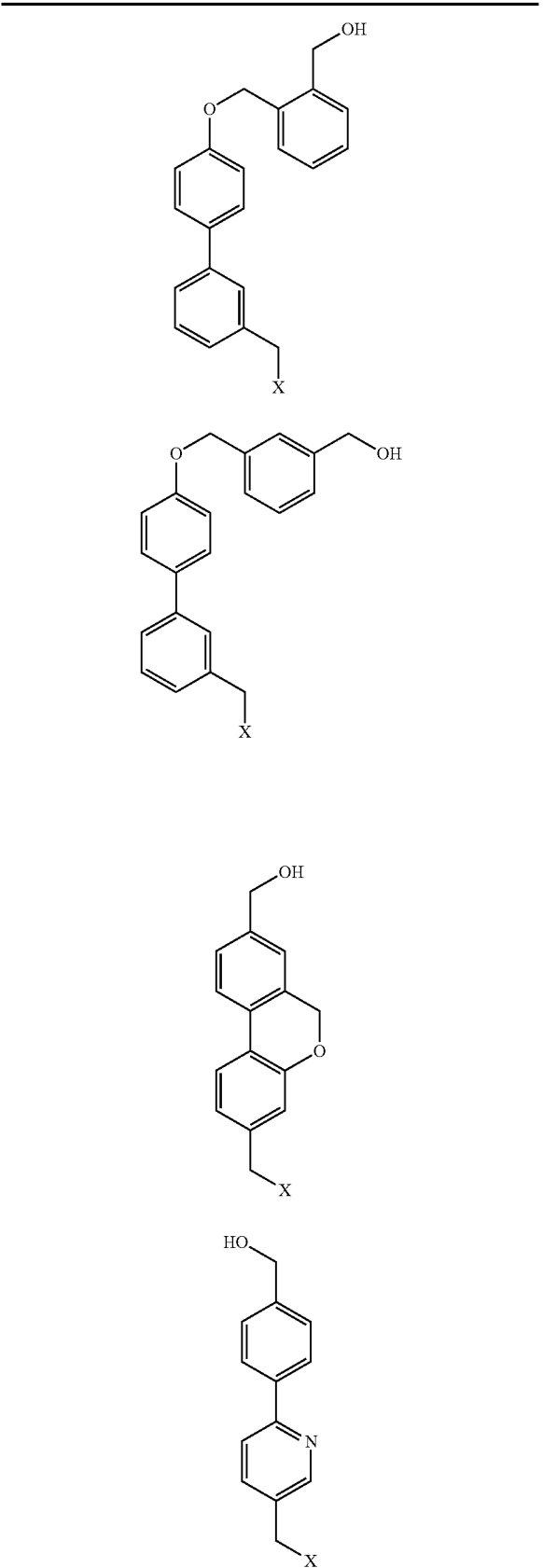
TABLE 5D-continued
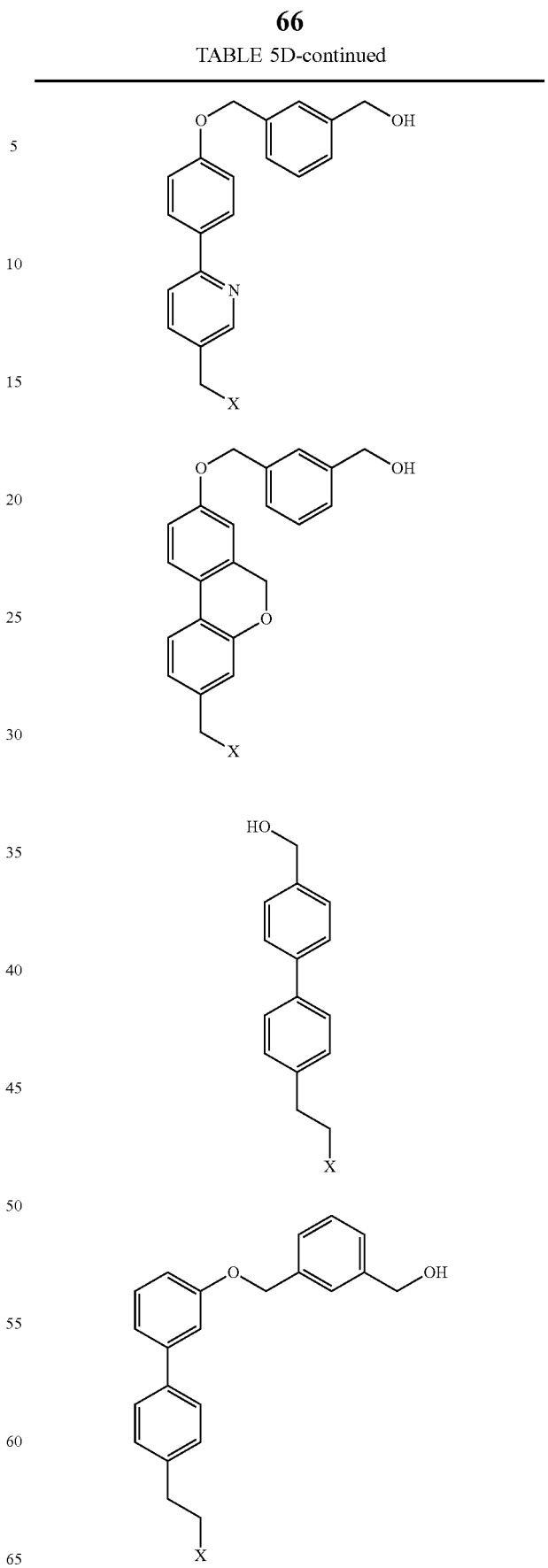

TABLE 5D-continued
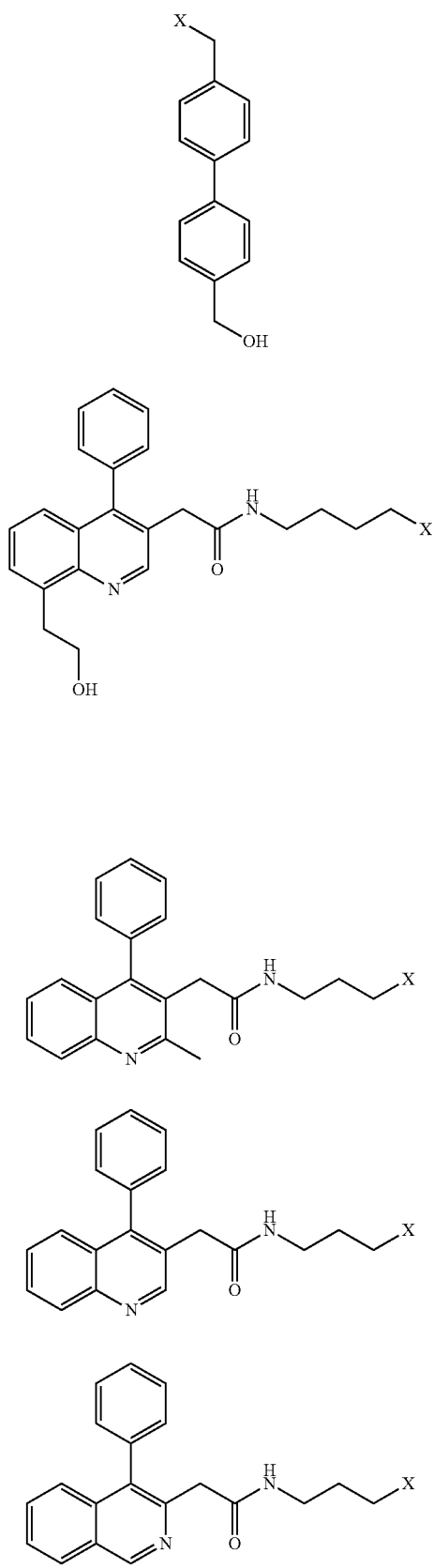
TABLE 5D-continued
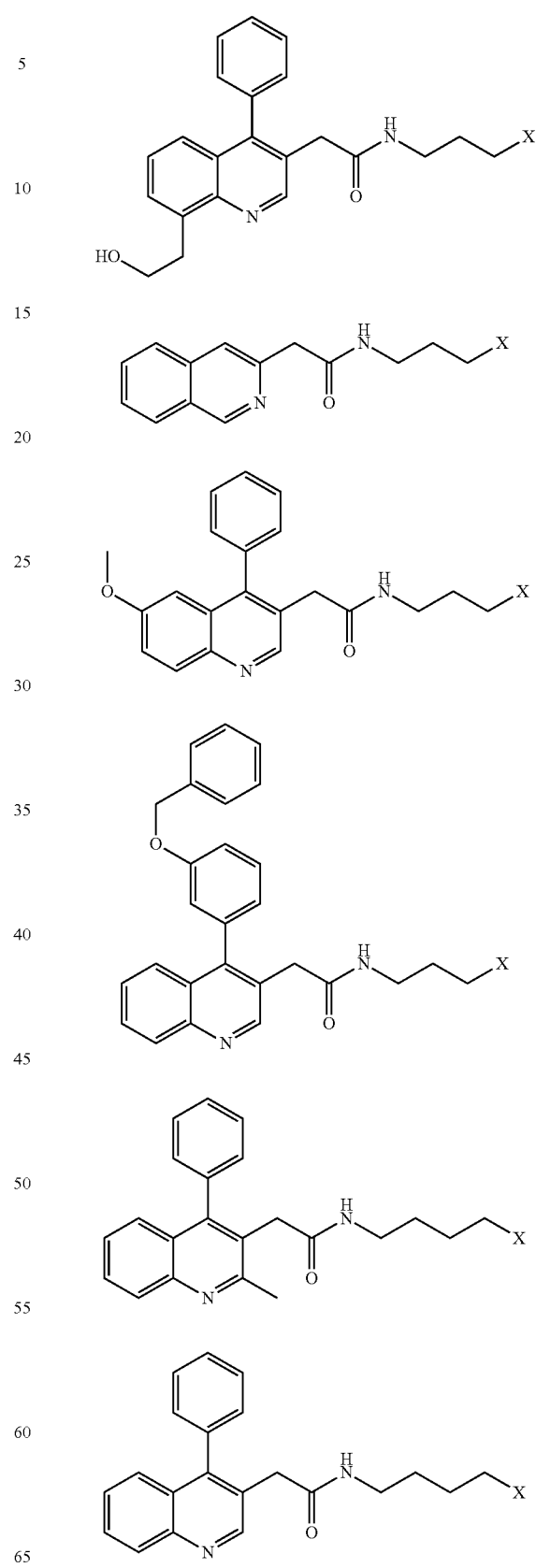

TABLE 5D-continued
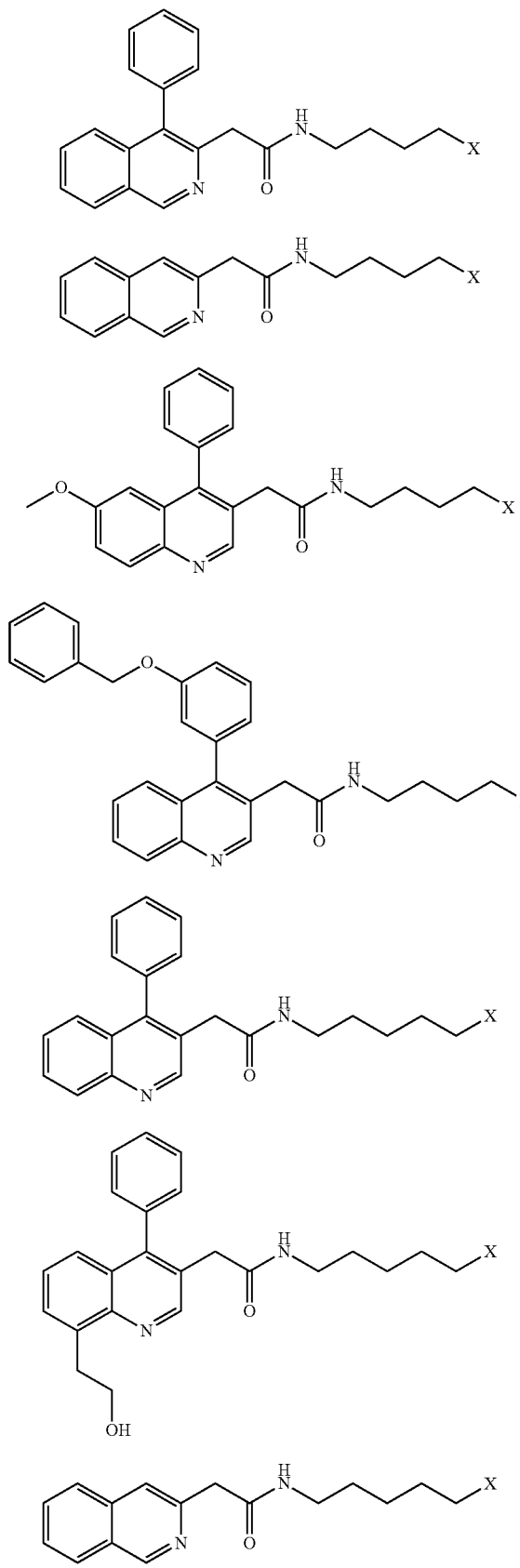
TABLE 5D-continued
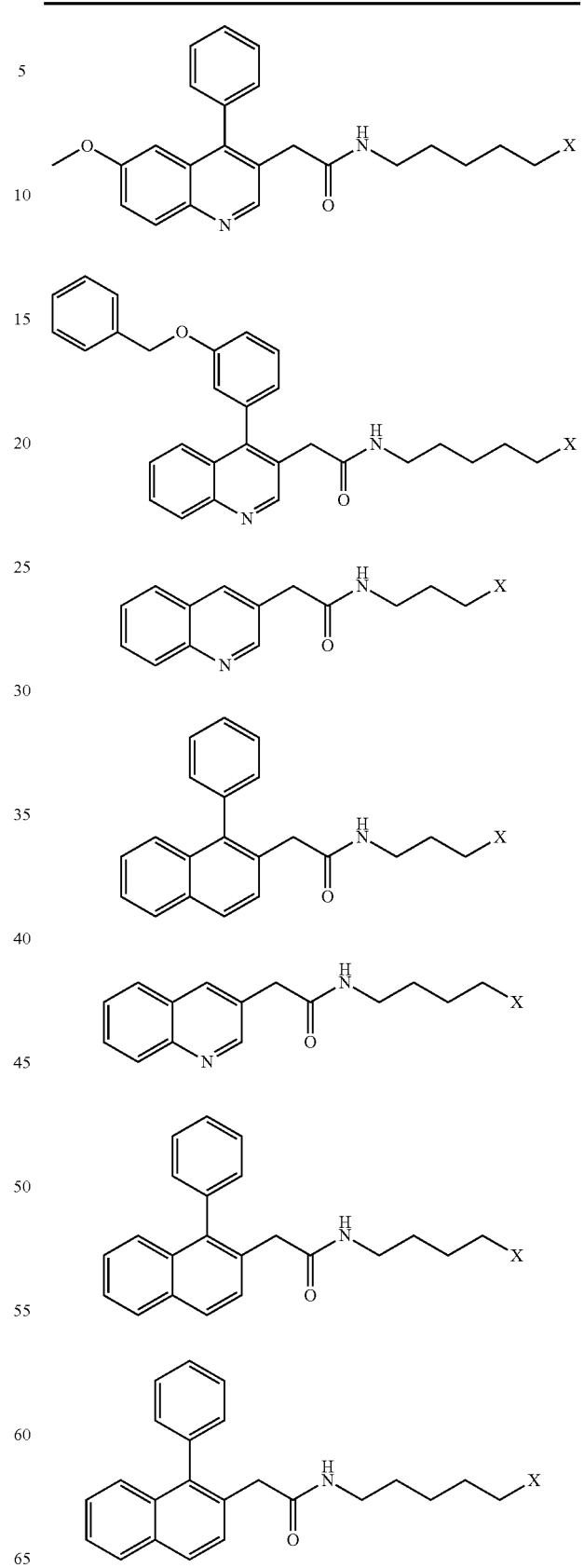

TABLE 5D-continued
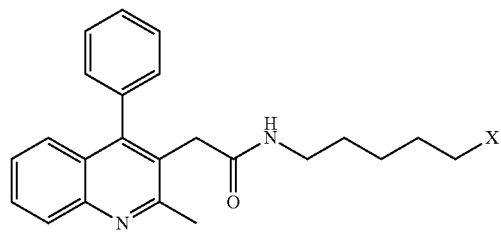
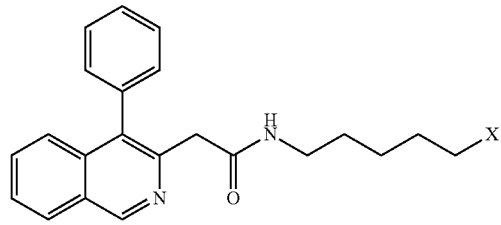
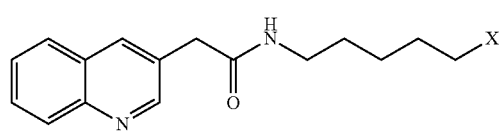
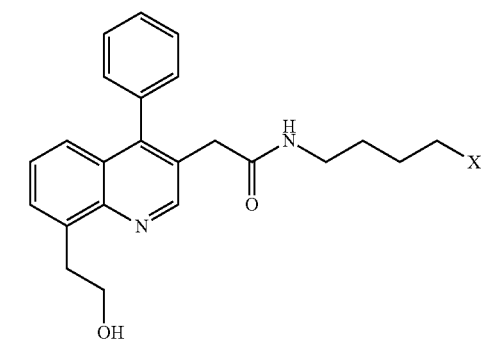
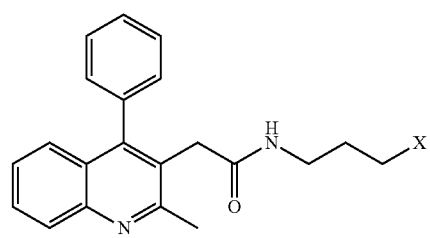
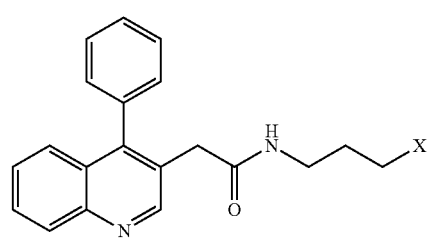
TABLE 5D-continued
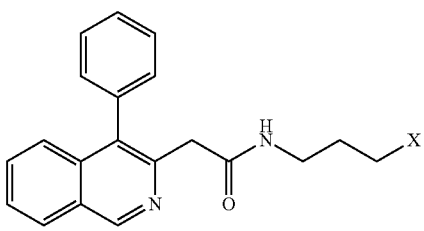
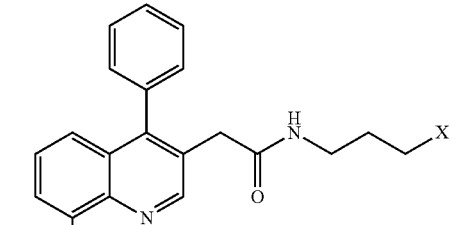
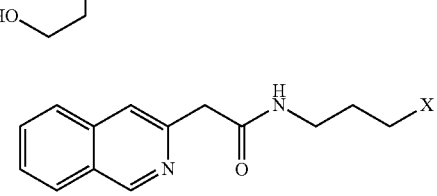
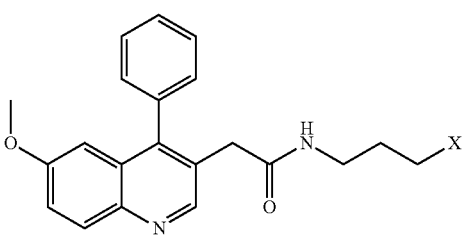
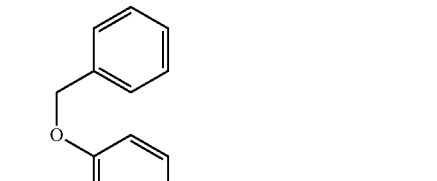
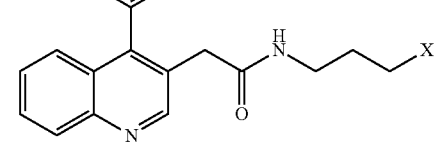
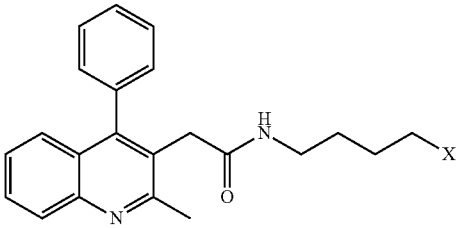

TABLE 5D-continued
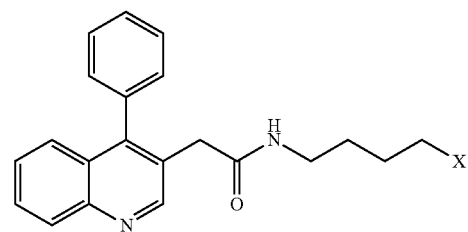
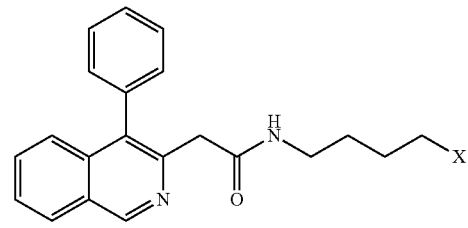
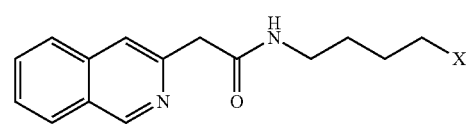
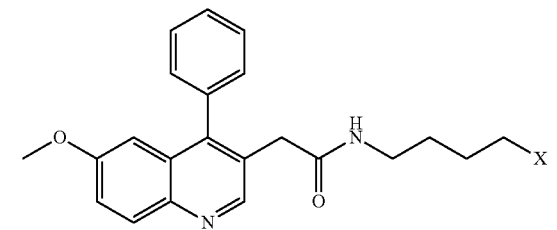
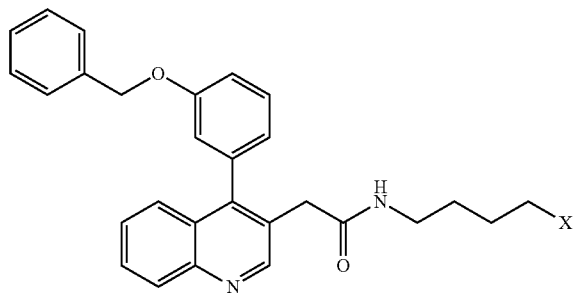
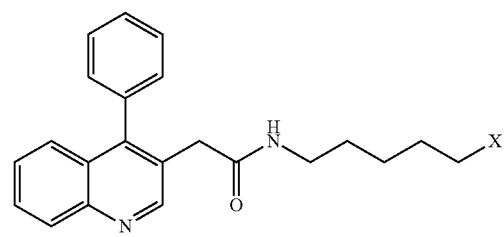
TABLE 5D-continued
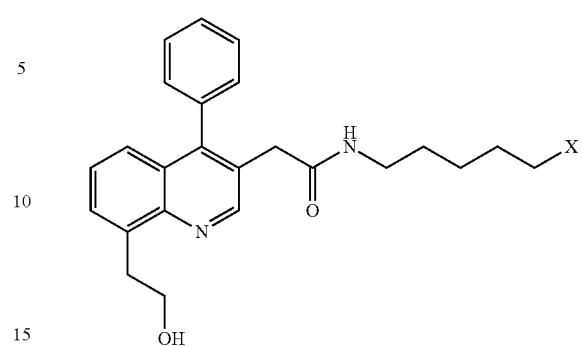
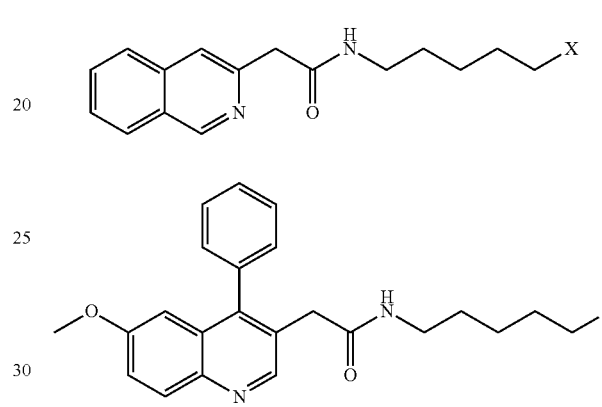
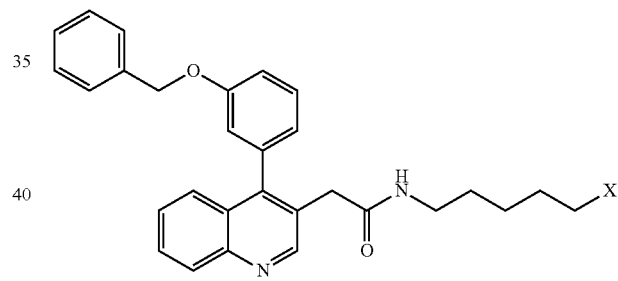
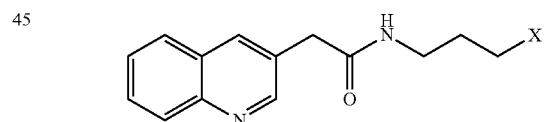
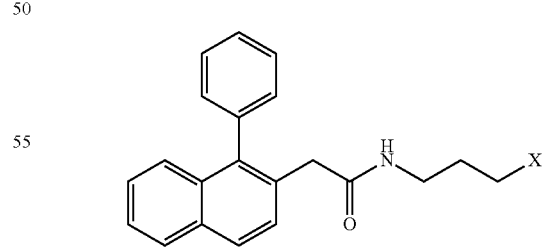
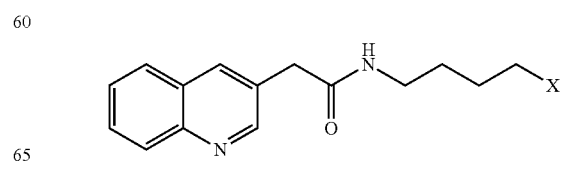

TABLE 5D-continued

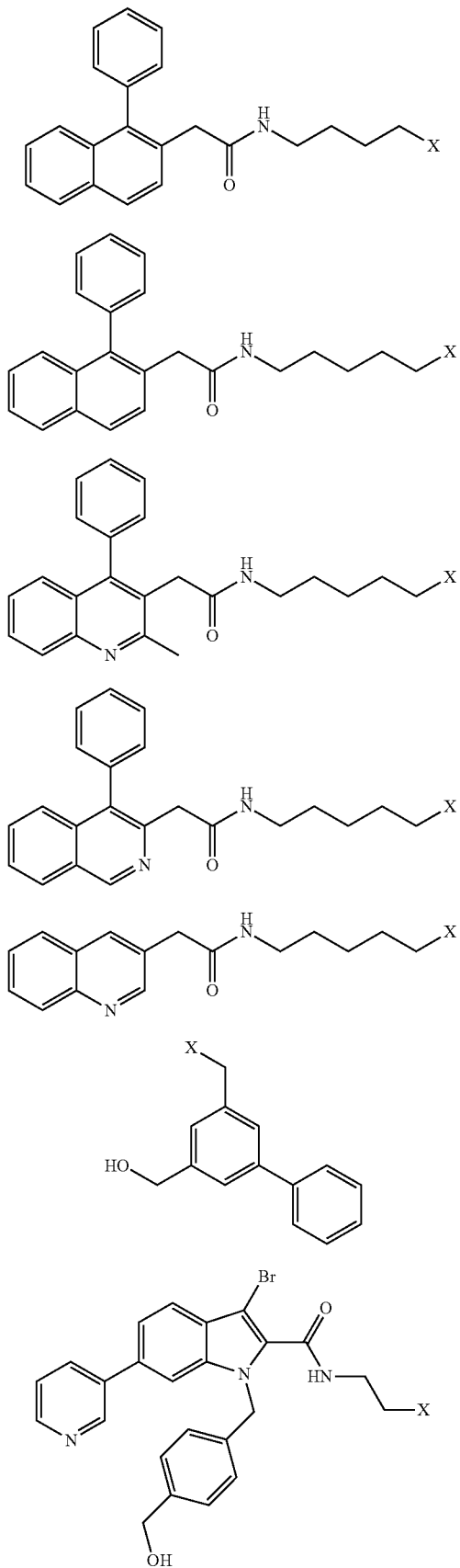

TABLE 5D-continued

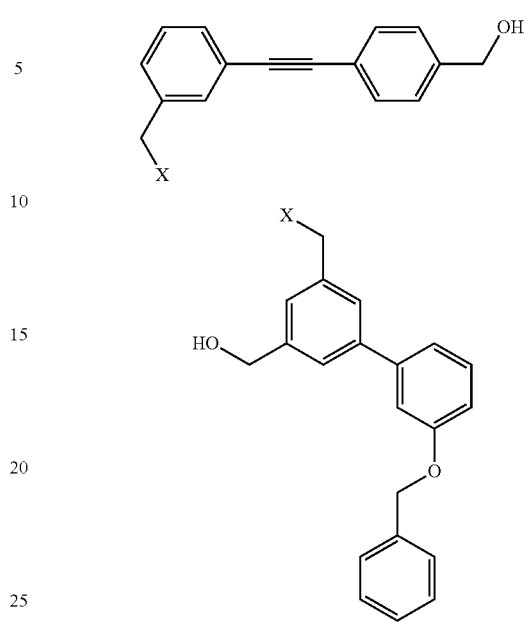

in which:
X is a 3' end of a molecule comprising: a strand of an APOC3 RNAi agent, wherein the 3' end of the strand terminates in a phosphate or modified internucleoside linker and optionally further comprises, in 5' to 3' order: a spacer and a second phosphate or modified internucleoside linker.

In various embodiments, the 3' end cap encompasses a compound selected from Table 5E.

TABLE 5E

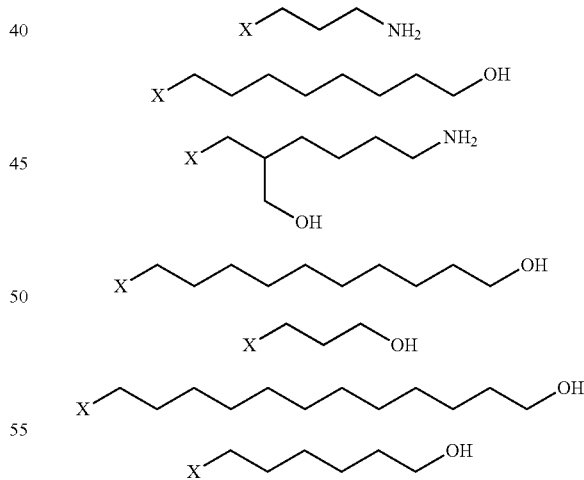

X is a 3' end of a molecule comprising: a strand of an APOC3 RNAi agent, wherein the 3' end of the strand terminates in a phosphate or modified internucleoside linker and optionally further comprises, in 5' to 3' order: a spacer and a second phosphate or modified internucleoside linker.

Suitable 3' end caps, including but not limited to: C3, C6, C12, Triethylene glycol, Cyclohexyl (or Cyclohex), Phenyl, Biphenyl, Adamantane and Lithocholic acid (or Lithochol), are described herein and/or in U.S. Pat. Nos. 8,097,716; 8,084,600; 8,344,128; 8,404,831; and 8,404,832.

In some embodiments, the 3' end cap is a ribitol. Thus, in some embodiments, the RNAi agent comprises an 18-mer strand further comprising at the 3' terminus, in 5' to 3' order, a spacer (e.g., a sugar or alkyl, cycloakyl, ribitol or other type of abasic nucleotide, C3, C4, C5, C6, etc.), a phosphate or modified internucleoside linker, and a 3' end cap (e.g., a second ribitol or other type of abasic nucleotide).

In some embodiments, the 3' end cap is a diribitol. Thus: In some embodiments, the RNAi agent comprises an 18-mer strand further comprising at the 3' terminus, in 5' to 3' order, a spacer (e.g., a ribitol, C3, C4, C5, C6, etc.), a phosphate or modified internucleoside linker, and a 3' end cap (e.g., a diribitol).

Additional Aspects of an APOC3 RNAi Agent

As noted above, the disclosure thus relates to compositions comprising an APOC3 RNAi agent. These APOC3 RNAi agents can be of any format. These include, in some embodiments, the 18-mer format, the 19-mer format, the internal spacer format, the shortened sense strand format, or any other format or length of RNAi agent known in the art. RNAi agents of the various formats can comprise strands of various lengths, one or more spacer, modified internucleoside linker, and 3' end cap. RNAi agents of the 18-mer format, for example, comprise a sense and an anti-sense strand, each strand being an 18-mer and the strands together forming a blunt-ended duplex, wherein the 3' end of at least one strand terminates in a phosphate or modified internucleoside linker and further comprises, in 5' to 3' order: a spacer; a second phosphate or modified internucleoside linker; and a 3' end cap. In some embodiments, the 3' end of both the sense and anti-sense strand further comprise, in 5' to 3' order: a spacer; a second phosphate or modified internucleoside linker; and a 3' end cap. The two strands can have the same or different spacers, phosphate or modified internucleoside linker, and/or 3' end caps. In various embodiments, one or more nt can be modified and/or substituted. Various spacers, modified internucleoside linkers and 3' end caps are described below.

Spacers: Ribitol, Diribitol, 2'-Deoxyribitol, 2'-Methoxyethoxy Ribitol, C3, C4, C5, C6, or 4-Methoxybutane-1,3-Diol (5300)

In the present disclosure, in an APOC3 RNAi agent, any of various spacers can be used in combination with strands of any sequence, with or without substitutions and/or modifications of nt, with phosphates or modified nucleoside spacers, and with any 3' end cap, in any combination without limitation.

A spacer is a chemical moiety intended or used to create or maintain a space (e.g., a proper or functional spacing) between two other chemical moieties; e.g., between two phosphates or modified internucleoside linkers. In various embodiments, the spacer is a ribitol, diribitol, 2'-deoxyribitol, or 2'-methoxyethoxy ribitol (ribitol with 2'-MOE) or an equivalent abasic nucleotide known to one skilled in the art, or a lower alkyl or alkoxy group such as a C3, C4, C5 or C6, or 4-methoxybutane-1,3-diol. Various embodiments are described in more detail below.

Ribitol Spacer.

In some embodiments, the spacer is ribitol.

In one embodiment, the RNAi agent comprises, in 5' to 3' order: an 18-mer strand (comprising a 3' terminal phosphate or a modified internucleoside linker); a spacer which is ribitol; a phosphate or a modified internucleoside linker; and a 3' end cap (e.g., any 3' end cap described herein or otherwise known in the art). In one embodiment, the RNAi agent comprises, in 5' to 3' order: an 18-mer strand comprising a 3' terminal phosphate; a spacer which is ribitol; a phosphate or a modified internucleoside linker; and a 3' end cap.

The structure of a 3' terminal phosphate and ribitol spacer is shown here:

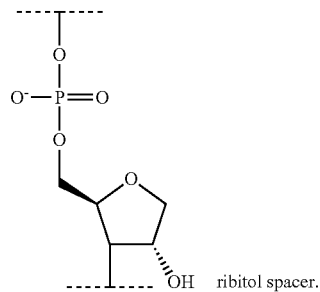

ribitol spacer.

In some documents, the ribitol spacer is designated as N027 (C027, etc.).

One embodiment the RNAi agent comprises, in 5' to 3' order: an 18-mer strand, wherein the 3' end of the 18-mer strand terminates in a phosphate and further comprises, in 5' to 3' order: a spacer which is ribitol, a phosphate, and a 3' end cap which is X058. This structure can be on any RNAi strand of any sequence or target. In addition, any 3' end cap disclosed herein can be used.

In one embodiment, ribitol with X058, wherein the last nucleotide of the 18-mer strand is a 2'-MOE and the 3' end of the 18-mer strand terminates in a phosphate and further comprises, in 5' to 3' order: a spacer which is ribitol, a second phosphate, and a 3' end cap which is X058.

In another embodiment, ribitol with C6 cap, wherein the last nucleotide of the 18-mer strand is and the 3' end of the 18-mer strand terminates in a phosphate and further comprises, in 5' to 3' order: a spacer which is ribitol, a phosphate, and a 3' end cap which is C6. In another embodiment, the RNAi agent comprises, in 5' to 3' order: an 18-mer strand terminating in a 3' phosphate, a ribitol spacer, a phosphate, and a C6 3' end cap. In another embodiment, the RNAi agent comprises, in 5' to 3' order: an 18-mer strand terminating in a 3' phosphate, a ribitol spacer, a phosphate, and a BP 3' end cap. In another embodiment, the RNAi agent comprises, in 5' to 3' order: an 18-mer strand terminating in a 3' phosphate, a ribitol spacer, a phosphate, and a C10 3' end cap.

In some embodiments, the 3' end cap is a ribitol. Thus, the RNAi agent comprises an 18-mer strand, wherein the 3' end of the 18-mer strand terminates in a phosphate or modified internucleoside linker and further comprises, in 5' to 3' order: a spacer which is ribitol, a second phosphate or modified internucleoside linker, and a 3' end cap which is a second ribitol. In one embodiment, the 3' end of the 18-mer strand terminates in a phosphate and further comprises, in 5' to 3' order: a spacer which is ribitol, a second phosphate, and a 3' end cap which is a second ribitol.

The structure comprising an RNAi agent comprising, in 5' to 3' order, an 18-mer strand terminating in a 3' terminal phosphate or a modified internucleoside linker, a ribitol spacer, a phosphate or a modified internucleoside linker, and a 3' end cap can be used on any RNAi agent of sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, FANA, ANA, HNA, CeNA, and/or UNA.

Diribitol Spacer.

In some embodiments the spacer is Diribitol.

In one embodiment, the RNAi agent comprises, in 5' to 3' order: an 18-mer strand wherein the 3' end of the strand terminates in a phosphate or modified internucleoside linker and further comprises in 5' to 3' order: a spacer (wherein the spacer comprises in 5' to 3' order: a first ribitol; a phosphate or a modified internucleoside linker; a second ribitol; and a phosphate or a modified internucleoside linker); and a 3' end cap.

Thus: In one embodiment, the RNAi agent comprises, in 5' to 3' order: an 18-mer strand comprising a 3' terminal phosphate; a first ribitol; a phosphate; a second ribitol; a phosphate or a modified internucleoside linker; and a 3' end cap.

This structure of a 3' terminal phosphate, a first ribitol, a phosphate, and a second ribitol is shown here:

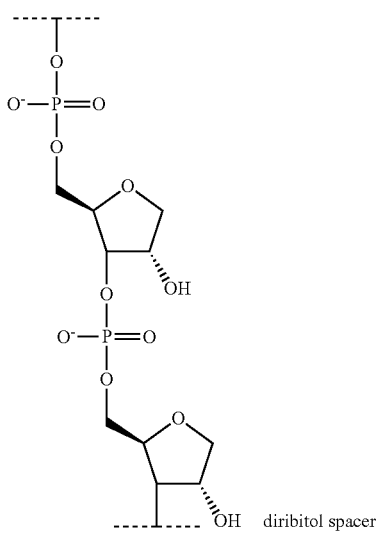

diribitol spacer

In one embodiment, the RNAi agent comprises, in 5' to 3' order: an 18-mer strand comprising a 3' terminal phosphate; a first ribitol spacer; a phosphate; a second ribitol spacer; a phosphate or a modified internucleoside linker; and a 3' end cap.

In one embodiment, the RNAi agent comprises, in 5' to 3' order: an 18-mer strand terminating in a 3' terminal phosphate or a modified internucleoside linker, a first ribitol spacer, a phosphate or a modified internucleoside linker, a second ribitol spacer, a phosphate or a modified internucleoside linker, and a 3' end cap which is a ribitol; this structure is designated a triribitol.

The structure comprising an RNAi agent comprising, in 5' to 3' order, an 18-mer strand terminating in a 3' terminal phosphate or a modified internucleoside linker, a first ribitol spacer, a phosphate or a modified internucleoside linker, a second ribitol spacer, a phosphate or a modified internucleoside linker, and a 3' end cap can be used on any RNAi agent of sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, FANA, CeNA, and/or UNA.

2'-Methoxyethoxy Ribitol Spacer.

In some embodiments, the spacer is 2'-methoxyethoxy ribitol or other type of abasic nucleotide.

In one embodiment, the RNAi agent comprises a strand, wherein the 3' end of the strand terminates in a phosphate or modified internucleoside linker and further comprises, in 5' to 3' order: a spacer which is 2'-methoxyethoxy ribitol, a second phosphate or modified internucleoside linker, and a 3' end (e.g., any 3' end cap described herein or known in the art). In other words: In one embodiment, the RNAi agent comprises, in 5' to 3' order: a strand comprising a 3' terminal phosphate or a modified internucleoside linker; a spacer which is 2'-methoxyethoxy ribitol; a phosphate or a modified internucleoside linker; and a 3' end cap (e.g., any 3' end cap described herein or known in the art). Thus: In one embodiment, the RNAi agent comprises, in 5' to 3' order: a strand comprising a 3' terminal phosphate; a spacer which is 2'-methoxyethoxy ribitol; a phosphate or a modified internucleoside linker; and a 3' end cap.

The structure of the 3' terminal phosphate and 2'-methoxyethoxy ribitol spacer is shown here:

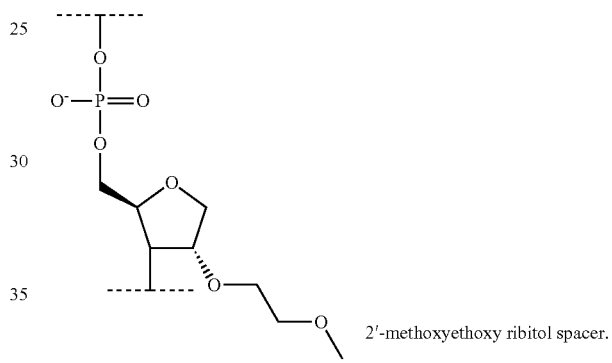

2'-methoxyethoxy ribitol spacer.

In one embodiment, the RNAi agent comprises, in 5' to 3' order: an 18-mer strand, wherein the 3' end of the 18-mer strand terminates in a phosphate and further comprises, in 5' to 3' order: a spacer which is 2'-methoxyethoxy ribitol, a phosphate, and a 3' end cap which is X058. This structure can be on any RNAi strand of any sequence or target. In addition, any 3' end cap disclosed herein can be used in place of X058.

A related structure is 2'-methoxyethoxy ribitol with X058, wherein the last nucleotide of the 18-mer strand is a 2'-MOE), and the 3' end of the 18-mer strand terminates in a phosphate and further comprises, in 5' to 3' order: a spacer which is 2'-methoxyethoxy ribitol, a second phosphate, and a 3' end cap which is X058.

Another embodiment is 2'-methoxyethoxy ribitol with C6 cap, wherein the last nucleotide of the 18-mer strand is a 2'-MOE), and the 3' end of the 18-mer strand terminates in a phosphate and further comprises, in 5' to 3' order: a spacer which is 2'-methoxyethoxy ribitol, a phosphate, and a 3' end cap which is C6.

In one embodiment, the RNAi agent comprises, in 5' to 3' order: an 18-mer strand terminating in a 3' phosphate, a 2'-methoxyethoxy ribitol spacer, a phosphate, and a C6 3' end cap.

In one embodiment, the RNAi agent comprises, in 5' to 3' order: an 18-mer strand terminating in a 3' phosphate, a 2'-methoxyethoxy ribitol spacer, a phosphate, and a BP 3' end cap.

In one embodiment, the RNAi agent comprises, in 5' to 3' order: an 18-mer strand terminating in a 3' phosphate, a 2'-methoxyethoxy ribitol spacer, a phosphate, and a C10 3' end cap.

In another embodiment, the RNAi agent comprises a strand, wherein the 3' end of the strand terminates in a phosphate and further comprises, in 5' to 3' order: a spacer which is 2'-methoxyethoxy ribitol, a phosphate, and a 3' end cap which is X058.

In some embodiments, the 3' end cap is a 2'-methoxyethoxy ribitol. Thus, the RNAi agent comprises an 18-mer strand, wherein the 3' end of the 18-mer strand terminates in a phosphate or modified internucleoside linker and further comprises, in 5' to 3' order: a spacer which is 2'-methoxyethoxy ribitol, a second phosphate or modified internucleoside linker, and a 3' end cap which is a second 2'-methoxyethoxy ribitol. In one embodiment, the 3' end of the 18-mer strand terminates in a phosphate and further comprises, in 5' to 3' order: a spacer which is 2'-methoxyethoxy ribitol, a second phosphate, and a 3' end cap which is a second 2'-methoxyethoxy ribitol.

In various embodiments, the structure comprises an RNAi agent comprising, in 5' to 3' order, a strand terminating in a 3' terminal phosphate or a modified internucleoside linker, a 2'-methoxyethoxy ribitol spacer, a phosphate or a modified internucleoside linker, and a 3' end cap (e.g., any 3' end cap known in the art) can be used on any RNAi agent of any length, sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

2'-Deoxyribitol Spacer.

In some embodiments the spacer is 2'-deoxyribitol.

In one embodiment, the RNAi agent comprises, in 5' to 3' order: an 18-mer strand terminating in a 3' phosphate or a modified internucleoside linker, a spacer which is 2'-deoxyribitol (2'-deoxyrib), a phosphate or a modified internucleoside linker, and a 3' end cap.

In one embodiment, the RNAi agent comprises, in 5' to 3' order: an 18-mer strand terminating in a 3' phosphate, a spacer which is 2'-deoxyribitol (2'-deoxyrib), a phosphate or a modified internucleoside linker, and a 3' end cap. The structure of a 3' terminal phosphate and a 2'-deoxyribitol is shown here:

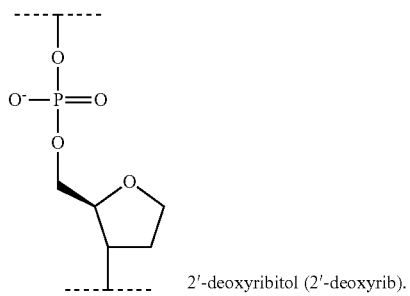

2'-deoxyribitol (2'-deoxyrib).

In one embodiment, the RNAi agent comprises, in 5' to 3' order: an 18-mer strand terminating in a 3' phosphate, a 2'-deoxyribitol spacer, a phosphate, and a C12 3' end cap.

The structure comprising an RNAi agent comprising, in 5' to 3' order, an 18-mer strand terminating in a 3' terminal phosphate or a modified internucleoside linker, a 2'-deoxyribitol spacer, a phosphate or a modified internucleoside linker, and a 3' end cap can be used on any RNAi agent of any sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

C3 Spacer.

In various embodiments, the spacer is C3.

In one embodiment, the RNAi agent comprises an 18-mer strand, wherein the 3' end of the 18-mer strand terminates in a 3' phosphate or a modified internucleoside linker, and further comprises a spacer which is C3, a phosphate or a modified internucleoside linker, and a 3' end cap.

In one embodiment, the RNAi agent comprises two 18-mer strands, wherein the 3' end of each 18-mer strand terminates in a 3' phosphate or a modified internucleoside linker, and further comprises a spacer, a second phosphate or a modified internucleoside linker, and a 3' end cap, wherein the spacer in one or both strands is C3.

The C3 spacer has the chemical formula $-(CH_2)_3-$. The structure of a 3' terminal phosphate and a C3 spacer is shown here:

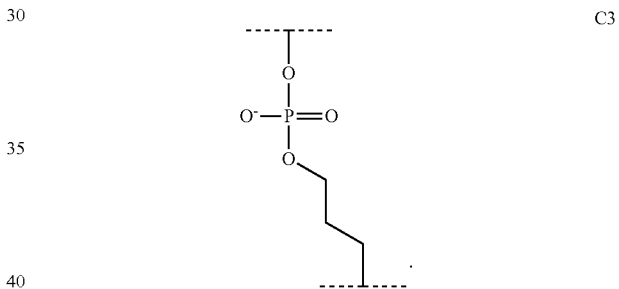

One embodiment the RNAi agent comprises, in 5' to 3' order: an 18-mer strand terminating in a 3' phosphate, a C3 spacer, a phosphate, and a 3' end cap which is X058. This structure can be on any RNAi strand of any sequence or target. In addition, any 3' end cap disclosed herein or known in the art can be used in place of X058, and any modified internucleoside linker can be used in place of phosphate.

In one embodiment a portion of a RNAi agent comprising an 18-mer strand, wherein the 18-mer strand terminates in a phosphate and further comprises in 5' to 3' order: a C3 spacer, a phosphate and a 3' end cap which is C6. This is designated "C3pC6 overhang". This structure can be on any RNAi strand of any sequence or target. In addition, any 3' end cap disclosed herein or known in the art can be used in place of C6, and any modified internucleoside linker can be used in place of phosphate.

The structure comprising an RNAi agent comprising, in 5' to 3' order, an 18-mer strand terminating in a 3' terminal phosphate or a modified internucleoside linker, a C3 spacer, a phosphate or a modified internucleoside linker, and a 3' end cap can be used on any RNAi agent of any sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

In Various Embodiments, the Spacer is C4 or C5 or C6.

In one embodiment, the APOC3 RNAi agent comprises an 18-mer strand, wherein the 3' end of the 18-mer strand terminates in a 3' phosphate or a modified internucleoside linker, and further comprises a spacer which is C4 or C5 or C6, a phosphate or a modified internucleoside linker, and a 3' end cap.

In one embodiment, the RNAi agent comprises two 18-mer strands, wherein the 3' end of each 18-mer strand terminates in a 3' phosphate or a modified internucleoside linker, and further comprises a spacer, a second phosphate or a modified internucleoside linker, and a 3' end cap, wherein the spacer in one or both strands is C4 or C5 or C6.

The C3 to C6 spacers can be defined as: C3=1,3-propane-diol, C4=1,4-butane-diol, C5=1,5-pentane-diol, or C6=1,6-hexane-diol In some contexts: the C4 spacer has the chemical formula —(CH$_2$)$_4$—, the C5 spacer has the chemical formula —(CH$_2$)$_5$—, and the C6 spacer has the chemical formula —(CH$_2$)$_6$—.

In one embodiment, the structure comprising an RNAi agent comprises in 5' to 3' order, an 18-mer strand terminating in a 3' terminal phosphate or a modified internucleoside linker, a C4 or C5 or C6 spacer, a phosphate or a modified internucleoside linker, and a 3' end cap can be used on any RNAi agent of any sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

As a note of clarification, this disclosure notes that the terms "C3" [—(CH$_2$)$_3$—], "C4" [—(CH$_2$)$_4$—], and "C5" [—(CH$_2$)$_5$-] are generally used herein to designate spacers, similar terms (C3, C4, C5 "linkers") are also used to designate a portion of a 3' end cap. It is also noted that the term "C3" is used to designate a C3 3' end cap (see, e.g, U.S. Pat. No. 8,097,716), a C3 spacer, and a C3 linker. The C6 spacer should also be differentiated from the C6 3' end cap.

4-Methoxybutane-1,3-Diol (5300) Spacer.

In various embodiments, the spacer is 4-methoxybutane-1,3-diol. 4-methoxybutane-1,3-diol is also designated 5300, A5300, C5300, G5300, and UG5300.

In one embodiment, the APOC3 RNAi agent comprises, in 5' to 3' order: an 18-mer strand, wherein the 3' end terminates in a 3' phosphate (a 3' terminal phosphate) or a modified internucleoside linker and further comprises: a spacer which is 4-methoxybutane-1,3-diol, a phosphate or a modified internucleoside linker, and a 3' end cap.

The structure of a 3' terminal phosphate and a 4-methoxybutane-1,3-diol spacer is shown here:

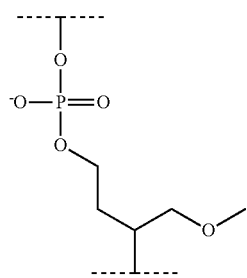

In one embodiment, the RNAi agent comprises, in 5' to 3' order: an 18-mer strand terminating in a 3' phosphate, a spacer which is 4-methoxybutane-1,3-diol, a phosphate or a modified internucleoside linker, and a 3' end cap.

In one embodiment the RNAi agent comprises, in 5' to 3' order: an 18-mer strand terminating in a 3' phosphate, a 4-methoxybutane-1,3-diol spacer, a phosphate, and a 3' end cap which is X058. This structure can be on any RNAi strand of any sequence or target. In addition, any 3' end cap disclosed herein or known in the art can be used in place of X058, and any modified internucleoside linker can be used in place of phosphate.

In one embodiment the RNAi agent comprises, in 5' to 3' order, an 18-mer strand terminating in a 3' terminal phosphate or a modified internucleoside linker, a 4-methoxybutane-1,3-diol spacer, a phosphate or a modified internucleoside linker, and a 3' end cap can be used on any RNAi agent of any sequence or target, including but not limited to a double-stranded RNA, wherein optionally one or more phosphates are replaced by a modified internucleoside linker, optionally one or more nucleotides are modified, and optionally one or more RNA nucleotides are replaced by DNA, PNA, LNA, morpholino, TNA, GNA, ANA, HNA, CeNA, FANA, and/or UNA.

Phosphate or Modified Internucleoside Linker.

In various embodiments, the modified internucleoside linker is: phosphorothioate, phosphorodithioate, phosphoramidate, boranophosphonate, an amide linker, or a compound of formula (I).

The disclosure relates to compositions comprising an APOC3 RNAi agent having a novel format. These RNAi agents comprise a sense and an anti-sense strand, each strand being an 18-mer and the strands together forming a blunt-ended duplex, wherein the 3' end of at least one strand terminates in a phosphate or modified internucleoside linker and further comprises, in 5' to 3' order: a spacer; a second phosphate or modified internucleoside linker; and a 3' end cap. In some embodiments, the 3' end of both the sense and anti-sense strand further comprise, in 5' to 3' order: a spacer; a second phosphate or modified internucleoside linker; and a 3' end cap. The two strands can have the same or different spacers, phosphate or modified internucleoside linker, and/or 3' end caps. In various embodiments, one or more nt can be modified and/or substituted. Various spacers are described below. Various phosphates or modified internucleoside linkers can be used in combination with strands of any sequence, with or without substitutions and/or modifications of nt, with any spacers, and with any 3' end cap, in any combination without limitation.

In some embodiments, the modified internucleoside linker is interposed between the spacer and the 3' end cap.

In various embodiments, one or more of the phosphates of one or both strands of the RNAi agent are replaced. Thus: In various embodiments, one or more nucleotide of one or both strands has a modified internucleoside linker. In some embodiments, the 3' terminal phosphate is replaced. In some embodiments, one or more nucleotide of one or both strands has a modified internucleoside linker, and/or a modified internucleoside linker is interposed between the spacer and the 3' end cap.

In one embodiment, the present disclosure encompasses a RNAi agent comprising a sense and an anti-sense strand, each strand being an 18-mer and the strands together forming a blunt-ended duplex, wherein the 3' end of at least one strand terminates in a phosphate or modified internucleoside linker and further comprises, in 5' to 3' order: a spacer; a second phosphate or modified internucleoside linker; and a 3' end cap, wherein the 3' end cap is selected from the 3' end caps listed in any Table herein or otherwise disclosed herein, and wherein at least one nucleotide has a modified internucleoside linker a modified internucleoside linker (e.g., wherein at least one phosphate of a nucleotide is replaced by a modified internucleoside linker), where the modified internucleoside linker is:

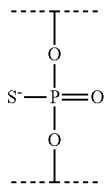

phosphorothioate (PS),

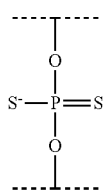

phosphorodithioate, phosphoramidate, boranophosphonoate, an amide linker, or a compound of formula (I):

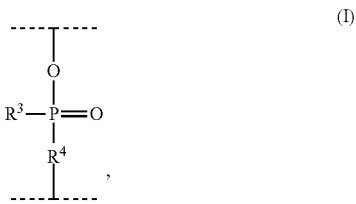

where $R^3$ is selected from $O^-$, $S^-$, $NH_2$, $BH_3$, $CH_3$, $C_{1-6}$ alkyl, $C_{6-10}$ aryl, $C_{1-6}$ alkoxy and $C_{6-10}$ aryl-oxy, wherein $C_{1-6}$ alkyl and $C_{6-10}$ aryl are unsubstituted or optionally independently substituted with 1 to 3 groups independently selected from halo, hydroxyl and $NH_2$; and $R^4$ is selected from O, S, NH, or $CH_2$.

In one embodiment, the present disclosure encompasses a RNAi agent comprising a sense and an anti-sense strand, each strand being an 18-mer and the strands together forming a blunt-ended duplex, wherein the 3' end of at least one strand terminates in a phosphate or modified internucleoside linker and further comprises, in 5' to 3' order: a spacer; a second phosphate or modified internucleoside linker; and a 3' end cap, wherein the 3' end cap is selected from the 3' end caps listed in any Table herein or otherwise disclosed herein, and wherein at least the 3' terminal nucleotide on one or both strands has a modified internucleoside linker (e.g., wherein the phosphate of the 3' nucleotide on one or both strands is replaced by a modified internucleoside linker), wherein the modified internucleoside linker is phosphorothioate, phosphorodithioate, phosphoramidate, boranophosphonoate, an amide linker, or a compound of formula (I).

In various embodiments, the 3' end cap is linked via a terminal phosphate group (i.e., a phosphate group at the 3' end of a RNAi agent strand). Such compounds are shown in, for example, Table 5A-E. Alternatively, in 3' to 5' order, a 3' end cap can be bound to a phosphate or modified internucleoside linker, which is bound to a spacer, which is bound to a phosphate or modified internucleoside linker bound to the 3' carbon at the 3' end of at least one RNAi agent strand.

In one embodiment, compounds of table 5A-E have a terminal phosphorothioate group bound to the 3' carbon at the 3' end of at least one RNAi agent strand. Thus, in various embodiments, in the 3' end caps listed in Table 5A-E, the phosphate group is replaced by a phosphorothioate. In other words, the composition comprises a RNAi agent comprising a strand, wherein the 3' end of the strand terminates in a phosphorothioate and further comprises a compound of Table 5A-E (or any other 3' end cap described herein or known in the art). In additional embodiments, the phosphate group of various 3' end caps listed herein as C3, C6, C12, Triethylene glycol, Cyclohexyl, Phenyl, Biphenyl, Adamantane, Lithocholic acid can be replaced by phosphorothioate. In one embodiment, the phosphate group in the C3 3' end cap is replaced by phosphorothioate. In another embodiment, the phosphate group in the C6 3' end cap is replaced by phosphorothioate. In another embodiment, the phosphate group in the C10 3' end cap is replaced by phosphorothioate. In another embodiment, the phosphate group in the biphenyl (BP) 3' end cap is replaced by phosphorothioate.

Various Additional Embodiments of APOC3 RNAi Agents in the 18-Mer Format

In some embodiments, the APOC3 RNAi agent comprises a 18-mer strand further comprising at the 3' terminus a 3' end cap (but no spacer, or phosphate or internucleoside linker). Thus: In some embodiments, the RNAi agent comprises an 18-mer strand further comprising at the 3' terminus a 3' end cap (e.g., BP or C6).

In some embodiments, the APOC3 RNAi agent comprises an 18-mer strand further comprising at the 3' terminus a spacer (but no phosphate or internucleoside linker, or 3' end cap). Thus: In some embodiments, the RNAi agent comprises an 18-mer strand further comprising at the 3' terminus a spacer (e.g., ribitol).

In various embodiments, one or both strands can comprise ribonucleotide subunits, or one or more nucleotide can optionally be modified or substituted. Thus, in various embodiments, the RNAi agent can either contain only naturally-occurring ribonucleotide subunits, or one or more modifications to the sugar, phosphate or base of one or more of nucleotide subunits. In one embodiment, the modifications improve efficacy, stability and/or reduce immunogenicity of the RNAi agent.

Some embodiments of the present disclosure relates to an APOC3 RNAi agent comprising at least one non-natural nucleobase. In certain embodiments, the non-natural nucleobase is difluorotolyl, nitroindolyl, nitropyrrolyl, or nitroimidazolyl. In a particular embodiment, the non-natural nucleobase is difluorotolyl. In certain embodiments, only one of the two strands contains a non-natural nucleobase. In certain embodiments, both of the strands contain a non-natural nucleobase.

In one embodiment, the first two base-pairing nucleotides on the 3' end of the sense and/or anti-sense strand are modified. In one embodiment, the first two base-pairing nucleotides on the 3' end of the sense and/or anti-sense strand are 2'-MOE (a 2' MOE clamp).

In one embodiment, the 3' terminal phosphate of the sense and/or anti-sense strands is replaced by a modified internucleoside linker.

In various embodiments, one of more nucleotides is substituted with DNA, a peptide nucleic acid (PNA), locked nucleic acid (LNA), morpholino nucleotide, threose nucleic acid (TNA), glycol nucleic acid (GNA), arabinose nucleic acid (ANA), 2'-fluoroarabinose nucleic acid (FANA), cyclohexene nucleic acid (CeNA), anhydrohexitol nucleic acid (HNA), or unlocked nucleic acid (UNA). In some embodiments, the replacement or substitution of RNA with DNA, or a nucleotide of a different backbone, or PNA, LNA, Morpholino, TNA, GNA, ANA, HNA, CeNA, FANA, and/or UNA can be considered a "modification".

In various embodiments, at least one nucleotide comprises a modified internucleoside linker, wherein the modified internucleoside linker is selected from phosphorothioate, phosphorodithioate, phosphoramidate, boranophosphonate, an amide linker, and a compound of formula (I).

In various embodiments, optionally the 3' terminal phosphate of the sense and/or anti-sense strands is replaced by a modified internucleoside linker.

In various embodiments, the RNAi agent can be modified on one or both 5' end. In various embodiments, the sense strand can comprise a 5' end cap which reduces the amount of the RNA interference mediated by this strand.

In various embodiments, the sense strand comprises a 5' end cap selected: a nucleotide lacking a 5' phosphate or 5'-OH; a nucleotide lacking a 5' phosphate or a 5'-OH and also comprising a 2-OMe or 2'-MOE modification; 5'-deoxy-2'-O-methyl modification; 5'-OME-dT; ddT; and 5'-OTr-dT.

In various embodiments, the RNAi agent is optionally attached to a ligand. The ligand can be selected to improve one or more characteristic, such as, e.g., stability, distribution and/or cellular uptake of the agent, e.g., cholesterol or a derivative thereof.

In various embodiments, the RNAi agent can be isolated or be part of a pharmaceutical composition used for the methods described herein.

In various embodiments, the pharmaceutical composition can be a lipid nanoparticle.

In various embodiments, the pharmaceutical composition can be a lipid nanoparticle Optionally, the pharmaceutical compositions can further comprise or be used in conjunction with any known treatment for any target gene-related disease.

The present disclosure further provides methods for reducing the level of target gene mRNA in a cell, particularly in the case of a disease characterized by over-expression or hyper-activity of the target gene product. The present disclosure also encompasses a method of treating a human subject having a pathological state mediated at least in part by target gene expression, the method comprising the step of administering to the subject a therapeutically effective amount of a RNAi agent target gene. Such methods comprise the step of administering one of the RNAi agents of the present disclosure to a subject. Reduction of target gene mRNA in a cell results in a reduction in the amount of encoded target gene protein produced.

In another embodiment, the invention provides an RNAi agent with any one or more of the above properties for use as a medicament.

The methods and compositions of the present disclosure, e.g., the methods and target gene RNAi agent compositions, can be used with any dosage and/or formulation described herein, as well as with any route of administration described herein.

In various embodiments, the RNAi agent can be combined with one or more additional RNAi agents in the same formulation. The one or more additional RNAi agents can have the same or different sequences, targets, spacers, 3' end caps, nucleotide replacements modifications, and/or ligands, etc. In various embodiments, the one or more additional RNAi agents can have a sense and an anti-sense strand wherein each is an 18-mer and together form a blunt-ended duplex. The one or more additional RNAi agent can target the same or different sequence and/or the same or different target gene.

Thus: Multiple RNAi agents can be administered separately or co-administered. The multiple RNAi agents can be administered in the same delivery vehicle, the same type of delivery vehicle, or in different delivery vehicles.

Various additional embodiments are described below.

Any of the various 3' end caps (e.g., ligands or PAZ ligands) can be used with the APOC3 RNAi agents described herein.

A 3' end cap is a non-nucleotidic chemical moiety bound to the 3' end of a molecule comprising a RNAi agent, e.g., the 3' terminus (or 3' end) of (a) a molecule comprising a strand, wherein the 3' end of the strand terminates in a phosphate or modified internucleoside linker; or (b) a molecule comprising, in 5' to 3' order: a strand (wherein the 3' end of the strand terminates in a phosphate or modified internucleoside linker), a spacer, and a second phosphate or modified internucleoside linker. The 3' end cap performs at least one of the following functions: allowing RNA interference mediated by the molecule, protecting the molecule from degradation or reducing the amount or rate of degradation of the molecule (e.g., by nucleases), reducing the off-target effects of the sense strand, or increasing the activity, duration or efficacy of RNA interference mediated by the molecule. By describing a 3' end cap as "non-nucleotidic", it is meant that a nucleotide comprises three components: a phosphate, a pentose (e.g., a ribose or deoxyribose) and a nucleobase, and a 3' end cap does not comprise all three components.

3' end caps include, but are not limited to compounds designated "PAZ ligands". These ligands can provide increased potency and/or higher siRNA turnover.

Various PAZ ligands and 3' end caps have been tested with various APOC3 RNAi agents. It is noted that some documents also refer to C6, C8, C10, C12, BP and other 3' end caps as PAZ ligands.

Human APOC3 RNAi agents were constructed, with the guide strand, with or without (+ or −) the MOE clamp (wherein the first two nt on the 3' end of each strand are 2'-MOE), with or without (+ or −) the ribitol spacer, and with each of the 17 listed PAZ ligands, C6 and BP as the 3' end caps. The passenger strands were constructed with or without (+ or −) the MOE clamp, with or without (+ or −) the ribitol spacer, and with C6 as the 3' end cap.

The RNAi agents are tested in a 3 point dose response.

RNAi agents are introduced into Huh7 cells (10,000) using Optifect.

Three RNAi agent concentrations are used: 30, 15, 10 and 5 nM.

A group of siRNA agents are tested.

7×96-well plates are transfected in duplicate (with randomized distribution of siRNAs across the plates).

qRT-PCR is performed and duplicate, and the gene product is normalized to GAPDH mRNA.

Plate-to-plate normalization is also performed.

Modification of Human APOC3 RNAi agents is also described herein.

Once efficacious siRNA sequences are identified, these siRNAs can be optimized by performing various modifications and testing those modifications to find those which improve efficacy, duration and/or stability and/or reduce off-target effects, or otherwise improve the performance of the siRNA.

The efficacious human APOC3 RNAi agents can be modified by replacing a RNA with 2'-OMe-RNA, DNA, 2'-F-RNA, 2'-MOE-RNA, and/or addition of a spacer (e.g., ribitol), and/or additional of a 3' end cap (X058, C6 or other 3' end cap).

Human ApoC3 RNAi agents were thus modified in numerous ways and tested for activity.

Human APOC3 RNAi Agents can also be modified by replacement of RNA with DNA. In particular, nucleotides in the seed region (positions 2-7) can be replaced by DNA. It is noted that various references define the exact limit of the seed region differently; some describe it as nt 4-8, 2-8 or 2-7, counting from the 5' end of the anti-sense strand. In this disclosure, the seed region refers to nt 2-7. RNAi names sometimes have suffixes identifying a base as DNA (e.g., "pos4_DNA" indicates that the nucleotide at position 4 is DNA; "pos8_DNA" indicates that that at position 8 is DNA, etc.). These modifications reduce off-target effects by weakening the binding affinity of the guide strand seed region. Off-target effects can be measured, for example, as EC50 in nM in HeLa cells. The data show that DNA is thus well-tolerated, e.g., in the seed region and can reduce the off-target phenotype. In some cases, other positions (e.g., position 2) can be replaced by DNA, or more than one nucleotide can be replaced by DNA (e.g., positions 2 and 4).

Modifications can be made to increase the serum stability of the molecules.

In various experiments, off-target effects are measured in HeLa cells (1000 cells, using HiPerFect, 166 hours post-transfection); and potency is measured (e.g., 12 dose-response, time course, in Huh7 cells, using 8000 cells, using OptiFect, at 24, 48, 72, 120 and 166 hours). Potency reporter: human/cyno (6 dose-response): COS1 (5000 cells), Fugene/Oligofectamine, 72 hours; antisense reporter human, sense reporter human, and antisense reporter cyno.

Modified variants of APOC3 RNAi agents include conjugate formats for 18-mers and 19-mers.

Modified variants of APOC3 RNAi agents include those with modifications of 5' and/or 3' end of the passenger strand to components which increase targeting to and uptake by the liver; and/or modification of the 5' end of the anti-sense strand to stabilize it; and/or modification of the 3' end of the anti-sense strand, e.g., by conjugation with a 3' end cap, to increase stability and/or potency.

Delivery

Any pharmaceutical carrier known in the art can be used to deliver APOC3 siRNAs.

Criteria for an effective delivery vehicle include effective target knockdown in the liver at a reasonable dosage and duration, and acceptable pharmacokinetics and toxicity.

Delivery vehicles include, for example, lipid nanoparticles (LNPs), non-LNP delivery, peptide conjugation, and lipoprotein particles (LLPs). Particles can be, for example 10-100 nM in size, and can, for example, self-assemble in aqueous media.

Lipid nanoparticle (LNP)

For example, APOC3 siRNAs can be delivered using a lipid nanoparticle (LNP).

Such an LNP can comprise, for example, a cationic lipid, cholesterol, a neutral lipid, and a shielding lipid.

Several in vivo studies were done using APOC3 18-mer RNAi agents at 1 mg/kg administered to mice using LNPs. In one study, APOC3 RNAi agents were able to deduce gene expression by over 70% compared to PBS control at 48 hours. Other studies demonstrated the efficacy of APOC3 siRNAs in vivo using a variety of LNPs.

The use of one LNP and an 18-mer APOC3 RNAi yielded a 60% KD in mice 48 and 96 hrs post IV injection.

Additional Definitions

For convenience, the meaning of certain terms and phrases used in the specification, examples, and appended claims, are provided below. If there is an apparent discrepancy between the usage of a term in other parts of this specification and its definition provided in this section, the definition in this section shall prevail.

As used throughout this disclosure, articles such as "a" and "an" refer to one or more than one (at least one) of the grammatical object of the article.

RNAi Agent

In some embodiments, the present disclosure pertains to an APOC3 RNAi agent. An RNAi agent is a composition comprising at least an antisense nucleic acid sequence complementary to a target nucleic acid (or portion thereof) and capable of mediating RNA interference against the target, or pertains to a recombinant expression vector encoding an shRNA or composition comprising the antisense nucleic acid that can function as an RNAi as defined below; an RNAi agent generally, but not always, also comprises a sense strand at least partially complementary to the antisense strand. As used herein, an "antisense" nucleic acid comprises a nucleotide sequence complementary to a "sense" nucleic acid encoding the target protein (e.g., complementary to the coding strand of a double-stranded DNA, complementary to an mRNA or complementary to the coding strand of a target gene or nucleic acid).

RNAi agents include, as non-limiting examples, siRNAs (small interfering RNAs), dsRNAs (double stranded RNAs), shRNAs (short hairpin RNAs) and miRNAs (micro RNAs). A canonical siRNA comprises two strands, each a 21-mer, forming a 19-bp double-stranded region and two 3' overhangs of 2 nt each. However, other structures or formats of RNAi agents are known to be active, including blunt-ended 19-mers, or, as disclosed herein, blunt-ended 18-mers, or siRNAs with a shortened sense strand. RNAi agents can comprise RNA subunits (ribonucleotides); however, one or more ribonucleotides can be modified and/or substituted. Modifications and substitutions include, as additional non-limiting examples, locked nucleic acid (LNA), Morpholino, threose nucleic acid (TNA), or glycol nucleic acid (GNA), arabinose nucleic acid (ANA), 2'-fluoroarabinose nucleic acid (FANA), cyclohexene nucleic acid (CeNA), anhydrohexitol nucleic acid (HNA), peptide nucleic acid (PNA), or UNA (unlocked nucleic acid), 2'-MOE, 2'-OMe, 2'-F, 2'-alkyl, or any other modification or substitution described herein or known in the art. RNAi agents also include molecules in which one or more strands are a mixture of RNA, DNA, LNA, morpholino, TNA, GNA, ANA, HNA, CeNA, FANA, UNA, and/or FANA, etc. As a non-limiting example, one or both strands of an RNAi agent could be, for example, RNA, except that one or more RNA nucleotides is replaced by DNA, LNA, morpholino, TNA, GNA, UNA, and/or FANA, etc. In various aspects, one or both strands of the RNAi agent can be nicked, and both strands can be the same length, or one (e.g., the passenger strand), can be shorter than the other.

In various aspects, the present disclosure pertains to any RNAi agent comprising a RNA sequence disclosed herein and/or a RNA sequence corresponding to any DNA sequence disclosed herein (e.g., wherein the DNA nucleotides are replaced by the corresponding RNA nucleotide, for example, with T in DNA replaced by U in RNA, and with ribose instead of deoxyribose in the sugar-phosphate backbone).

The RNAi agent(s) of the present disclosure target (e.g., bind to, anneal to, hybridize, etc.) the APOC3 mRNA. The use of the RNAi agent specific to APOC3 results in a decrease of APOC3 activity, level and/or expression, e.g., a "knock-down" (KD) or "knock-out" of the target gene or target sequence. In some embodiments, in the case of a disease state characterized by over-expression or hyper-activity of APOC3, administration of a RNAi agent to APOC3 knocks down the APOC3 target enough to provide a more normal or therapeutic level of APOC3 activity or expression. Thus, a minimal expression of APOC3 in normal tissues can be beneficial. In various aspects of the disclosure, the patient or individual may have a disease state characterized by excessively high levels of APOC3 and the RNAi agent can restore a normal level. In some embodiments of the disclosure, the levels of APOC3 throughout the body are modulated such that APOC3 levels in one area (e.g., areas afflicted by an APOC3-related disease) are lower, while areas of the body not afflicted by the disease are closer to normal APOC3 levels. In some embodiments of the disclosure, the RNAi agent can be delivered locally so that levels of APOC3 outside the diseased areas can be maintained as close to normal as possible. In another aspect, the level of APOC3 in the body can be modulated such that it is low enough to improve the disease state, but not so low that organ pathology occurs.

In some embodiments, the RNAi comprises a single strand. This single-stranded RNAi agent oligonucleotide or polynucleotide can comprise the sense or antisense strand, as described by Sioud 2005 J. Mol. Biol. 348:1079-1090, and references therein. Thus the disclosure encompasses RNAi agents with a single strand comprising either the sense or antisense strand of an RNAi agent described herein. The disclosure also encompasses RNAi agents comprising a single strand, wherein the single strand comprises the sequences of both the antisense and sense strands of any RNAi agent disclosed herein, e.g., wherein the strands are contiguous, connected by a loop or otherwise linked. Examples of such molecules include those with a hairpin between the sense and anti-sense sequences (e.g., shRNA).

In various aspects, one or both strands contain one or more nicks, i.e., a break or missing bond in the phosphate backbone, such that at least one nucleotide subunit is not covalently linked to the adjacent nucleotide subunit in any given sequence. In some aspects, the passenger strand is nicked (see, for example, WO 2007/107162). In various aspects, one or both strands contain one or more gaps, e.g., wherein at least one entire nucleotide subunit is absent from the disclosed sequence. Where a sense or antisense sequence contains a gap, that strand is envisioned to comprise two separate oligonucleotides.

Particularly useful siRNAs include those which can bind specifically to those regions of the APOC3 mRNA that have one or more of the following qualities: binding in the coding segment of APOC3; binding at or near the junction of the 5' untranslated region and the start of the coding segment; binding at or near the translational start site of the mRNA; binding at, across or near junctions of exons and introns; little or no binding to the mRNAs or transcripts of other genes (little or no "off-target effects"); binding to the APOC3 mRNA in or near a region or regions that is not double-stranded or a stem region, e.g., those in a loop or single-stranded portion; eliciting little or no immunogenicity; binding in a segment of the APOC3 mRNA sequence which is conserved among various animal species (including human, mouse, rat, cyno, etc.), as the presence of a conserved sequence facilitates testing using various laboratory animals; binding to double-stranded region(s) of the mRNA; binding to an AT-rich region (e.g., at least about 50, 51, 52, 53, 54, 55, 56, 57, 58, 59, or 60% AT-rich); and/or lacking particular sequences known or suspected to decrease siRNA activity, e.g., the presence of a GG sequence at the 5' end, which may decrease separation of the double-stranded portion of the siRNA. In some embodiments, the RNAi agent specific to APOC3 can be a double-stranded RNA having any one or more of these qualities.

The term "double-stranded RNA" or "dsRNA," as used herein, refers to a RNAi agent comprising a first and a second strand; e.g., a composition that includes an RNA molecule or complex of molecules having a hybridized duplex region (i.e., a region where the nucleotide bases from the first strand and the second strand are paired) that comprises two anti-parallel and substantially complementary nucleic acid strands, which will be referred to as having "sense" and "antisense" orientations with respect to a target RNA. The antisense strand, with respect to the mRNA target, is also called the "guide" strand, and the sense strand is also called the "passenger" or "anti-guide" strand. The passenger strand can include at least one or more of the following: one or more extra nucleotides (e.g., a bulge or 1 nt loop) compared to the other strand, and/or a nick, a gap, a mismatch, etc., compared to the other strand. In various aspects, the RNAi agent comprises a first strand and a second strand. In various aspects, and as used herein and as is clear by context, terminology referring to the first strand refers to the sense strand and the second strand refers to the anti-sense strand as listed in any Table herein. In other aspects, and as used herein and as is clear by context, the first strand refers to the anti-sense strand, and the second strand refers to the sense strand as listed in any Table herein.

The duplex region can be of any length that permits specific degradation of a desired target RNA through a RISC pathway, but will typically range from 9 to 36 base pairs ("bp") in length, e.g., 15-30 bp in length. Considering a duplex between 9 and 36 bp, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 bp and any sub-range therebetween, including, but not limited to 15-30 bp, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 20 basepairs, 21-30 bp, 21-26 bp, 21-25 bp, 21-24 bp, 21-23 bp, 21-22 bp, 21 bp, 22 bp, or 23 bp. The dsRNAs generated in the cell by processing with Dicer and similar enzymes are generally in the range of about 19 to about 22 bp in length, though the strands of artificial dsRNAs can be shorter or longer. siRNAs wherein one or both strands are as short as 16 or 15 nt still demonstrate RNA interference activity. (Chu and Rana 2008 RNA 14: 1714-1719). One strand of the duplex region of a dsRNA comprises a sequence that is substantially complementary to a region of a target RNA. The two strands forming the duplex structure can be from a single RNA molecule having at least one self-complementary duplex region, or can be formed from two or more separate RNA molecules that hybridize to form the duplex. Where the duplex region is formed from two self-complementary regions of a single molecule, the molecule can have a duplex region separated by a single-stranded chain of nucleotides (herein referred to as a "hairpin loop", e.g., such as found in an shRNA construct) between the 3'-end of one strand and the 5'-end of the respective other strand forming the duplex structure. The hairpin loop can comprise at least one unpaired nucleotide; in some aspects the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can, be covalently connected. Where the two strands are connected covalently by a hairpin loop, the construct is generally referred to herein and in the art as a "shRNA". Where the two strands are connected covalently by means other than a hairpin loop, the connecting structure is referred to as a "linker."

RNAi Agents to APOC3 Comprising Mismatches from the Disclosed Sequences.

Various specific aspects of a RNAi agent to APOC3 are disclosed herein; example sequences are provided in the Tables. Specific aspects of the present disclosure include RNAi agents which comprise sequences differing by 0, 1, 2, or 3 nt (nucleotides) or bp [basepair(s)] (e.g., with 0, 1, 2 or 3 mismatches) from any of the RNAi agents listed in any of the tables herein, and modified and unmodified variants thereof.

A mismatch is defined herein as a difference between the base sequence or length when two sequences are maximally aligned and compared. A mismatch is defined as a position wherein the base of one sequence does not match the base of the other sequence. Thus, a mismatch is counted, for example, if a position in one sequence has a particular base (e.g., A), and the corresponding position on the other sequence has a different base (e.g., G). Substitution of A, for example, with T, C, G or U would constitute a mismatch. Substitution of G with T, A, C or U would also constitute a mismatch. Substitution of C with T, G, A or U would also constitute a mismatch. Substitution of U with A, C or G would constitute a mismatch. Note, however, that on a given strand, a U can be replaced by T (either as RNA or, preferably, DNA, e.g., 2'-deoxy-thymidine); the replacement of a U with a T is not a mismatch as used herein, as either U or T can pair with A on the opposite strand. The RNAi agent can thus comprise one or more DNA bases, e.g., T. In some cases, in a portion or portions of the RNAi agent, DNA can be used in place of RNA (e.g., in the seed region), to form a DNA-RNA hybrid. See, for example, Yamato et al. 2011 cancer Gene Ther. 18: 587-597. No mismatch is counted between a DNA portion(s) of the RNAi agent and the corresponding target mRNA if basepairing occurs (e.g., between A, G, C, or T in the DNA portion, and the corresponding U, C, G, or A, respectively in the mRNA).

A mismatch is also counted, e.g., if a position in one sequence has a base (e.g., A), and the corresponding position on the other sequence has no base (e.g., that position is a spacer [e.g., in the internal spacer format described herein] or an abasic nucleotide, which comprises a phosphate-sugar backbone but no base). For example, if the anti-sense strands of two different duplexes are identical except that, at one position, the nucleobase unit (i.e., sugar+base) has been replaced by a spacer (e.g., a spacer described herein), the sequences are considered to have one mismatch (e.g., to differ by 1 nt). A single-stranded nick in either sequence (or in the sense or anti-sense strand) is not counted as mismatch. Thus, as a non-limiting example, no mismatch would be counted if one sequence comprises the sequence AG, but the other sequence comprises the sequence AG with a single-stranded nick between the A and the G. A nucleotide modification in the sugar or phosphate is also not considered a mismatch. Thus, if one sequence comprises a C, and the other sequence comprises a modified C (e.g., 2'-modification) at the same position, no mismatch would be counted.

Thus, no mismatches are counted if modifications are made to the sugar, phosphate, or backbone of the RNAi agent without modifying the base. Thus, a strand having a particular sequence of as an RNA would have zero mismatches from another strand having the same sequence as a PNA; or morpholino; or LNA; or TNA; or GNA; or UNA; or FANA; or a mix or chimera of RNA and DNA, TNA, GNA, UNA, FANA, morpholino, LNA, and/or PNA, etc.

It is also noted that the sequences of the RNAi agents in the Tables include sequences which comprise modifications. It is noted that dTdT (2'-deoxy-thymidine-5'-phosphate and 2'-deoxy-thymidine-5'-phosphate), or in some cases, TT or UU, can be added as a terminal dinucleotide cap or extension to one or both 3'-ends, but this cap or extension is not included in the calculation of the total number of mismatches and is not considered part of the target sequence. This is because the terminal dinucleotide protects the ends from nuclease degradation but does not contribute to target specificity (Elbashir et al. 2001 Nature 411: 494-498; Elbashir et al. 2001 EMBO J. 20: 6877-6888; and Kraynack et al. 2006 RNA 12:163-176).

In addition, a modified variant can have one or more modifications from the corresponding unmodified sequence. In this case, lowercase "c" represents 2'-O-methylcytidine-5'-phosphate, and lowercase "u" represents 2'-O-methyluridine-5'-phosphate. Uppercase "A", "C", "G" and "U" represent the un-modified adenosine-5'-phosphate, cytidine-5'-phosphate, guanosine-5'-phosphate, and uridine-5'-phosphate, respectively. The substitution, for example, of modified c for unmodified C does not count as a mismatch in numbering the 0, 1, 2, or 3 mismatches between sequences. This nomenclature is used for all sequences in any of the tables herein. Thus, an equal number of mismatches would be calculated (a) between a test sequence and that of another RNAi agent, and (b) between the same test sequence and the corresponding unmodified sequence from the APOC3 gene, and (c) between a modified sequence and a differently modified sequence which have the same base sequence.

In some embodiments, the present disclosure comprises a RNAi agent comprising a anti-sense strand comprising at least 15 to 19 contiguous nucleotides differing by 0, 1, 2, or 3 nt from the sequence of the anti-sense strand of: any of the RNAi agents listed in any of the tables herein, and modified and unmodified variants thereof.

The present disclosure pertains to "modified and unmodified variants" of the disclosed sequences.

An "unmodified variant" of a particular sequence is the corresponding portion of APOC3 without any modifications. Example modified sequences are disclosed herein. The "unmodified variants" of the sequences of the Tables disclosed herein have the identical sequence, without base modifications or terminal dTdT. A given sequence and an "unmodified variant" of it differ by 0 nt (and have no mismatches).

A "modified variant" of a particular sequence comprises one or more (or one or more fewer) modifications to the backbone, sugar, phosphate or base, and/or addition of a terminal dinucleotide (e.g., TT, dTdT, TsT or UU), but do not have any base substitutions (e.g., G for C, or A for G); thus a given sequence and a modified variant thereof differ by 0 nt (and have no mismatches). As another example, a given sequence as a RNA and the same sequence as a PNA are modified variants of each other and differ by 0 nt (and have no mismatches). Similarly, the same sequence (with no base substitutions) as a locked nucleic acid (LNA), Morpholino, threose nucleic acid (TNA), or glycol nucleic acid (GNA) or unlocked nucleic acid (UNA) or FANA or ANA or HNA or CeNA, etc. would be a modified variant which has 0 mismatches. In addition, the same sequence could be used in strands which are a mixture of RNA, DNA, LNA, morpholino, TNA, GNA, ANA, HNA, CeNA, UNA, and/or FANA, etc. As a non-limiting example, one or both strands could be, for example, RNA except that one or more nucleotides is replaced by DNA, LNA, morpholino, TNA, GNA, ANA, HNA, CeNA, UNA, and/or FANA, etc.

As detailed below, substituting a single nucleotide at a given position with a modified version of the same nucleotide would produce a modified variant (with 0 mismatches).

In another particular aspect, the RNAi agent comprises a sense strand comprising at least 14 contiguous nucleotides differing by 0, 1, 2, or 3 nt from the sense strand of any of the RNAi agents listed in the Tables and modified and unmodified variants thereof.

RNAi agents to APOC3 of the present disclosure can be used in RNA interference.

Modifications of RNAi Agents.

The present disclosure encompasses both unmodified and example modified RNAi agents, such as those disclosed in the Tables.

The present disclosure further encompasses any other modification of a disclosed RNAi agent (e.g., a modified variant).

For example, the disclosure encompasses a RNAi agent with a substitution of a single nucleotide at a given position with a modified version of the same nucleotide. Thus a nucleotide (A, G, C or U) can be replaced by the corresponding 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, or 2,6-diaminopurine.

Additional modified variants include the addition of any other moiety (e.g., a radiolabel or other tag or conjugate) to the RNAi agent; provided that the base sequence is identical, the addition of other moieties produces a "modified variant" (with no mismatches).

Various sets of modifications can be used. These include the following formats, which are used in various screens disclosed herein.

In addition to these modifications and patterns (e.g., formats) for modifications, other modifications or sets of modifications of the sequences provided can be generated using common knowledge of nucleic acid modification. These various aspects of the RNAi agents to APOC3 of the present disclosure can be used in RNA interference.

RNA Interference.

RNA interference (RNAi) is a post-transcriptional, targeted gene-silencing technique that uses double-stranded RNA (dsRNA) to degrade messenger RNA (mRNA) containing the same sequence as the dsRNA. The process of RNAi occurs when ribonuclease III (Dicer) cleaves the longer dsRNA into shorter fragments called siRNAs. siRNAs (small interfering RNAs) produced by Dicer are typically about 21 to 23 nucleotides long and comprise about 19 base pair duplexes (though artificial siRNAs or RNAi agents can be shorter or longer, and/or blunt-ended, and/or comprises one or more endcaps). The smaller RNA segments then mediate the degradation of the target mRNA. Dicer has also been implicated in the excision of 21- and 22-nucleotide small temporal RNAs (stRNAs) from precursor RNA of conserved structure that are implicated in translational control. (Hutvagner et al. 2001 Science 293: 834). The RNAi response also features an endonuclease complex, commonly referred to as an RNA-induced silencing complex (RISC), which mediates cleavage of single-stranded mRNA complementary to the anti-sense strand of the RNAi agent. Cleavage of the target RNA takes place in the middle of the region complementary to the anti-sense strand of the siRNA duplex.

In some embodiments, an RNA interference agent includes a single-stranded RNA that interacts with a target RNA sequence to direct the cleavage of the target RNA. Without wishing to be bound by theory, the present disclosure contemplates a long double-stranded RNA introduced into plants and invertebrate cells is broken down into siRNA by a Type III endonuclease known as Dicer. (Sharp et al. 2001 Genes Dev. 15:485. Dicer), a ribonuclease-III-like enzyme, processes the dsRNA into 19-23 base pair short interfering RNAs with characteristic two base 3' overhangs. (Bernstein, et al. 2001 Nature 409:363). The siRNAs are then incorporated into an RNA-induced silencing complex (RISC) where one or more helicases unwind the siRNA duplex, enabling one of the now unpaired siRNA strands to act as a "guide" strand to guide target recognition. (Nykanen, et al. 2001 Cell 107:309). Upon binding of the antisense guide strand to the appropriate target mRNA, one or more endonucleases within the RISC cleaves the target to induce silencing. (Elbashir, et al. 2001 Genes Dev. 15:188). Thus, in some embodiments the present disclosure relates to a single-stranded RNA that promotes the formation of a RISC complex to effect silencing of the target gene.

A suitable RNAi agent can be selected by any process known in the art or conceivable by one of ordinary skill in the art. For example, the selection criteria can include one or more of the following steps: initial analysis of the APOC3 gene sequence and design of RNAi agents; this design can take into consideration sequence similarity across species (human, cynomolgus, mouse, etc.) and dissimilarity to other (non-APOC3) genes; screening of RNAi agents in vitro (e.g., at 10 nM in RKO cells); determination of EC50 in RKO cells; determination of viability of cells treated with RNAi agents, including insensitive cells which do not require APOC3 for survival, or sensitive cells, which do require APOC3 for survival; testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCP1 (monocyte chemotactic protein 1)], wherein Immunostimulatory sequences are less desired; determination of gene knockdown in vivo using subcutaneous tumors in test animals; APOC3 target gene modulation analysis, e.g., using a pharmacodynamic (PD) marker, for example, other factors whose expression is affected by APOC3, wherein APOC3 knockdown leads to a dose-dependent reduction of abundance of those components; and optimization of specific modifications of the RNAi agents.

The dsRNA molecules (RNAi agents) described herein are thus useful in RNA interference of APOC3.

Features of a RNAi Agent: Sense Strand, Antisense Strand and (Optional) Overhangs.

In various aspects, the RNAi agents comprise a first strand and a second strand, e.g., a sense strand and an antisense strand (or an antisense and a sense strand), optionally, either or both ends of either or both strands can comprise unpaired nucleotides (referred to herein as "overhangs").

The term "antisense strand" refers to the strand of a RNAi agent which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand," as used herein, refers to the strand of a RNAi agent that includes a region that is substantially complementary to a region of the antisense strand as that term is defined herein.

The sequence of a gene may vary from individual to individual, especially at wobble positions within the coding segment, or in the untranslated region; individuals may also differ from each other in coding sequence, resulting in additional differences in mRNA. The sequence of the sense and antisense strands of the RNAi agent can thus be designed to correspond to that of an individual patient, if and where needed. RNAi agents can also be modified in sequence to reduce immunogenicity, binding to undesired mRNAs (e.g., "off-target effects") or to increase stability in the blood. These sequence variants are independent of chemical modification of the bases or 5' or 3' or other end-caps of the RNAi agents.

The RNAi agents can also have overhangs of 0, 1, or 2 overhangs; in the case of a 0 nt overhang, they are blunt-ended. A RNAi agent can thus have 0, 1 or 2 blunt ends. In a "blunt-ended RNAi agent" both strands terminate in a base-pair; thus a blunt-ended molecule lacks either 3' or 5' single-stranded nucleotide overhangs.

The RNAi agents can comprise overhang(s), blunt end(s), and/or 5' and 3' endcap(s).

As used herein, the term "overhang" or "nucleotide overhang" refer to at least one unpaired nucleotide that protrudes from the end of at least one of the two strands of the duplex structure of a RNAi agent. For example, when a 3'-end of one strand of a dsRNA extends beyond the 5'-end of the other strand, or vice versa, this forms a nucleotidic overhang, e.g., the unpaired nucleotide(s) form the overhang. A dsRNA can comprise an overhang of at least one nucleotide; alternatively the overhang can comprise at least two nucleotides, at least three nucleotides, at least four nucleotides, at least five nucleotides or more. An overhang can comprise or consist of a nucleotide/nucleoside analog, including a deoxynucleotide/nucleoside. The overhang(s) may be on the sense strand, the antisense strand or any combination thereof. Furthermore, the nucleotide(s) of an overhang can be present on the 5' end, 3' end or both ends of either an antisense or sense strand of a dsRNA. The RNAi agent can also optionally comprise a cap. The term "Cap" and the like include a chemical moiety attached to the end of a double-stranded nucleotide duplex, but is used herein to exclude a chemical moiety that is a nucleotide or nucleoside. A "3' Cap" is attached at the 3' end of a nucleotide or oligonucleotide and protects the molecule from degradation, e.g., from nucleases, such as those in blood serum or intestinal fluid. A non-nucleotidic 3' cap is not a nucleotide and can replace a TT or UU dinucleotide at the end of a blunt-ended RNAi agent. In some embodiments, non-nucleotidic 3' end caps are as disclosed in, for example, WO 2005/021749 and WO 2007/128477; and U.S. Pat. No. 8,097,716; U.S. Pat. No. 8,084,600; and U.S. Pat. No. 8,344,128. A "5' cap" is attached at the 5' end of a nucleotide or oligonucleotide. A cap should not interfere (or unduly interfere) with RNAi activity.

The present disclosure thus contemplates a RNAi agent specific to APOC3 comprising an antisense strand (which may be contiguous or connected via a linker or loop) in a RNAi agent. In a more specific aspect, an RNAi agent comprises an antisense strand and a sense strand which together comprise a double-stranded or complementary region. In some embodiments, it can also optionally comprise one or two overhangs and/or one or two caps. The RNAi agent is used to induce RNA interference of the target gene, APOC3.

Target and Complementary Sequences

The RNAi agents of the present disclosure target (e.g., specifically bind to, anneal to, etc.) the mRNA encoding APOC3. The use of the RNAi agent specific to APOC3 results in a decrease of APOC3 activity, level and/or expression. Particularly in some embodiments, in the case of a disease state characterized by over-expression or hyperactivity of APOC3, administration of a RNAi agent to APOC3 knocks down the APOC3 gene enough to restore a normal level of APOC3 activity or expression.

In some embodiments, the first or second strand of the RNAi comprises a sequence complementary to that of the target nucleic acid, APOC3.

As used herein, the term "strand comprising a sequence" refers to an oligonucleotide comprising a chain of nucleotides that is described by the sequence referred to using the standard nucleotide nomenclature.

As used herein, "target sequence" or "target gene" refer to a contiguous portion of the nucleotide sequence of an mRNA molecule formed during the transcription of a gene, e.g., an APOC3 gene, including mRNA that is a product of RNA processing of a primary transcription product. The target portion of the sequence will be at least long enough to serve as a substrate for RNAi-directed cleavage at or near that portion. For example, the target sequence will generally be from 9-36 nucleotides ("nt") in length, e.g., 15-30 nt in length, including all sub-ranges therebetween. As non-limiting examples, the target sequence can be from 15-30 nt, 15-26 nt, 15-23 nt, 15-22 nt, 15-21 nt, 15-20 nt, 15-19 nt, 15-18 nt, 15-17 nt, 18-30 nt, 18-26 nt, 18-23 nt, 18-22 nt, 18-21 nt, 18-20 nt, 19-30 nt, 19-26 nt, 19-23 nt, 19-22 nt, 19-21 nt, 19-20 nt, 19 nt, 20-30 nt, 20-26 nt, 20-25 nt, 20-24 nt, 20-23 nt, 20-22 nt, 20-21 nt, 20 nt, 21-30 nt, 21-26 nt, 21-25 nt, 21-24 nt, 21-23 nt, or 21-22 nt, 21 nt, 22 nt, or 23 nt. The sense and antisense strands of the RNAi comprise a sequence complementary to that of the target nucleic acid, APOC3.

As used herein, and unless otherwise indicated, the term "complementary" refers to the ability of an oligonucleotide or polynucleotide comprising a first nucleotide sequence to hybridize and form a duplex structure under certain conditions with an oligonucleotide or polynucleotide comprising a second nucleotide sequence. Such conditions can, for example, be stringent, e.g., 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. The skilled person will be able to determine the set of conditions most appropriate for a test of complementarity of two sequences in accordance with the ultimate application of the hybridized nucleotides.

Complementary sequences within a RNAi agent, e.g., within a dsRNA as described herein, include base-paired oligonucleotides or polynucleotides comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they may form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single-stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein. The term "overhang" describes an unpaired nucleotide at the 3' or 5' end of a double-stranded nucleotide duplex, as described above. In some embodiments, the overhang is 1 to 4 nt long and is on the 3' end.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but are not limited to, Wobble or Hoogstein base pairing. The terms "complementary," "fully complementary" and "substantially complementary" herein may furthermore be used with respect to the base matching between the sense strand and the antisense strand of a dsRNA, or between the antisense strand of a RNAi agent and a target sequence, as will be understood from the context of their use. As used herein, a polynucleotide that is "substantially complementary to at least part of" a messenger RNA (mRNA) refers to a polynucleotide that is substantially complementary to a contiguous portion of the mRNA of interest (e.g., an mRNA encoding APOC3). For example, a polynucleotide is complementary to at least a part of an APOC3 mRNA if the sequence is substantially complementary to a non-interrupted portion of an mRNA encoding APOC3.

Thus, in some embodiments, the RNAi agent of the present disclosure is complimentary or substantially complimentary to a target sequence in the target APOC3 and is double-stranded, comprising a sense and an antisense strand (which can be contiguous, linked via a loop, or otherwise joined), where the double-stranded region is 9 to 36 bp long (particularly for example, 19-22 bp or 19-23 bp long), and can furthermore optionally comprise a 3' or 5' overhang, and the RNAi agent can furthermore comprise a 3' cap. The RNAi agent mediates RNA interference, down-regulating or inhibiting or reducing the level, expression and/or activity of APOC3, and/or establishing or re-establishing an approximately normal level of APOC3 and/or APOC3 activity, or other biological function related to APOC3.

Thus, in some embodiments, the RNAi agent of the present disclosure is complimentary or substantially complimentary to a target sequence in the target APOC3 and is double-stranded, comprising a sense and an antisense strand (which can be contiguous, linked via a loop, or otherwise joined), where the double-stranded region is 9 to 36 bp long (particularly for example, 19-22 bp or 19-23 bp long), and can furthermore optionally comprise a 3' or 5' overhang, and the RNAi agent can furthermore comprise a 3' cap. The RNAi agent mediates RNA interference, down-regulating or inhibiting the level, expression and/or activity of APOC3, and/or establishing or re-establishing an approximately normal level of APOC3 activity or expression.

The term "double-stranded RNA" or "dsRNA," as used herein, refers to an RNAi agent comprising a first and a second strand; e.g., a composition that includes an RNA molecule or complex of molecules having a hybridized duplex region that comprises two anti-parallel and substantially complementary nucleic acid strands, which will be referred to as having "sense" and "antisense" orientations with respect to a target RNA. The antisense strand, with respect to the mRNA target, is also called the "guide" strand, and the sense strand is also called the "passenger" strand. As used herein, depending on the context, the "first" strand can be the guide or antisense strand, and the "second" strand can be the passenger or sense strand. Also as used herein, again depending on the context, the "first" strand can be the passenger or sense strand, and the "second" strand can be the guide or antisense. The passenger strand can include at least one or more of the following: one or more extra nucleotides (e.g., a bulge or 1 nt loop) compared to the other strand, a nick, a gap, etc., compared to the other strand. In various aspects, the first strand is the sense strand and the second strand is the anti-sense strand. In other aspects, the first strand is the anti-sense strand, and the second strand is the sense strand.

The duplex region can be of any length that permits loading into the RISC complex and subsequent specific degradation of a desired target RNA through a RISC pathway, but will typically range from 9 to 36 base pairs ("bp") in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 bp and any sub-range therebetween, including, but not limited to 15-30 base pairs, 15-26 bp, 15-23 bp, 15-22 bp, 15-21 bp, 15-20 bp, 15-19 bp, 15-18 bp, 15-17 bp, 18-30 bp, 18-26 bp, 18-23 bp, 18-22 bp, 18-21 bp, 18-20 bp, 19-30 bp, 19-26 bp, 19-23 bp, 19-22 bp, 19-21 bp, 19-20 bp, 19 bp, 20-30 bp, 20-26 bp, 20-25 bp, 20-24 bp, 20-23 bp, 20-22 bp, 20-21 bp, 20 bp, 21-30 bp, 21-26 bp, 21-25 bp, 21-24 bp, 21-23 bp, 21-22 bp, 21 bp, 22 bp, or 23 bp.

The dsRNAs generated in the cell by processing with Dicer and similar enzymes are generally in the range of about 19 to about 22 base pairs in length, although artificial RNAi agents can be synthesized or made by any method known in the art. One strand of the duplex region of a dsRNA comprises a sequence that is substantially complementary to a region of a target RNA. The two strands forming the duplex structure can be from a single RNA molecule having at least one self-complementary duplex region, or can be formed from two or more separate RNA molecules that hybridize to form the duplex. Where the duplex region is formed from two self-complementary regions of a single molecule, the molecule can have a duplex region separated by a single stranded chain of nucleotides (herein referred to as a "hairpin loop", e.g., such as found in an shRNA construct) between the 3'-end of one strand and the 5'-end of the respective other strand forming the duplex structure. The hairpin loop can comprise at least one unpaired nucleotide; in some aspects the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by a hairpin loop, the construct is generally referred to herein and in the art as a "shRNA". Where the two strands are connected covalently by means other than a hairpin loop, the connecting structure is referred to as a "linker." The term "siRNA" is also used herein to refer to a dsRNA as described above.

RNAi Agents Lowering or Normalizing APOC3 Level, Expression and/or Activity

RNAi agents for targeting APOC3 include those which bind to an APOC3 sequence provided herein and which work to reduce APOC3 through a RNAi mechanism. Example RNAi agents (e.g., siRNAs) to APOC3 are provided herein.

Any method known in the art can be used to measure changes in APOC3 activity, level, and/or expression induced by an APOC3 RNAi agent. Measurements can be performed at multiple timepoints, prior to, during and after administration of the RNAi agent, to determine the effect of the RNAi agent.

The RNAi agents of the present disclosure silence, inhibit the expression of, down-regulate the expression of, and/or suppress the expression of APOC3, such that an approximately normal level of APOC3 activity or expression is restored.

In addition, in various aspects, depending on the disease condition and biological context, it is acceptable to use the RNAi agents of the present disclosure to establish a level of APOC3 expression, activity and/or level which is below the normal level, or above the normal level, depending on the therapeutic outcome that is desired.

Any method known in the art can be used to measure changes in APOC3 activity, level and/or expression induced by an APOC3 siRNA. Measurements can be performed at multiple timepoints, prior to, during and after administration of the siRNA, to determine the effect of the siRNA.

The terms "silence," "inhibit the expression of," "down-regulate the expression of," "suppress the expression of," and the like, in so far as they refer to an APOC3 gene, herein refer to the at least partial suppression of the expression of an APOC3 gene, as manifested by a reduction of the amount of APOC3 mRNA which may be isolated from or detected in a first cell or group of cells in which an APOC3 gene is transcribed and which has or have been treated such that the expression of an APOC3 gene is inhibited, as compared to a second cell or group of cells substantially identical to the first cell or group of cells but which has or have not been so treated (control cells). The degree of inhibition is usually expressed in terms of $$\frac{(mRNA \text{ in control cells}) - (mRNA \text{ in treated cells})}{(mRNA \text{ in control cells})} \cdot 100\% \quad \text{Equation 1}$$

Alternatively, the degree of inhibition may be given in terms of a reduction of a parameter that is functionally linked to APOC3 gene expression, e.g., the amount of protein encoded by an APOC3 gene, alteration in expression of a protein whose expression is dependent on APOC3, etc. In principle, APOC3 gene silencing may be determined in any cell expressing APOC3, either constitutively or by genomic engineering, and by any appropriate assay. However, when a reference or control is needed in order to determine whether a given RNAi agent inhibits the expression of APOC3 by a certain degree and therefore is encompassed by the instant disclosure, the assays provided in the Examples below shall serve as such reference.

For example, in certain instances, expression of APOC3 is suppressed by at least about 10%, 15%, 20%, 25%, 30%, 35%, 40%, 45%, or 50% by administration of a RNAi agent featured in the present disclosure. In some aspects, APOC3 is suppressed by at least about 60%, 70%, or 80% by administration of a RNAi agent featured in the present disclosure. In some aspects, APOC3 is suppressed by at least about 85%, 90%, or 95% or more by administration of a RNAi agent, as described herein. In some embodiments, the degree of APOC3 suppression is determined by loss of full length APOC3 mRNA in a treated cell compared to an untreated cell. In some embodiments, the degree of APOC3 suppression is determined with a phenotypic assay that monitors loss of proliferative activity and/or cell death. Other aspects are as provided in the Examples.

A suitable RNAi agent can be selected by any process known in the art or conceivable by one of ordinary skill in the art. For example, the selection criteria can include one or more of the following steps: initial analysis of the APOC3 gene sequence and design of RNAi agents; this design can take into consideration sequence similarity across species (human, cynomolgus, mouse, etc.) and dissimilarity to other (non-APOC3) genes; screening of RNAi agents in vitro (e.g., at 10 nM and 1 nM in Huh-7 cells); selection of RNAi agents with high knock-down at 10 nM and 1 nM in Huh-7 cells; determination of EC50 in Huh-7 cells; confirmation of EC50 in a RCC cell line (Huh-7 cells); analysis of a lack of effect on cell growth relative to a control siRNA; reduction in Huh-7 cells of expression of a HRE-luc (luciferase) reporter gene and not control UB6-luc (luciferase) reporter gene; Western blots to measure Hif-1, Hif-2, and ARNT levels; testing with human PBMC (peripheral blood mononuclear cells), e.g., to test levels of TNF-alpha to estimate immunogenicity, wherein immunostimulatory sequences are less desired; testing in human whole blood assay, wherein fresh human blood is treated with an RNAi agent and cytokine/chemokine levels are determined [e.g., TNF-alpha (tumor necrosis factor-alpha) and/or MCP1 (monocyte chemotactic protein 1)], wherein immunostimulatory sequences are less desired; determination of gene knock-down in vivo using subcutaneous tumors in test animals; APOC3 target gene modulation analysis, e.g., using a pharmacodynamic (PD) marker, for example, EGLN3, SLC2A1 and VEGF, wherein APOC3 knockdown leads to a dose-dependent alteration of EGLN3, SLC2A1 and VEGF expression in cells; and optimization of specific modifications of the RNAi agents. As appropriate, other cell lines can be used in place of those listed above to identify RNAi agents capable of lowering APOC3 levels or decrease symptoms of an APOC3-related disease.

By "lower" in the context of APOC3 or a symptom of an APOC3-related disease is meant a statistically significant decrease in such level. The decrease can be, for example, at least 10%, at least 20%, at least 30%, at least 40% or more. If, for a particular disease, or for an individual suffering from a particular disease, the levels or expression of APOC3 are elevated, treatment with an APOC3 RNAi agent of the present disclosure can particularly reduce the level or expression of APOC3 to a level considered in the literature as within the range of normal for an individual without such disorder, or to a level that reduces or ameliorates symptoms of a disease. The level or expression of APOC3 can be measured by evaluation of mRNA (e.g., via Northern blots or PCR), or protein (e.g., Western blots). The effect of a RNAi agent on APOC3 expression can be determined by measuring APOC3 gene transcription rates (e.g., via Northern blots; or reverse transcriptase polymerase chain reaction or real-time polymerase chain reaction).

As used herein, "down-regulates" refers to any statistically significant decrease in a biological activity and/or expression of APOC3, including full blocking of the activity (i.e., complete inhibition) and/or expression. For example, "down-regulation" can refer to a decrease of at least about 10, 20, 30, 40, 50, 60, 70, 80, 90 or 100% in APOC3 level, activity and/or expression.

As used herein, the term "inhibit" or "inhibiting" APOC3 refers to any statistically significant decrease in biological level, activity and/or expression of APOC3, including full blocking of the activity and/or expression. For example, "inhibition" can refer to a decrease of at least about 10, 20, 30, 40, 50, 60, 70, 80, 90 or 100% in APOC3 level, activity and/or expression. As used herein, the term "inhibit" similarly refers to a significant decrease in level, activity and/or expression, while referring to any other biological agent or composition.

By "level", it is meant that the APOC3 RNAi agent can alter the level of APOC3, e.g., the level of APOC3 mRNA or the level of APOC3 protein, or the level of activity of APOC3.

Some diseases include any APOC3-related disease disclosed herein or known in the literature. Particularly in some embodiments, in the case of a disease characterized by over-expression and/or hyper-activity of APOC3, administration of a RNAi agent to APOC3 reduces the level, expression and/or activity of APOC3. Thus, in various aspects, administration of a RNAi agent to APOC3 particularly establishes or re-establishes a normal or approximately normal level of APOC3 activity, expression and/or level.

By "normal" or "approximately normal" in terms of level, expression and/or activity, is meant at least: about 50%, about 60%, about 70%, about 80%, about 90%, and/or about 100%; and/or no more than: about 100%, about 120%, about 130%, about 140%, or about 150% of the level, expression and/or activity of APOC3 in a healthy cell, tissue, or organ. This can be measured using, for example, lung or kidney homogenates, as described in Gambling et al. 2 Kidney Intl. 65: 1774-1781. Particularly in some embodiments, administration of the appropriate amount of the appropriate APOC3 RNAi agent restores APOC3 level, activity and/or expression to about 50% to about 150%, more particularly about 60% to about 140%, more particularly to about 70% to about 130%, more particularly to about 80% to about 120%, more particularly to about 90% to about 110%, and most particularly to about 100% of that of a healthy cell, tissue or organ. Administration of an APOC3 RNAi to a patient with an APOC3-related disease thus particularly restores the level, activity, and/or expression of APOC3 and the level of $Na^+$ reabsorption to an approximately normal level, as determined by direct measurements of APOC3 mRNA or protein levels, or indirect determinations. In addition, the preferred target amount of APOC3 level, expression and/or activity after APOC3 RNAi agent administration can be calculated to take into account any other perturbations in an APOC3-related pathway. For example, if another factor in an APOC3-related pathway is either over- or under-expressed, APOC3 level, expression or activity may be modulated to attain a more normal state.

In addition, in various aspects, depending on the disease condition and biological context, it is acceptable to use the RNAi agents of the present disclosure to establish a level of APOC3 expression, activity and/or level which is below the normal level, or above the normal level.

Types of RNAi Agents and Modification Thereof

The use of RNAi agents or compositions comprising an antisense nucleic acid to down-modulate the expression of a particular protein in a cell is well known in the art. A RNAi agent comprises a sequence complementary to, and is capable of hydrogen bonding to, the coding strand of another nucleic acid (e.g., an mRNA). Thus, in various aspects, the RNAi agents of the present disclosure encompass any RNAi agents which target (e.g., are complementary, capable of hybridizing or hydrogen bonding to, etc.) any sequence presented, e.g., in any of the Tables.

Once a functional guide strand has been identified, many variations to the guide and/or passenger strand can be made. For example, the RNAi agent may have modifications internally, or at one or both ends. The modifications at the ends can help stabilize the RNAi agent, protecting it from degradation by nucleases in the blood. The RNAi agents may optionally be directed to regions of the APOC3 mRNA known or predicted to be near or at splice sites of the gene.

A RNAi agent can be constructed using chemical synthesis and enzymatic ligation reactions using procedures known in the art. For example, RNAi agent can be chemically synthesized using naturally-occurring nucleotides or variously modified nucleotides designed to decrease off-target effects, and/or increase the biological stability of the molecules or to increase the physical stability of the duplex formed between the antisense and sense nucleic acids, e.g., phosphorothioate derivatives and acridine substituted nucleotides can be used.

"G," "C," "A," "T" and "U" each generally stand for a nucleotide that contains guanine, cytosine, adenine, thymidine and uracil as a base, respectively. However, the terms "ribonucleotide", "deoxynucleotide", or "nucleotide" can also refer to a modified nucleotide or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of dsRNA featured in the present disclosure by a nucleotide containing, for example, inosine. In another example, adenine and cytosine anywhere in the oligonucleotide can be replaced with guanine and uracil, respectively to form Wobble base pairing with the target mRNA. Sequences containing such replacement moieties are suitable for the compositions and methods featured in the present disclosure.

The skilled artisan will recognize that the term "RNA molecule" or "ribonucleic acid molecule" encompasses not only RNA molecules as expressed or found in nature (i.e., are naturally occurring), but also non-naturally occurring analogs and derivatives of RNA comprising one or more ribonucleotide/ribonucleoside analogs or derivatives as described herein or as known in the art. The RNA can be modified in the nucleobase structure or in the ribose-phosphate backbone structure, e.g., as described herein below. However, the molecules comprising ribonucleoside analogs or derivatives can retain the ability to form a duplex. As non-limiting examples, either or both strand of an RNAi agent can comprise at least one modified ribonucleoside, including but not limited to a 2'-O-methyl modified nucleotide, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, an unlocked ribonucleotide (e.g., an acyclic nucleotide monomer, as described in WO 2008/147824), a phosphoramidate or a non-natural base comprising nucleoside, or any combination thereof. Alternatively, an RNA molecule can comprise at least two modified ribonucleosides, at least 3, at least 4, at least 5, at least 6, at least 7, at least 8, at least 9, at least 10, at least 15, at least 20 or more, up to the entire length of the dsRNA molecule. The modifications need not be the same for each of such a plurality of modified ribonucleosides in an RNA molecule. In some embodiments, modified RNAs contemplated for use in methods and compositions described herein are peptide nucleic acids (PNAs) that have the ability to form the required duplex structure and that permit or mediate the specific degradation of a target RNA via a RISC pathway. In addition, the RNAi agent can comprise one or two strands which are a RNA, or a mixture of RNA, DNA, LNA, morpholino, TNA, GNA, ANA, HNA, CeNA, UNA, and/or FANA, etc. As a non-limiting example, one or both strands could be, for example, RNA except that one or more nucleotides is replaced by DNA, LNA, morpholino, TNA, GNA, ANA, HNA, CeNA, FANA, and/or UNA, etc.

Examples of modified nucleotides which can be used to generate the RNAi agent include 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxy acetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurin (Usman et al. 1992 TIBS 17:34; Usman et al. 1994 Nucl. Acids Symp. Ser. 31: 163; Burgin et al. 1996 Biochem. 35: 14090).

A "modified variant" of a sequence disclosed herein includes any variant comprising the same sequence, but with a modification in the base, sugar, phosphate or backbone (but not a base substitution, e.g., A for G, or C for U). Thus, a modified variant can comprise any modified nucleotide described above (e.g., 5-fluorouracil, 5-bromouracil, 5-chlorouracil, 5-iodouracil, hypoxanthine, xantine, 4-acetylcytosine, 5-(carboxyhydroxylmethyl) uracil, etc.). When a base is replaced by a corresponding modified base (e.g., A for modified A), these modified nucleotides do not constitute a mismatch or base difference. Thus a given sequence with a U at a particular position and a modified variant comprising a 5-fluorouracil, 5-bromouracil, 5-chlorouracil, or 5-iodouracil at the same sequence would differ by 0 nt (or have no mismatches); however, a given sequence with a C at a particular position and a different sequence with a 5-fluorouracil (wherein the two sequences are otherwise identical) would differ by 1 nt (1 mismatch).

Replacing the 3'-terminal nucleotide overhanging segments of a 21-mer siRNA duplex having two-nucleotide 3'-overhangs with deoxyribonucleotides does not have an adverse effect on RNAi activity. Replacing up to four nucleotides on each end of the siRNA with deoxyribonucleotides has been well tolerated, whereas complete substitution with deoxyribonucleotides results in no RNAi activity. International PCT Publication No. WO 00/44914, and Beach et al. International PCT Publication No. WO 01/68836 preliminarily suggest that siRNA may include modifications to either the phosphate-sugar backbone or the nucleoside to include at least one of a nitrogen or sulfur heteroatom. Kreutzer et al. Canadian Patent Application No. 2,359,180, also describe certain chemical modifications for use in dsRNA constructs in order to counteract activation of double-stranded RNA-dependent protein kinase PKR, specifically 2'-amino or 2'-O-methyl nucleotides, and nucleotides containing a 2'-O or 4'-C methylene bridge. Additional 3'-terminal nucleotide overhangs include dT (deoxythimidine), 2'-O,4'-C-ethylene thymidine (eT), and 2-hydroxyethyl phosphate (hp). 4-thiouracil and 5-bromouracil substitutions can also be made. Parrish et al. 2000 Molecular Cell 6: 1077-1087.

Those skilled in the art will appreciate that it is possible to synthesize and modify the siRNA as desired, using any conventional method known in the art (see Henschel et al. 2004 DEQOR: a web-based tool for the design and quality control of siRNAs. Nucleic Acids Research 32 (Web Server Issue): W113-W120). In addition, if the RNAi agent is a shRNA, it will be apparent to those skilled in the art that there are a variety of regulatory sequences (for example, constitutive or inducible promoters, tissue-specific promoters or functional fragments thereof, etc.) which are useful for shRNA expression construct/vector.

There are several examples in the art describing sugar, base, phosphate and backbone modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-O-allyl, 2'-H, nucleotide base modifications (for a review see Usman and Cedergren 1992 TIBS. 17: 34; Usman et al. 1994 Nucleic Acids Symp. Ser.

31: 163; Burgin et al. 1996 Biochemistry 35: 14090). Sugar modification of nucleic acid molecules are extensively described in the art.

In various aspects, the RNAi agent comprises a 2'-modification selected from the group consisting of: 2'-deoxy, 2'-deoxy-2'-fluoro, 2'-O-methyl, 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), and 2'-O—N-methylacetamido (2'-O-NMA).

Additional modifications and conjugations of RNAi agents have been described. Soutschek et al. 2004 Nature 432: 173-178 presented conjugation of cholesterol to the 3'-end of the sense strand of a siRNA molecule by means of a pyrrolidine linker, thereby generating a covalent and irreversible conjugate. Chemical modifications (including conjugation with other molecules) of RNAi agents may also be made to improve the in vivo pharmacokinetic retention time and efficiency.

In various aspects, the RNAi agent to APOC3 comprises at least one 5'-uridine-adenine-3' (5'-ua-3') dinucleotide, wherein the uridine is a 2'-modified nucleotide; at least one 5'-uridine-guanine-3' (5'-ug-3') dinucleotide, wherein the 5'-uridine is a 2'-modified nucleotide; at least one 5'-cytidine-adenine-3' (5'-ca-3') dinucleotide, wherein the 5'-cytidine is a 2'-modified nucleotide; and/or at least one 5'-uridine-uridine-3' (5'-uu-3') dinucleotide, wherein the 5'-uridine is a 2'-modified nucleotide. In certain aspects, the RNAi agent can comprise a non-natural nucleobase, wherein the non-natural nucleobase is difluorotolyl, nitroindolyl, nitropyrrolyl, or nitroimidazolyl. In a particular aspect, the non-natural nucleobase is difluorotolyl. In certain aspects, only one of the two oligonucleotide strands contains a non-natural nucleobase. In certain aspects, both of the oligonucleotide strands contain a non-natural nucleobase.

In another aspect, the RNAi comprises a gap or contains mismatch comprising an abasic nucleotide.

In another aspect, the RNAi agent has a single-stranded nick (e.g., a break or missing bond in the backbone). In various aspects, a single-stranded nick can be in either the sense or anti-sense strand, or both.

This nick can be, for example, in the sense strand, producing a small internally segmented interfering RNA, or sisiRNA, which may have less off-target effects than the corresponding RNAi agent without a nick. (See, for example, WO 2007/107162 to Wengels and Kjems).

The antisense nucleic acid or RNAi agent can also have an alternative backbone such as locked nucleic acids (LNA), Morpholinos, peptidic nucleic acids (PNA), threose nucleic acid (TNA), or glycol nucleic acid (GNA), arabinose nucleic acid (ANA), 2'-fluoroarabinose nucleic acid (FANA), cyclohexene nucleic acid (CeNA), anhydrohexitol nucleic acid (HNA), or unlocked nucleic acid (UNA), and/or it can be labeled (e.g., radiolabeled or otherwise tagged). FANA are described in Dowler et al. 2006 Nucl. Acids Res. 34: 1669-1675.

One or both strands can comprise an alternative backbone.

In yet another aspect, the RNAi agent employed by the methods of the present disclosure can include an α-anomeric nucleic acid molecule. An α-anomeric nucleic acid molecule forms specific double-stranded hybrids with complementary RNA in which, contrary to the usual β-units, the strands run parallel to each other. Gaultier et al. 1987 Nucleic Acids. Res. 15: 6625-6641.

The antisense nucleic acid molecule can also comprise a 2'-o-methylribonucleotide (Inoue et al. 1987 Nucleic Acids Res. 15: 6131-6148) or a chimeric RNA-DNA analogue (Inoue et al. 1987 FEBS Lett. 215: 327-330).

Other modifications and/or other changes can be made to the RNAi agent. A portion of the RNAi agent can be double-stranded DNA, while another portion is double-stranded RNA, forming a DNA-RNA chimera (See, for example, Yamato et al. 2011. Cancer Gene Ther. 18: 587-597). Mismatches between the guide and passenger stand can also be introduced, though some positions may be better suited than others (See, for example, U.S. Patent App. No. 2009/0209626 to Khvorova). The passenger strand can also be shortened, to as short as 15 or 16 nt, while the guide strand remains 19 nt or longer (See, for example, Sun et al. 2008 Nature Biotech. 26: 1379-1382; and Chu and Rana 2008 RNA 14: 1714-1719). This can increase incorporation of the guide strand into the RNA-induced Silence Complex (RISC), and decrease incorporation of the passenger strand, than reducing off-target effects. In some cases, the passenger strand may be more amenable to modification (e.g., single-stranded nicking, nucleotide modifications, and shortening) than the guide strand.

These and many other modifications can be made once a functional guide strand is identified.

Pharmaceutical Compositions of RNAi Agents

As used here, a "pharmaceutical composition" comprises a pharmaceutically effective amount of one or more APOC3 RNAi agent, a pharmaceutically acceptable carrier, and, optionally, an additional disease treatment which works synergistically with the RNAi agent. As used herein, "pharmacologically effective amount," "therapeutically effective amount" or simply "effective amount" refers to that amount of a RNAi agent effective to produce the intended pharmacological, therapeutic or preventive result. For example, if a given clinical treatment is considered effective where there is at least a 10% reduction in a measurable parameter associated with a disease or disorder, a therapeutically effective amount of a drug for the treatment of that disease or disorder is the amount necessary to effect at least a 10% reduction in that parameter. In this aspect, a therapeutically effective amount of a RNAi agent targeting APOC3 can reduce APOC3 protein levels by at least 10%. In additional aspects, a given clinical treatment is considered effective where there is at least a 15, 20, 25, 30, 35, 40, 45, 50, 55, 60, 65, 70, 75, 80, 85, 90 or 95% reduction in a measurable parameter associated with a disease or disorder, and the therapeutically effective amount of a drug for the treatment of that disease or disorder is the amount necessary to effect at least a 15, 20, 25, 30, 35, 40, 45, 50, 55, 60, 65, 70, 75, 80, 85, 90 or 95% reduction, respectively, in that parameter.

The term "pharmaceutically acceptable carrier" refers to a carrier for administration of a therapeutic agent. Such carriers include, but are not limited to, lipid nanoparticles, saline, buffered saline, dextrose, water, glycerol, ethanol, and combinations thereof. The term specifically excludes cell culture medium. Any appropriate pharmaceutical carrier known in the art can be used in conjunction with the RNAi agents disclosed herein.

Pharmaceutical Composition Comprising a RNAi Agent to APOC3

Additional components of a pharmaceutical composition comprising a RNAi Agent to APOC3 are contemplated to aid in delivery, stability, efficacy, or reduction of immunogenicity.

Liposomes have been used previously for drug delivery (e.g., delivery of a chemotherapeutic). Liposomes (e.g., cationic liposomes) are described in PCT publications WO02/100435A1, WO03/015757A1, WO04029213A2;

and WO/2011/076807; U.S. Pat. Nos. 5,962,016; 5,030,453; and 6,680,068; and U.S. Patent Application 2004/0208921. A process of making liposomes is also described in WO04/002453A1. Furthermore, neutral lipids have been incorporated into cationic liposomes (e.g., Farhood et al. 1995), as well as PEGylated lipids.

Cationic liposomes have been used to deliver RNAi agent to various cell types (Sioud and Sorensen 2003; U.S. Patent Application 2004/0204377; Duxbury et al., 2004; Donze and Picard, 2002).

Use of neutral liposomes disclosed in Miller et al. 1998, and U.S. Patent Application 2003/0012812.

As used herein, the term "SNALP" refers to a stable nucleic acid-lipid particle. A SNALP represents a vesicle of lipids coating a reduced aqueous interior comprising a nucleic acid such as an RNAi or a plasmid from which an RNAi is transcribed. SNALPs are described, e.g., in U.S. Patent Application Publication Nos. 20060240093, 20070135372, and in International Application No. WO 2009082817.

Chemical transfection using lipid-based, amine-based and polymer-based techniques is disclosed in products from Ambion Inc., Austin, Tex.; and Novagen, EMD Biosciences, Inc, an Affiliate of Merck KGaA, Darmstadt, Germany); Ovcharenko D (2003) "Efficient delivery of siRNAs to human primary cells." Ambion TechNotes 10 (5): 15-16). Additionally, Song et al. (Nat Med. published online (Feb. 10, 2003) doi: 10.1038/nm828) and others [Caplen et al. 2001 Proc. Natl. Acad. Sci. (USA), 98: 9742-9747; and McCaffrey et al. Nature 414: 34-39] disclose that liver cells can be efficiently transfected by injection of the siRNA into a mammal's circulatory system.

A variety of molecules have been used for cell-specific RNAi agent delivery. See, for example, WO/2011/076807. For example, the nucleic acid-condensing property of protamine has been combined with specific antibodies to deliver siRNAs. Song et al. 2005 Nat Biotech. 23: 709-717. The self-assembly PEGylated polycation polyethylenimine (PEI) has also been used to condense and protect siRNAs. (Schiffelers et al. 2004 Nucl. Acids Res. 32: e149, 141-1 10).

The RNAi agents of the present disclosure can be delivered via, for example, Lipid nanoparticles (LNP); neutral liposomes (NL); polymer nanoparticles; double-stranded RNA binding motifs (dsRBMs); or via modification of the RNAi agent (e.g., covalent attachment to the dsRNA) or by any method known in the art for delivery of a RNAi agent comprising nucleic acids.

Lipid nanoparticles (LNP) are self-assembling cationic lipid based systems. These can comprise, for example, a neutral lipid (the liposome base); a cationic lipid (for siRNA loading); cholesterol (for stabilizing the liposomes); and PEG-lipid (for stabilizing the formulation, charge shielding and extended circulation in the bloodstream).

The cationic lipid can comprise, for example, a headgroup, a linker, a tail and a cholesterol tail. The LNP can have, for example, good delivery to the diseased area, extended circulation in the blood, small particles (e.g., less than 100 nm), and stability in the microenvironment of the diseased area (which may have low pH and/or be hypoxic).

Neutral Liposomes (NL) are Non-Cationic Lipid Based Particles.

Polymer nanoparticles are self-assembling polymer-based particles.

Double-stranded RNA binding motifs (dsRBMs) are self-assembling RNA binding proteins, which will need modifications.

APOC3 RNAi Agent Compositions in a Lipid Nanoparticles (LNP) Comprising a Neutral Lipid; a Cationic Lipid; Cholesterol; and PEG-Lipid Lipid nanoparticles (LNP) are self-assembling cationic lipid based systems. These can comprise, for example, a neutral lipid (the liposome base); a cationic lipid (for siRNA loading); cholesterol (for stabilizing the liposomes); and PEG-lipid (for stabilizing the formulation, charge shielding and extended circulation in the bloodstream).

A neutral lipid is, for example, the liposome base. A cationic lipid is, for example, for siRNA loading. Cholesterol is, for example, for stabilizing the liposomes. PEG-lipid is, for example, for stabilizing the formulation, charge shielding and extended circulation in the bloodstream.

Additional Pharmaceutical Compositions

In various aspects, the RNAi agent to APOC3 is packaged as a monotherapy into a delivery vehicle, or may be further ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

The RNAi agents of the present disclosure can be prepared in a pharmaceutical composition comprising various components appropriate for the particular method of administration of the RNAi agent.

Aspects of Some Embodiments

In some embodiments, the present disclosure is a composition comprising one or more APOC3 RNAi agents.

In some embodiments, the disclosure encompasses a composition comprising any one or more of the following:

A RNAi agent comprising a first and a second strand, wherein the sequence of the first strand is the sequence of SEQ ID NO: 1, or modified or unmodified variants thereof.

A RNAi agent comprising a first and a second strand, wherein the sequence of the first strand is the sequence of SEQ ID NO: 2, or modified or unmodified variants thereof.

A RNAi agent comprising a first and a second strand, wherein the sequence of the first strand is the sequence of SEQ ID NO: 41, or modified or unmodified variants thereof.

A RNAi agent comprising a first and a second strand, wherein the sequence of the first strand is the sequence of SEQ ID NO: 48, or modified or unmodified variants thereof.

A RNAi agent comprising a first and a second strand, wherein the sequence of the first strand is the sequence of SEQ ID NO: 56, or modified or unmodified variants thereof.

A RNAi agent comprising a first and a second strand, wherein the sequence of the first strand is the sequence of SEQ ID NO: 71, or modified or unmodified variants thereof.

A RNAi agent comprising a first and a second strand, wherein the sequence of the first strand is the sequence of SEQ ID NO: 102, or modified or unmodified variants thereof.

Particular Specific Aspects of Some Embodiments

In a particular specific aspect of some embodiments, the present disclosure is a composition comprising one or more APOC3 RNAi agents.

In some embodiments, the disclosure encompasses a composition comprising any one or more of the following:

A RNAi agent comprising a first and a second strand, wherein the sequence of the first strand is the sequence of SEQ ID NO: 1, and the sequence of the second strand is the sequence of SEQ ID NO: 45, or modified or unmodified variants thereof.

A RNAi agent comprising a first and a second strand, wherein the sequence of the first strand is the sequence of SEQ ID NO: 2, and the sequence of the second strand is the sequence of SEQ ID NO: 100, or modified or unmodified variants thereof.

A RNAi agent comprising a first and a second strand, wherein the sequence of the first strand is the sequence of SEQ ID NO: 41, and the sequence of the second strand is the sequence of SEQ ID NO: 9, or modified or unmodified variants thereof.

A RNAi agent comprising a first and a second strand, wherein the sequence of the first strand is the sequence of SEQ ID NO: 48, and the sequence of the second strand is the sequence of SEQ ID NO: 39, or modified or unmodified variants thereof.

A RNAi agent comprising a first and a second strand, wherein the sequence of the first strand is the sequence of SEQ ID NO: 56, and the sequence of the second strand is the sequence of SEQ ID NO: 23, or modified or unmodified variants thereof.

A RNAi agent comprising a first and a second strand, wherein the sequence of the first strand is the sequence of SEQ ID NO: 102, and the sequence of the second strand is the sequence of SEQ ID NO: 23, or modified or unmodified variants thereof.

Additional Particular Specific Aspects of Some Embodiments

In a particular specific aspect, the present disclosure is a composition comprising one or more APOC3 RNAi agents.

In some embodiments, the disclosure encompasses a composition comprising any one or more of the following:

A RNAi agent comprising a first and a second strand, wherein the sequence of the first strand comprises the sequence of SEQ ID NO: 41, wherein the length of the first and second strand are each no more than about 30 nt, or modified or unmodified variants thereof.

A RNAi agent comprising a first and a second strand, wherein the sequence of the first strand comprises the sequence of SEQ ID NO: 71, wherein the length of the first and second strand are each no more than about 30 nt, or modified or unmodified variants thereof.

A RNAi agent comprising a first and a second strand, wherein the sequence of the first strand comprises the sequence of SEQ ID NO: 56, wherein the length of the first and second strand are each no more than about 30 nt, or modified or unmodified variants thereof.

A RNAi agent comprising a first and a second strand, wherein the sequence of the first strand comprises the sequence of SEQ ID NO: 102, wherein the length of the first and second strand are each no more than about 30 nt, or modified or unmodified variants thereof.

A RNAi agent comprising a first and a second strand, wherein the sequence of the first strand comprises the sequence of SEQ ID NO: 1, wherein the length of the first and second strand are each no more than about 30 nt, or modified or unmodified variants thereof.

A RNAi agent comprising a first and a second strand, wherein the sequence of the first strand comprises the sequence of SEQ ID NO: 2, wherein the length of the first and second strand are each no more than about 30 nt, or modified or unmodified variants thereof.

Additional Particular Specific Aspects of Some Embodiments

In some embodiments, the disclosure comprises a RNAi agent comprising a first and a second strand, wherein the sequence of the first strand comprises at least 18 contiguous nucleotides of the sequence of any one or more RNAi agent disclosed herein, or modified or unmodified variants thereof.

In some embodiments, the disclosure encompasses a composition comprising any one or more of the following:

A RNAi agent comprising a first and a second strand, wherein the sequence of the first strand comprises at least 18 contiguous nucleotides of the sequence of SEQ ID NO: 41, or modified or unmodified variants thereof.

A RNAi agent comprising a first and a second strand, wherein the sequence of the first strand comprises at least 18 contiguous nucleotides of the sequence of SEQ ID NO: 48, or modified or unmodified variants thereof.

A RNAi agent comprising a first and a second strand, wherein the sequence of the first strand comprises at least 18 contiguous nucleotides of the sequence of SEQ ID NO: 56, or modified or unmodified variants thereof.

A RNAi agent comprising a first and a second strand, wherein the sequence of the first strand comprises at least 18 contiguous nucleotides of the sequence of SEQ ID NO: 102, or modified or unmodified variants thereof.

A RNAi agent comprising a first and a second strand, wherein the sequence of the first strand comprises at least 18 contiguous nucleotides of the sequence of SEQ ID NO: 1, or modified or unmodified variants thereof.

A RNAi agent comprising a first and a second strand, wherein the sequence of the first strand comprises at least 18 contiguous nucleotides of the sequence of SEQ ID NO: 2, or modified or unmodified variants thereof.

Additional Particular Specific Aspects of Some Embodiments

In some embodiments, the disclosure comprises a RNAi agent comprising a first and a second strand, wherein the sequence of the first strand comprises at least 18 contiguous nucleotides differing by 0, 1, 2, or 3 nt from a first strand, or modified or unmodified variants thereof.

In some embodiments, the disclosure encompasses a composition comprising any one or more of the following:

A RNAi agent comprising a first and a second strand, wherein the sequence of the first strand comprises at least 18 contiguous nucleotides differing by 0, 1, 2, or 3 nt from the sequence of SEQ ID NO: 41, or modified or unmodified variants thereof.

A RNAi agent comprising a first and a second strand, wherein the sequence of the first strand comprises at least 18 contiguous nucleotides differing by 0, 1, 2, or 3 nt from the sequence of SEQ ID NO: 48, or modified or unmodified variants thereof.

A RNAi agent comprising a first and a second strand, wherein the sequence of the first strand comprises at least 18 contiguous nucleotides differing by 0, 1, 2, or 3 nt from the sequence of SEQ ID NO: 56, or modified or unmodified variants thereof.

A RNAi agent comprising a first and a second strand, wherein the sequence of the first strand comprises at least 18 contiguous nucleotides differing by 0, 1, 2, or 3 nt from the sequence of SEQ ID NO: 102, or modified or unmodified variants thereof.

A RNAi agent comprising a first and a second strand, wherein the sequence of the first strand comprises at least 18 contiguous nucleotides differing by 0, 1, 2, or 3 nt from the sequence of SEQ ID NO: 1, or modified or unmodified variants thereof.

A RNAi agent comprising a first and a second strand, wherein the sequence of the first strand comprises at least 18 contiguous nucleotides differing by 0, 1, 2, or 3 nt from the sequence of SEQ ID NO: 2, or modified or unmodified variants thereof.

Additional Particular Specific Aspects of Some Embodiments

In some embodiments, the disclosure comprises a RNAi agent comprising a first and a second strand, wherein the sequence of the first strand comprises at least 14 contiguous nucleotides of the sequence of any one or more RNAi agent disclosed herein, or modified or unmodified variants thereof.

In some embodiments, the disclosure encompasses a composition comprising any one or more of the following:

A RNAi agent comprising a first and a second strand, wherein the sequence of the first strand comprises at least 14 contiguous nucleotides of the sequence of SEQ ID NO: 41, or modified or unmodified variants thereof.

A RNAi agent comprising a first and a second strand, wherein the sequence of the first strand comprises at least 14 contiguous nucleotides of the sequence of SEQ ID NO: 48, or modified or unmodified variants thereof.

A RNAi agent comprising a first and a second strand, wherein the sequence of the first strand comprises at least 14 contiguous nucleotides of the sequence of SEQ ID NO: 56, or modified or unmodified variants thereof.

A RNAi agent comprising a first and a second strand, wherein the sequence of the first strand comprises at least 14 contiguous nucleotides of the sequence of SEQ ID NO: 102, or modified or unmodified variants thereof.

A RNAi agent comprising a first and a second strand, wherein the sequence of the first strand comprises at least 14 contiguous nucleotides of the sequence of SEQ ID NO: 1, or modified or unmodified variants thereof.

A RNAi agent comprising a first and a second strand, wherein the sequence of the first strand comprises at least 14 contiguous nucleotides of the sequence of SEQ ID NO: 2, or modified or unmodified variants thereof.

Additional Particular Specific Aspects of Some Embodiments

In some embodiments, the disclosure comprises a RNAi agent comprising a first and a second strand, wherein the sequence of the first strand comprises at least 14 contiguous nucleotides differing by 0, 1, 2, or 3 nt from a first strand, or modified or unmodified variants thereof.

In some embodiments, the disclosure encompasses a composition comprising any one or more of the following:

A RNAi agent comprising a first and a second strand, wherein the sequence of the first strand comprises at least 14 contiguous nucleotides differing by 0, 1, 2, or 3 nt from the sequence of SEQ ID NO: 41, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 48, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 56, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 102, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 1, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 2, or modified or unmodified variants thereof.

Additional Particular Specific Aspects of Some Embodiments

In a particular specific aspect, the present disclosure is a composition comprising one or more APOC3 RNAi agents.

In some embodiments, the disclosure encompasses a composition comprising any one or more of the following:

A RNAi agent comprising a first and a second strand, wherein the sequence of the first strand is the sequence of SEQ ID NO: 41, and/or the sequence of the second strand is the sequence of SEQ ID NO: 9, or modified or unmodified variants thereof.

A RNAi agent comprising a first and a second strand, wherein the sequence of the first strand is the sequence of SEQ ID NO: 48, and/or the sequence of the second strand is the sequence of SEQ ID NO: 39, or modified or unmodified variants thereof.

A RNAi agent comprising a first and a second strand, wherein the sequence of the first strand is the sequence of SEQ ID NO: 56, and/or the sequence of the second strand is the sequence of SEQ ID NO: 23, or modified or unmodified variants thereof.

A RNAi agent comprising a first and a second strand, wherein the sequence of the first strand is the sequence of SEQ ID NO: 102, and/or the sequence of the second strand is the sequence of SEQ ID NO: 81, or modified or unmodified variants thereof.

A RNAi agent comprising a first and a second strand, wherein the sequence of the first strand is the sequence of SEQ ID NO: 1, and/or the sequence of the second strand is the sequence of SEQ ID NO: 45, or modified or unmodified variants thereof.

A RNAi agent comprising a first and a second strand, wherein the sequence of the first strand is the sequence of SEQ ID NO: 2, and/or the sequence of the second strand is the sequence of SEQ ID NO: 100, or modified or unmodified variants thereof.

Additional Particular Specific Aspects of Some Embodiments

In a particular specific aspect, the present disclosure is a composition comprising one or more APOC3 RNAi agents.

In some embodiments, the disclosure encompasses a composition comprising any one or more of the following:

A RNAi agent comprising a first and a second strand, wherein the sequence of the first strand comprises the sequence of SEQ ID NO: 41, and/or the sequence of the second strand comprises the sequence of SEQ ID NO: 9, wherein the length of the first and second strand are each no more than about 30 nt, or modified or unmodified variants thereof.

A RNAi agent comprising a first and a second strand, wherein the sequence of the first strand comprises the sequence of SEQ ID NO: 48, and/or the sequence of the second strand comprises the sequence of SEQ ID NO: 39, wherein the length of the first and second strand are each no more than about 30 nt, or modified or unmodified variants thereof.

A RNAi agent comprising a first and a second strand, wherein the sequence of the first strand comprises the sequence of SEQ ID NO: 56, and/or the sequence of the second strand comprises the sequence of SEQ ID NO: 23, wherein the length of the first and second strand are each no more than about 30 nt, or modified or unmodified variants thereof.

A RNAi agent comprising a first and a second strand, wherein the sequence of the first strand comprises the sequence of SEQ ID NO: 102, and/or the sequence of the second strand comprises the sequence of SEQ ID NO: 81, wherein the length of the first and second strand are each no more than about 30 nt, or modified or unmodified variants thereof.

A RNAi agent comprising a first and a second strand, wherein the sequence of the first strand comprises the sequence of SEQ ID NO: 1, and/or the sequence of the second strand comprises the sequence of SEQ ID NO: 45, wherein the length of the first and second strand are each no more than about 30 nt, or modified or unmodified variants thereof.

A RNAi agent comprising a first and a second strand, wherein the sequence of the first strand comprises the sequence of SEQ ID NO: 2, and/or the sequence of the second strand comprises the sequence of SEQ ID NO: 100, wherein the length of the first and second strand are each no more than about 30 nt, or modified or unmodified variants thereof.

Additional Particular Specific Aspects of Some Embodiments

In some embodiments, the disclosure comprises a RNAi agent comprising a first and a second strand, wherein the sequence of the first strand comprises at least 14 contiguous nucleotides of a first strand, and/or the sequence of the second strand comprises at least 14 contiguous nucleotides of the second strand of any one or more RNAi agent disclosed herein.

In some embodiments, the disclosure encompasses a composition comprising any one or more of the following:

A RNAi agent comprising a first and a second strand, wherein the sequence of the first strand comprises at least 14 contiguous nucleotides of the sequence of SEQ ID NO: 41, and/or the sequence of the second strand comprises at least 14 contiguous nucleotides of the sequence of SEQ ID NO: 9, wherein the length of the first and second strand are each no more than about 30 nt, or modified or unmodified variants thereof.

A RNAi agent comprising a first and a second strand, wherein the sequence of the first strand comprises at least 14 contiguous nucleotides of the sequence of SEQ ID NO: 48, and/or the sequence of the second strand comprises at least 14 contiguous nucleotides of the sequence of SEQ ID NO: 39, wherein the length of the first and second strand are each no more than about 30 nt, or modified or unmodified variants thereof.

A RNAi agent comprising a first and a second strand, wherein the sequence of the first strand comprises at least 14 contiguous nucleotides of the sequence of SEQ ID NO: 56, and/or the sequence of the second strand comprises at least 14 contiguous nucleotides of the sequence of SEQ ID NO: 23, wherein the length of the first and second strand are each no more than about 30 nt, or modified or unmodified variants thereof.

A RNAi agent comprising a first and a second strand, wherein the sequence of the first strand comprises at least 14 contiguous nucleotides of the sequence of SEQ ID NO: 102, and/or the sequence of the second strand comprises at least 14 contiguous nucleotides of the sequence of SEQ ID NO: 81, wherein the length of the first and second strand are each no more than about 30 nt, or modified or unmodified variants thereof.

A RNAi agent comprising a first and a second strand, wherein the sequence of the first strand comprises at least 14 contiguous nucleotides of the sequence of SEQ ID NO: 1, and/or the sequence of the second strand comprises at least 14 contiguous nucleotides of the sequence of SEQ ID NO: 45, wherein the length of the first and second strand are each no more than about 30 nt, or modified or unmodified variants thereof.

A RNAi agent comprising a first and a second strand, wherein the sequence of the first strand comprises at least 14 contiguous nucleotides of the sequence of SEQ ID NO: 2, and/or the sequence of the second strand comprises at least 14 contiguous nucleotides of the sequence of SEQ ID NO: 100, wherein the length of the first and second strand are each no more than about 30 nt, or modified or unmodified variants thereof.

Additional Particular Specific Aspects of Some Embodiments

In some embodiments, the disclosure comprises a RNAi agent comprising a first and a second strand, wherein the sequence of the first strand comprises at least 14 contiguous nucleotides differing by 0, 1, 2, or 3 nt from a first strand, and/or the sequence of the second strand comprises at least 14 contiguous nucleotides differing by 0, 1, 2, or 3 nt from the second strand of any one or more RNAi agent disclosed herein.

In some embodiments, the disclosure encompasses a composition comprising any one or more of the following:

A RNAi agent comprising a first and a second strand, wherein the sequence of the first strand comprises at least 14 contiguous nucleotides differing by 0, 1, 2, or 3 nt from the sequence of SEQ ID NO: 41, and/or the sequence of the second strand comprises at least 14 contiguous nucleotides differing by 0, 1, 2, or 3 nt from the sequence of SEQ ID NO: 9, wherein the length of the first and second strand are each no more than about 30 nt, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 48, and/or the sequence of the second strand comprises at least 14 contiguous nucleotides differing by 0, 1, 2, or 3 nt from the sequence of SEQ ID NO:

39, wherein the length of the first and second strand are each no more than about 30 nt, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 56, and/or the sequence of the second strand comprises at least 14 contiguous nucleotides differing by 0, 1, 2, or 3 nt from the sequence of SEQ ID NO: 23, wherein the length of the first and second strand are each no more than about 30 nt, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 102, and/or the sequence of the second strand comprises at least 14 contiguous nucleotides differing by 0, 1, 2, or 3 nt from the sequence of SEQ ID NO: 81, wherein the length of the first and second strand are each no more than about 30 nt, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 1, and/or the sequence of the second strand comprises at least 14 contiguous nucleotides differing by 0, 1, 2, or 3 nt from the sequence of SEQ ID NO: 45, wherein the length of the first and second strand are each no more than about 30 nt, or modified or unmodified variants thereof.

A RNAi agent comprising a first and a second strand, wherein the sequence of the first strand comprises at least 14 contiguous nucleotides differing by 0, 1, 2, or 3 nt from the sequence of SEQ ID NO: 2, and/or the sequence of the second strand comprises at least 14 contiguous nucleotides differing by 0, 1, 2, or 3 nt from the sequence of SEQ ID NO: 100, wherein the length of the first and second strand are each no more than about 30 nt, or modified or unmodified variants thereof.

Additional Particular Aspects

In some embodiments, the disclosure comprises a RNAi agent comprising a sense and an antisense strand, wherein the antisense strand comprises at least 14 contiguous nucleotides differing by 0, 1, 2, or 3 nt from the antisense strand of any RNAi agent disclosed herein, or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

Thus, in some embodiments, the disclosure comprises a RNAi agent comprising a sense and an antisense strand, wherein the antisense strand comprises at least 14 contiguous nucleotides differing by 0, 1, 2, or 3 nt from any of: SEQ ID NOs in Table 2, or modified or unmodified variants thereof, wherein the antisense strand optionally further comprises 0, 1, 2, 3, 4, 5, 6, 7, 8, 9, or 10 or more nt (or any range thereof, e.g., 0-1, 1-2, 1-3, 1-4 nt, etc.).

In some embodiments, the disclosure comprises any one or more RNAi agent listed herein.

Additional Particular Specific Aspects of Some Embodiments

Other particular specific aspects include compositions comprising 1, 2, 3, 4, or more of these RNAi agents. Another aspect is a composition comprising any single RNAi agent, along with any other RNAi agents which overlap it. Another aspect comprises two, three, four or more APOC3 RNAi agents which do not overlap and thus target different parts of the RNA molecule. When two or more RNAi agents are used, they can be administered simultaneously or sequentially.

Another particular specific aspect comprises an RNAi agent, wherein the RNAi agent comprises a sense strand comprising at least 14 contiguous nucleotides (identical in sequence) to the sense strand of any of the listed RNAi agents, and an antisense strand comprising at least 14 contiguous nucleotides (identical in sequence) to the antisense strand of the same RNAi agent. In another aspect, the composition comprises one, two, three, four, or more such RNAi agents.

In some embodiments, the composition comprises an RNAi agent which comprises an antisense strand comprising at least 14 contiguous nucleotides differing by 0, 1, 2 or 3 mismatches from the antisense strand of a RNAi agent described herein.

In some embodiments, the composition comprises an RNAi agent which comprises an antisense strand comprising at least 14 contiguous nucleotides differing by 0, 1, 2 or 3 mismatches from the antisense strand of a RNAi agent described herein.

In another aspect, the composition comprises an RNAi agent which comprises a sense strand comprising at least 14 contiguous nucleotides differing by 0, 1, 2, or 3 mismatches from the sense strand of one of the listed RNAi agents, and an antisense strand comprising at least 14 contiguous nucleotides differing by 0, 1, 2 or 3 mismatches from the antisense strand of the same RNAi agent.

A "mismatch" is defined herein as a difference between the base sequence or length when two sequences are maximally aligned and compared. As a non-limiting example, a mismatch is counted if a difference exists between the base at a particular location in one sequence and the base at the corresponding position in another sequence (e.g., between the sequence of a given RNAi agent and an RNAi agent listed herein). Thus, a mismatch is counted, for example, if a position in one sequence has a particular base (e.g., A), and the corresponding position on the other sequence has a different base (e.g., G, C or U). A mismatch is also counted, e.g., if a position in one sequence has a base (e.g., A), and the corresponding position on the other sequence has no base (e.g., that position is an abasic nucleotide which comprises a phosphate-sugar backbone but no base). A single-stranded nick in either sequence (or in the sense or antisense strand) is not counted as mismatch. Thus, as a non-limiting example, no mismatch would be counted if one sequence comprises the sequence A-G, but the other sequence comprises the sequence A-G with a single-stranded nick between the A and the G. A base modification is also not considered a mismatch. If one sequence comprises a C, and the other sequence comprises a modified C (e.g., with a 2'-modification) at the same position, no mismatch would be counted. Thus, modifications of a nucleotide other than replacement or alteration of the base would not constitute a mismatch. For example, no mismatch would occur between a nucleotide which is A, and a nucleotide which is A with a 5' modification and/or a 2'-modification. The key feature of a mismatch (base replacement) is that it would not be able to base-pair with the corresponding base on the opposite strand. In addition, terminal overhangs such as "UU" or "dTdT" are not counted when counting the number of mismatches; the terminal "UU" and "dTdT" overhangs are also not included when calculating "15 contiguous nucleotides."

In these aspects, a mismatch is defined as a position wherein the base of one sequence does not match the base of the other sequence.

In another aspect, the composition comprises 1, 2, 3, 4, or more such RNAi agents.

In another aspect, the composition comprises an RNAi agent which comprises a sense strand comprising at least 14 contiguous nucleotides differing by 0, 1, 2 or 3 mismatches from the sense strand of one of the listed RNAi agents, and an antisense strand comprising at least 14 contiguous nucleotides differing by 0, 1, 2 or 3 mismatches from the antisense strand of the same RNAi agent Variants of RNAi agents (e.g., comprising different modifications, caps, etc.) are disclosed herein, e.g., in the Tables. An unmodified and an example modified variant of various RNAi agents are provided. The disclosure thus encompasses groups of overlapping modified and/or unmodified RNAi agents. More aspects are provided herein, and are included in the scope of each RNAi agents of the disclosure.

Other modifications known to one skilled in the art are contemplated as being encompassed within the invention. Exemplary modifications include, but are not limited to, the presence of gaps or mismatches between the base pairs in the sense and antisense strands, the presence of nicks or breaks in the internucleoside linkages in the sense strand, and the like.

Pharmaceutical Compositions

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be, for example, inert diluents; such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets can be uncoated or they can be coated by known techniques. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Aqueous suspensions contain the active materials in a mixture with excipients suitable for the manufacture of aqueous suspensions.

Oral administration of the compositions of the invention include all standard techniques for administering substances directly to the stomach or gut, most importantly by patient controlled swallowing of the dosage form, but also by other mechanical and assisted means of such delivery.

Dosage levels of the order of from about 0.1 mg to about 140 mg per kilogram of body weight per day are useful in the treatment of the above-indicated conditions (about 0.5 mg to about 7 g per subject per day). The amount of active ingredient that can be combined with the carrier materials to produce a single dosage form varies depending upon the host treated and the particular mode of administration.

Dosage unit forms generally contain between from about 1 mg to about 500 mg of an active ingredient. It is understood that the specific dose level for any particular subject depends upon a variety of factors including the activity of the specific compound employed, the age, body weight, general health, sex, diet, time of administration, route of administration, and rate of excretion, drug combination and the severity of the particular disease undergoing therapy.

Therapeutic effect of the therapeutic agents of the invention may be enhanced by combination with other agents. Typically such other agents will include agents known for use in treating similar diseases, such as angiogenic disorders.

The RNAi agents of the invention and formulations thereof can be administered orally, topically, parenterally, by inhalation or spray, or rectally in dosage unit formulations containing conventional non-toxic pharmaceutically acceptable carriers, adjuvants and/or vehicles. The term parenteral as used herein includes percutaneous, subcutaneous, intravascular (e.g., intravenous), intramuscular, intraperitoneal, or intrathecal injection, or infusion techniques and the like. Where two or more different RNAi agents are administered, each may be administered separately or co-administered. Where each is administered separately, the method and/or site of administration may be the same or different, e.g., both RNAi agents may be administered intravenously or subcutaneously, or a first RNAi agent may be administered intravenously with a second Rai agent administered subcutaneously, etc.

In various embodiments, the disclosure encompasses a composition or pharmaceutical composition comprising a RNAi agent, wherein one or both strands comprises a 3' end cap, the composition further comprising a helper lipid, a neutral lipid, and/or a stealth lipid.

In one particular specific embodiment, the present disclosure relates to a method of treating a target gene-related disease in an individual, comprising the step of administering to the individual a therapeutically effective amount of a composition comprising a RNAi agent comprising a first strand and a second strand, wherein the first and/or second strand comprise a 3' end cap selected from the 3' end caps listed in Table 5A-E. In one particular specific embodiment, the present disclosure relates to a method of inhibiting the expression of target gene in an individual, comprising the step of administering to the individual a therapeutically effective amount of a composition comprising a RNAi agent of the present disclosure.

In one embodiment of the method, the composition further comprises a pharmaceutically effective formulation.

Various particular specific embodiments of these embodiments are described below.

In one embodiment, the method further comprises the administration of an additional treatment. In one embodiment, the additional treatment is a therapeutically effective amount of a composition.

In one embodiment, the additional treatment is a method (or procedure).

In one embodiment, the additional treatment and the RNAi agent can be administered in any order, or can be administered simultaneously.

In one embodiment, the method further comprises the step of administering an additional treatment for the disease.

In one embodiment, the method further comprises the step of administering an additional treatment or therapy selected from the list of an additional antagonist to a target gene-related disease.

In one embodiment, the composition comprises a second RNAi agent to target gene. In various embodiments, the second RNAi agent is physically separate from the first, or the two are physically connected (e.g., covalently linked or otherwise conjugated).

Other Embodiments

Various particular specific embodiments of this disclosure are described below.

In one embodiment, the disclosure pertains to a composition according to any of the embodiments described herein, for use in a method of treating a target gene-related disease in an individual, the method comprising the step of administering to the individual a therapeutically effective amount of a composition according to any of the claims.

One embodiment of the disclosure is the use of a composition according to any of these embodiments, in the manufacture of a medicament for treatment of an target gene-related disease.

In one embodiment, the disclosure pertains to the composition of any of the above embodiments, for use in the treatment of an target gene-related disease.

Additional Definitions

Unless defined otherwise, the technical and scientific terms used herein have the same meaning as that usually understood by a specialist familiar with the field to which the present disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein.

Claims to the present disclosure are non-limiting and are provided below.

Although particular embodiments and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the present disclosure without departing from the spirit and scope of the present disclosure as defined by the claims. The choice of nucleic acid starting material, clone of interest, or library type is believed to be a matter of routine for a person of ordinary skill in the art with knowledge of the embodiments described herein or known in the art. Other aspects, advantages, and modifications considered to be within the scope of the following claims. Redrafting of claim scope in later-filed corresponding applications may be due to limitations by the patent laws of various countries and should not be interpreted as giving up subject matter of the claims.

Various additional formulations and obvious variants of the described 3' end caps can be devised by those of ordinary skill in the art. Non-limiting example RNAi agents wherein one or both strands comprises a 3' end cap are described in the Examples below, which do not limit the scope of the present disclosure as described in the claims.

EXAMPLES

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

Example 1: siRNA Lipid Formulations

The siRNAs of the present invention can be encapsulated in lipid nanoparticles as follows. The siRNA lipid nanoparticles were formed by mixing solutions of lipids dissolved in ethanol with siRNA dissolved in a citrate buffer as described generally above. Mixing chambers were used having passages with inner diameters of 0.5, 1.0, or 2.0 mm. The processing chambers had lengths of from 50 mm to 1000 mm. The dilution chambers had passages with inner diameters equivalent to or of at least to 2 times that of the mixing chamber about 0.5 or 1.0 or 2.0 or 4.0 mm. The lipid solution contained a cationic lipid, a helper lipid (cholesterol), a neutral lipid (DSPC) and a stealth lipid.

The concentrations of total lipids were either 16.7 mg/mL or 25 mg/mL. The total lipid to siRNA ratio for these experiments was about 18.3:1. The concentration of siRNA solutions were 0.225, 0.3, 0.3375, or 0.45 mg/mL in a sodium citrate: sodium chloride buffer with pH 5. The concentration of NaCl was 50 mM, 66 mM, 75 mM, or 100 mM. The flow rates and linear velocities were varied as described below.

For siRNA encapsulation experiments, the cationic lipids and stealth lipids (i.e., PEG lipid) used are shown in the Table below.

TABLE 4

| lipid ID | lipid type | Chemical name |
|---|---|---|
| A1 | cationic lipid | ((5-((dimethylamino)methyl)-1,3-phenylene)bis(oxy))bis(octane-8,1-diyl) bis(decanoate) |
| A2 | cationic lipid | (9Z,9'Z,12Z,12'Z)-2-((4-(((3-(dimethylamino)propoxy)carbonyl)oxy)hexadecanoyl)oxy)propane-1,3-diyl bis(octadeca-9,12-dienoate) |
| A3 | cationic lipid | (9Z,12Z)-3-((4,4-bis(octyloxy)butanoyl)oxy)-2-((((3-(diethylamino)propoxy)carbonyl)oxy)methyl)propyl octadeca-9,12-dienoate |
| A4 | cationic lipid | (9Z,9'Z,12Z,12'Z)-((5-((dimethylamino)methyl)-1,3-phenylene)bis(oxy))bis(butane-4,1-diyl) bis(octadeca-9,12-dienoate) |
| B1 | PEG lipid | PEG-dimyristylglycerol |
| B2 | PEG lipid | 2,3-bis(tetradecyloxy)propyl (158-hydroxy-3,6,9,12,15,18,21,24,27,30,33,36,39,42,45,48,51,54,57,60,63,66,69,72,75,78,81,84,87,90,93,96,99,102,105,108,111,114,117,120,123,126,129,132,135,138,141,144,147,150,153,156-dopentacontaoxaoctapentacontahectyl)carbamate |

The siRNA used for these experiments had sequences and SEQ ID NOs. as shown in Table below.

TABLE 5

| Position | Location | SEQ ID NO: Antisense generic sequence | SEQ ID NO: Sense generic sequence | Gene |
|---|---|---|---|---|
| 457 | 3'UTR | 14: A<u>GCACTG</u>AGAATACTGTC | 162: GACAGTATTCTCAGTGC<u>T</u> | APOC3 |
| 524 | 3'UTR | 97: T<u>TCTTGT</u>CCAGCTTTATT | 125: AATAAAGCTGGACAAGAA | APOC3 |
| 72 | CDS | 7: A<u>CAACAA</u>GGAGTACCCG | 152: CCGGGTACTCCTTGTTG<u>T</u> | APOC3 |

Process Example 1 Encapsulation of siRNA

Preparation of Lipid Mixture in Ethanol.

The following is an example of siRNA encapsulated at a cationic lipid amine to siRNA phosphate (N:P) molar ratio of 4.5:1. Lipids (cationic lipid, DSPC, cholesterol and lipidated PEG) in the amounts shown in Table 6 are dissolved in 150 mL of ethanol. The molar ratios of lipids are 45:9:44:2, respectively. The mixture is sonicated briefly, then gently agitated for 5 minutes and then maintained at 37° C. until use.

TABLE 6

Lipid mixture components

| Reagent | Amount (mg) | MW | Final Concentration (mM) |
|---|---|---|---|
| Cationic lipid A1 | 1315.9 | 732.15 | 12 |
| DSPC | 284 | 790.16 | 2.4 |
| Cholesterol | 679.5 | 386.67 | 11.7 |
| PEG lipid B1 | 226.6 | 2837 | 0.53 |

Preparation of siRNA in Citrate Buffer.

The buffer for the siRNA streams is 100 mM sodium chloride and 25 mM sodium citrate at a pH of 5. The pH of the citrate buffer is first confirmed to be pH 5.00. If it is not, the pH is adjusted before proceeding. Enough siRNA in water for the encapsulation is thawed from −80° C. storage. The siRNA is added to citrate buffer solution and the concentration of the dissolved siRNA is measured by optical density at 260 nm in a UV spectrophotometer. The final concentration of the siRNA is adjusted to 0.45 mg/ml in 150 ml of citrate buffer in a sterile PETG bottle and is held at room temperature until use.

Encapsulation of siRNA in Lipid Nanoparticles.

Sterile syringes are loaded with an equal volume (25 ml) of lipids in ethanol (syringe (a)), siRNA in citrate buffer (syringes (b1) and (b2)), and water alone (syringe (c)). Tubing leading from Luer fittings on the syringe (a) containing 16.7 mg/mL lipids is attached to the center input of a cross junction with a 0.5 mm inner diameter. Tubing leading from Luer fittings on syringes (b1) and (b2) containing siRNA at 0.45 mg/ml are attached to the side inputs of the cross junction. The tubing is fluorinated ethylene propylene (FEP) tubing with 1.55 mm inner diameter. Syringes (a), (b1) and (b2) are installed on syringe pump A. Tubing leading from the center input of the cross opposite the lipid input is attached to a T junction with a 1 mm inner diameter. Tubing leading from a Luer fitting on syringe (c) containing water alone is attached to the T junction to enable in-line dilution of siRNA lipid nanoparticles, and syringe (c) is installed on syringe pump B. Have the output line from the T junction positioned over a sterile PETG bottle for collection of the diluted siRNA lipid nanoparticles. It is important to make sure that all fittings are tight on the syringes. The syringe pumps are set to the appropriate syringe manufacturer and size and a flow rate of 40 ml per minute. Start both pumps simultaneously, and start collecting material after approximately 0.5 seconds. Approximately 90 ml of encapsulated siRNA lipid nanoparticles will be collected and which contains 25% ethanol by volume, 0.23 mg/mL of the siRNA, 4.2 mg/mL of the lipids, and 50 mM NaCl. After a 60 min. post mixing incubation period, particle sizes are determined using a Malvern Zetasizer.

Dilution of siRNA Lipid Nanoparticles.

A 1.0 mm inner diameter T junction is set up for further dilution of the siRNA lipid nanoparticle suspension. This dilution step is run with two syringes on one syringe pump. One 140 mL syringe contains the siRNA lipid nanoparticles and a second 140 mL syringe contains water. The flow rate is set to 25 ml per minute. The siRNA stream and the water stream enter the T junction at 180 degrees from each other. The diluted siRNA lipid nanoparticle suspension is collected into a sterile PETG bottle. The final volume will be approximately 280 ml, with an ethanol concentration of 12.5%.

Dialysis and Concentration of siRNA Lipid Nanoparticles by Tangential Flow Filtration.

For every 50 mg of siRNA in the encapsulation run, use a Vivaflow 50 cartridge. For a 100 mg siRNA encapsulation run, use 2 Vivaflow 50 cartridges attached in series. The regenerated cellulose cartridges is first rinsed to remove any storage solution from the manufacturer. This is done by filling an empty TFF reservoir with 500 ml of DI water and recirculate with a peristaltic pump at a flow rate of 115 ml/min. The permeate line should not be restricted and the rinsing process is complete when the entire 500 ml of water is flushed through the membrane.

Load the siRNA lipid nanoparticle suspension into the Minimate TFF reservoir. Concentrate the mixture while maintaining an overall pressure of 20-25 psi. The filtrate should elute at approximately 4 ml per minute throughout the concentration step. This rate is achieved by restricting the permeate line with a pinch valve until the proper flow rate is achieved. Concentrate until the liquid level in the reservoir is at the 15 ml graduation. Diafilter the concentrated siRNA lipid nanoparticle suspension against 225 ml of pyrogen-free, nuclease-free 1×PBS. Increase the flow rate to 80 ml/min. After diafiltration, resume concentration of the material to the holdup volume of the TFF system. Collect the siRNA lipid nanoparticle suspension from the reservoir. It is possible to rinse the TFF system with additional 2 ml of 1×PBS and to collect this wash that contains diluted siRNA lipid nanoparticle suspension, but this wash should be collected separately from the concentrated siRNA lipid nanoparticle suspension. Store materials at 4° C. until analysis.

Sterile Filtration Step.

The siRNA lipid nanoparticles are filtered by heating approximately 10 ml of the suspension in a glass vial which is placed in a aluminum block heater preheated to 50° C. for 10 min. The vial is then removed and the solution is removed with a syringe and filtered through a 0.22 μm PES syringe filter directly into a sterile vial. This final product is stored at 4° C.

Percent Encapsulation Determination (SYBR GOLD).

To determine the efficiency of the siRNA formulation into lipid nanoparticles, the percent encapsulation of the siRNA can be determined by measuring sybr gold fluorescence. When bound to siRNA, sybr gold fluoresces. The intensity of sybr gold fluorescence is proportional to the amount of siRNA.

A standard solution of siRNA stock at approximately 0.9 mg/mL is prepared in PBS. The concentration of siRNA stock is verified by UV measurement. The siRNA stock is diluted with PBS to 8 μg/mL. Serial dilution is done to prepare 4, 2, 1, 0.5 and 0.25 μg/mL siRNA solutions. 6 μg/mL of siRNA is prepared by mixing equal volumes of 8 μg/mL and 4 μg/mL solutions.

To prepare test samples, 10 μL of siRNA lipid nanoparticle suspension are diluted with 990 μL of PBS (this is now solution A). Note: This first dilution step applies for the formulations with expected siRNA concentration of ~3.6 mg/mL or less. If the concentration is higher than ~3.6 mg/mL, the dilution should be greater. 40 uL of solution A is diluted with 160 μL of PBS (this is now solution 1).

For the measurement of free siRNA in a formulation, a solution of 0.02% sybr gold in PBS is prepared (e.g., 34 of sybr gold in 15 mL of PBS) (solution 2). In a 96-well black, clear-bottom plate 10 μL of solution 1 is mixed with 190 μL of solution 2 to provide sample mixture 1. In this mix, sybr gold will bind only to the nonencapsulated (i.e. free) siRNA. It will not have access to the siRNA encapsulated in the liposome.

For the measurement of total siRNA in a formulation, a solution of 0.02% sybr gold and 0.2% triton-x in PBS is prepared (e.g., 3 μL of sybr gold in 15 mL of 0.2% triton in PBS) (solution 3). In a 96-well black, clear-bottom plate 10 μL of solution 1 is mixed with 190 μL of solution 3 to provide sample mixture 2. In this mix, triton-x disrupts the liposomes and exposes previously encapsulated siRNA to sybr gold binding. Hence, sybr gold will bind to the non-encapsulated (i.e. free) siRNA and to all newly exposed siRNA. The free siRNA+newly exposed siRNA=total siRNA The standard solutions described above (10 μL each) are mixed with either 190 μL solution 2 to provide standard mixtures 1 or 190 μL solution 3 to provide standard mixtures 2.

The fluorescence of all mixes is measured on the SpectraMax M5 spectrophotometer using software SoftMax pro 5.2 and the following parameters:

$\lambda_{ex}$=485 nm $\lambda_{em}$=530 nm

Read Mode: Fluorescence, Top read

Wavelengths: Ex 485 nm, Em 530 nm, Auto Cutoff On 530 nm

Sensitivity: Readings 6, PMT: Auto

Automix: Before: Off

Autocalibrate: On

Assay plate type: 96 Well costarblk/clrbtm

Wells to read: Read entire plate

Settling time: Off

Column Way. Priority: Column priority

Carriage Speed: Normal

Auto read: Off

The fluorescence intensity values obtained from standard mixtures 1 are used to create the calibration curve for free siRNA. The fluorescence intensity of a sample 1 mixture is then plugged into the equation provided by the calibration curve for free siRNA. The found concentration of the sample is then multiplied by the dilution magnitude to obtain the free siRNA in the lipid nanoparticle formulation.

The fluorescence intensity values obtained from standard mixtures 2 are used to create the calibration curve for total siRNA. The fluorescence intensity of a sample 2 mixture is then plugged into the equation provided by the calibration curve for total siRNA. The found concentration of the sample is then multiplied by the dilution magnitude to obtain the total siRNA in the lipid nanoparticle formulation.

The encapsulated siRNA is calculated by the formula: [(total siRNA−free siRNA)/(total siRNA)]×100%.

Percent Encapsulation Determination Using Size Exclusion Chromatography (SEC).

Because the size of free siRNA (5 nm) is different than the size of a liposome (50-200 nm), they will elute at different times in the size exclusion column. Free siRNA elutes after the liposomes. Retention time for siRNA is ~17 minutes whereas the retention time for liposomes is ~10 minutes. Detection of eluted siRNA is carried out via UV detector with absorption wavelength set at 260 nm.

siRNA stock at approximately 0.9 mg/mL is prepared in PBS. To a 200 μL aliquot of stock, 10 μL of TRITON X-100 are added. The concentration of siRNA stock is verified by UV measurement. Serial dilutions are done to prepare standards at ½, ¼, ⅛, 1/16 and 1/32 concentration of the siRNA stock. 10 μL of TRITON X-100 are added to 200 μL of each standard. The concentration of each standard is verified by UV measurement.

In a HPLC vial, 25 μL of lipid nanoparticle formula are added to 185 μL of 1×PBS (10×PBS (FISHER, BP399) diluted with deionized water to 1×). The dispersion is gently vortexed until homogeneous (dispersion 1). In another HPLC vial, 25 μL of lipid nanoparticle formula are added to 185 μL of 20% TRITON-X. The dispersion is gently vortexed until clear and homogeneous (dispersion 2).

The size exclusion chromatography is performed on an AGILENT 1200 HPLC using EMPOWER PRO software. The parameters are:
Column temperature: 30° C.
Mobile Phase rate flow: 1 ml/min for 30 minutes
UV detector wavelength: 260 nm
Injection volume: 20 µL
Number of injections: 2

20 µL of standards and dispersions are injected onto size exclusion column, mobile phase 1×PBS with pH adjusted to 7.7 flowing at 1 mL/min for 30 minutes. The eluted material is detected by UV detector with 260 nm absorption wavelength.

From the siRNA standards, the peak at ~17 minutes represents the siRNA. From dispersion 1, the peak at ~10 minutes represents the lipid nanoparticle containing encapsulated siRNA and the peak at ~17 minutes represents the nonencapsulated (i.e. free) siRNA.

In dispersion 2, TRITON-X disrupts the lipid nanoparticle enabling previously encapsulated siRNA to elute together with already free siRNA at 17 minutes. The peak at ~10 minutes disappears, and only one peak in the chromatogram remains, i.e. the peak at ~17 minutes, representing both non-encapsulated (i.e. free) siRNA and newly free siRNA. Free siRNA+newly free siRNA=total siRNA.

The peak area values obtained from siRNA standards are used to create the siRNA concentration calibration curve. The integrated area of the peak at ~17 minutes in dipersion 1 is plugged into the equation provided by calibration curve for free siRNA to obtain the concentration of the free siRNA in the dispersion. The found concentration of the sample is then multiplied by the dilution magnitude to obtain the free siRNA in the lipid nanoparticle formulation.

The integrated area of the peak at ~17 minutes in dispersion 2 is plugged into the equation provided by calibration curve for free siRNA to obtain the concentration of the total siRNA in the dispersion. The found concentration of sample is then multiplied by the dilution magnitude to obtain the total siRNA in the lipid nanoparticle formulation.

Encapsulated siRNA is calculated by formula:
[(total siRNA−free siRNA)/(total siRNA)]×100%.

Particle Analytics.

The siRNA lipid nanoparticles are analyzed for size and polydispersity using a Zetasizer Nano ZS from Malvern Instruments. For formulated siRNA at an encapsulated siRNA concentration of >1 mg/ml, dilute 5 µl of sample with 115 µl of 1×PBS. Add to a small volume disposable microcuvette. Insert the cuvette into the Zetasizer Nano ZS. For the machine settings, set material to be polystyrene latex, dispersant to be water, and cell to be ZEN040. Measure the sample at 25° C. with no wait time. Record Z-Ave (set as diameter, in nanometer units) and polydispersity index (PDI).

In Table 7 are shown the results obtained for siRNA and lipid nanoparticle combinations using the procedures described above. Encapsulation percentages were determined using the SEC method.

TABLE 7 siRNA Lipid Nanoparticle Encapsulation Results

| Cationic lipid | PEG lipid | Z-Ave (nm) | # Ave | PDI | % Encapsulation |
|---|---|---|---|---|---|
| A1 | B1 | 65.1 | 49.6 | 0.089 | 92.9 |
| A2 | B2 | 72.9 | 52.2 | 0.092 | 93.1 |
| A3 | B2 | 81.7 | 66.5 | 0.026 | 97.0 |
| A3 | B1 | 72.4 | 56.6 | 0.03 | 98.1 |
| A1 | B1 | 71.0 | 50.5 | 0.145 | 94.7 |

Process Example 2: Effect of Dilution

Using the system substantially as described herein, two aqueous nucleic acids streams having concentrations of 0.45 mg/mL of siRNA, 100 mM NaCl, and 25 mM sodium citrate at a pH of 5 were introduced from opposing directions into a cross-shaped mixing chamber having passages with inner diameters of 0.5 mm with flow rates of 40 mL/min each. Simultaneously, a lipid stream was introduced into the cross-shaped mixing chamber from a direction orthogonal to the two nucleic acid streams at a flow rate of 40 mL/min. The lipid stream was made up of 45% cationic lipid A1, 44% cholesterol, 9% DSPC, and 2% PEG-lipid B1 in ethanol. The total concentration of lipids was 16.7 mg/mL. In one run, the joined stream from the cross-shaped mixing chamber was subjected to a dilution step with water using a T-shaped chamber (1.0 mm inner diameter).

The water was introduced into the T-shaped chamber at a rate of 40 mL/min. The resultant solution was collected and the encapsulated nucleic acid nanoparticles analyzed for size and uniformity with the results shown in entry 1 in Table 8. The solution obtained from entry 1 included 25% ethanol by volume, 0.23 mg/mL of the siRNA, 4.2 mg/mL of the lipids, and 50 mM NaCl. In a separate experiment using the same concentrations, flow rates, and initial cross-shaped mixing chamber, the joined streams from the mixing chamber were diluted in a volume of water equivalent to the dilution volume used in entry 1. These results are shown in entry 2 in Table 8. The concentrations of the collected solution were the same as in entry 1. For comparison, another experiment was conducted under the same process conditions but without any dilution step. These results are shown in entry 3 in Table 6. Without any dilution step, the collected solution in entry 3 included 33% ethanol, 0.3 mg/mL siRNA, 5.6 mg/mL lipids and 66 mM NaCl. The Z-Avg, #-Avg, and PDI for entries 1 and 2 were less than entry 3, which lacked the dilution step. The Z-Avg, #-Avg, and PDI in Table were determined 60 minutes post-mixing.

TABLE 8

| Entry | Dilution chamber | Dilution flow (mL/min) | Z-Avg | #-Avg | PDI |
|---|---|---|---|---|---|
| 1 | T | 40 | 58 | 46 | 0.063 |
| 2 | pool | — | 58 | 47 | 0.063 |
| 3 | — | — | 82 | 69 | 0.083 |

Uniformly-sized lipid nanoparticles were produced. Replacing the cross-shaped mixing chamber with a T-shaped mixing chamber (0.5 mm inner diameter) while increasing the concentration of siRNA to 0.9 mg/mL at a flow rate of 40 mg/mL (same total amount of siRNA in one-half the volume) produced the less uniformly-sized lipid nanoparticles.

Process Example 3 Effect of Flow Rates, Velocities, and Solution Concentrations

In a series of experiments using a T-shaped mixing chamber and having an inner diameter of 0.5 mm, a single nucleic acid stream and a single lipid stream were mixed at various flow rates/velocities and concentrations. The nucleic acid and lipid streams included the same constituents as described above in Process Example 2. No dilution step was used in these examples since the initial siRNA concentrations were adjusted to obtain a final solution concentration the same as entry 1 in Table 8. The concentration of lipids in ethanol in these experiments was either 16.7 mg/mL (1×) or 25 mg/mL (1.5×). The results are shown in Table 9 below with the Z-Avg, #-Avg, and PDI determined 60 minutes post-mixing.

TABLE 9

| Lipid Flow (mL/min) | Lipid linear velocity (m/s) | [lipid] | Total siRNA Flow (mL/min) | siRNA linear velocity (m/s) | [siRNA] (mg/mL) | NaCl (mM) | Z-Avg | #-Avg | PDI |
|---|---|---|---|---|---|---|---|---|---|
| 40 | 3.4 | 1x | 80 | 6.8 | 0.45 | 100 | 60 | 44 | 0.089 |
| 40 | 3.4 | 1x | 120 | 10.2 | 0.3 | 66 | 58 | 46 | 0.048 |
| 40 | 3.4 | 1x | 160 | 13.6 | 0.225 | 50 | 60 | 42 | 0.110 |
| 20 | 1.7 | 1x | 60 | 5.1 | 0.3 | 66 | 59 | 47 | 0.037 |
| 20 | 1.7 | 1x | 80 | 6.8 | 0.225 | 50 | 59 | 43 | 0.100 |
| 40 | 3.4 | 1.5x | 120 | 10.2 | 0.45 | 100 | 66 | 54 | 0.032 |
| 40 | 3.4 | 1.5x | 160 | 13.6 | 0.3375 | 75 | 64 | 43 | 0.108 |
| 20 | 1.7 | 1.5x | 60 | 5.1 | 0.45 | 100 | 66 | 50 | 0.051 |
| 20 | 1.7 | 1.5x | 80 | 6.8 | 0.3375 | 75 | 67 | 46 | 0.067 |

Process Example 4: Effect of Flow Rates and Velocities

In a series of experiments using a T-shaped mixing chamber, a single nucleic acid stream and a single lipid stream were mixed from opposing directions at various flow rates/linear velocities and subsequently diluted with water at a 1 mm inner diameter dilution tee. The siRNA, cationic lipid A1, PEG lipid B1, cholesterol, and DSPC were used in Process Example 4 in amounts as described above. The total concentration of lipids in the ethanol stream was 16.7 mg/mL. The concentration of siRNA in the nucleic acid stream was 0.9 mg/mL. The results in Table 10 show that increasing linear velocity decreases the particle size and the PDI.

TABLE 10

| Lipid Flow (mL/min) | Lipid linear velocity (m/s) | Total siRNA Flow (mL/min) | siRNA linear velocity (m/s) | dilution Flow (mL/min) | Z-Avg | PDI |
|---|---|---|---|---|---|---|
| 5 | 0.43 | 5 | 0.42 | 5 | 168 | 0.118 |
| 10 | 0.85 | 10 | 0.85 | 10 | 130 | 0.137 |
| 20 | 1.7 | 20 | 1.7 | 20 | 97 | 0.070 |
| 30 | 2.6 | 30 | 2.6 | 30 | 95 | 0.047 |
| 40 | 3.4 | 40 | 3.4 | 40 | 85 | 0.039 |

Process Example 5: Effect of Orientation of T-Shaped Mixing Chamber

Table 11 shows the results from two experiments using an alternate mixing chamber (0.5 mm inner diameter). In entry 1 are shown the results obtained where the siRNA enters from the branch and in entry 2 are shown the results obtained where the lipids enter from the branch. For both experiments, the siRNA and lipids were the same as those described above in Process Example 2. The flow rate for the siRNA streams was 120 mL/min and the flow rate of the lipid streams was 40 mL/min. The siRNA concentration was 0.3 mg/mL in a buffer solution containing 66 mM NaCl. The concentration of the lipids was 16.7 mg/mL. The Z-Avg, #-Avg, and PDI were determined 60 minutes post-mixing.

TABLE 11

| entry | Initial mixing chamber | Z-Avg | #-Avg | PDI |
|---|---|---|---|---|
| 1 | T, siRNA into branch | 62 | 48 | 0.070 |
| 2 | T, lipid into branch | 66 | 46 | 0.106 |

Process Example 6: Effect of Mixing Chamber Configurations

A series of experiments were conducted using mixing chambers having various configurations of nucleic acid and lipid streams with the total number of streams ranging from 3 to 6. In each case the mixing chamber had a 1 mm inner diameter chamber and the flow rates were adjusted to maintain the combined flow of 240 mL/min for the siRNA streams and 80 mL/min for the lipid streams. The concentration of siRNA in these experiments was 0.3 mg/mL and the concentration of lipids was 16.7 mg/mL. The linear velocity of the combined siRNA streams was 5.1 meters/second. The linear velocity of the combined lipid streams was 1.7 meters/second. Where the number of streams allows for more than one arrangement of streams, Table 11 indicates the angle between lipid or siRNA streams. For example, in the case of three lipid streams and three siRNA streams, each lipid stream is separated from the next lipid stream by either 60 degrees (i.e., 3 adjacent lipid streams) or 120 degrees (i.e., lipid streams separated by 120 degrees with intervening siRNA streams also separated by 120 degrees). For the experimental results summarized in Table 11, siRNA was used with cationic lipid A4, DSPC, cholesterol, and PEG lipid B1, in a ratio of 45:9:44:2. The results shown in Table 11 indicate that substantially the same results are obtained for the various mixing configurations where the total flow rates/velocities remained constant.

TABLE 11 b
| #siRNA streams | #Lipid streams | siRNA flow/strm (ml/min) | Lipid flow/strm (ml/min) | lipid or siRNA angle | 60 min Z-avg. (nm) | 60 min #avg. (nm) | % Encap. @60 min |
|---|---|---|---|---|---|---|---|
| 2 | 1 | 120 | 80 | — | 76 | 66 | 90 |
| 3 | 1 | 80 | 80 | — | 78 | 68 | 89 |
| 2 | 2 | 120 | 40 | 90 | 81 | 70 | 90 |
| 2 | 2 | 120 | 40 | 180 | 81 | 70 | 89 |
| 1 | 3 | 240 | 26.6 | — | 90 | 76 | 91 |
| 4 | 2 | 60 | 40 | 60 | 80 | 70 | 83 |
| 4 | 2 | 60 | 40 | 120 | 80 | 70 | 84 |
| 4 | 2 | 60 | 40 | 180 | 81 | 71 | 84 |
| 3 | 3 | 80 | 26.6 | 60 | 81 | 70 | 86 |
| 3 | 3 | 80 | 26.6 | 120 | 78 | 67 | 86 |
| 2 | 4 | 120 | 20 | 60 | 85 | 74 | 85 |
| 2 | 4 | 120 | 20 | 120 | 83 | 72 | 87 |
| 2 | 4 | 120 | 20 | 180 | 82 | 71 | 85 |
Example 2: Conjugation of a Fatty Acid to APOC 3-siRNA
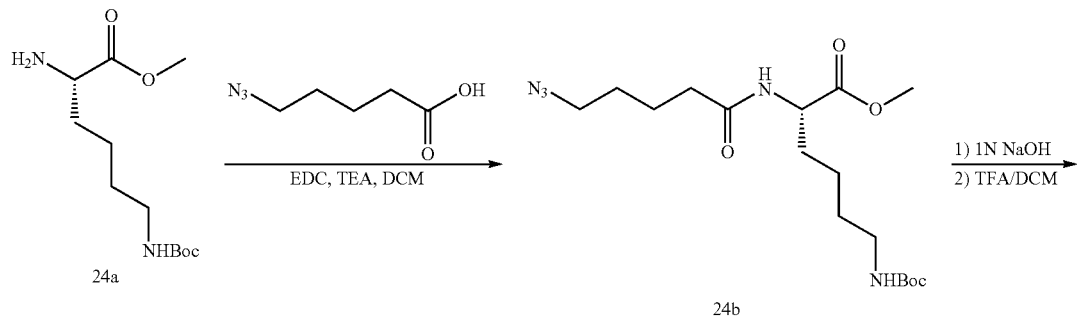
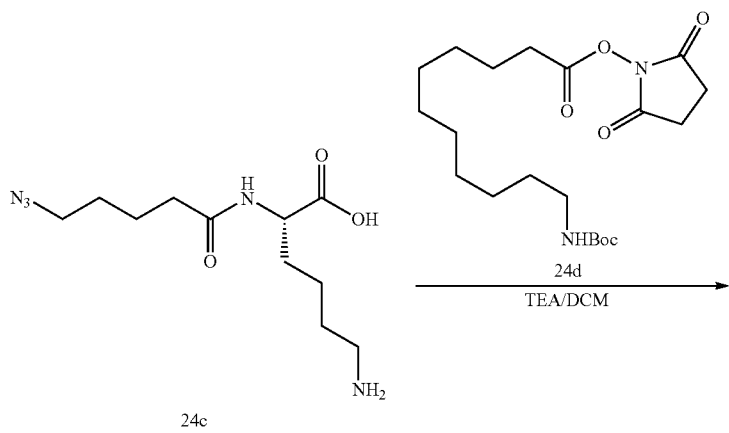

133
134
-continued
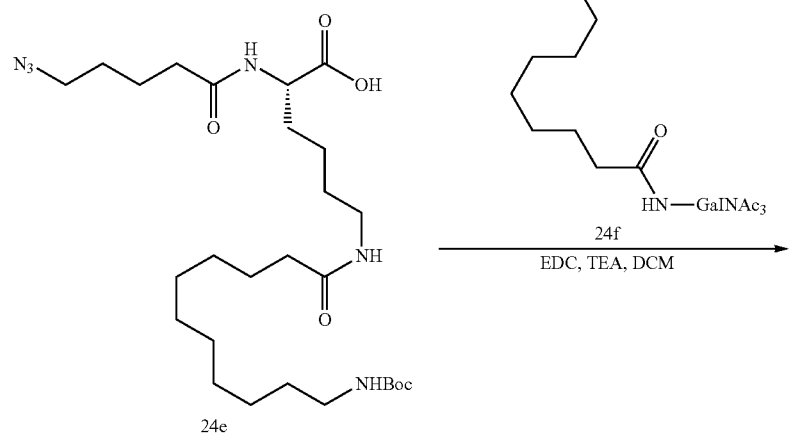
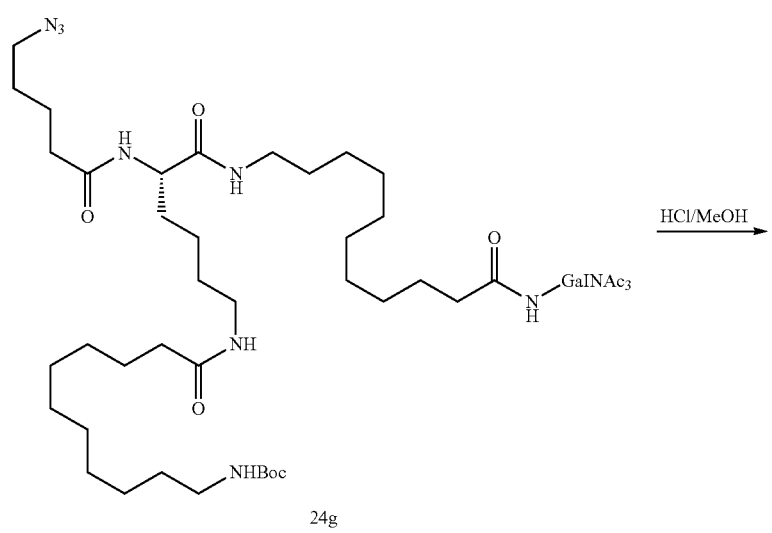
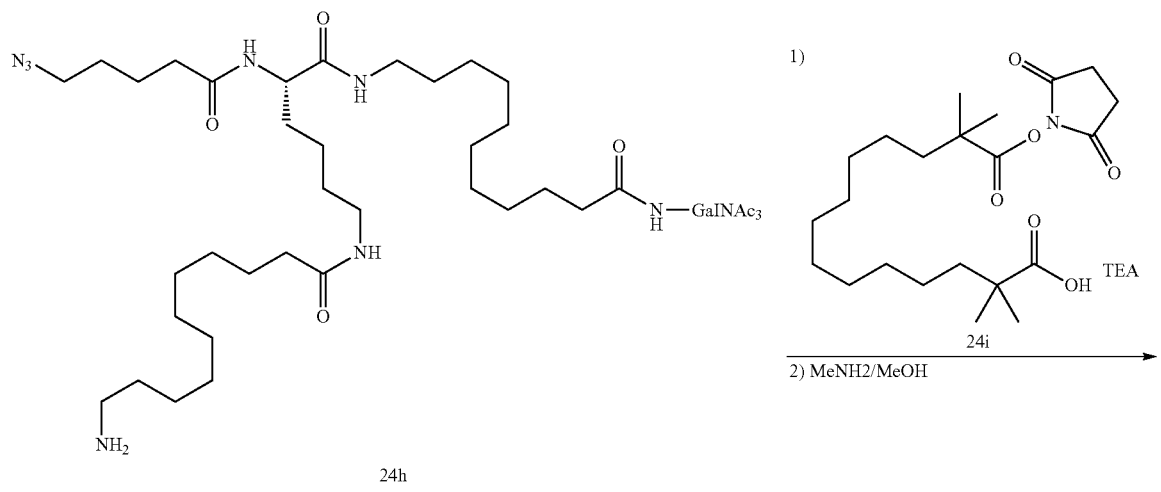

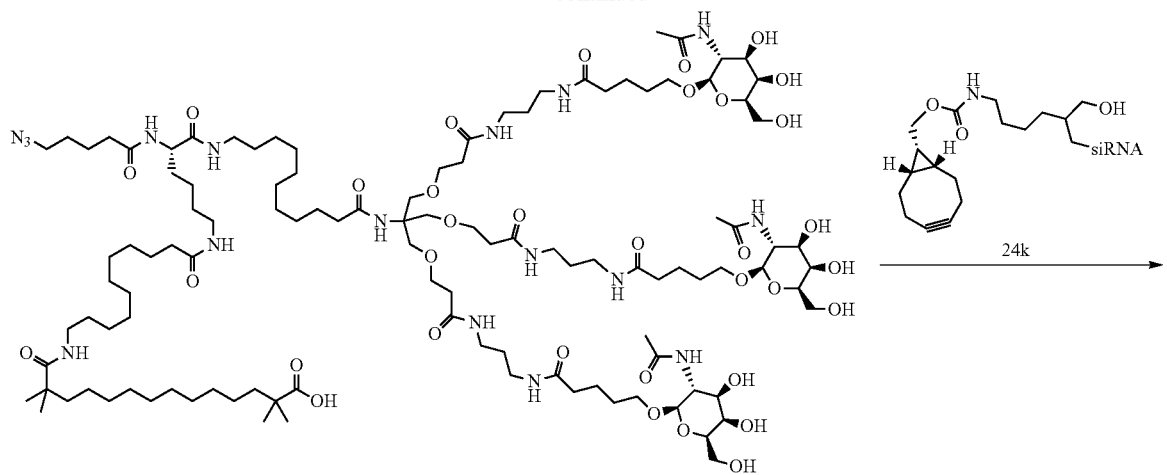
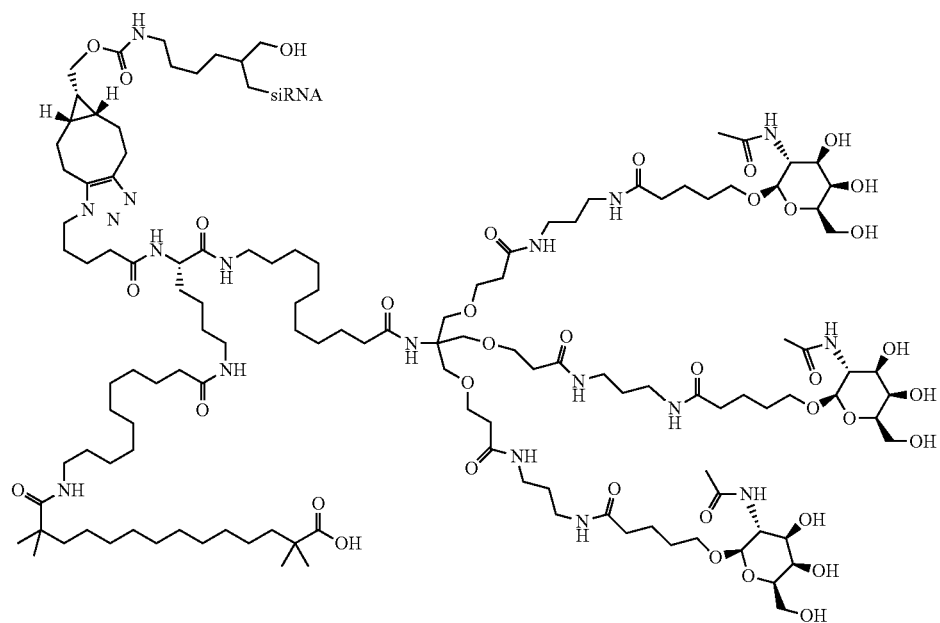

-continued

GalNAc3 = 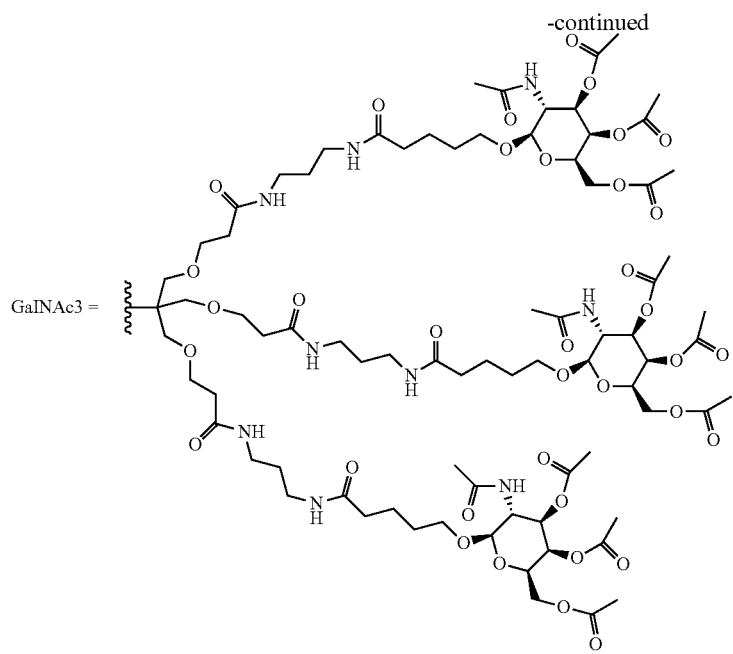

Preparation of 24b: To a solution of 24a (1.244 g, 4.19 mmol) in 25 ml DCM, TEA (0.58 ml, 4.19 mmol) was added, followed by N3-pentanoic acid (500 mg, 3.49 mmol). EDC (804 mg, 4.19 mmol) was added at last. The reaction stirred at room temperature for 4 hr. The reaction was extracted between brine and DCM. Combined all organics, dried, concentrated and purified over SiO2 gel with 60% ethylacetate/heptane to afford 1.20 g compound 24b (89% yield). $^1$H NMR (CHLOROFORM-d, 400 NHz) d: 5.88-6.37 (m, 1H), 4.60 (d, J=4.8 Hz, 2H), 3.77 (s, 3H), 3.33 (t, J=6.7 Hz, 2H), 3.13 (d, J=6.5 Hz, 2H), 2.30 (t, J=7.2 Hz, 2H), 1.81-1.95 (m, 1H), 1.63-1.81 (m, 5H), 1.48-1.57 (m, 2H), 1.46 (s, 9H), 1.36 (d, J=6.8 Hz, 2H)

Preparation of 24c: To a solution of 24b (860 mg, 2.23 mmol) in 12 ml THF, 1N NaOH (5.58 ml, 5.58 mmol) was added. The reaction stirred at room temperature for 0.5 hr. The reaction was diluted with brine and 20 ml DCM was added. The pH of aqueous layer was adjusted to pH ~5 with 1N HCl, then extracted with DCM. Combined all organics, dried, concentrated and the crude solid was redissolved into 6 ml DCM. 0.6 ml TFA was added and the reaction stirred at room temperature for 2 hr. The reaction was concentrated and afforded the crude 24c (400 mg, 54%), which was used directly without further purification. Under LC-MS method I, the product showed a major peak at 0.43 min. with a mass of 272.5 (M+H$^+$).

Preparation of 24e: To a solution of 24c (400 mg, 1.04 mmol) in 10 ml DCM, TEA (0.434 ml, 3.11 mmol) was added, followed by the addition of 24d (538 mg, 1.35 mmol). The reaction stirred at room temperature for 3 hr. The reaction was extracted between H2O and DCM. Combined all organics, dried, concentrated and purified over SiO2 gel with 8% MeOH/DCM to afford 475 mg of 24e (82% yield). 1H NMR (CHLOROFORM-d, 400 MHz) d: 6.74-6.98 (m, 1H), 5.95-6.13 (m, 1H), 4.55 (dd, J=7.2, 2.4 Hz, 2H), 3.32 (t, J=6.7 Hz, 4H), 3.11 (d, J=5.8 Hz, 2H), 2.30-2.37 (m, 2H), 2.20-2.26 (m, 2H), 1.90 (br. s., 2H), 1.71-1.80 (m, 2H), 1.59-1.71 (m, 4H), 1.51-1.59 (m, 2H), 1.35-1.51 (m, 13H), 1.20-1.35 (m, 13H)

Preparation of 24f

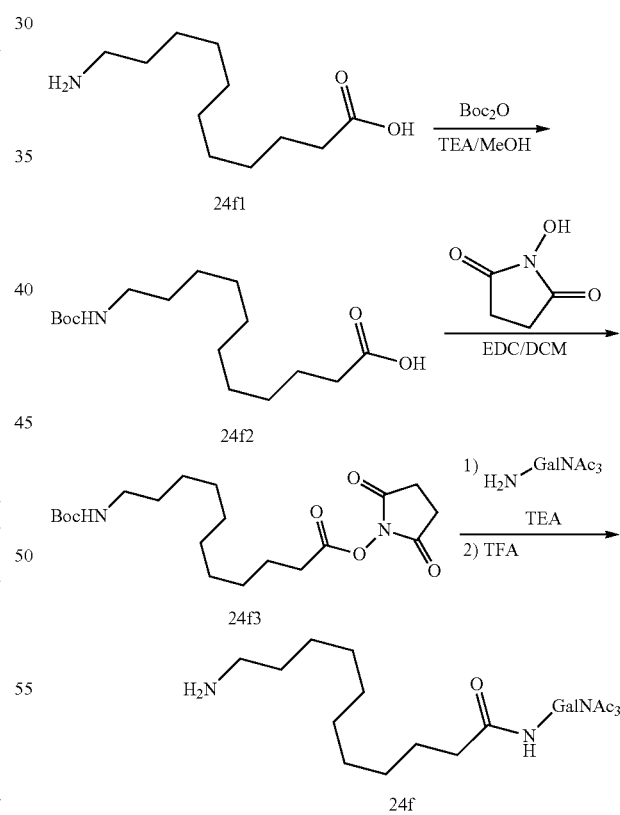

Preparation of intermediate 24f2: To a solution of 24f1 (1.0 g, 4.97 mmol) in MeOH (40 ml), TEA (1.04 ml, 7.45 mmol) was added, followed by di t-butyl dicarbonate (2.17 g, 9.94 mmol). The reaction was heated at 60° C. for 1.5 hr. The reaction was concentrated and purified over SiO2 column with 5% MeOH/DCM to afford 1.2 g compound 24f2 (80% yield). $^1$H NMR (CHLOROFORM-d, 400 MHz)

d: 4.51 (br. s, 1H), 3.00-3.22 (m, 2H), 2.37 (t, J=7.4 Hz, 2H), 1.59-1.71 (m, 2H), 1.46 (s, 11H), 1.29 (br. s., 12H).

Preparation of intermediate 24f3: To a solution of 24f2 (1.2 g, 3.98 mmol) in DCM (30 ml), N-hydroxyl succinimide (0.60 g, 5.18 mmol) was added, followed by EDC (1.0 g, 5.18 mmol). The solution was stirred at room temperature for overnight. The reaction was concentrated, directly loaded onto SiO2 column and purified with 40% ethylacetate/heptane to afford 1.46 g compound 24f3 (92% yield). 1H NMR (CHLOROFORM-d, 400 MHz) d: 4.49 (br. s, 1H), 3.04-3.19 (m, 2H), 2.86 (d, J=4.5 Hz, 4H), 2.62 (t, J=7.4 Hz, 2H), 1.70-1.82 (m, 2H), 1.37-1.53 (m, 13H), 1.30 (br. s., 10H)

Preparation of intermediate 24f: To a solution of Gal-NAc3-NH2 (300 mg, 0.16 mmol) in DCM (1.5 ml), TEA (0.11 ml, 0.79 mmol) was added, followed by the addition of 24l3 (188 mg, 0.47 mmol). The reaction stirred at room temperature for overnight. Then trifluoroacetic acid (1.0 ml) was added. After 2 hrs, LC-MS showed the disappearance of the intermediate. The reaction was concentrated and purified on open access HPLC under acidic condition with ELSD as a detection. The HPLC fractions containing the product were collected and the solvent was evaporated to afford 220 mg compound 24f (67% yield). LC-MS showed that partial product lost one acetyl group. HPLC conditions for purification: column: Sunfire 30×100 mm 5 um column; organic solvent: ACN w/7.5% TFA; aqueous solvent: $H_2O$ w/7.5% TFA; flow rate: 75 ml/min. Gradient: 15-40% H2O/AcCN; Time: 9.5 min. detection: ELSD (Evaporative Light Scattering Detector) as detection. Under LC-MS method I, the product showed a peak at 0.83 min. with a mass of 989.9 (M/2+H$^+$).

Preparation of 24g: To a solution of 24e (172 mg, 0.31 mmol) in 3 ml DCM, 24f (250 mg, 0.12 mmol) was added, followed by TEA (0.069 ml, 0.50 mmol). EDC (95 mg, 0.5 mmol) was added at last. The reaction stirred at room temperature for overnight. The reaction was concentrated and purified over $SiO_2$ column with 5% MeOH/DCM to afford 230 mg 24g (74% yield). Under LC-MS method I, the product showed a peak 1.30 min. with a mass of 1258.2 (M/2+H$^+$).

Preparation of 24h: To a solution of 24g (230 mg, 0.091 mmol) in 1 ml THF, 0.457 ml 4N HCl (in dioxane, 1.83 mmol) was added. The reaction stirred at room temperature for 1 hr. The reaction was concentrated and purified over HPLC to afford 50 mg 24h (23% yield), which lost one acetyl group on the sugar. HPLC conditions for purification: column: Sunfire 30×100 mm 5 um column; organic solvent: ACN w/7.5% TFA; aqueous solvent: $H_2O$ w/7.5% TFA; flow rate: 75 ml/min. Gradient: 15-40% H2O/AcCN; Time: 9.5 min. detection: ELSD (Evaporative Light Scattering Detector) as detection. Under LC-MS method I, the product showed a peak at 0.95 min. with a mass of 1187.1 (M/2+H$^+$).

Preparation of 24i: To a solution of 2,2,13,13-tetramethyltetradecanedioic acid (40 mg, 0.127 mmol) in 2 ml DCM, N—OH succinimide (9.81 mg, 0.085 mmol) was added, followed by the addition of EDC (16.34 mg, 0.085 mmol). The reaction was stirred at room temperature for overnight. The reaction was concentrated and purified over HPLC to afford 20 mg 24i (38% yield). HPLC conditions for purification: column: Sunfire 30×100 mm 5 um column; organic solvent: ACN w/7.5% TFA; aqueous solvent: $H_2O$ w/7.5% TFA; flow rate: 75 ml/min. Gradient: 45-70% H2O/AcCN; Time: 9.5 min. detection: ELSD (Evaporative Light Scattering Detector) as detection. Under LC-MS method I, the product showed a peak at 1.55 min. with a mass of 434.3 (M+Na$^+$).

Preparation of 24j: To a solution of 24h (20 mg, 8.05 µmol) in 0.5 ml DCM, TEA (4.5 µl, 32 µmol) was added, followed by the addition of 24i (6.62 mg, 16 µmol) and DMAP (3.93 mg, 32 µmol). The reaction stirred at room temperature for overnight. Then 0.5 ml 2N MeNH$_2$/MeOH was added for the deprotection. The reaction stirred at room temperature for another overnight. The reaction was concentrated and acetone was added to precipitate the product and remove excess reagents and lipids to afforded 12 mg 24j (64% yield). Under LC-MS method I, the product showed a peak at 0.69 min. with a mass of 1166.9 (M/2+H$^+$).

Preparation of 24K

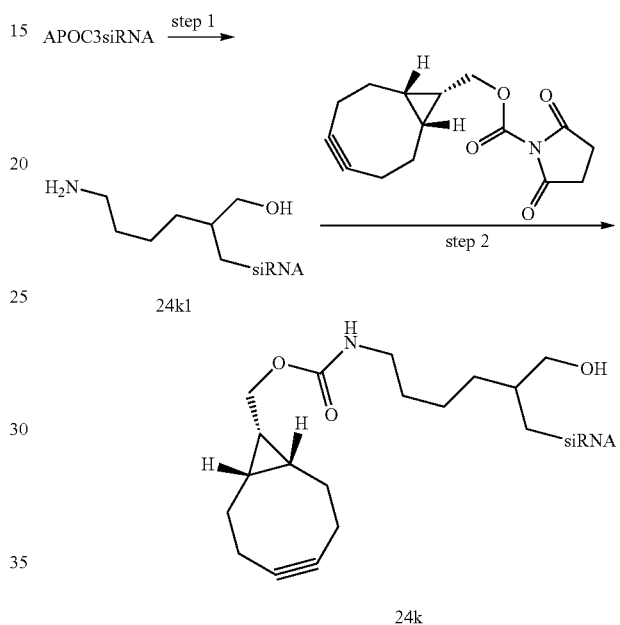

Step 1:
Sequence of APOCIII siRNA (Synthesized using conventional methods known in the art):
Antisense strand: AGCACuGAGAAuACuGuc-rib-X058. (SEQ ID NO: 544 (SEQ ID. NO: 543 with shown modifications)).
wherein:
A is DNA, uppercase letters indicate non-modified nucleotide, lowercase letters indicate a 2'-OMe modified nucleotide, italics letters indicate a 2'-MOE modified nucleotide, rib is ribitol, and X058 is a non-nucleotidic linker of Formula:

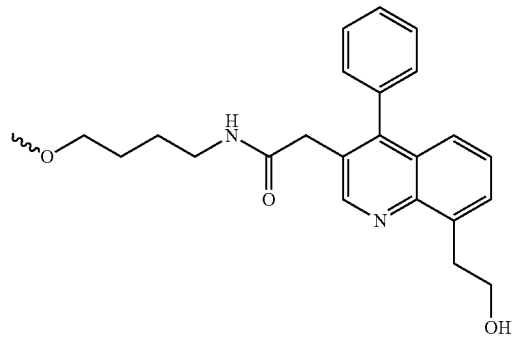

Sense Strand: GAcAGuAuucucAGuGcu-rib-C6OH. (SEQ ID NO: 546 (SEQ ID NO: 545 with shown modifications)).

APOCIII siRNA was reacted with 2-Dimethoxytrityloxymethyl-6-fluorenylmethoxycarbonylamino-hexane-1-succinoyl-long chain alkylamino-CPG (Glen Research Catalog No 20-2957) to generate product 24k1.

Step 2: APOCIII siRNA (24k1: 401 μL, 11.2 mM in H2O, 4.49 μmol) was mixed with 401 □l DMF to get a clear solution. Then TEA (180 μl, 0.25M in DMF, 45 μmol) was added, followed by BCN-NHS (((1R,8S,9S)-Bicyclo[6.1.0]non-4-yn-9-ylmethyl N-succinimidyl carbonate) (9.16 mg, 31 μmol). The reaction stirred at room temperature for 1 hr. The reaction was diluted with H₂O to 10 ml and extracted with ethylacetate 3 times. The aqueous layer was separated and concentrated to ~5 ml and purified over PD-10 desalting column (GE healthcare).

Preparation of 24: 24j (5.8 mg, 2.5 μmol) was added into 105 μl compound 24k (Apoc 3 siRNA 9.5 mM in H₂O, 0.993 μmol). After 1 hr, the reaction became viscous. So another 60 μl H₂O was added and the reaction stirred at room temperature for overnight. The reaction was diluted with H₂O and purified over HPLC to afford 5 mg conjugate 24 (57% yield). HPLC conditions for purification: Column: Xselect Prep phenylhexyl 5 um OBD 19×50 mm; organic solvent: AcCN modified with 100 mM TEA.HOAc; aqueous solvent: H₂O modified with 100 mM TEA.HOAc; Gradient: 5-50% AcCN/H₂O; Time: 10 min. Under LC-MS method H, the product showed a peak at 5.96 min. with the desired mass of 8896 after deconvolution.

Reference Example 3: APOC3 siRNA Conjugated with GalNAc

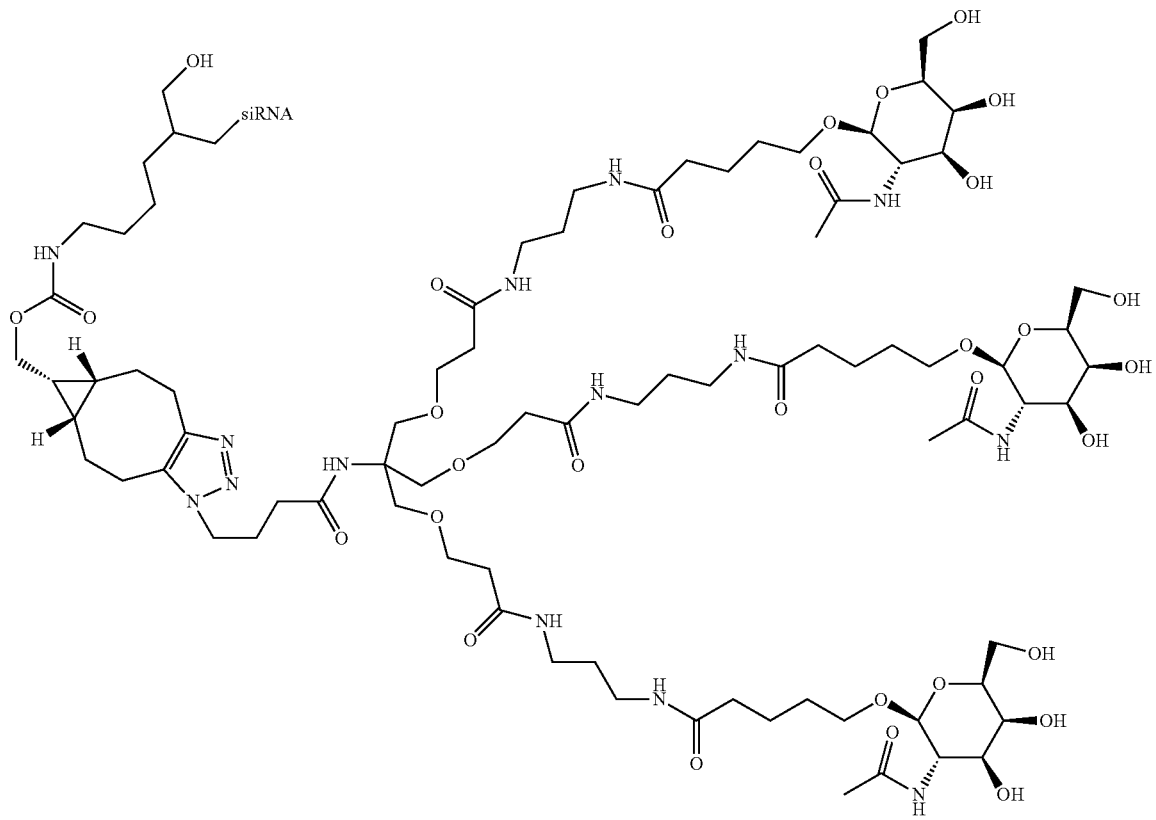

Reference Example 3 was prepared according to procedure of Example 24 (replacing 24j with GalNac3-N3 (below).

Preparation of GalNac3-N3

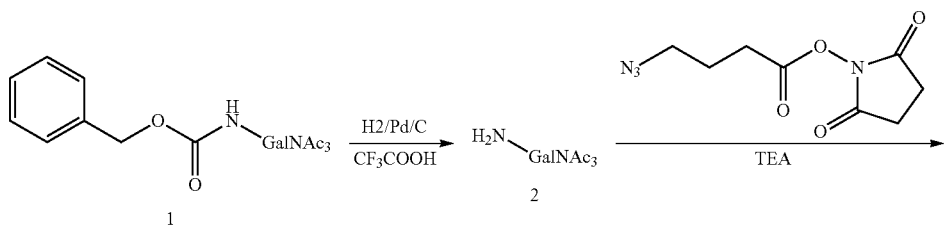

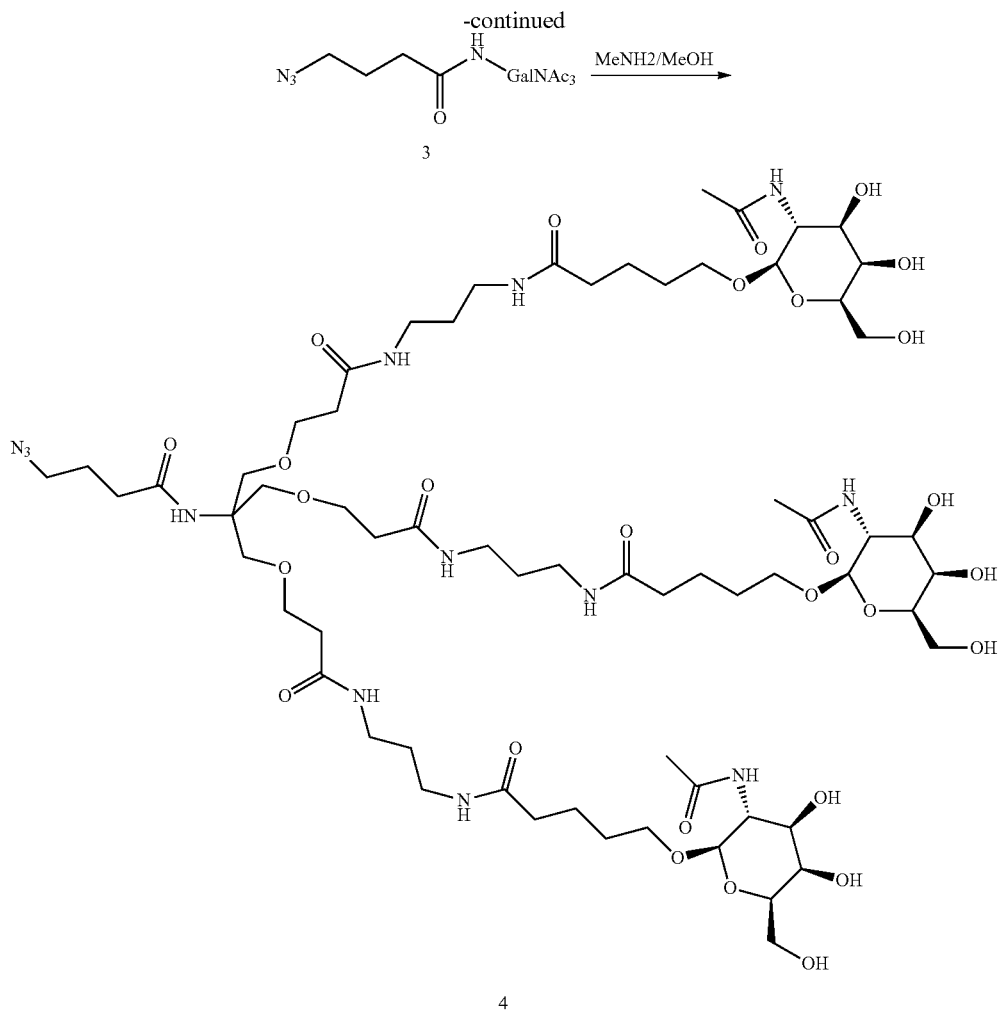

Preparation of intermediate 2: Compound 1 (2.06 g, 1.07 mmol) was dissolved in 20 ml ethanol, TFA (82 ul, 1.07 mmol) was added, followed by 10% Pd/C (0.114 g, 0.11 mmol). The reaction was treated under H2 balloon for 6 hours. The reaction was filtered, washed with ethanol and concentrated to get white solid, which was used directly for next step. Under LC-MS method I, the product showed a peak at 0.81 min. with a mass of 898.5 (M/2+H$^+$).

Preparation of intermediate 3: Compound 2 (4.848 g, 0.479 mmol) was dissolved in 10 ml anhdrous DMF, 2,5-dioxopyrrolidin-1-yl-4 azidobutenoate (0.325 g, 1.436 mmol) was added, followed by the addition of DIPEA (0.418 ml, 2.394 mmol). The reaction was to react overnight at room temperature. The reaction was concentrated with no heating, directly loaded onto a pre-equilibrated SiO2 column and purified with 0-20% methanol/DCM step gradient to afford 2.383 g compound 3 (49.25% yield).

Under LC-MS method I, the product showed a peak at 1.27 min. with a mass of 953.7 (M/2+H$^+$).

Preparation of intermediate 4: Mixed compound 3 (1.33 g, 0.70 mmol) with MeNH2 (17.45 ml, 2.0M in Methanol, 34.9 mmol). The reaction stirred at room temperature for 2 hr. LC-MS only showed the product peak. The reaction was concentrated. Then the solid redissolved into ethanol and was precipitated with acetone to afford 1.0 g compound 4 (94% yield). Under LC-MS method I, the product showed a peak at 0.53 min. with a mass of 764.5 (M/2+H$^+$).

We claim:

1. A double-stranded RNAi agent for inhibiting expression of an APOC3 gene in a cell, the RNAi anent comprising a first strand and a second strand, wherein said first strand is less than about 49 nucleotides in length and comprises at least 19 contiguous nucleotides differing by 0 or 1 nucleotides from the nucleotide sequence (5' to 3') AGCACUGAGAAUACUGUCC (SEQ ID NO: 132), wherein the second strand is substantially complementary to the first strand, wherein the first strand comprises at least one modified nucleotide or modified internucleoside linkage, wherein the 3' end of the first strand and/or the second strand comprises a 3' end cap, and wherein the 3' end of the first and/or second strand terminates in a phosphate or modified internucleoside linker and further comprises, in 5' to 3' order: a spacer, a second phosphate or modified internucleoside linker, and a 3' end cap.

2. The RNAi agent of claim 1, wherein the spacer is selected from a sugar, alkyl, cycloalkyl, ribitol, 2'-deoxyribitol, diribitol, 2'-methoxyethoxy-ribitol, C3 [—(CH$_2$)$_3$—], C4 [—(CH$_2$)$_4$—], C5 [—(CH$_2$)$_5$—], C6 [—(CH$_2$)$_6$—], or 4-methoxybutane-1,3-diol.

3. The RNAi agent of claim 1, wherein the RNAi agent is ligated to one or more diagnostic compound, reporter group, cross-linking agent, nuclease-resistance conferring moiety, natural or unusual nucleobase, lipophilic molecule, cholesterol, lipid, lectin, steroid, uvaol, hecigenin, diosgenin, terpene, triterpene, sarsasapogenin, Friedelin, epifriedelanol-derivatized lithocholic acid, vitamin, carbohydrate, dextran, pullulan, chitin, chitosan, synthetic carbohydrate, oligo lactate 15-mer, natural polymer, low- or medium-molecular weight polymer, inulin, cyclodextrin, hyaluronic acid, protein, protein-binding agent, integrin-targeting molecule, polycationic, peptide, polyamine, peptide mimic, and/or transferrin.

4. The RNAi agent of claim 1, wherein the RNAi agent is ligated to one or more carbohydrates.

5. The RNAi agent of claim 1, wherein the RNAi agent is ligated to one or more N-Acetylgalactosamines.

6. A double-stranded RNAi agent for inhibiting expression of an APOC3 gene in a cell, the RNAi agent comprising a first strand and a second strand, wherein said first strand is less than about 49 nucleotides in length and comprises at least 19 continuous nucleotides differing by 0 or 1 nucleotides from the nucleotide sequence (5' to 3') AGCACUGA-GAAUACUGUCC (SEQ ID NO: 132), and wherein the second strand is substantially complementary to the first strand, wherein the RNAi agent is ligated to an N-Acctyl-galactosamine-containing compound that comprises the following structure:

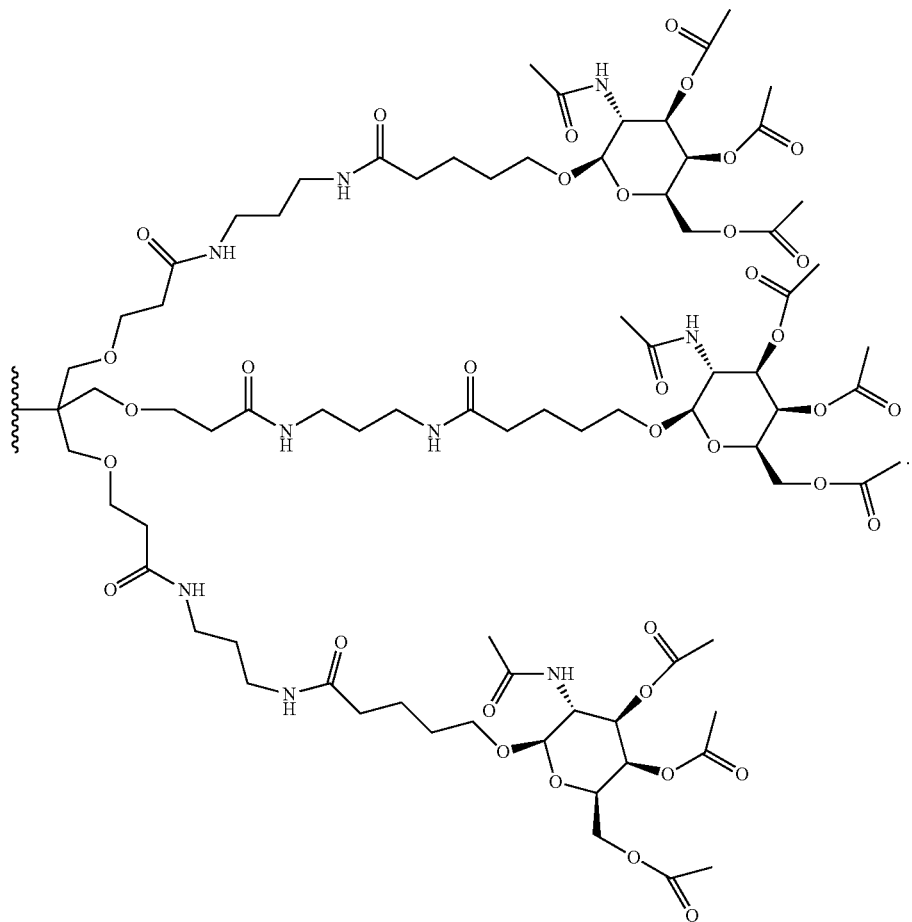 [SMILES: *C(COCCC(=O)NCCCNC(=O)CCCCO[C@@H]1O[C@H](COC(C)=O)[C@H](OC(C)=O)[C@H](OC(C)=O)[C@H]1NC(C)=O)(COCCC(=O)NCCCNC(=O)CCCCO[C@@H]1O[C@H](COC(C)=O)[C@H](OC(C)=O)[C@H](OC(C)=O)[C@H]1NC(C)=O)COCCC(=O)NCCCNC(=O)CCCCO[C@@H]1O[C@H](COC(C)=O)[C@H](OC(C)=O)[C@H](OC(C)=O)[C@H]1NC(C)=O]

7. The RNAi agent of claim 1, wherein the 3' end cap comprises:

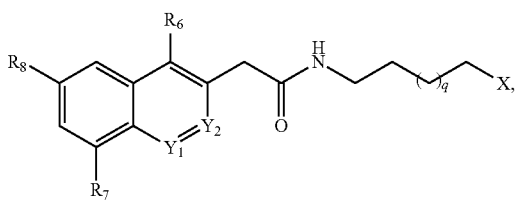

wherein,

X is (a) the 3' end of a strand of a RNAi agent; (b) the 3' end of a molecule comprising a strand of a RNAi agent, wherein the 3' end of the strand terminates in a phosphate or modified internucleoside linker and further comprises in 5' to 3' order: a spacer, and a second phosphate or modified internucleoside linker; or (c) is a 3' end of a molecule comprising: a strand of an APOC3 RNAi agent, wherein the 3' end of the strand terminates in a phosphate or modified internucleoside linker and optionally further comprises, in 5' to 3' order: a spacer and a second phosphate or modified internucleoside linker;

q is 0, 1, or 2;
$R_6$ is phenyl which is unsubstituted or substituted with a group selected from benzoxy and 3,4-dihydroxybutyl;
$R_7$ is hydrogen or hydroxy-ethyl, wherein if $R_7$ is hydroxy-ethyl, the hydroxyl can be optionally functionalized as succinate or attached to a solid support;
$R_8$ is hydrogen or methoxy;
$Y_1$ is CH or N; and
$Y_2$ is N or $CR_9$; wherein $R_9$ is selected from hydrogen and methyl.

8. A pharmaceutical composition comprising one or more RNAi agents of claim 1, and at least one pharmaceutically acceptable excipient.

9. A cell or vector containing the RNAi agent of claim 1.

10. The RNAi agent of claim 1, wherein the second strand is less than about 49 nucleotides in length and comprises at least 19 contiguous nucleotides differing by 0, or 1 nucleotides from the nucleotide sequence (5' to 3') GACA-GUAUUCUCAGUGCUU (SEQ ID NO: 71).

11. The RNAi agent of claim 10, wherein the first strand and second strand comprise the duplex pair of SEQ ID NOs: 378/290; 484/438; 485/438; 486/438; 487/438; 488/438; 489/438; 490/438; 491/438; 492/438; 493/438; 494/438; 495/438; 496/438; 497/438; 498/438; 499/438; 500/438; 501/438; 502/438; or 503/439.

12. A double-stranded RNAi agent for inhibiting expression of an APOC3 gene in a cell, the RNAi agent comprising a first strand and a second strand wherein the first strand and second strand comprise the duplex pair of SEQ ID NOs: 484/438, 485/438, 486/438; 487/438; 488/438; 489/438; 491/438; 496/438; 497/438; 498/438; 499/438; 501/438; 502/438; or 503/439.

13. The RNAi agent of claim 12, wherein the 3' end of the first strand and/or the second strand comprises a 3' end cap.

14. The RNAi agent of claim 12, wherein the first strand and the second strand form a duplex region of about 15 to about 30 nucleotide base pairs.

15. The RNAi agent of claim 12, wherein one or more nucleotides of the first strand or the second strand has been replaced by a spacer.

16. A pharmaceutical composition comprising one or more RNAi agents of claim 6, and at least one pharmaceutically acceptable excipient.

17. A pharmaceutical composition comprising one or more RNAi agents of claim 12, and at least one pharmaceutically acceptable excipient.

* * * * *

UNITED STATES PATENT AND TRADEMARK OFFICE
CERTIFICATE OF CORRECTION

PATENT NO. : 10,240,153 B2  
APPLICATION NO. : 15/403919  
DATED : March 26, 2019  
INVENTOR(S) : Jan Weiler et al.

Page 1 of 1

It is certified that error appears in the above-identified patent and that said Letters Patent is hereby corrected as shown below:

In the Claims

In Column 313, Claim 1, Line 51, delete "anent" and insert -- agent --.

In Column 314, Claim 3, Line 55, delete "hecigenin," and insert -- hecogenin, --.

In Column 315, Claim 6, Line 5, delete "continuous" and insert -- contiguous --.

In Column 315, Claim 6, Lines 9-10, delete "N-Acctylgalactosamine" and insert -- N-Acetylgalactosamine --.

In Column 316, Claim 7, Line 3, after "(c)" delete "is".

In Column 317, Claim 12, Line 12, after "491/438;" insert -- 494/438; 495/438; --.

Signed and Sealed this  
Twenty-eighth Day of April, 2020

Andrei Iancu  
*Director of the United States Patent and Trademark Office*